US007473694B2

(12) United States Patent
Unoki et al.

(10) Patent No.: US 7,473,694 B2
(45) Date of Patent: Jan. 6, 2009

(54) PYRAZOLOPYRIMIDINE DERIVATIVES OR PHARMACEUTICALLY ACCEPTABLE SALTS THEREOF

(75) Inventors: Gen Unoki, Tokyo (JP); Tomomi Kosugi, Tokyo (JP); Mika Takakuwa, Tokyo (JP); Hiroaki Makino, Yamaguchi (JP); Kenichiro Kataoka, Tokyo (JP); Yuko Yamakoshi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 179 days.

(21) Appl. No.: 11/377,363

(22) Filed: Mar. 17, 2006

(65) Prior Publication Data

US 2007/0173519 A1 Jul. 26, 2007

(30) Foreign Application Priority Data

Mar. 17, 2005 (JP) ............................ 2005-077509

(51) Int. Cl.

| | |
|---|---|
| ***A01N 43/54*** | (2006.01) |
| ***A61K 31/505*** | (2006.01) |
| ***C07D 239/00*** | (2006.01) |
| ***C07D 471/00*** | (2006.01) |
| ***C07D 487/00*** | (2006.01) |
| ***C07D 491/00*** | (2006.01) |

(52) U.S. Cl. ...................................... 514/267; 544/251

(58) Field of Classification Search ...................... None
See application file for complete search history.

(56) References Cited

FOREIGN PATENT DOCUMENTS

| | | | |
|---|---|---|---|
| WO | WO 2004/054504 | A2 | 7/2004 |
| WO | WO 2004/054505 | A2 | 7/2004 |
| WO | WO 2004/055015 | A1 | 7/2004 |
| WO | WO 2004/055019 | A1 | 7/2004 |
| WO | WO 2004/058176 | A2 | 7/2004 |
| WO | WO 2004/058762 | A1 | 7/2004 |
| WO | WO 2004/076458 | * | 9/2004 |
| WO | WO 2004/076458 | A1 | 9/2004 |
| WO | WO 2004/081013 | A1 | 9/2004 |
| WO | WO 2004/099127 | A1 | 11/2004 |
| WO | WO 2005/007092 | A3 | 1/2005 |
| WO | WO 2005/009370 | A2 | 2/2005 |

OTHER PUBLICATIONS

Enrique Martin-Blanco, "P38 MAPK signalling cascades: ancient roles and new functions", Bioessays 22 637-645, 2000.

H.Y. Shin, et al: "Regulatory Effect of Cytokine Production in Patients with Cerebral infarction by Yulda-Hanson-Tang", Immunopharmacology and Immunotoxicology 22 (2), 183-193, Marcel Dekker, Inc. 2000.

David Stokoe, et al. "Identification of MAPKAP kinase 2 as a major enzyme responsible for the phosphorylation of the small mammalian heat shock proteins", Federation of European Biochemical Societies, vol. 313, No. 3, 307-313, FEBS 11807, Elsevier Science Publishers B.V., Nov. 1992.

Oliver Werz, et al: "5-Lipoxygenase is phosphorylated by p38 kinase-dependent MAPKAP kinases", May 9, 2000, vol. 97, No. 10, pp. 5261-5266.

Olaf Heidenreich, et al.: "MAPKAP Kinase 2 Phosphorylates Serum Response Factor in Vitro and In Vivo", The Journal of boil. Chem., vol. 274, No. 20, May 14, pp. 14434-14443; 1999.

Yi Tan, et al.: "FGF and stress regulate CREB and ATF-1 via a pathway involving P38 MAP kinase and MAPKAP kinase-2", The EMBO Journal, vol. 15, No. 17, pp. 4629-4642; 1996.

Bernd Neufeld, et al: "Serine/Threonine Kinases 3pk and MAPK-activated Protein Kinase 2 Interact with the Basic Helix-Loop-Helix Transcription Factor E47 and Repress Its Transcriptional Activity", The Journal of Biological Chemistry, vol. 275, No. 27, Jul. 7, pp. 20239-20424: 2000.

David Stokoe, et al: "The substrate specificity and structure of mitogen-activated protein (MAP) kinase-activated protein kinase-2", Biochem. J. (1993) 296 843-849.

Alexey Kotlyarov, et al: "MAPKAP kinase 2 is essential for LPS-induced TNF-α biosynthesis", Nature Cell Biology, vol. 1, Jun. 1999, pp. 94-97.

Xinkang Wang, et al: "Mitogen-activated Protein Kinase-activated Protein (MAPKAP) Kinase 2 Deficiency Protects Brain from Ischemic Injury in Mice", The Journal of Biological Chemistry, vol. 277, No. 46, Nov. 15, pp. 43968-43972; 2002.

Isaac A. Manke, et al: "MAPKAP Kinase-2 Is a Cell Cycle Checkpoint Kinase that Regulates the $G_2$/M Transition and S Phase Progression in Response to UV Irradiation", Molecular Cell, vol. 17, pp. 37-48, Jan. 7, 2005.

* cited by examiner

*Primary Examiner*—Mark Berch
*Assistant Examiner*—Erich A. Leeser
(74) *Attorney, Agent, or Firm*—Sughrue Mion, PLLC

(57) ABSTRACT

A pyrazolopyrimidine derivative represented by formula (1) and pharmaceutically acceptable salt thereof exhibit excellent inhibitory activity against MAPKAP-K2. Accordingly, medicines containing this compound as an active ingredient are expected to be effective for treating diseases mediated by MAPKAP-K2 such as, for example, inflammatory disorder, autoimmune diseases, destructive osteopathy, cancer and/or tumor growth.

(1)

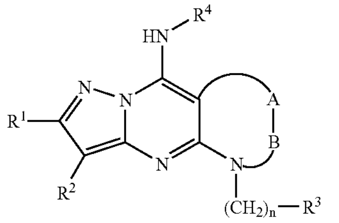

42 Claims, 1 Drawing Sheet

[Figure 1]
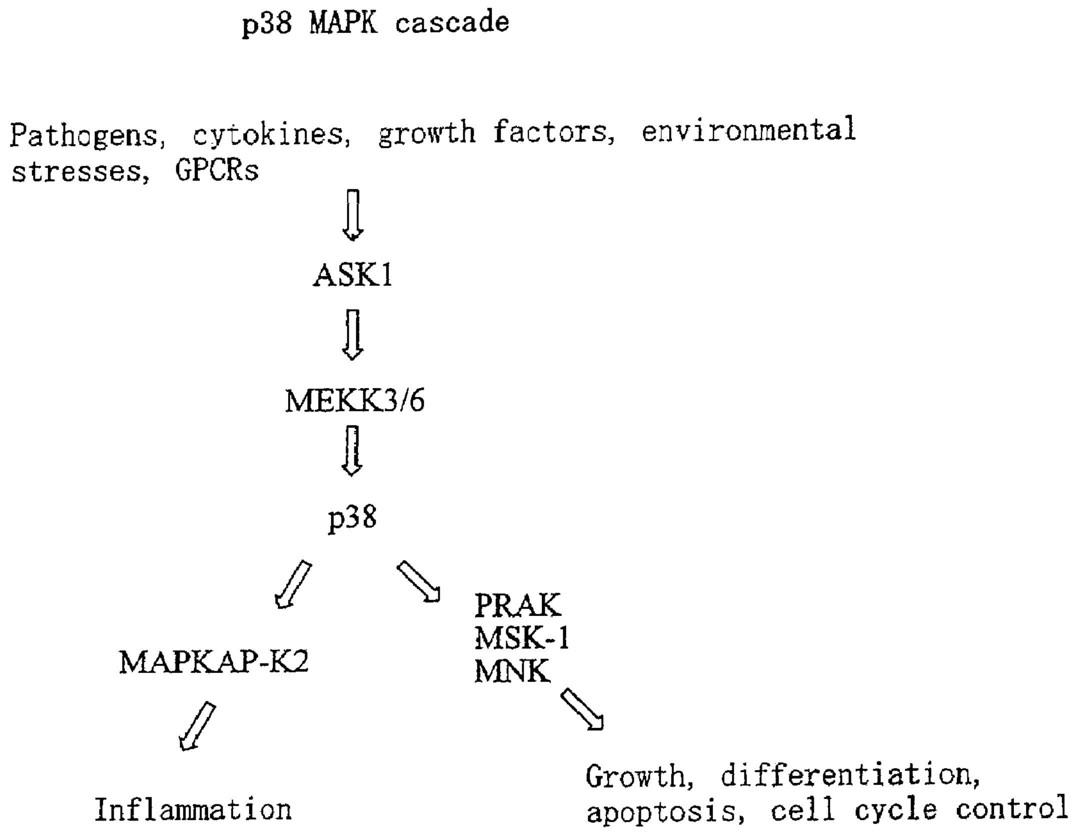

PYRAZOLOPYRIMIDINE DERIVATIVES OR PHARMACEUTICALLY ACCEPTABLE SALTS THEREOF

This application claims benefit under 35 U.S.C. §119(e) of U.S. Provisional Application No. 60/663,205 filed on Mar. 21, 2005, incorporated herein by reference in its entirety.

FIELD OF THE INVENTION

The present invention relates to a novel pyrazolopyrimidine derivative or a medically acceptable salt thereof, a pharmaceutical composition comprising them as an active ingredient, a MAPKAP-K2 (mitogen-activating protein kinase activating protein kinase 2) inhibitor comprising them as an active ingredient and a novel intermediate thereof. The present invention also relates to a therapeutic agent comprising these compounds as an active ingredient for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

BACKGROUND ART

MAPKAP-K2 (mitogen-activating protein kinase activating protein kinase 2) is a serine/threonine kinase and operates at immediate downstream of p38 kinase in a stress-induced MAPK pathway (FIG. 1).

This p38 kinase pathway is activated by various stress-related extracellular stimuli such as heat, ultraviolet ray, bacterial lipopolysaccharide or inflammatory cytokines. The activation of this pathway causes phosphorylation of transcription and initiation factors and affects cell division, apoptosis, cell differentiation, inflammatory response and infiltration of cancer cells (Martin-Blanco, Bioessays 22, 637-645).

p38 Kinase itself activates many protein kinases other than MAPKAP kinase, for example, Mnkl/2, PRAK and MSK1 (FIG. 1). This pathway is particularly important for discovery of novel anti-inflammatory drugs. A p38 kinase-selective inhibitor is effective for suppressing inflammatory cytokines in both cell base model and model animals of chronic inflammation (Lee et al., Immunopharmacology 47, 185-201 (2000)). However, a p38 kinase-knockout mouse is embryonic lethal. Moreover, it has been proved that cells derived from such an embryo exhibit a lot of anomaly in fundamental cellular responses. As another strategy for developing anti-inflammatory drugs, there may be mentioned a drug inhibiting this pathway in the level of MAPKAP-K2. MAPKAP-K2 exists in the nucleus in an unstimulated cell, and is transferred to cytosol when the cell is stimulated. It is known that this kinase phosphorylates many nuclear transcription factors and cytosolic proteins such as heat-shock protein involved in cell protection and 5-lipoxygenase involved in bioprotection and inflammation (Stokoe et al., FEBS Lett. 313, 307-313 (1992); Werz et al., Proc. Natl. Acad. Sci. USA 97, 5261-5266 (2000); Heindenreich et al., J. Biol. Chem. 274, 14434-14443 (1999); Tan et al., EMBO J. 15, 4629-4642 (1996); Neufeld, J. Biol. Chem. 275, 20239-20242 (2000)). All of these substrates contain a unique amino acid motif (XX-Hyd-XRXXSXX where Hyd represents a bulky hydrophobic residue) which is required for effective phosphorylation by MAPKAP-K2 (Stokoe et al., Biochem. J. 296, 843-849 (1993)).

MAPKAP-K2 is the only substrate of p38 kinase whose special function is currently identified. The special roll of MAPKAP-K2 in mediation of inflammatory response is remarkably demonstrated in a phenotype of MAPKAP-K2 knockout mouse (MAPKAP-K2$^{-/-}$) (Kotlyarov et al., Nature Cell Biol. 1, 94-97 (1999)). This mouse is not lethal and normal except for particularly reduced inflammatory response. Recently, it has been proved that lack of MAPKAP-K2 causes particular protection of neurons from ischemic brain injury (Wang et al., J. Biol. Chem. 277, 43968-43972 (29002)). It is considered that MAPKAP-K2 regulates translation and/or stabilization of mRNA of important inflammatory cytokines. This is likely because MAPKAP-K2 phosphorylates proteins which bind to AU-rich elements found in untranslated regions of these cytokines. Identification of these proteins is now under investigation.

Furthermore, it is reported that MAPKAP-K2 has activity of repairing anomaly in DNA induced by ultraviolet ray (Isaac A. Manke et al., Molecular Cell 17, 37-48 (2005)). Inhibition of MAPKAP-K2 activity may disable repairing damaged DNA and cause death in some types of cancer cell.

From the above, a MAPKAP-K2 inhibitor is effective for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

As MAPKAP-K2 inhibitors there have been disclosed in WO2004/054504, WO2004/054505, WO2004/055015, WO2004/055019, WO2004/058176, WO2004/058762, WO2004/099127, WO2005/009370, WO2005/007092, WO2004/076458 and WO2004/081013, but these compounds are different in the structure from the compound of the present invention.

DISCLOSURE OF THE INVENTION

An object of the present invention is to provide a novel compound useful as a MAPKAP-K2 inhibitor.

Another object of the present invention is to provide a novel MAPKAP-K2 inhibitor or a novel therapeutic agent for neurodegenerative and/or neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD). A still other object of the present invention is to provide a novel intermediate of the novel MAPKAP-K2 inhibitor.

The present inventors pursued zealous study, found that novel pyrazolopyrimidine derivatives and pharmaceutically acceptable salts thereof represented by the following formula (1) exhibit excellent MAPKAP-K2 inhibitory activity, and accomplished the present invention.

Namely, the present invention is

<1> A pyrazolopyrimidine derivative or medically acceptable salt thereof represented by formula (1):

(1)

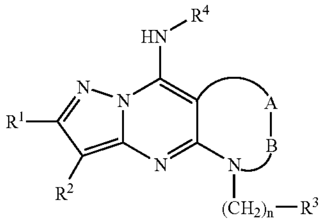

[wherein, $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally substituted heterocyclic group, an optionally substituted C6-C14 aryl group or $—OR^5$;

$R^5$ represents a hydrogen atom, an optionally substituted C1-C8 alkyl group or $—(C{=}O)R^6$;

$R^6$ represents an optionally substituted C1-C8 alkyl group;

n represents 0 or 1, or n represents 0 when $R^3$ is $—OR^5$;

$R^4$ represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted heterocyclylalkyl group or an optionally substituted C7-C16 aralkyl group;

the substituents in the optionally substituted C6-C14 aryl group as $R^4$ are one or more substituents selected from the group consisting of halogen, —CN, $—NO_2$, —CHO, —OH, —COOH, optionally substituted C1-C8 alkyl group, optionally substituted C2-C8 alkenyl, optionally substituted C2-C8 alkynyl, optionally substituted C3-C8 cycloalkyl group, $—O—(CH_2)_m—W$, optionally substituted C6-C14 aryl group, optionally substituted heterocyclic group, $—C({=}O)—R^{133}$, $—O—C({=}O)R^{26}$, $—C({=}O)OR^{27}$, $—NR^{28}C({=}O)R^{29}$, $—NR^{30}R^{31}$, $—C({=}O)NR^{32}R^{33}$, $—NR^{34}C({=}X^1)OR^{35}$, $—NR^{36}C({=}X^2)NR^{37}R^{38}$, $—NR^{39}—SO_2R^{40}$, $—S(O)_r—R^{41}$ and $—SO_2NR^{42}R^{43}$, wherein $X^1$ or $X^2$ represents O, S, N—CN or NH and r represents 0 to 2;

W represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group or an optionally substituted heterocyclic group, and in this case m represents 0 to 4; or W represents an optionally substituted C1-C8 alkoxy group, $—NR^{150}R^{151}$ or an optionally substituted phenoxy group and in this case m represents 1 to 4;

$R^{26}$ to $R^{43}$, $R^{133}$, $R^{150}$ and $R^{151}$ may be identical or different and each represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted aralkyl group or an optionally substituted heterocyclylalkyl group, or, when $R^{30}$ and $R^{31}$, $R^{32}$ and $R^{33}$, $R^{37}$ and $R^{38}$, $R^{42}$ and $R^{43}$ or $R^{150}$ and $R^{151}$ are optionally substituted alkyl groups, the substituents in each combination may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(\text{-}Z^1)\text{-}$, $—(CH_2)_p—$, $—CH_2—CH{=}CH—CH_2—$, $—CH{=}C(\text{-}Z^2)\text{-}$ or $—(CH_2)_q—C({=}O)—$;

p represents 3 or 4 and q represents 1 or 2;

$Z^1$ and $Z^2$ may be identical or different and each represents a hydrogen atom or $—CH_2—OR^{11}$; and $R^{11}$ represents a hydrogen atom, an optionally substituted C1-C8 alkyl group or a substituted silyl group.]

<2> A pyrazolopyrimidine derivative or medically acceptable salt thereof represented by formula (1):

(1)

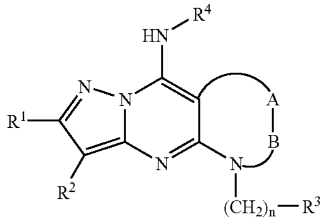

[wherein, $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally substituted heterocyclic group, an optionally substituted C6-C14 aryl group or $—OR^5$;

$R^5$ represents a hydrogen atom, an optionally substituted C1-C8 alkyl group or $—(C{=}O)R^6$;

$R^6$ represents an optionally substituted C1-C8 alkyl group;

n represents 0 or 1 or n represents 0 and when $R^3$ is $—OR^5$;

$R^4$ represents an optionally substituted C1-C8 alkyl group, an optionally substituted C3-C8 cycloalkyl group, an optionally substituted C6-C14 aryl group, an optionally substituted heterocyclic group or an optionally substituted C7-C16 aralkyl group; the substituents in the optionally substituted C6-C14 aryl group as $R^4$ are one or more substituents selected from the group consisting of halogen, —CN, $—NO_2$, optionally substituted C1-C8 alkyl group, $—O—(CH_2)_m—W$, optionally substituted C6-C14 aryl group, optionally substituted heterocyclic group, $—C({=}O)OR^7$, $—NR^8C({=}O)R^9$, $—NR^{10}R^{127}$, $—C({=}O)NR^{128}R^{129}$ and $—SO_2NR^{130}R^{131}$;

W represents a hydrogen atom, an optionally substituted C1-C8 alkyl group, an optionally substituted C3-C8 cycloalkyl group, an optionally substituted C6-C14 aryl group or an optionally substituted heterocyclic group and in this case m represents 0 to 4; or W represents an optionally substituted C1-C8 alkoxy group or an optionally substituted phenoxy group and in this case m represents 1 to 4;

$R^7$ to $R^{10}$ and $R^{127}$ to $R^{131}$ may be identical or different and each represents a hydrogen atom, an optionally substituted C1-C8 alkyl group, an optionally substituted C3-C8 cycloalkyl group or an optionally substituted C6-C14 aryl group, or, when $R^{10}$ and $R^{127}$, $R^{128}$ and $R^{129}$ or $R^{130}$ and $R^{131}$ are optionally substituted alkyl groups, they may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(-Z^3)-$, $—(CH_2)_p—$, $—CH_2—CH═CH—CH_2—$, $—CH═C(-Z^4)-$ or $—(CH_2)_q—C(═O)—$;

p represents 3 or 4 and q represents 1 or 2;

$Z^3$ and $Z^4$ may be identical or different and each represents a hydrogen atom or $—CH_2—OR^{11}$; and $R^{11}$ represents a hydrogen atom or an optionally substituted C1-C8 alkyl group.]

<3> The pyrazolopyrimidine derivative or medically acceptable salt thereof according to either <1> or <2>, wherein $R^1$ is a hydrogen atom.

<4> The pyrazolopyrimidine derivative or medically acceptable salt thereof according to any of <1> to <3>, wherein $R^2$ is a hydrogen atom.

<5> The pyrazolopyrimidine derivative or medically acceptable salt thereof according to any of <1> to <3>, wherein $R^3$ is a halogen.

<6> The pyrazolopyrimidine derivative or medically acceptable salt thereof according to any of <1> to <5>, wherein $R^3$ is an optionally substituted C1-C8 alkyl group, an optionally substituted C3-C8 cycloalkyl group or an optionally substituted heterocyclic group.

<7> The pyrazolopyrimidine derivative or medically acceptable salt thereof according to any of <1> to <5>, wherein $R^3$ is an unsubstituted C1-C4 alkyl group, a substituted C1-C4 alkyl group (wherein the substituents are 1 to 3 substituents selected from the group consisting of halogen, phenyl group, C1-C4 alkyl group substituted with 1 to 9 halogens, C1-C4 alkoxy group, C1-C4 alkoxy group substituted with 1 to 9 halogens, —CN, —CHO, —OH, —(C═O)OH, $—(C═O)OR^{86}$, $—(C═O)NR^{87}R^{88}$ and $—NR^{89}R^{90}$; $R^{86}$ represents a C1-C4 alkyl group, a C3-C8 cycloalkyl group or a phenyl group; $R^{87}$ and $R^{88}$ may be identical or different and each represents a hydrogen atom, a C1-C8 alkyl group, a C3-C8 cycloalkyl group, a phenyl group or an aralkyl group; $R^{89}$ represents a hydrogen atom, a C1-C4 alkyl group, a phenyl group or a benzyl group, $R^{90}$ represents a hydrogen atom, a C1-C4 alkyl group, a benzyl group, an acetyl group, a tert-butoxycarbonyl group or a benzyloxycarbonyl group, or, when $R^{89}$ and $R^{90}$ are alkyl groups, they may form a saturated or unsaturated 5- to 7-membered ring together with the nitrogen atom to which they bond; further this ring may contain 1 or 2 heteroatoms selected from the group consisting of oxygen atom, nitrogen atom and sulfur atom besides the nitrogen atom to which $R^{89}$ and $R^{90}$ bond), an unsubstituted C3-C8 cycloalkyl group, a substituted C3-C8 cycloalkyl group (wherein the substituents are 1 to 3 substituents selected from the group consisting of halogen, —OH, —(C═O)OH, C1-C4 alkyl group, C1-C4 alkoxy group and $—NR^{91}R^{92}$, wherein $R^{91}$ represents a hydrogen atom, a C1-C8 alkyl group, a phenyl group or a benzyl group and $R^{92}$ represents a hydrogen atom, a C1-C8 alkyl group, a benzyl group, an acetyl group, a tert-butoxycarbonyl group or a benzyloxycarbonyl group), an unsubstituted heterocyclic group or a substituted heterocyclic group (wherein, when carbon atom(s) in the substituted heterocyclic group are substituted, the substituent(s) are 1 to 3 substituents selected from the group consisting of halogen, —(C═O)OH, C1-C4 alkyl group, C1-C4 alkyl group substituted with 1 to 9 halogens, phenyl group, benzyl group, C1-C4 alkoxy group, C1-C4 alkoxy group substituted with 1 to 9 halogens and $—NR^{93}R^{94}$, wherein $R^{93}$ represents a hydrogen atom, a C1-C8 alkyl group, a phenyl group or a benzyl group and $R^{94}$ represents a hydrogen atom, a C1-C8 alkyl group, a benzyl group, an acetyl group, a tert-butoxycarbonyl group or a benzyloxycarbonyl group, wherein, when nitrogen atom(s) in the heterocycle are substituted, the substituents are one or more substituents selected from the group consisting of C1-C4 alkyl group, benzyl group, acetyl group, tert-butoxycarbonyl group and benzyloxycarbonyl group).

<8> The pyrazolopyrimidine derivative or medically acceptable salt thereof according to any of <1> to <5>, wherein $R^3$ is an unsubstituted heterocyclic group (wherein the heterocyclic group represents a monocyclic 5- to 8-membered heterocyclic group containing 1 or 2 heteroatoms selected from the group consisting of N, O and S), a substituted saturated heterocyclic group (wherein the heterocyclic group represents a monocyclic 5- to 8-membered heterocyclic group containing 1 or 2 heteroatoms selected from the group consisting of N, O and S, and the substituent bonds to a nitrogen atom in the heterocycle and the substituents represent one or more substituents selected from the group consisting of C1-C4 alkyl group, benzyl group and tert-butoxycarbonyl group), a C1-C4 alkyl group substituted with one amino group or a C3-C8 cycloalkyl group substituted with one amino group.

<9> The pyrazolopyrimidine derivative or medically acceptable salt thereof according to any of <1> to <5>, wherein $R^3$ is a piperidyl group, a pyrrolidinyl group or a cyclohexyl group substituted with an amino group.

<10> The pyrazolopyrimidine derivative or medically acceptable salt thereof according to any of <1> to <9>, wherein n is 0.

<11> The pyrazolopyrimidine derivative or medically acceptable salt thereof according to any of <1> to <10>, wherein $R^4$ is an optionally substituted C6-C14 aryl group.

<12> The pyrazolopyrimidine derivative or medically acceptable salt thereof according to any of <1> to <10>, wherein $R^4$ is an optionally substituted C6-C14 aryl group and the substituents are one or more substituents selected from the group consisting of halogen, —CN, optionally substituted C1-C8 alkyl group, $—O—(CH_2)_m—W$, optionally substituted C6-C14 aryl group, optionally substituted heterocyclic group, $—C(═O)OR^7$ and $—C(═O)NR^9R^{10}$.

<13> The pyrazolopyrimidine derivative or medically acceptable salt thereof according to any of <1> to <10>, wherein $R^4$ is an optionally substituted C6-C14 aryl group and the substituents are one or more substituents selected from the group consisting of halogen, —CN, optionally substituted C1-C8 alkyl group and $—O—(CH_2)_m—W$.

<14> The pyrazolopyrimidine derivative or medically acceptable salt thereof according to any of <1> to <10>, wherein $R^4$ is an optionally substituted C6-C14 aryl group and the substituents are one or more $—O—(CH_2)_m—W$, wherein W is a hydrogen atom, an optionally substituted C1-C8 alkyl group, an optionally substituted heterocyclic group or an optionally substituted C1-C8 alkoxy group.

<15> The pyrazolopyrimidine derivative or medically acceptable salt thereof according to any of <1> to <8>, wherein $R^4$ is an optionally substituted C6-C14 aryl group and the substituents are one or more substituents selected from the group consisting of halogen, —CN, optionally substituted C1-C8 alkyl group, optionally substituted C6-C14 aryl group and optionally substituted heterocyclic group.

<16> The pyrazolopyrimidine derivative or medically acceptable salt thereof according to any of <1> to <10>, wherein $R^4$ is an optionally substituted C6-C14 aryl group and the substituents are one or more substituents selected from the group consisting of halogen, —CN, optionally substituted C1-C8 alkyl group, —C(═O)OR$^7$ and —C(═O)NR$^9$R$^{10}$.

<17> The pyrazolopyrimidine derivative or medically acceptable salt thereof according to any of <1> to <10>, wherein $R^4$ is an optionally substituted C6-C14 aryl group (wherein the substituents are 1 to 3 substituents selected from the group consisting of halogen, —CN, optionally substituted C1-C8 alkyl group, —O—$(CH_2)_m$—W and —C(═O)OR$^{13}$, wherein W represents a hydrogen atom, an optionally substituted C1-C4 alkyl group, an optionally substituted C3-C8 cycloalkyl group, an optionally substituted phenyl group or an optionally substituted monocyclic or bicyclic heterocyclic group and m represents 0 to 4; or W represents an optionally substituted C1-C4 alkoxy group and m represents 1 to 4, and $R^{113}$ represents an optionally substituted C1-C8 alkyl group, an optionally substituted C3-C8 cycloalkyl group or an optionally substituted phenyl group).

<18> The pyrazolopyrimidine derivative or medically acceptable salt thereof according to any of <1> to <10>, wherein $R^4$ is an optionally substituted phenyl group (wherein the substituent is one —O—$(CH_2)_m$—W, wherein W represents a hydrogen atom or an optionally substituted C1-C4 alkyl group and m represents 0 to 4; or W represents an optionally substituted C1-C4 alkoxy group and m represents 1 to 4).

<19> The pyrazolopyrimidine derivative or medically acceptable salt thereof according to any of <1> to <10>, wherein $R^4$ is an optionally substituted C6-C14 aryl group (wherein the substituents are one or more substituents selected from the group consisting of halogen, —CN, optionally substituted C1-C4 alkyl group, optionally substituted phenyl group and optionally substituted monocyclic or bicyclic heterocyclic group).

<20> The pyrazolopyrimidine derivative or medically acceptable salt thereof according to any of <1> to <10>, wherein $R^4$ is an optionally substituted C6-C14 aryl group (wherein the substituents are one or more substituents selected from the group consisting of halogen, —CN, optionally substituted C1-C4 alkyl group, —C(═O)OR$^{13}$ and —C(═O)NR$^{118}$R$^{119}$, wherein $R^{113}$, $R^{18}$ and $R^{119}$ may be identical or different and each represents a hydrogen atom, an optionally substituted C1-C8 alkyl group, an optionally substituted C3-C8 cycloalkyl group or an optionally substituted C6-C14 aryl group; and when $R^{118}$ and $R^{119}$ are alkyl groups, they may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which they bond).

<21> The pyrazolopyrimidine derivative or medically acceptable salt thereof according to any of <1> to <10>, wherein $R^4$ is an optionally substituted heterocyclic group.

<22> The pyrazolopyrimidine derivative or medically acceptable salt thereof according to any of <1> to <10>, wherein $R^4$ is an optionally substituted bicyclic heteroaryl group (wherein, when carbon atom(s) in the bicyclic heteroaryl group are substituted, the substituents are 1 to 3 substituents selected from the group consisting of halogen, —CN, C1-C8 alkyl group, C1-C4 alkyl group substituted with 1 to 9 halogens, C1-C8 alkoxy group, C1-C4 alkoxy group substituted with 1 to 9 halogens, phenyl group, monocyclic or bicyclic heterocyclic group, —C(═O)OR$^{122}$, —NR$^{123}$R$^{124}$ and —C(═O)NR$^{125}$R$^{126}$, wherein $R^{123}$ represents a hydrogen atom, a C1-C8 alkyl group, a phenyl group or a benzyl group, $R^{124}$ represents a hydrogen atom, a C1-C8 alkyl group, a benzyl group, an acetyl group, a tert-butoxycarbonyl group or a benzyloxycarbonyl group, $R^{122}$ represents a C1-C8 alkyl group, a C3-C8 cycloalkyl group or a phenyl group, and $R^{125}$ and $R^{126}$ may be identical or different and each represents a hydrogen atom, a C1-C8 alkyl group, a C3-C8 cycloalkyl group, a phenyl group or a benzyl group; when nitrogen atom(s) in the heterocycle are substituted, the substituents are one or more substituents selected from the group consisting of C1-C4 alkyl group, benzyl group, acetyl group, tert-butoxycarbonyl group and benzyloxycarbonyl group).

<23> The pyrazolopyrimidine derivative or medically acceptable salt thereof according to any of <1> to <10>, wherein $R^4$ is an optionally substituted bicyclic heteroaryl group (wherein the bicyclic heteroaryl group means a bicyclic heteroaryl group wherein a phenyl group is fused with an aromatic heterocycle containing 1 or 2 heteroatoms selected from the group consisting of N, O and S; when carbon atom(s) in the bicyclic heteroaryl group are substituted, the substituents are 1 to 3 substituents selected from the group consisting of halogen, C1-C4 alkyl group and C1-C4 alkyl group substituted with 1 to 9 halogens; when nitrogen atom(s) in the heterocycle are substituted, the substituent represents one or more C1-C4 alkyl group).

<24> The pyrazolopyrimidine derivative or medically acceptable salt thereof according to any of <1> to <10>, wherein $R^4$ is a hydrogen atom, an optionally substituted C1-C8 alkyl group, an optionally substituted C3-C8 cycloalkyl group, an optionally substituted C7-C16 aralkyl group or an optionally substituted heterocyclylalkyl group.

<25> The pyrazolopyrimidine derivative or medically acceptable salt thereof according to any of <1> to <10>, wherein $R^4$ is an optionally substituted heterocyclylalkyl group.

<26> The pyrazolopyrimidine derivative or medically acceptable salt thereof according to any of <1> to <25>, wherein -A-B- is —$CH_2$—$CH_2$—, —$(CH_2)_p$—, —$CH_2$—CH═CH—$CH_2$— or —CH═CH—.

<27> The pyrazolopyrimidine derivative or medically acceptable salt thereof according to any of <1> to <25>, wherein -A-B- is —$CH_2$—$CH_2$.

<28> A pyrazolopyrimidine derivative represented by formula (2):

(2)

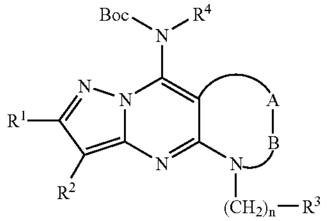

[wherein, $R^1$, $R^2$, $R^3$, $R^4$, n and -A-B- are as defined in either claim 1 or 2, and Boc represents tert-butoxycarbonyl].

<29> The pyrazolopyrimidine derivative according to <28>, wherein $R^1$ and $R^2$ are a hydrogen atom.

<30> The pyrazolopyrimidine derivative according to <28>, wherein $R^1$ is a hydrogen atom and $R^2$ is a halogen.

<31> The pyrazolopyrimidine derivative according to any of <28> to <30>, wherein $R^3$ is an optionally substituted C1-C8 alkyl group, an optionally substituted cyclohexyl group or an optionally substituted heterocyclic group (wherein the heterocyclic group means a 3- to 10-membered monocyclic or bicyclic heterocyclic group containing 1 to 4 heteroatoms selected from the group consisting of N, O and S).

<32> The pyrazolopyrimidine derivative according to any of <28> to <30>, wherein $R^3$ is an unsubstituted heterocyclic group (wherein the heterocyclic group means a 5- to 8-membered monocyclic heterocyclic group containing 1 or 2 heteroatoms selected from the group consisting of N, O and S), a substituted heterocyclic group (wherein the heterocyclic group means a 5- to 8-membered monocyclic heterocyclic group containing 1 or 2 heteroatoms selected from the group consisting of N, O and S, and the substituent bonds to a nitrogen atom in a saturated heterocyclic group and the substituents represent one or more substituents selected from the group consisting of C1-C4 alkyl group, benzyl group, acetyl group, tert-butoxycarbonyl group and benzyloxycarbonyl group), a C1-C4 alkyl group substituted with an amino group or a C3-C8 alkyl group substituted with an amino group.

<33> The pyrazolopyrimidine derivative according to any of <28> to <32>, wherein $R^4$ is an optionally substituted C1-C8 alkyl group, an optionally substituted C3-C8 cycloalkyl group, an optionally substituted C6-C14 aryl group, an optionally substituted heterocyclic group or an optionally substituted heterocyclylalkyl group.

<34> The pyrazolopyrimidine derivative according to any of <28> to <32>, wherein $R^4$ is an optionally substituted phenyl group or an optionally substituted bicyclic heteroaryl group.

<35> The pyrazolopyrimidine derivative according to any of <28> to <32>, wherein $R^4$ is an optionally substituted phenyl group (wherein the substituents are one or more $—O—(CH_2)_m—W$, wherein W represents a hydrogen atom or an optionally substituted C1-C4 alkyl group and m is 0 to 4, or W represents an optionally substituted C1-C4 alkoxy group and m is 2 to 4).

<36> The pyrazolopyrimidine derivative according to any of <28> to <32>, wherein $R^4$ is an optionally substituted bicyclic heteroaryl group (wherein the substituents are 1 to 3 substituents selected from the group consisting of halogen, C1-C4 alkyl group and C1-C4 alkyl group substituted with 1 to 9 halogens.).

<37> The pyrazolopyrimidine derivative according to any of <28> to <36>, wherein -A-B- is $—CH_2—CH_2—$, $—(CH_2)_p—$, $—CH_2—CH{=}CH—CH_2—$ or $—CH{=}CH—$.

<38> The pyrazolopyrimidine derivative according to any of <28> to <36>, wherein -A-B- is $—CH_2—CH_2$.

<39> The pyrazolopyrimidine derivative according to any of <28> to <38>, wherein n is 0.

<40> A pharmaceutical composition comprising the pyrazolopyrimidine derivative or medically acceptable salt thereof according to any of <1> to <27> and a pharmaceutically acceptable carrier.

<41> A MAPKAP-K2 inhibitor comprising the pyrazolopyrimidine derivative or medically acceptable salt thereof according to any of <1> to <27> as an active ingredient.

<42> A therapeutic agent comprising the pyrazolopyrimidine derivative or medically acceptable salt thereof according to any of <1> to <27> as an active ingredient for neurodegenerative and/or neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma or chronic obstructive pulmonary disease (COPD).

<43> The therapeutic agent according to <42>, wherein the autoimmune disease is rheumatoid arthritis, ankylosing spondylitis, juvenile rheumatoid arthritis, psoriatic arthritis, graft-versus-host disease, diabetes mellitus or Crohn's disease.

BRIEF DESCRIPTION OF DRAWINGS

FIG. 1 is a FIGURE illustrating p38MAPK cascade.

BEST MODE FOR CARRYING OUT THE INVENTION

The compounds represented by formula (1) in the present invention are defined as follows.

"Alkyl group" in the present specification represents either a linear or branched alkyl group. Preferably it is an alkyl group having 1 to 8 carbon atoms. For example, although not limited thereto, there may be mentioned methyl, ethyl, n-propyl, isopropyl, n-butyl, sec-butyl, isobutyl, tert-butyl, n-pentyl, isopentyl, neopentyl, tert-pentyl, 2-methylpentyl, 4-methylpentyl, 3-hexyl, n-hexyl, n-heptyl, 2-methylhexyl, 5-methylhexyl, 2-methyl-2-hexyl, 6-methylheptyl and n-octyl. More preferably, it is an alkyl group having 1 to 6 carbon atoms, and still more preferably it is an alkyl group having 1 to 4 carbon atoms. For example, although not limited thereto, there may be mentioned methyl, ethyl, n-propyl, isopropyl, n-butyl, sec-butyl, isobutyl, and tert-butyl.

"Alkenyl group" in the present specification represents a linear, branched or cyclic alkenyl group having one or more C—C double bonds. When the group exists as either trans or cis form, it includes both isomers. Preferably it is an alkenyl group having 2 to 8 carbon atoms. For example, although not limited thereto, there may be mentioned vinyl, allyl, isopropenyl, 1-propenyl, 2-butenyl, 1-butenyl, 2-methyl-1-propenyl, 2-methyl-3-pentenyl, 1-pentenyl, 2-pentenyl, 4-methyl-1-pentenyl, 1-hexenyl, 2-hexenyl, 2-cyclopentenyl, 2-cyclohexenyl, 2-heptenyl, 2-octenyl, 3-cyclopentenyl, 1,3-butadienyl and 1,5-hexadienyl. More preferably, it is an alkenyl group having 2 to 6 carbon atoms, and still more preferably it is an alkenyl group having 2 to 4 carbon atoms. For example, although not limited thereto, there may be mentioned vinyl, allyl, isopropenyl, 1-propenyl, 2-butenyl, 1-butenyl and 2-methyl-1-propenyl.

"Alkynyl group" in the present specification represents either a linear or a branched alkynyl group having one or more C—C triple bonds. Preferably it is an alkynyl group having 2 to 8 carbon atoms. For example, although not limited thereto, there may be mentioned ethynyl, 2-propynyl, 1-propynyl, 1-butynyl, 2-butynyl, 3-hexynyl, 3-methyl-1-butynyl, 3,3-dimethyl-1-butynyl, 3-pentynyl, 2-petynyl, 2-hexynyl, 3-hexynyl, 4-hexynyl, 1-methyl-3-pentynyl, 1-methyl-3-hexynyl, 2-heptynyl and 2-octynyl. More preferably, it is an alkynyl group having 2 to 6 carbon atoms, and still more preferably it is an alkynyl group having 2 to 4 carbon atoms. For example, although not limited thereto, there may be mentioned ethynyl, 2-propynyl, 1-propynyl and 1-butynyl.

"Cycloalkyl group" in the present specification represents a cyclic alkyl group. Preferably it is a cycloalkyl group having 3 to 8 carbon atoms. For example, although not limited thereto, there may be mentioned cyclopropyl, cyclobutyl, cyclopentyl, cyclohexyl, cycloheptyl and cyclooctyl.

"Aryl group" in the present specification represents a monocyclic, bicyclic or tricyclic aromatic hydrocarbon group having 6 or 14 carbon atoms; or an aromatic hydrocarbon group having totally 6 to 14 carbon atoms wherein such an aromatic hydrocarbon group is fused with one or more saturated or partially saturated carbocycles. For example, although not limited thereto, there may be mentioned phenyl, naphthyl, anthracenyl, 5-indanyl and 5,6,7,8-tetrahydro-2-naphthyl. Preferably it is an aryl group having 6 to 10 carbon atoms. For example, although not limited thereto, there may be mentioned phenyl, naphthyl, 5-indanyl and 5,6,7,8-tetrahydro-2-naphthyl. More preferably it is phenyl.

"Heterocyclic group" in the present specification means a monovalent group derived from a 3- to 14-membered monocyclic, bicyclic or tricyclic heterocycle containing 1 to 4 heteroatoms selected from the group consisting of N, O and S. The heterocyclic group may be completely saturated, partially saturated or aromatized. The heterocyclic group may contain one or two —C(═O) or —C(═S)—. As example of the heterocyclic group, although not limited thereto, there may be mentioned a monovalent group derived from furan, thiophene, pyrrole, pyrroline, pyrrolidine, oxazole, oxazolidine, isoxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzoxazole, chroman, isochroman, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazne, quinuclidine, acridine, carbazole, cinnoline, dioxane, dioxolane, dithiane, dithiazine, dithiazole, dithiolane, indolizine, indazole, isoindole, isoxazole, isobenzofuan, naphthyridine, oxathiazole, oxathiazolidine, oxazine, oxadiazine, phthalazine, quinolizine, tetrahydrofuran, tetrazine, thiadiazine, thiatriazole, thiazine, thianaphthalene, triazine, 1,3-dioxane, 2,5-dihydrofuran, oxazoline, trithiane, piperidin-2-one, 3H-isobenzofuran-1-one, ϵ-caprolactam, 2-furanone, 2-pyrrolidone, tetrahydro-3H-pyrazol-3-one, piperazin-2-one, coumarin, tetrahydro-2-pyrimidinone, glutarimide or morpholine-3,5-dione. Preferably it means a 3- to 10-membered monocyclic or bicyclic heterocyclic group containing 1 to 4 heteroatoms selected from the group consisting of N, O and S.

"Heteroaryl group" in the present specification means, among the above "heterocyclic group", a monocyclic, bicyclic or tricyclic heterocyclic group wherein the ring forming a monovalent group is aromatized. In the case of a bicyclic or tricyclic group, rings other than the ring forming a monovalent group may be completely saturated, partially saturated or aromatized. The heteroaryl group may contain one or two —C(═O)— or —C(═S)—. For example, although not limited thereto, there may be mentioned a monovalent group derived from furan, thiophene, pyrrole, oxazole, thiazole, isothiazole, isoxazole, imidazole, pyrazole, pyridine, pyrazine, pyrimidine, pyridazine, benzofuran, benzothiophene, indole, benzimidazole, benzothiazole, benzoxazole, indazole, isobenzofuran, quinoline, isoquinoline, quinazoline, purine or acridine, 7-chromanyl, 6-isochromanyl and 5-indolinyl. Preferably it means a bicyclic heteroaryl group wherein a phenyl group is fused with a heterocycle containing 1 to 4 heteroatoms selected from the group consisting of N, O and S. As examples of such a group, although not limited thereto, there may be mentioned 4-benzothiazolyl, 5-benzothiazolyl, 6-benzothiazolyl, 7-benzothiazolyl, 5-benzoxazolyl, 6-benzoxazolyl, 5-benzothienyl, 6-benzofuranyl, 6-indazolyl, 5-quinolyl, 7-phthalazinyl, 6-quinoxalinyl, 6-quinazolinyl, 6-cinnolinyl, 7-chromanyl, 5-indolinyl and 6-isoindolinyl. More preferably, it means a bicyclic heteroaryl group wherein a phenyl group is fused with a heteroaryl containing 1 or 2 heteroatoms selected from the group consisting of N, O and S. As examples of such a group, although not limited thereto, there may be mentioned 4-benzothiazolyl, 5-benzothiazolyl, 6-benzothiazolyl, 7-benzothiazolyl, 5-benzoxazolyl, 6-benzoxazolyl, 5-benzothienyl, 6-benzofuranyl, 6-indazolyl, 5-quinolyl, 7-phthalazinyl, 6-quinoxalinyl, 6-quinazolinyl and 6-cinnolinyl.

"Saturated heterocyclic group" in the present specification represents, among the above "heterocyclic group", a monocyclic, bicyclic or tricyclic heterocyclic group wherein the ring forming a monovalent group is completely or partially saturated. In the case of a bicyclic or tricyclic group, rings other than the ring forming a monovalent group may be completely saturated, partially saturated or aromatized. The saturated heterocyclic group may contain one or two —C(═O)— or —C(═S)—. For example, although not limited thereto, there may be mentioned a monovalent group derived from pyrrolidine, imidazolidine, pyrazolidine, morpholine, thiomorpholine, piperidine, homopiperidine, piperazine, homopiperazine or tetrahydrofuran, 3-chromanyl and 3-indolyl. Preferably it represents a 5- to 8-membered monocyclic saturated heterocyclic group containing 1 or 2 heteroatoms selected from the group consisting of N, O and S. For example, although not limited thereto, there may be mentioned a monovalent group derived from pyrrolidine, imidazolidine, pyrazolidine, morpholine, thiomorpholine, piperidine, homopiperidine, piperazine, homopiperazine or tetrahydrofuran.

"Heterocyclylalkyl group" in the present specification represents a group composed of a heterocyclic group and an alkyl group. Here, the heterocyclic group and the alkyl group correspond to "heterocyclic group" and "alkyl group" defined above, respectively. As preferred examples of the heterocyclylalkyl group, there may be mentioned a group composed of a group included in the above definition and one of the preferred groups or a combination of one of the referred groups for each moiety. Preferably, it is a group composed of a 3- to 10-membered monocyclic or bicyclic "heterocyclic group" containing 1 to 4 heteroatoms selected from the group consisting of N, O and S and an "alkyl group" having 1 to 8 carbon atoms. More preferably, it is a group containing a combination of a 3- to 10-membered monocyclic or bicyclic "heterocyclic group" containing 1 to 4 heteroatoms selected from the group consisting of N, O and S and an "alkyl group" having 1 to 4 carbon atoms. As examples, although not limited thereto, there may be mentioned (2-furyl)methyl, (3-thienyl)methyl, (5-isobenzofuranyl)methyl, (5-benzothienyl)methyl, (6-benzoxazolyl)methyl, 2-(4-morpholyl)ethyl, 2-(3-thienyl)ethyl, 2-(1-pyrazinyl)ethyl, 3-(2-pyridyl)propyl and 3-(4-piperidyl)propyl.

"Aralkyl group" in the present specification represents a group composed of an aryl group and an alkyl group. Here, the aryl group and the alkyl group correspond to "aryl group" and "alkyl group" defined above, respectively. Preferably it is a group composed of an "aryl group" having 6 to 10 carbon atoms and an "alkyl group" having 1 to 8 carbon atoms. As examples, although not limited thereto, there may be mentioned benzyl, phenethyl, (2-naphthyl)methyl, 3-phenylpropyl, 4-phenylbutyl and 5-(1-naphthyl)pentyl. More preferably, it is a group composed of a phenyl group and an alkyl group having 1 to 4 carbon atoms. As examples of such a group, although not limited thereto, there may be mentioned benzyl, phenethyl, (2-naphthyl)methyl, 3-phenylpropyl and 4-phenylbutyl.

"Alkoxy group" in the present specification represents a linear, branched or cyclic alkoxy group. Preferably it is an alkoxy group having 1 to 8 carbon atoms. As examples, although not limited thereto, there may be mentioned methoxy, ethoxy, n-propoxy, isopropoxy, n-butoxy, tert-butoxy, n-pentyloxy, n-hexyloxy and n-heptyloxy. More preferably, it is an alkoxy group having 1 to 6 carbon atoms, and still more preferably it is an alkoxy group having 1 to 4 carbon atoms. As examples of such a group, although not limited thereto, there may be mentioned methoxy, ethoxy, n-propoxy, isopropoxy, n-butoxy and tert-butoxy.

"Halogen" in the present specification represents F, Cl, Br or I. Preferably it is F, Cl or Br.

In the present specification, the figure following "C" in, for example, "C1" represents the number of carbon atoms, and "C1-C6" represents the range of number of carbon atoms of 1 to 6. Needless to say, in the present invention, each group different in number of carbon atoms means the same type of group having each number of carbon atoms. For example, "C1-C6 alkyl group" means an alkyl group, which is defined for "C1-C8 alkyl group", having 1 to 6 carbon atoms. Numbers of carbon atoms in other groups are interpreted in the same way.

"Substituted silyl group" in the present specification represents a silyl group that can be used as a protecting group for a hydroxyl group. Preferably it is trimethylsilyl, tert-butyldimethylsilyl, tert-butyldiphenylsilyl or triethylsilyl, and more preferably it is tert-butyldimethylsilyl.

The substituents in the "optionally substituted alkyl group" in the present invention are one or more substituent(s) selected from the group consisting of a halogen, —CN, —CHO, —(C═O)—$R^{50}$, —$NO_2$, —OH, —(C═O)OH, —(C═O)$OR^{51}$, —(C═O)$NR^{52}R^{53}$, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{12}R^{13}$. Preferably, they are one or more substituents selected from the group consisting of a halogen, —OH, —(C═O)OH, a phenyl group, a C1-C4 alkoxy group, a C1-C4 alkoxy group substituted with 1 to 9 halogens and —$NR^{12}R^{13}$. The preferred number of substituents is 1 to 3. Here, $R^{12}$ represents a hydrogen atom, a C1-C8 alkyl group, a phenyl group or a benzyl group, and preferably it is a hydrogen atom or a C1-C4 alkyl group. $R^{13}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. When $R^{12}$ and $R^{13}$ are alkyl groups, they may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which $R^{12}$ and $R^{13}$ bond. $R^{50}$ represents a C1-C8 alkyl group, a C3-C8 cycloalkyl group or a C6-C14 aryl group, and preferably it is a C1-C4 alkyl group or a phenyl group. $R^{51}$ represents a C1-C8 alkyl group, a C3-C8 cycloalkyl group or a C6-C14 aryl group, and preferably it is a C1-C4 alkyl group. $R^{52}$ and $R^{53}$ may be identical or different and each represents a hydrogen atom, a C1-C8 alkyl group, a C3-C8 cycloalkyl group, a C6-C14 aryl group or an aralkyl group. When $R^{52}$ and $R^{53}$ are alkyl groups, they may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which $R^{52}$ and $R^{53}$ bond. Preferably each of $R^{52}$ and $R^{53}$, which may be identical or different, is a hydrogen atom or a C1-C4 alkyl group.

The substituents in "optionally substituted alkenyl" in the present invention are one or more substituents selected from the group consisting of a halogen, —CN, —CHO, —(C═O)—$R^{54}$, —$NO_2$, —OH, —(C═O)OH, —(C═O)$OR^{55}$, —(C═O)$NR^{56}R^{57}$, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{44}R^{45}$. Preferably, they are one or more substituents selected from the group consisting of a halogen, a C1-C4 alkyl group, a phenyl group and an amino group. The preferred number of substituents is 1 to 3. Here, $R^{44}$ represents a hydrogen atom, a C1-C8 alkyl group or a benzyl group, and preferably it is a hydrogen atom or a C1-C4 alkyl group. $R^{45}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{54}$ represents a C1-C8 alkyl group, a C3-C8 cycloalkyl group or a C6-C14 aryl group, and preferably it is a C1-C4 alkyl group or a phenyl group. $R^{55}$ represents a C1-C8 alkyl group, a C3-C8 cycloalkyl group or a C6-C14 aryl group, and preferably it is a C1-C4 alkyl group. $R^{56}$ and $R^{57}$ may be identical or different and each represents a hydrogen atom, a C1-C8 alkyl group, a C3-C8 cycloalkyl group, a C6-C14 aryl group or an aralkyl group. Preferably they are a hydrogen atom or a C1-C4 alkyl group.

The substituents in "optionally substituted alkynyl" in the present invention are one or more substituents selected from the group consisting of a halogen, —CN, —CHO, —(C═O)—$R^{58}$, —$NO_2$, —OH, —(C═O)OH, —(C═O)$R^{59}$, —(C═O)$NR^{60}R^{61}$, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{46}R^{47}$. Preferably, they are one or more substituents selected from the group consisting of a halogen, a C1-C4 alkyl group, a phenyl group and an amino group. Preferably the number of substituents is 1 to 3. Here, $R^{46}$ represents a hydrogen atom, a C1-C8 alkyl group or a benzyl group, and preferably it is a hydrogen atom or a C1-C4 alkyl group. $R^{47}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{58}$ represents a C1-C8 alkyl group, a C3-C8 cycloalkyl group or a C6-C14 aryl group, and preferably it is a C1-C4 alkyl group or a phenyl group. $R^{59}$ represents a C1-C8 alkyl group, a C3-C8 cycloalkyl group or a C6-C14 aryl group, and preferably it is a C1-C4 alkyl group. $R^{60}$ and $R^{61}$ may be identical or different and each represents a hydrogen atom, a C1-C8 alkyl group, a C3-C8 cycloalkyl group, a C6-C14 aryl group or an aralkyl group, and preferably they are a hydrogen atom or a C1-C4 alkyl group.

The substituents in "optionally substituted cycloalkyl group" in the present invention are one or more substituents selected from the group consisting of a halogen, —CN, —CHO, —(C═O)—$R^{62}$, —$NO_2$, —OH, —(C═O)OH, —(C═O)$OR^{63}$, —(C═O)$NR^{64}R^{65}$, a C1-C8 alkyl group, a C3-C8 cycloalkyl group or a C6-C14 aryl group, a C1-C8 alkoxy group and —$NR^{14}R^{15}$. Preferably they are one or more substituents selected from the group consisting of a halogen, —OH, —(C═O)OH, a C1-C4 alkyl group, a phenyl group and —$NR^{14}R^{15}$. More preferably they are one or more substituents selected from the group consisting of —OH, a C1-C4 alkoxy group and —$NR^{14}R^{15}$. Preferably the number of substituents is 1 to 3. Here, $R^{14}$ represents a hydrogen atom, a C1-C8 alkyl group, a phenyl group or a benzyl group, and preferably it is a hydrogen atom or a C1-C4 alkyl group. $R^{15}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{62}$ represents a C1-C8 alkyl group, a C3-C8 cycloalkyl group or a C6-C14 aryl group, and preferably it is a C1-C4 alkyl group or a phenyl group. $R^{63}$ represents a C1-C8 alkyl group, a C3-C8 cycloalkyl group or a C6-C14 aryl group, and preferably it is a C1-C4 alkyl group. $R^{64}$ and $R^{65}$ may be identical or different and each represents a hydrogen atom, a C1-C8 alkyl group, a C3-C8 cycloalkyl group, a C6-C14 aryl group or an aralkyl group. When $R^{64}$ and $R^{65}$ are alkyl groups, they may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which $R^{64}$ and $R^{65}$ bond. Preferably, $R^{64}$ and $R^{65}$, which may be identical or different, are a hydrogen atom or a C1-C4 alkyl group.

The substituents in "optionally substituted aralkyl group" in the present invention are one or more substituents selected from the group consisting of a halogen, —CN, —CHO, —(C═O)—$R^{66}$, —$NO_2$, —OH, —(C═O)OH, —(C═O)$OR^{67}$, —(C═O)$NR^{68}R^{69}$, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogen atoms and —$NR^{16}R^{17}$. Preferably, they are one or more substituents selected from the group consisting of a halogen, a C1-C4 alkyl group, a C1-C8 alkoxy group, a phenyl group and an amino group. Preferably the number of substituents is 1 to 3. Here, $R^{16}$ represents a hydrogen atom, a C1-C8 alkyl group or a benzyl group, and preferably it is a hydrogen atom or a C1-C4 alkyl group. $R^{17}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{66}$ represents a C1-C8 alkyl group, a C3-C8 cycloalkyl group or a C6-C14 aryl group, and preferably it is a C1-C4 alkyl group or a phenyl group. $R^{67}$ represents a C1-C8 alkyl group, a C3-C8 cycloalkyl group or a C6-C14 aryl group, and preferably it is a C1-C4 alkyl group. $R^{68}$ and $R^{69}$ may be identical or different and each represents a hydrogen atom, a C1-C8 alkyl group, a C3-C8 cycloalkyl group, a C6-C14 aryl group or an aralkyl group, and preferably they are a hydrogen atom or a C1-C4 alkyl group.

The substituents in "optionally substituted alkoxy group" in the present invention are one or more substituents selected from the group consisting of a halogen, —CN, —CHO, —(C═O)—$R^{70}$, —$NO_2$, —OH, —(C═O)OH, —(C═O)$OR^{71}$, —(C═O)$NR^{72}R^{73}$, a C1-C8 alkyl group, a C3-C8 cycloalkyl group, a C6-C14 aryl group, a C1-C8 alkoxy group and —$NR^{18}R^{19}$. Preferably they are one or more substituents selected from the group consisting of a halogen, a C1-C4 alkyl group, a phenyl group and an amino group. Preferably the number of substituents is 1 to 3. Here, $R^{18}$ represents a hydrogen atom, a C1-C8 alkyl group or a benzyl group, and preferably it is a hydrogen atom or a C1-C4 alkyl group. $R^{19}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{70}$ represents a C1-C8 alkyl group, a C3-C8 cycloalkyl group or a C6-C14 aryl group, and preferably it is a C1-C4 alkyl group or a phenyl group. $R^{71}$ represents a C1-C8 alkyl group, a C3-C8 cycloalkyl group or a C6-C14 aryl group, and preferably it is a C1-C4 alkyl group. $R^{72}$ and $R^{73}$ may be identical or different and each represents a hydrogen atom, a C1-C8 alkyl group, a C3-C8 cycloalkyl group, a C6-C14 aryl group or an aralkyl group, and preferably each of them is a hydrogen atom or a C1-C4 alkyl group.

The substituents in "optionally substituted phenoxy group" in the present invention are one or more substituents selected from the group consisting of a halogen, —CN, —CHO, —(C═O)—$R^{74}$, —$NO_2$, —OH, —(C═O)OH, —(C═O)$OR^{75}$, —(C═O)$NR^{76}R^{77}$, a C1-C8 alkyl group, a C3-C8 cycloalkyl group, a C6-C14 aryl group, a C1-C8 alkoxy group and —$NR^{20}R^{21}$ Preferably, they are one or more substituents selected from the group consisting of a halogen, a C1-C4 alkyl group, a C1-C4 alkoxy group, a phenyl group and an amino group. Preferably the number of substituents is 1 to 3. Here, $R^{20}$ represents a hydrogen atom, a C1-C8 alkyl group or a benzyl group, and preferably it is a hydrogen atom or a C1-C4 alkyl group. $R^{21}$ represents a hydrogen atom, a C1-C 8 alkyl group, a benzyl group, an acetyl group, a tert-butoxycarbonyl group or a benzyloxycarbonyl group, and preferably it is a hydrogen atom or a C1-C4 alkyl group. $R^{74}$ represents a C1-C8 alkyl group, a C3-C8 cycloalkyl group or a C6-C14 aryl group, and preferably it is a C1-C4 alkyl group or a phenyl group. $R^{75}$ represents a C1-C8 alkyl group, a C3-C8 cycloalkyl group or a C6-C14 aryl group, and preferably it is a C1-C4 alkyl group. $R^{76}$ and $R^{77}$ may be identical or different and each represents a hydrogen atom, a C1-C8 alkyl group, a C3-C8 cycloalkyl group, a C6-C14 aryl group or an aralkyl group, and preferably they are a hydrogen atom or a C1-C4 alkyl group.

The substituents on carbon atom(s) in "optionally substituted heterocyclic group" in the present invention are one or more substituents selected from the group consisting of a halogen, —(C═O)—$R^{78}$, —CN, —$NO_2$, —OH, —(C═O)OH, —(C═O)$OR^{79}$, —(C═O)$NR^{80}R^{81}$, a C1-C8 alkyl group, a C1-C4 alkyl group substituted with 1 to 9 halogens, a C2-C8 alkenyl, a C2-C8 alkynyl, a C3-C8 cycloalkyl group, a C6-C14 aryl group, a heterocyclic group, a C7-C16 aralkyl group, a C1-C8 alkoxy group, a C1-C4 alkoxy group substituted with 1 to 9 halogens and —$NR^{22}R^{23}$. Preferably they are one or more substituents selected from the group consisting of a halogen, —CN, —$NO_2$, —OH, —(C═O)OH, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{22}R^{23}$. Still more preferably they are one or more substituents selected from the group consisting of a halogen, —(C═O)OH, a C1-C4 alkyl group, a C1-C4 alkyl group substituted with 1 to 9 halogens, a phenyl group, a C1-C4 alkoxy group and an amino group. Preferably the number of substituents is 1 to 3. Here, $R^{22}$ represents a hydrogen atom, a C1-C8 alkyl group, a phenyl group and a benzyl group, and preferably it is a hydrogen atom or a C1-C4 alkyl group. $R^{23}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{78}$ represents a hydrogen atom, a C1-C8 alkyl group, a C3-C8 cycloalkyl group or a C6-C14 aryl group, and preferably it is a C1-C4 alkyl group or a phenyl group. $R^{79}$ represents a C1-C8 alkyl group, a C3-C8 cycloalkyl group or a C6-C14 aryl group, and preferably it is a C1-C4 alkyl group. $R^{80}$ and $R^{81}$ may be identical or different and each represents a hydrogen atom, a C1-C8 alkyl group, a C3-C8 cycloalkyl group, a C6-C14 aryl group or an aralkyl group, and preferably they are a hydrogen atom or a C1-C4 alkyl group. When nitrogen atom(s) in the heterocyclic group are substituted, the substituents are one or more substituents selected from the group consisting of a C1-C4 alkyl group, a benzyl group, an acetyl group, a tert-butoxycarbonyl group and a benzyloxycarbonyl group.

When $R^4$ is an "optionally substituted aryl group" in the present invention, the substituents are one or more substituents selected from the group consisting of a halogen, —CN, —$NO_2$, —CHO, —OH, —COOH, an optionally substituted C1-C8 alkyl group, an optionally substituted C2-C8 alkenyl, an optionally substituted C2-C8 alkynyl, an optionally substituted C3-C8 cycloalkyl group, —O—$(CH_2)_m$—W, an optionally substituted C6-C14 aryl group, an optionally substituted heterocyclic group, —C(=O)—$R^{133}$, —O—C(=O)$R^{26}$, —C(=O)$OR^{27}$, —$NR^{28}$C(=O)$R^{29}$, —$NR^{30}R^{31}$, —C(=O)$NR^{32}R^{33}$, —$NR^{34}$—C(=X)$OR^{35}$, —$NR^{36}$—C(=X)$NR^{37}R^{38}$, —$NR^{39}$—$SO_2R^{40}$, —$S(O)_r$—$R^{41}$ and —$SO_2NR^{42}R^{43}$. Preferably they are one or more substituents selected from the group consisting of a halogen, —CN, —$NO_2$, an optionally substituted C1-C8 alkyl group, —O—$(CH_2)_m$—W, an optionally substituted phenyl group, an optionally substituted heterocyclic group, —(C=O)$OR^7$, —$NR^7$(C=O)$R^8$, —$NR^9R^{10}$, —(C=O)$NR^9R^{10}$ and —$SO_2NR^9R^{10}$. More preferably they are one or more substituents selected from the group consisting of a halogen, an optionally substituted C1-C4 alkyl group, —O—$(CH_2)_m$—W and —C(=O)$OR^{27}$; and —O—$(CH_2)_m$—W is still more preferred. The number of substituents is 1 to 3, and preferably 1.

W represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group or an optionally substituted heterocyclic group and m is 0 to 4; or W represents an optionally substituted C1-C8 alkoxy group or an optionally substituted phenoxy group and m is 1 to 4. Preferably, W is a hydrogen atom, an optionally substituted C1-C4 alkyl group, an optionally substituted C3-C8 cycloalkyl group, an optionally substituted phenyl group or an optionally substituted monocyclic or bicyclic heterocyclic group and m is 0 to 4; or W is an optionally substituted C1-C4 alkoxy group and m is 1 to 4. More preferably, W is a hydrogen atom or an optionally substituted C1-C4 alkyl group and m is 0 to 4; or W is an optionally substituted C1-C4 alkoxy group and m is 1 to 4. Still more preferably, W is a C1-C4 alkyl group and m is 0; or W is a C1-C4 alkoxy group and m is 2.

$R^7$, $R^8$, $R^9$ and $R^{10}$ may be identical or different and each represents a hydrogen atom, an optionally substituted C1-C8 alkyl group, an optionally substituted C3-C8 cycloalkyl group or an optionally substituted C6-C14 aryl group. When $R^9$ and $R^{10}$ are alkyl groups, they may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which $R^9$ and $R^{10}$ bond. Preferably $R^7$, $R^8$, $R^9$ and $R^{10}$, which may be identical or different, are a hydrogen atom or an optionally substituted C1-C4 alkyl group.

$R^{26}$-$R^{43}$, $R^{133}$, $R^{150}$ and $R^{151}$ may be identical or different and each represents is a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted aralkyl group or an optionally substituted heterocyclylalkyl group. When $R^{30}$ and $R^{31}$, $R^{32}$ and $R^{33}$, $R^{37}$ and $R^{38}$, $R^{42}$ and $R^{43}$, or $R^{150}$ and $R^{151}$ are alkyl groups, the substituents in each combination may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which the substituents bond. Preferably $R^{26}$-$R^{43}$, $R^{33}$, $R^{150}$ and $R^{151}$, which may be identical or different, are a hydrogen atom, an optionally substituted C1-C8 alkyl group, an optionally substituted C3-C8 cycloalkyl group or an optionally substituted C6-C14 aryl group. More preferably they are a hydrogen atom or an optionally substituted C1-C4 alkyl group. Each of $X^1$ and $X^2$ represents O, S, N—CN or NH, and preferably O. r represents an integer ranging from 0 to 2, and preferably it is 0 or 2.

The substituents in "optionally substituted aryl group" other than "optionally substituted aryl group as $R^4$" in the present invention are one or more substituents selected from the group consisting of a halogen, —CN, —CHO, —(C=O)—$R^{82}$, —$NO_2$, —OH, —(C=O)OH, —(C=O)$OR^{83}$, —(C=O)$NR^{84}R^{85}$, a C1-C8 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{24}R^{25}$. Preferably they are one or more substituents selected from the group consisting of a halogen, —CN, —OH, —(C=O)OH, a C1-C6 alkyl group, a C1-C4 alkyl group substituted with 1 to 9 halogens, a C1-C6 alkoxy group, a C1-C4 alkoxy group substituted with 1 to 9 halogens and —$NR^{24}R^{25}$. A halogen is further preferred. The number of substituents is 1 to 3 and preferably 1. Here, $R^{24}$ represents a hydrogen atom, a C1-C8 alkyl group or a benzyl group, and preferably it is a hydrogen atom or a C1-C4 alkyl group. $R^{25}$ represents a hydrogen atom, a C1-C8 alkyl group or a benzyl group, an acetyl group, a tert-butoxycarbonyl group or a benzyloxycarbonyl group, and preferably it is a hydrogen atom or a C1-C4 alkyl group. $R^{82}$ represents a C1-C8 alkyl group, a C3-C8 cycloalkyl group or a C6-C14 aryl group, and preferably it is a C1-C4 alkyl group or a phenyl group. $R^{25}$ represents a C1-C8 alkyl group, a C3-C8 cycloalkyl group or a C6-C14 aryl group, and preferably it is a C1-C4 alkyl group. $R^{84}$ and $R^{85}$ may be identical or different and each represents is a hydrogen atom, a C1-C8 alkyl group, a C3-C8 cycloalkyl group, a C6-C14 aryl group or an aralkyl group. Preferably they are a hydrogen atom or a C1-C4 alkyl group.

The substituents on carbon atom(s) in "optionally substituted heterocyclylalkyl group" in the present invention are one or more substituents selected from the group consisting of a halogen, —(C=O)—$R^{127}$, —CN, —$NO_2$, —OH, —(C=O)OH, —(C=O)$OR^{128}$, —(C=O)$NR^{129}R^{130}$, a C1-C8 alkyl group, a C1-C4 alkyl group substituted with 1 to 9 halogens, a C6-C14 aryl group, a C1-C8 alkoxy group, a C1-C4 alkoxy group substituted with 1 to 9 halogens and —$NR^{131}R^{132}$. Preferably the alkyl moiety in the heterocyclylalkyl group is unsubstituted and substituents on carbon atom(s) in the heterocycle moiety are one or more substituents selected from the group consisting of a halogen, —(C=O)OH, a C1-C4 alkyl group, a C1-C4 alkyl group substituted with 1 to 9 halogens, a C1-C4 alkoxy group, a C1-C4 alkoxy group substituted with 1 to 9 halogens and —$NR^{131}R^{132}$, further preferably, one or more substituents selected from the group consisting of a halogen, a C1-C4 alkyl group and a C1-C4 alkyl group substituted with 1 to 9 halogens. Preferably the number of substituents is 1 to 3.

Here, $R^{131}$ represents a hydrogen atom, a C1-C8 alkyl group, a phenyl group or a benzyl group, and preferably it is a hydrogen atom or a C1-C4 alkyl group. $R^{132}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{127}$ represents a hydrogen atom, a C1-C8 alkyl group, a C3-C8 cycloalkyl group or a C6-C14 aryl group, and preferably it is a C1-C4 alkyl group or a phenyl group. $R^{128}$ represents a C1-C8 alkyl group, a C3-C8 cycloalkyl group or a C6-C14 aryl group, and preferably it is a C1-C4 alkyl group. $R^{129}$ and $R^{130}$ may be identical or different and each represents a hydrogen atom, a C1-C8 alkyl group, a C3-C8 cycloalkyl group, a C6-C14 aryl group or an aralkyl group. Preferably they are a hydrogen atom or a C1-4 alkyl group. When nitrogen atom(s) in the heterocycle are substituted, the substituents are one or more substituents selected from the group consisting of a C1-4 alkyl group, a benzyl group, an acetyl group, a tert-butoxycarbonyl group and a benzyloxycarbonyl group.

$R^1$ is preferably hydrogen.

$R^2$ is preferably hydrogen.

$R^3$ is preferably an optionally substituted C1-8 alkyl group, an optionally substituted C3-8 cycloalkyl group or an optionally substituted heterocyclic group.

Among the optionally substituted C1-C8 alkyl groups, which are preferred groups as $R^3$, as more preferred example, there may be mentioned unsubstituted C1-C6 alkyl groups and substituted C1-C6 alkyl groups. (Here, the substituents are 1 to 3 substituents selected from the group consisting of a halogen, a phenyl group, a C1-C4 alkyl group substituted with 1 to 9 halogens, a C1-C4 alkoxy group, a C1-C4 alkoxy group substituted with 1 to 9 halogens, —CN, —CHO, —OH, —(C═O)OH, —(C═O)$OR^{86}$, —(C═O)$NR^{87}R^{88}$ and —$NR^{89}R^{90}$. Further preferably they are 1 to 3 substituents selected from the group consisting of a phenyl group, a C1-C4 alkoxy group, —CHO and —$NR^{89}R^{90}$. More preferably the substituent is one —$NR^{89}R^{90}$. Preferably the number of substituents is 1 to 3 for halogen or 1 for the others. $R^{86}$ represents a C1-C4 alkyl group, a C3-C8 cycloalkyl group or a phenyl group, and preferably it is a C1-C4 alkyl group. $R^{87}$ and $R^{88}$ may be identical or different, and each represents a hydrogen atom, a C1-C8 alkyl group, a C3-C8 cycloalkyl group, a phenyl group or an aralkyl group, and preferably they are a hydrogen atom or a C1-C4 alkyl group. $R^{89}$ represents a hydrogen atom, a C1-C4 alkyl group, a phenyl group or a benzyl group, and preferably it is a hydrogen atom or a C1-C4 alkyl group. $R^{90}$ represent a hydrogen atom, a C1-C4 alkyl group, a benzyl group, an acetyl group, a tert-butoxycarbonyl group or a benzyloxycarbonyl group, and preferably it is a hydrogen atom or a C1-C4 alkyl group. When $R^{89}$ and $R^{90}$ are alkyl groups, they may form a saturated or unsaturated 5- to 7-membered ring together with the nitrogen atom to which they bond. Further, this ring may contain 1 or 2 heteroatoms selected from the group consisting of an oxygen atom, a nitrogen atom and a sulfur atom besides the nitrogen atom to which $R^{89}$ and $R^{90}$ bond.)

Among the optionally substituted C3-C8 cycloalkyl groups, which are preferred groups as $R^3$, as more preferred examples, there may be mentioned unsubstituted C3-C8 cycloalkyl groups and substituted C3-C8 cycloalkyl groups. (Here, the substituents are 1 to 3 substituents selected from the group consisting of a halogen, —OH, —(C═O)OH, a C1-C4 alkyl group, a phenyl group, a C1-C4 alkoxy group and —$NR^{91}R^{92}$. Preferably they are 1 to 3 substituents selected from the group consisting of —OH, —(C═O)OH and —$NR^{91}R^{92}$. More preferably it is one —$NR^{91}R^{92}$. Preferably the number of substituents is 1 to 3 for halogens or 1 for the others. Here, $R^{91}$ represents a hydrogen atom, a C1-C8 alkyl group, a phenyl group or a benzyl group, and preferably it is a hydrogen atom or a C1-C4 alkyl group. $R^{92}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group.)

Among the optionally substituted heterocyclic groups, which are preferred groups as $R^3$, as more preferred examples, there may be mentioned an unsubstituted monocyclic heterocyclic group, an unsubstituted bicyclic heterocyclic group, a substituted monocyclic heterocyclic group and a substituted bicyclic heterocyclic group, and more preferably there may be mentioned an unsubstituted monocyclic heterocyclic group and a substituted monocyclic heterocyclic group. Here, when carbon atom(s) in the substituted monocyclic heterocyclic group or substituted bicyclic heterocyclic group are substituted, the substituent(s) are 1 to 3 substituents selected from the group consisting of a halogen, —(C═O)OH, a C1-C4 alkyl group, a C1-C4 alkyl group substituted with 1 to 9 halogens, a phenyl group, a benzyl group, a C1-C4 alkoxy group, a C1-C4 alkoxy group substituted with 1 to 9 halogens and —$NR^{93}R^{94}$. Preferably they are 1 to 3 substituents selected from the group consisting of a C1-C4 alkyl group and an amino group. Preferably the number of substituents is 1 to 3 for halogens or 1 for the others. Here, $R^{93}$ represents a hydrogen atom, a C1-C8 alkyl group, a phenyl group or a benzyl group, and preferably it is a hydrogen atom or a C1-C4 alkyl group. $R^{94}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. When nitrogen atom(s) in the heterocyclic group are substituted, the substituents are one or more substituents selected from the group consisting of a C1-C4 alkyl group, a benzyl group, an acetyl group, a tert-butoxycarbonyl group and a benzyloxycarbonyl group. Preferably the substituent is a C1-C4 alkyl group, a benzyl group or a tert-butoxycarbonyl group and more preferably a C1-C4 alkyl group or a tert-butoxycarbonyl group.

Preferably, $R^3$ is an unsubstituted 5- to 8-membered monocyclic heterocyclic group containing 1 or 2 heteroatoms selected from the group consisting of N, O and S, a C1-C4 alkyl group substituted with one amino group or a C3-C8 cycloalkyl group substituted with one amino group.

More preferably, $R^3$ is an unsubstituted 5- to 8-membered monocyclic saturated heterocyclic group containing one nitrogen atom, a C1-C4 alkyl group substituted with one amino group or a C3-C8 cycloalkyl group substituted with one amino group.

Still more preferably, $R^3$ is a piperidyl group, a pyrrolidinyl group or a cyclohexyl group substituted with one amino group.

Furthermore preferably $R^3$ is a piperidyl group or a pyrrolidinyl group.

Preferably $R^4$ is a hydrogen atom, an optionally substituted C1-C8 alkyl group, an optionally substituted C3-C8 cycloalkyl group, an optionally substituted aralkyl group, an optionally substituted heterocyclylalkyl group, an optionally substituted C6-C14 aryl group or an optionally substituted heterocyclic group.

Among the optionally substituted C1-C8 alkyl groups, which are preferred groups as $R^4$, as more preferred examples, there may be mentioned unsubstituted C1-C8 alkyl groups and substituted C1-C8 alkyl groups. (Here, the substituents are 1 to 3 substituents selected from the group consisting of a halogen, —(C═O)—$R^{95}$, —OH, —(C═O)OH, —(C═O)$OR^{96}$, —(C═O)$NR^{97}R^{98}$, a C1-C4 alkyl group, a C1-C4 alkyl group substituted with 1 to 9 halogens, a C3-C8 cycloalkyl group, a C6-C14 aryl group, a C1-C8 alkoxy group, a C1-C4 alkoxy group substituted with 1 to 9 halogens and —$NR^{99}R^{100}$. More preferably, they are 1 to 3 substituents selected from the group consisting of a halogen, a C3-C8 cycloalkyl group, a phenyl group, a C1-C8 alkoxy group and a C1-C4 alkoxy group substituted with 1 to 9 halogens. Preferably the number of the substituents is 1 to 3 for halogens or 1 for the others. $R^{95}$ represents a C1-C8 alkyl group, a C3-C8 cycloalkyl group or a phenyl group, and preferably it is a C1-C4 alkyl group or a phenyl group. $R^{96}$ represents a C1-C8 alkyl group, a C3-C8 cycloalkyl group or a phenyl group, and preferably it is a C1-C4 alkyl group. $R^{97}$ and $R^{98}$ may be identical or different and each represents a hydrogen atom, a C1-C8 alkyl group, a C3-C8 cycloalkyl group, a phenyl group or an aralkyl group. When $R^{97}$ and $R^{98}$ are alkyl groups, they may form a saturated or unsaturated 5- to 7-membered ring together with the nitrogen atom to which they bond. Further this ring may contain 1 or 2 heteroatoms selected from the group consisting of an oxygen atom, a nitrogen atom and a sulfur atom besides the nitrogen atom to which $R^{97}$ and $R^{98}$ bond. Preferably $R^{97}$ and $R^{98}$, which may be identical or different, are a hydrogen atom or a C1-C4 alkyl group. $R^{99}$ represents a hydrogen atom, a C1-C4 alkyl group, a phenyl group or a benzyl group, and preferably it is a hydrogen atom or a C1-C4 alkyl group. $R^{100}$ represents a hydrogen atom, a C1-C4 alkyl group, a benzyl group, an acetyl group, a tert-butoxycarbonyl group or a benzyloxycarbonyl group, and preferably it is a hydrogen atom or a C1-C4 alkyl group.)

Among the optionally substituted C3-C8 cycloalkyl groups, which are preferred groups as $R^4$, as more preferred examples, there may be mentioned unsubstituted C3-C8 cycloalkyl groups and substituted C3-C8 cycloalkyl groups. (Here, the substituents are 1 to 3 substituents selected from the group consisting of a halogen, —(C═O)—$R^{101}$, —OH, —(C═O)OH, —(C═O)$OR^{102}$, —(C═O)$NR^{103}R^{104}$, a C1-C8 alkyl group, a C6-C14 aryl group, a C1-C8 alkoxy group and —$NR^{105}R^{106}$. More preferably they are 1 to 3 substituents selected from the group consisting of a halogen, a C1-C4 alkyl group, a C1-C4 alkoxy group and a phenyl group. Preferably the number of the substituents is 1 to 3 for halogens or 1 for the others. Here, $R^{105}$ represents a hydrogen atom, a C1-C8 alkyl group, a phenyl group or a benzyl group, and preferably it is a hydrogen atom or a C1-C4 alkyl group. $R^{106}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{101}$ represents a C1-C8 alkyl group, a C3-C8 cycloalkyl group or a phenyl group, and preferably it is a C1-C4 alkyl group or a phenyl group. $R^{102}$ represents a C1-C8 alkyl group, a C3-C8 cycloalkyl group or a phenyl group, and preferably it is a C1-C4 alkyl group. $R^{103}$ and $R^{104}$ may be identical or different and each represents a hydrogen atom, a C1-C8 alkyl group, a C3-C8 cycloalkyl group, a phenyl group or a benzyl group. When $R^{103}$ and $R^{104}$ are alkyl groups, they may form a saturated or unsaturated 5- to 7-membered ring together with the nitrogen atom to which they bond. Further this ring may contain 1 or 2 heteroatoms selected from the group consisting of an oxygen atom, a nitrogen atom and a sulfur atom besides the nitrogen atom to which $R^{103}$ and $R^{104}$ bond. Preferably each of $R^{103}$ and $R^{104}$, which may be identical or different, is a hydrogen atom or a C1-C4 alkyl group.)

Among the optionally substituted aralkyl groups, which are preferred groups as $R^4$, as more preferred examples, there may be mentioned an aralkyl group composed of an unsubstituted C1-C4 alkyl group and an unsubstituted phenyl group or an aralkyl group composed of an unsubstituted C1-C4 alkyl group and a substituted phenyl group. Here, the substituents in the substituted phenyl group are one or more substituents selected from the group consisting of a halogen, —CN, —CHO, —(C═O)—$R^{107}$, —$NO_2$, —OH, —(C═O)OH, —(C═O)$OR^{108}$, —(C═O)$NR^{109}R^{110}$, a C1-C8 alkyl group, a C1-C4 alkyl group substituted with 1 to 9 halogens, a C3-C8 cycloalkyl group, a phenyl group, a C1-C8 alkoxy group, a C1-C4 alkoxy group substituted with 1 to 9 halogens and —$NR^{111}R^{112}$. Preferably they are 1 to 3 substituents selected from the group consisting of a halogen, a C1-C4 alkyl group, a C1-C8 alkoxy group, —(C═O)$OR^{108}$ and —(C═O)$NR^{109}R^{110}$. Preferably the number of the substituents is 1 to 3 for halogens or 1 for the others. $R^{111}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{112}$ represents a C1-C8 alkyl group, a C3-C8 cycloalkyl group or a phenyl group, and preferably it is a C1-C4 alkyl group or a phenyl group. $R^{107}$ represents a C1-C8 alkyl group, a C3-C8 cycloalkyl group or a phenyl group, and preferably it is a C1-C4 alkyl group. $R^{108}$ represents a C1-C8 alkyl group, a C3-C8 cycloalkyl group or a phenyl group, and preferably it is a C1-C4 alkyl group. $R^{109}$ and $R^{110}$ may be identical or different and each represents a hydrogen atom, a C1-C8 alkyl group, a C3-C8 cycloalkyl group, a phenyl group or a benzyl group, and preferably they are a hydrogen atom or a C1-C4 alkyl group.

Among the optionally substituted heterocyclylalkyl groups, which are preferred groups as $R^4$, as more preferred examples, there may be mentioned unsubstituted heterocyclylalkyl groups and substituted heterocyclylalkyl groups. More preferably there may be mentioned a heterocyclylalkyl group composed of an unsubstituted C1-C4 alkyl group and an unsubstituted heteroaryl group and a heterocyclylalkyl group composed of an unsubstituted C1-C4 alkyl group and a substituted heteroaryl group. Furthermore preferably there may be mentioned a heterocyclylalkyl group composed of an unsubstituted C1-C4 alkyl group and an unsubstituted monocyclic or bicyclic heteroaryl group and a heterocyclylalkyl group composed of an unsubstituted C1-C4 alkyl group and a substituted monocyclic or bicyclic heteroaryl group. Here, in the substituted heterocyclic group, the heterocyclylalkyl group composed of an unsubstituted C1-C4 alkyl group and a substituted heteroaryl group or the heterocyclylalkyl group composed of an unsubstituted C1-C4 alkyl group and a substituted monocyclic or bicyclic heteroaryl group, the substituents on carbon atom(s) are one or more substituents selected from the group consisting of a halogen, —(C═O)OH, a C1-C4 alkyl group, a C1-C4 alkyl group substituted with 1 to 9 halogens, a C1-C4 alkoxy group and a C1-C4 alkoxy group substituted with 1 to 9 halogens. Preferably, the alkyl moiety in the heterocyclylalkyl group is unsubstituted and the substituents on carbon atom(s) in the heterocyclic group are one or more substituents selected form the group consisting of a halogen, a C1-C4 alkyl group and a C1-C4 alkyl group substituted with 1 to 9 halogens. Preferably the number of the substituents is 1 to 3. When nitrogen atom(s) in the heterocyclic group are substituted, the substituents are one or more substituents selected from the group consisting of a C1-C4 alkyl group, a benzyl group, an acetyl group, a tert-butoxycarbonyl group and a benzyloxycarbonyl group. More preferably, the substituent is a C1-C4 alkyl group or a tert-butoxycarbonyl group.

Among the optionally substituted C6-C14 aryl groups, which are preferred groups as $R^4$, as more preferred examples, there may be mentioned unsubstituted C6-C10 aryl groups and substituted C6-C10 aryl groups, and more preferably there may be mentioned an unsubstituted phenyl group and a substituted phenyl group. Here, the substituents in the substituted C6-C10 aryl group or the substituted phenyl group are 1 to 3 substituents selected from the group consisting of a halogen, —CN, —$NO_2$, an optionally substituted C1-C8 alkyl group, —O—$(CH_2)_m$—W, an optionally substituted phenyl group, an optionally substituted heterocyclic group, —(C═O)O$R^{113}$, —N$R^{114}$(C—O)$R^{115}$, —N$R^{116}R^{117}$, —(C═O)N$R^{118}R^{119}$ and —$SO_2$N$R^{120}R^{121}$. More preferably they are 1 to 3 substituents selected from the group consisting of a halogen, an optionally substituted C1-C4 alkyl group, —O—$(CH_2)_m$—W and —(C═O)O$R^{113}$. Still more preferably the substituent is one —O—$(CH_2)_m$—W. Preferably the number of the substituents is 1.

W represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C10 aryl group or an optionally substituted heterocyclic group and in this case m is 0 to 4; or W represents an optionally substituted C1-C8 alkoxy group, —N$R^{150}R^{151}$ or an optionally substituted phenoxy group and in this case m is 1 to 4. Preferably W is a hydrogen atom, an optionally substituted C1-C4 alkyl group, an optionally substituted C3-C8 cycloalkyl group, an optionally substituted phenyl group or an optionally substituted monocyclic or bicyclic heterocyclic group and m is 0 to 4; or W is an optionally substituted C1-C4 alkoxy group and m is 1 to 4. More preferably, W is a hydrogen atom or an optionally substituted C1-C4 alkyl group and m is 0 to 4; or W is an optionally substituted C1-C4 alkoxy group and m is 1 to 4. Furthermore preferably W is a C1-C4 alkyl group and m is 0; or W is a C1-C4 alkoxy group and m is 2.

$R^{113}$-$R^{121}$ may be identical or different and each represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted aralkyl group or an optionally substituted heterocyclylalkyl group; or when $R^{116}$ and $R^{117}$, $R^{118}$ and $R^{119}$, or $R^{120}$ and $R^{121}$ are alkyl groups, they may form a saturated or unsaturated 5- to 7-membered ring together with the nitrogen atom to which they bond. Further this ring may contain 1 or 2 heteroatoms selected from the group consisting of an oxygen atom, a nitrogen atom and a sulfur atom besides the nitrogen atom to which these substituents bond. Preferably $R^{113}$-$R^{121}$, which may be identical or different, are a hydrogen atom, an optionally substituted C1-C8 alkyl group, an optionally substituted C3-C8 cycloalkyl group or an optionally substituted C6-C14 aryl group. More preferably $R^{113}$-$R^{121}$, which may be identical or different, are a hydrogen atom or an optionally substituted C1-C4 alkyl group, and still more preferably $R^{113}$-$R^{121}$, which may be identical or different, are a hydrogen atom or a C1-C4 alkyl group.

Among the optionally substituted heterocyclic groups, which are preferred groups as $R^4$, as more preferred examples, there may be mentioned unsubstituted monocyclic heterocyclic groups, unsubstituted bicyclic heterocyclic groups, substituted monocyclic heterocyclic groups and substituted bicyclic heterocyclic groups. Unsubstituted bicyclic heteroaryl groups and substituted bicyclic heteroaryl groups are more preferred. Here, in the substituted monocyclic heterocyclic group, the substituted bicyclic heterocyclic group or the substituted bicyclic heteroaryl group, when carbon atom(s) are substituted, the substituent(s) are 1 to 3 substituents selected from the group consisting of a halogen, —CN, —$NO_2$, a C1-C8 alkyl group, a C1-C4 alkyl group substituted with 1 to 9 halogens, a C1-C8 alkoxy group, a C1-C4 alkoxy group substituted with 1 to 9 halogens, a phenyl group, a monocyclic or bicyclic heterocyclic group, —(C═O)O$R^{122}$, —N$R^{123}R^{124}$ and —(C═O)N$R^{125}R^{126}$ Preferably they are 1 to 3 substituents selected from the group consisting of a halogen, a C1-C4 alkyl group and a C1-C4 alkyl group substituted with 1 to 9 halogens. More preferably the substituent is one C1-C4 alkyl group. Preferably the number of substituents is 1. Here, $R^{123}$ represents a hydrogen atom, a C1-C8 alkyl group, a phenyl group or a benzyl group, and preferably it is a hydrogen atom or a C1-C4 alkyl group. $R^{124}$ represents a hydrogen atom, a C1-C8 alkyl group, a benzyl group, an acetyl group, a tert-butoxycarbonyl group or a benzyloxycarbonyl group, and preferably it is a hydrogen atom or a C1-C4 alkyl group. $R^{122}$ represents a C1-C8 alkyl group, a C3-C8 cycloalkyl group or a phenyl group, and preferably it is a C1-C4 alkyl group. $R^{112}$ and $R^{126}$ may be identical or different and each represents a hydrogen atom, a C1-C8 alkyl group, a C3-C8 cycloalkyl group, a phenyl group or a benzyl group, and preferably they are a hydrogen atom or a C1-C4 alkyl group. When nitrogen atom(s) in the heterocycle are substituted, the substituents are one or more substituents selected from the group consisting of a C1-C4 alkyl group, a benzyl group, an acetyl group, a tert-butoxycarbonyl group or a benzyloxycarbonyl group. Preferably the substituent is a C1-C4 alkyl group or a tert-butoxycarbonyl group.

More preferably $R^4$ is an unsubstituted phenyl group, a phenyl group substituted with one —O—$(CH_2)_m$—W, an unsubstituted bicyclic heteroaryl group, a bicyclic heteroaryl group substituted with C1-C4 alkyl group(s) or a bicyclic heteroaryl group substituted with C1-C4 alkyl group(s) substituted with 1 to 9 halogens. (Here, W represents a C1-C4 alkyl group (in this case m is 0) or a C1-C4 alkoxy group (in this case m is 2). The bicyclic heteroaryl group means a bicyclic heteroaryl group wherein a phenyl group is fused with a heterocycle containing 1 to 4 heteroatoms selected from the group consisting of N, O and S, and preferably it is a bicyclic heteroaryl group wherein a phenyl group is fused with a heterocycle containing 1 or 2 heteroatoms selected from the group consisting of N, O and S.).

Still more preferably $R^4$ is an unsubstituted phenyl group, a phenyl group substituted with one —O—$(CH_2)_m$—W, an unsubstituted bicyclic heteroaryl group, a bicyclic heteroaryl group substituted with one C1-C4 alkyl group or a bicyclic heteroaryl group substituted with one C1-C4 alkyl group substituted with 1 to 9 halogens (Here, W represents a C1-C4 alkyl group (in this case m is 0) or a C1-C4 alkoxy group (in this case m is 2). As the bicyclic heteroaryl group, there may be mentioned 5-benzothiazolyl, 6-benzothiazolyl, 5-benzoxazolyl, 6-benzoxazolyl, 5-benzothienyl, 6-benzothienyl, 5-benzofuranyl, 6-benzofuranyl, 5-indazolyl, 6-indazolyl, 5-benzimidazolyl, 6-benzimidazolyl, 5-indolyl and 6-indolyl.)

Furthermore preferably $R^4$ is an unsubstituted phenyl group, a phenyl group substituted with one —O—$(CH_2)_m$—W (Wherein W is an ethyl group (in this case m is 0) or a methoxy group (in this case m is 2)), 6-indazolyl, 2-methyl-6-benzothiazolyl, 5-benzothienyl or 2-trifluoromethyl-5-benzimidazolyl.

Preferably n is 0.

Preferably -A-B- is $-CH_2-CH_2-$, $-CH_2-CH_2-CH_2-$, $-CH_2-CH_2-CH_2-CH_2-$, $-CH_2-CH=CH-CH_2-$ or $-CH=CH-$, and further preferably $-CH_2-CH_2-$.

Preferably $R^5$ is a hydrogen atom or $-(C=O)R^6$.

Preferably $R^6$ is a methyl group.

Preferably $X^1$ or $X^2$ is O.

Preferably r is 0 or 2.

Preferably each of $Z^1$-$Z^4$ is a hydrogen atom.

Preferably $R^{11}$ is a hydrogen atom.

For $R^1$-$R^4$, n and -A-B- in formula (2) in the present invention, groups like the corresponding groups in formula (1) described above are preferred.

As preferred combinations of $R^1$-$R^4$, n and -A-B- in formula (1) in the present invention, in addition to combinations of group(s) included in the above definition for the individual group(s) and group(s) mentioned as preferred example for the individual group(s) and combinations of groups mentioned above as preferred example for the individual groups, there may be mentioned the following 1) to 23).

1) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is an optionally substituted phenyl group (wherein the substituent in the optionally substituted phenyl group is a halogen, —CN, an optionally substituted C1-C8 alkyl group or $-O-(CH_2)_m-W$, wherein W represents a hydrogen atom, an optionally substituted C1-C8 alkyl group or an optionally substituted heterocyclic group and m is 0 to 4 or W represents an optionally substituted C1-C8 alkoxy group and m is 2 to 4); n is 0; and -A-B- is $-CH_2-CH_2-$.

2) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is an optionally substituted heterocyclic group; n is 0; and -A-B- is $-CH_2-CH_2-$.

3) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group, $R^4$ is an optionally substituted phenyl group (wherein, the substituent in the optionally substituted phenyl group is a halogen, —CN, an optionally substituted C1-C8 alkyl group or $-O-(CH_2)_m-W$, wherein W represents a hydrogen atom, an optionally substituted C1-C8 alkyl group or an optionally substituted heterocyclic group and m is 0 to 4 or W represents an optionally substituted C1-C8 alkoxy group and m is 2 to 4); n is 0; and -A-B- is $-CH_2-CH_2-CH_2-$ or $-CH_2-CH_2-CH_2-CH_2-$.

4) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is an optionally substituted heterocyclic group; n is 0; and -A-B- is $-CH_2-CH_2-CH_2-$ or $-CH_2-CH_2-CH_2-CH_2-$.

5) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is an optionally substituted phenyl group (wherein, the substituent in the optionally substituted phenyl group is a halogen, —CN, an optionally substituted C1-C8 alkyl group or $-O-(CH_2)_m-W$, wherein W represents a hydrogen atom, an optionally substituted C1-C8 alkyl group or an optionally substituted heterocyclic group and m is 0 to 4 or W represents an optionally substituted C1-C8 alkoxy group and m is 2 to 4); n is 0; and -A-B- is $-CH_2-CH=CH-CH_2-$ or $-CH=CH-$.

6) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is an optionally substituted heterocyclic group; n is 0; and -A-B- is $-CH_2-CH=CH-CH_2-$ or $-CH=CH-$.

7) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is a hydrogen atom, an optionally substituted C1-C8 alkyl group or an optionally substituted C3-C8 cycloalkyl group; n is 0; and -A-B- is $-CH_2-CH_2-$.

8) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is a hydrogen atom, an optionally substituted C1-C8 alkyl group or an optionally substituted C3-C8 cycloalkyl group; n is 0; and -A-B- is $-CH_2-CH_2-CH_2-$ or $-CH_2-CH_2-CH_2-CH_2-$.

9) In formula (1), $R^1$ is hydrogen; $R^2$ is hydrogen; $R^3$ is an optionally substituted C1-C8 alkyl group, an optionally substituted C3-C8 cycloalkyl group or an optionally substituted heterocyclic group; $R^4$ is a hydrogen atom, an optionally substituted C1-C8 alkyl group or an optionally substituted C3-C8 cycloalkyl group; n is 0; and -A-B- is $-CH_2-CH=CH-CH_2-$ or $-CH=CH-$.

10) In formula (1), $R^1$ is hydrogen; $R^2$ is hydrogen; $R^3$ is an optionally substituted C3-C8 cycloalkyl group; $R^4$ is an optionally substituted phenyl group (wherein the substituent in the optionally substituted phenyl group is a halogen or an optionally substituted C1-C4 alkyl group); n is 0; and -A-B- is $-CH_2-CH_2-$.

11) In formula (1), $R^1$ is hydrogen; $R^2$ is hydrogen; $R^3$ is an optionally substituted C3-C8 cycloalkyl group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4); n is 0; and -A-B- is $-CH_2-CH_2-$.

12) In formula (1), $R^1$ is hydrogen; $R^2$ is hydrogen; $R^3$ is an optionally substituted C3-C8 cycloalkyl group; $R^4$ is an optionally substituted heteroaryl group; n is 0; and -A-B- is $-CH_2-CH_2-$ 13) In formula (1), $R^1$ is hydrogen; $R^2$ is hydrogen; $R^3$ is an optionally substituted saturated heterocyclic group; $R^4$ is an optionally substituted phenyl group (wherein the substituent in the optionally substituted phenyl group is a halogen or an optionally substituted C1-C4 alkyl group); n is 0; and -A-B- is $-CH_2-CH_2-$.

14) In formula (1), $R^1$ is hydrogen; $R^2$ is hydrogen; $R^3$ is an optionally substituted saturated heterocyclic group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4); n is 0; and -A-B- is $-CH_2-CH_2-$.

15) In formula (1), $R^1$ is hydrogen; $R^2$ is hydrogen; $R^3$ is an optionally substituted saturated heterocyclic group; $R^4$ is an optionally substituted heteroaryl group; n is 0; and -A-B- is $-CH_2-CH_2-$.

16) In formula (1), $R^1$ is hydrogen; $R^2$ is halogen; $R^3$ is an optionally substituted saturated heterocyclic group; $R^4$ is an optionally substituted phenyl group (wherein the substituent in the optionally substituted phenyl group is a halogen or an optionally substituted C1-C4 alkyl group); n is 0; and -A-B- is $-CH_2-CH_2-$.

17) In formula (1), $R^1$ is hydrogen; $R^2$ is halogen; $R^3$ is an optionally substituted saturated heterocyclic group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4); n is 0; and -A-B- is $-CH_2-CH_2-$.

18) In formula (1), $R^1$ is hydrogen; $R^2$ is halogen; $R^3$ is an optionally substituted saturated heterocyclic group; $R^4$ is an optionally substituted heteroaryl group; n is 0; and -A-B- is $-CH_2-CH_2-$.

19) In formula (1), $R^1$ is hydrogen; $R^2$ is hydrogen; $R^3$ is an optionally substituted piperidyl group or a pyrrolidyl group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4.) or an optionally substituted bicyclic heteroaryl group; n is 0; and -A-B- is $-CH_2-CH_2-$.

20) In formula (1), $R^1$ is hydrogen; $R^2$ is hydrogen; $R^3$ is an optionally substituted piperidyl group or a pyrrolidyl group; $R^4$ is an optionally substituted heteroaryl group; n is 0; and -A-B- is $-CH_2-CH_2-$.

21) In formula (1), $R^1$ is hydrogen; $R^2$ is hydrogen; $R^3$ is an unsubstituted piperidyl group or a pyrrolidyl group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4.); n is 0; and -A-B- is $-CH_2-CH_2-$.

22) In formula (1), $R^1$ is hydrogen; $R^2$ is hydrogen; $R^3$ is a cyclohexyl group substituted with an amino group; $R^4$ is an optionally substituted phenyl group (wherein the substituent of the optionally substituted phenyl group is $-O-(CH_2)_m-W$, wherein W represents a hydrogen atom or an optionally substituted C1-C4 alkyl group and m is 0 to 4 or W represents an optionally substituted C1-C4 alkoxy group and m is 2 to 4.); n is 0; and -A-B- is $-CH_2-CH_2-$.

23) In formula (1), $R^1$ is hydrogen; $R^2$ is hydrogen; $R^3$ is a cyclohexyl group substituted with an amino group; $R^4$ is an optionally substituted heteroaryl group; n is 0; and -A-B- is $-CH_2-CH_2-$.

As preferred combinations of $R^1$-$R^4$, n and -A-B- in formula (2) in the present invention, in addition to combinations of group(s) included in the above definition for $R^1$-$R^4$, n and -A-B- in formula (1) and group(s) mentioned above as preferred example for the individual groups and combinations of groups mentioned as preferred example for the individual groups, there may be mentioned the above 1) to 23).

The compound of the present invention may contain a basic group in the molecule. In this case it may be converted to a medically acceptable acid-addition salt if necessary. As such acids, for example, there may be mentioned inorganic acids such as hydrochloric acid, hydrobromic acid, sulfuric acid, phosphoric acid and carbonic acid; and organic acids such as acetic acid, citric acid, malic acid, oxalic acid, tartaric acid, lactic acid, maleic acid, fumaric acid and methanesulfonic acid.

The compound of the present invention may contain an acidic group in the molecule. In this case it may be converted to a medically acceptable salt if necessary. As such salts, there may be mentioned salts with non-toxic cations. Specifically, there may be mentioned salts with alkali metal ions such as $Na^+$ and $K^+$, alkaline earth metal ions such as $Mg^{2+}$ and $Ca^{2+}$, metal ions such as $Al^{3+}$ and $Zn^{2+}$, ammonium ion, and organic bases such as triethylamine, ethylenediamine, propanediamine, pyrrolidine, piperidine, piperazine, pyridine, lysine, choline, ethanolamine, N,N-dimethylethanolamine, 4-hydroxypiperidine, glucosamine and N-methylglucamine.

When the compound of the present invention exists enantiomer, the present invention includes racemic and optically active forms. When the compound of the present invention contains two or more chiral carbon atoms, the present invention includes all diastereomers. When the compound of the present invention exists trans-cis geometrical isomer, the present invention includes either the trans form or the cis form.

As examples of compound represented by formula (1) in the present invention, there may be mentioned compounds listed in Tables A to G.

TABLE A

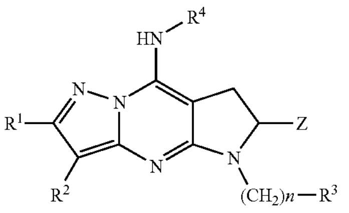

| Compound No. | $R^1$ | $R^2$ | $R^3$ | $R^4$ | n | Z |
|---|---|---|---|---|---|---|
| A-001 | H | H | 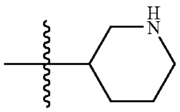 | 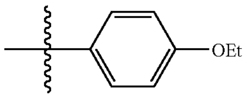 | 0 | H |

TABLE A-continued
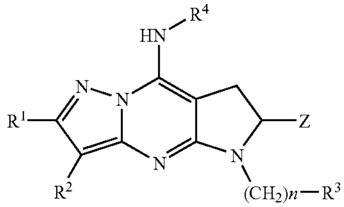
| Compound No. | $R^1$ | $R^2$ | $R^3$ | $R^4$ | n | Z |
|---|---|---|---|---|---|---|
| A-002 | H | H | 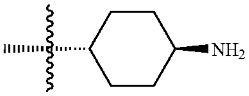 | 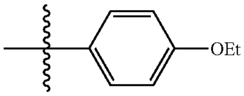 | 0 | H |
| A-003 | H | H | 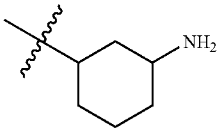 | 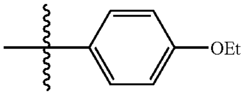 | 0 | H |
| A-004 | H | H | 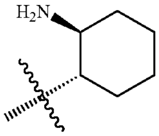 | 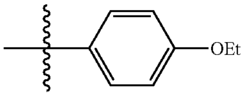 | 0 | H |
| A-005 | H | H | 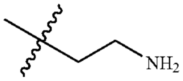 | 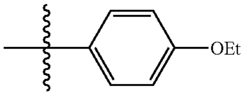 | 0 | H |
| A-006 | H | H | 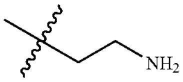 | 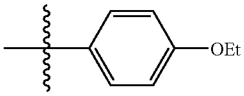 | 1 | H |
| A-007 | H | H | 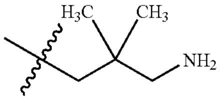 | 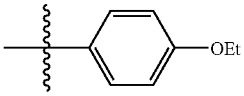 | 0 | H |
| A-008 | H | H | 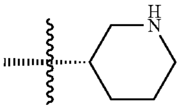 | 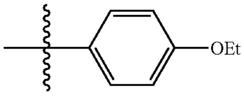 | 0 | H |
| A-009 | H | H | 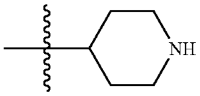 | 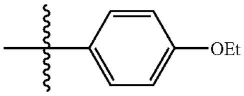 | 0 | H |
| A-010 | H | H | 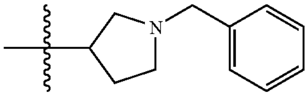 | 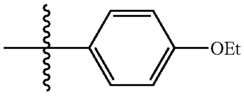 | 0 | H |
| A-011 | H | H | 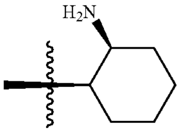 | 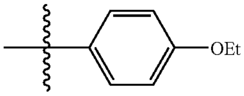 | 0 | H |

TABLE A-continued
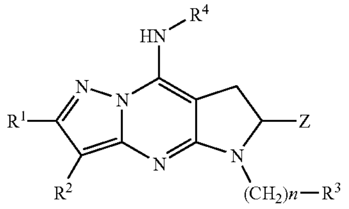
| Compound No. | $R^1$ | $R^2$ | $R^3$ | $R^4$ | n | Z |
|---|---|---|---|---|---|---|
| A-012 | H | H | 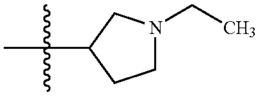 | 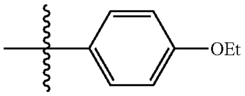 | 0 | H |
| A-013 | H | H | 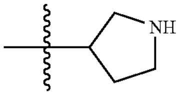 | 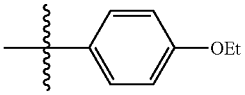 | 0 | H |
| A-014 | H | H | 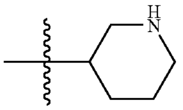 | 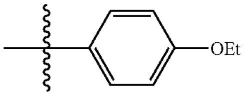 | 1 | H |
| A-015 | H | H | 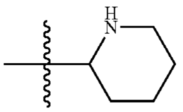 | 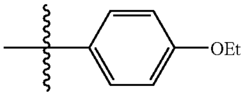 | 1 | H |
| A-016 | H | H | 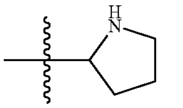 | 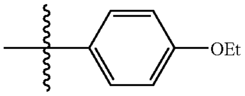 | 1 | H |
| A-017 | H | H | 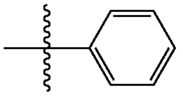 | 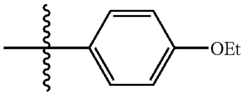 | 1 | H |
| A-018 | H | F | 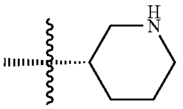 | 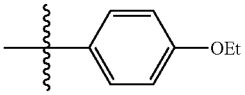 | 0 | H |
| A-019 | F | F | 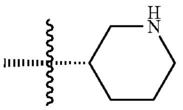 | 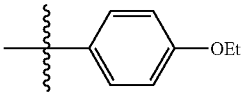 | 0 | H |
| A-020 | H | H | OH | 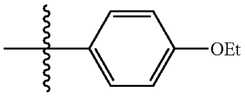 | 0 | H |
| A-021 | H | H | 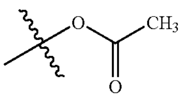 | 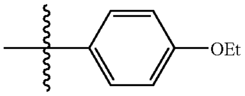 | 0 | H |
| A-022 | H | H | 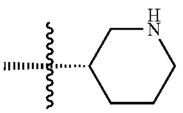 | 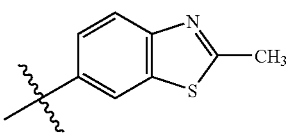 | 0 | H |

TABLE A-continued
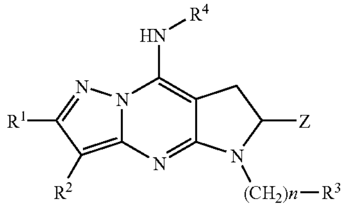
| Compound No. | $R^1$ | $R^2$ | $R^3$ | $R^4$ | n | Z |
|---|---|---|---|---|---|---|
| A-023 | H | H | 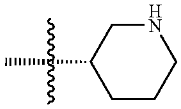 | 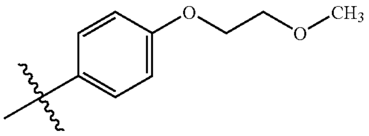 | 0 | H |
| A-024 | H | H | 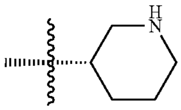 | 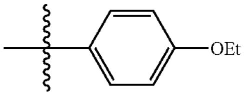 | 0 | 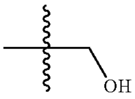 |
| A-025 | H | H | 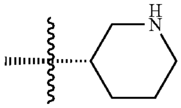 | 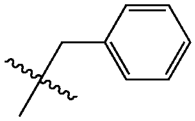 | 0 | H |
| A-026 | H | H | 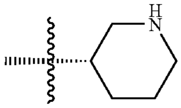 | 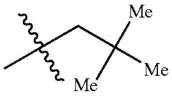 | 0 | H |
| A-027 | H | H | 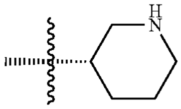 | 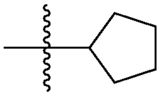 | 0 | H |
| A-028 | H | H | 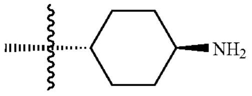 | 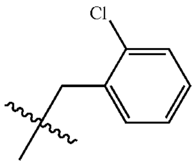 | 0 | H |
| A-029 | H | H | 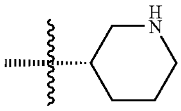 | 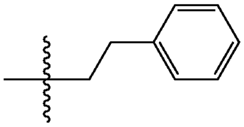 | 0 | H |
| A-030 | H | H | 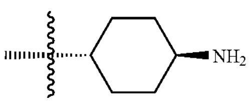 | 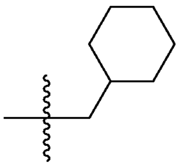 | 0 | H |
| A-031 | H | H | 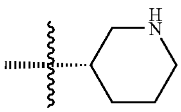 | 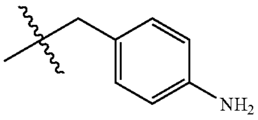 | 0 | H |

TABLE A-continued
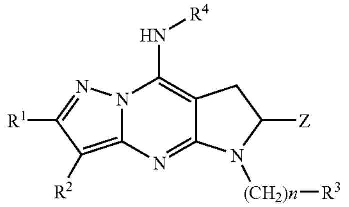
| Compound No. | $R^1$ | $R^2$ | $R^3$ | $R^4$ | n | Z |
|---|---|---|---|---|---|---|
| A-032 | H | H | 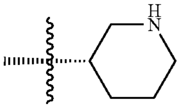 | 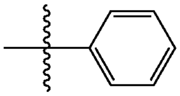 | 0 | H |
| A-033 | H | H | 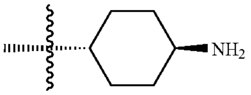 | 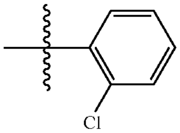 | 0 | H |
| A-034 | H | H | 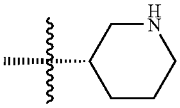 | 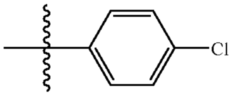 | 0 | H |
| A-035 | H | H | 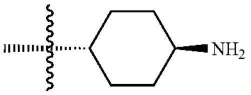 | 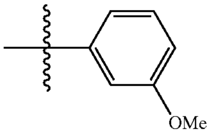 | 0 | H |
| A-036 | H | H | 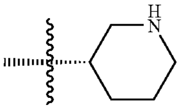 | 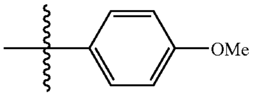 | 0 | H |
| A-037 | H | H | 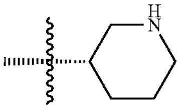 | 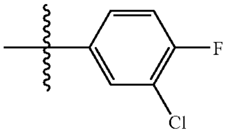 | 0 | H |
| A-038 | H | H | 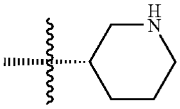 | 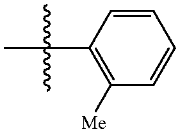 | 0 | H |
| A-039 | H | H | 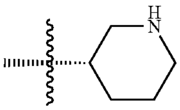 | 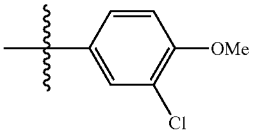 | 0 | H |
| A-040 | H | H | 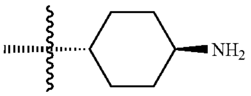 | 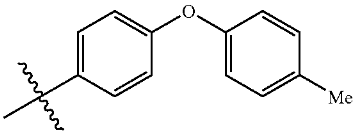 | 0 | H |

TABLE A-continued
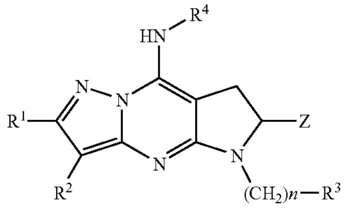
| Compound No. | $R^1$ | $R^2$ | $R^3$ | $R^4$ | n | Z |
|---|---|---|---|---|---|---|
| A-041 | H | H | 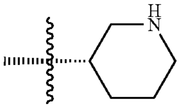 | 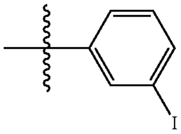 | 0 | H |
| A-042 | H | H | 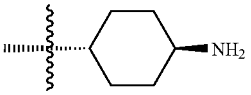 | 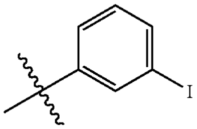 | 0 | H |
| A-043 | H | H | 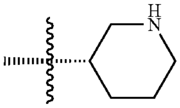 | 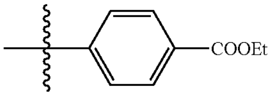 | 0 | H |
| A-044 | H | H | 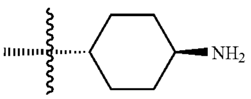 | 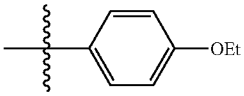 | 0 | H |
| A-045 | H | H | 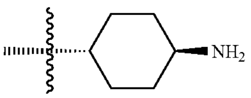 | 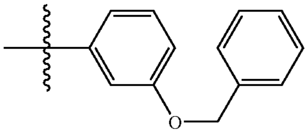 | 0 | H |
| A-046 | H | H | 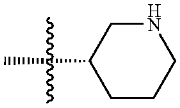 | 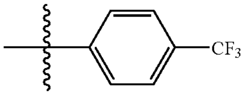 | 0 | H |
| A-047 | H | H | 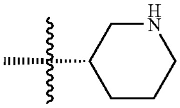 | 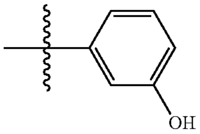 | 0 | H |
| A-048 | H | H | 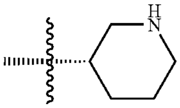 | 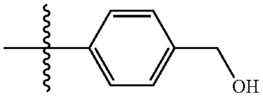 | 0 | H |
| A-049 | H | H | 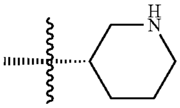 | 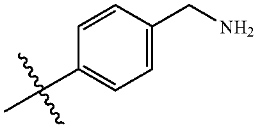 | 0 | H |
| A-050 | H | H | 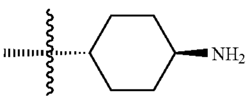 | 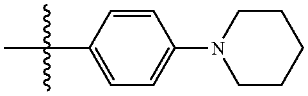 | 0 | H |

TABLE A-continued
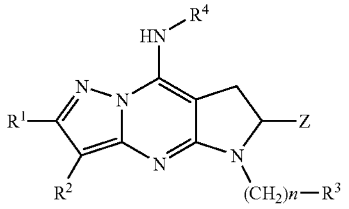
| Compound No. | $R^1$ | $R^2$ | $R^3$ | $R^4$ | n | Z |
|---|---|---|---|---|---|---|
| A-051 | H | H | 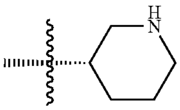 | 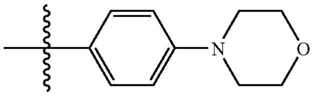 | 0 | H |
| A-052 | H | H | 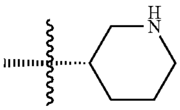 | 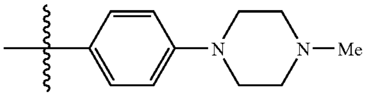 | 0 | H |
| A-053 | H | H | 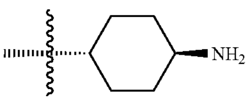 | 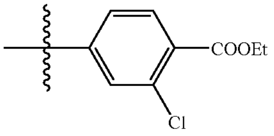 | 0 | H |
| A-054 | H | H | 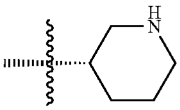 | 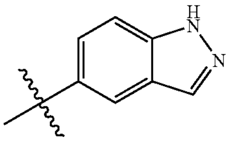 | 0 | H |
| A-055 | H | H | 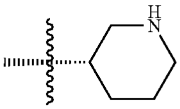 | 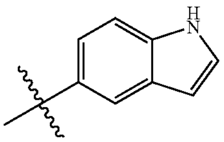 | 0 | H |
| A-056 | H | H | 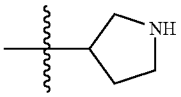 | 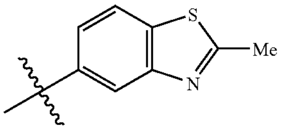 | 0 | H |
| A-057 | H | H | 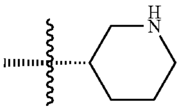 | 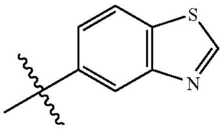 | 0 | H |
| A-058 | H | H | 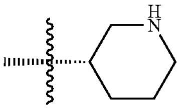 | 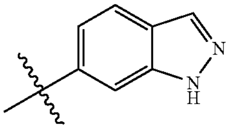 | 0 | H |
| A-059 | H | H | 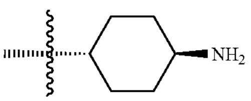 | 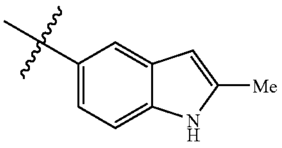 | 0 | H |

TABLE A-continued
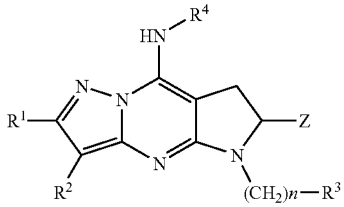
| Compound No. | $R^1$ | $R^2$ | $R^3$ | $R^4$ | n | Z |
|---|---|---|---|---|---|---|
| A-060 | H | H | 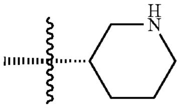 | 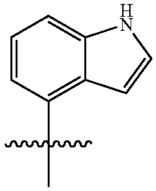 | 0 | H |
| A-061 | H | H | 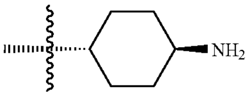 | 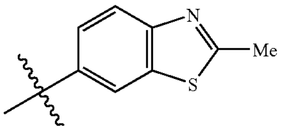 | 0 | H |
| A-062 | H | H | 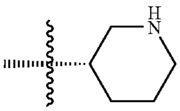 | 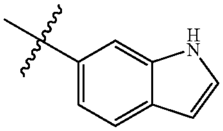 | 0 | H |
| A-063 | H | H | 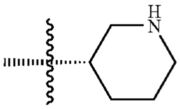 | 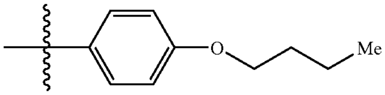 | 0 | H |
| A-064 | H | H | 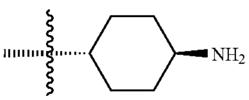 | 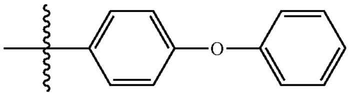 | 0 | H |
| A-065 | H | H | 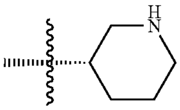 | 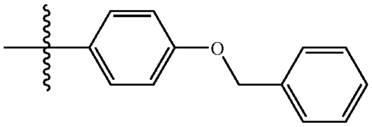 | 0 | H |
| A-066 | H | H | 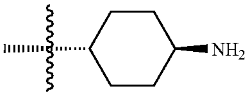 | 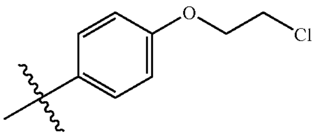 | 0 | H |
| A-067 | H | H | 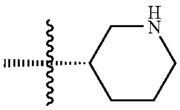 | 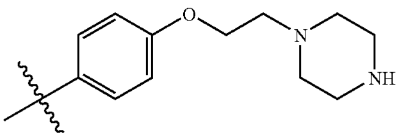 | 0 | H |
| A-068 | H | H | 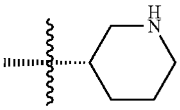 | 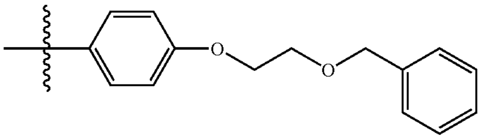 | 0 | H |

TABLE A-continued
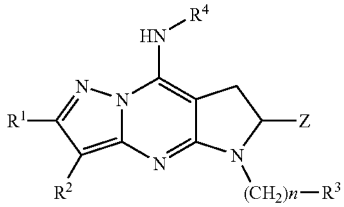
| Compound No. | $R^1$ | $R^2$ | $R^3$ | $R^4$ | n | Z |
|---|---|---|---|---|---|---|
| A-069 | H | H | 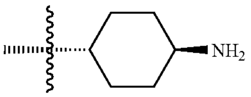 | 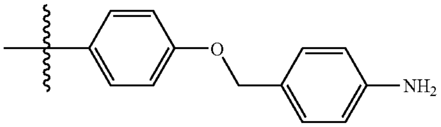 | 0 | H |
| A-070 | H | H | 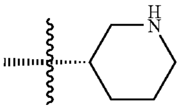 | 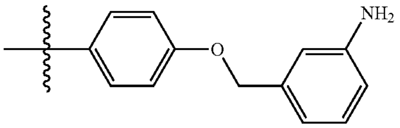 | 0 | H |
| A-071 | H | H | 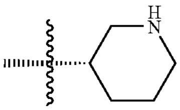 | 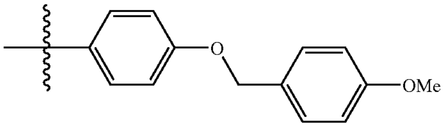 | 0 | H |
| A-072 | H | H | 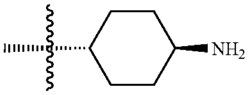 | 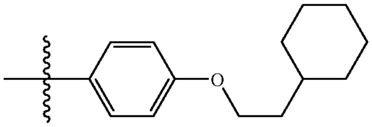 | 0 | H |
| A-073 | H | H | 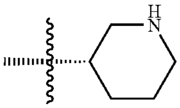 | 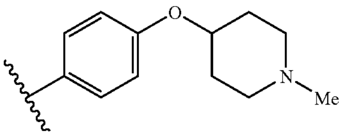 | 0 | H |
| A-074 | H | H | 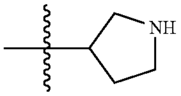 | 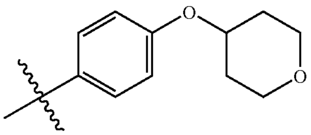 | 0 | H |
| A-075 | H | H | 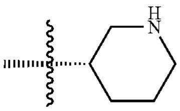 | 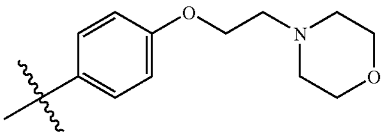 | 0 | H |
| A-076 | H | H | 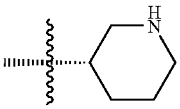 | 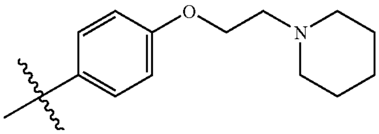 | 0 | H |
| A-077 | H | H | 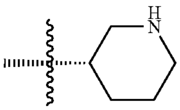 | 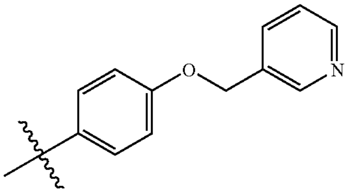 | 0 | H |

TABLE A-continued
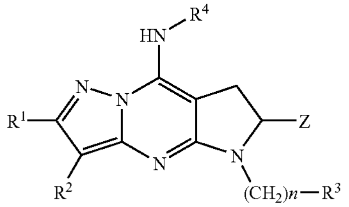
| Compound No. | $R^1$ | $R^2$ | $R^3$ | $R^4$ | n | Z |
|---|---|---|---|---|---|---|
| A-078 | H | H | 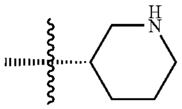 | 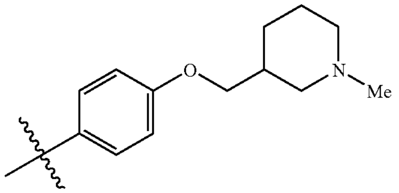 | 0 | H |
| A-079 | H | H | 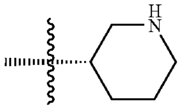 | 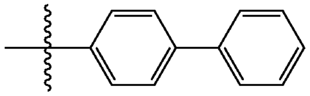 | 0 | H |
| A-080 | H | H | 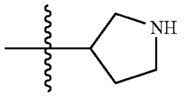 | 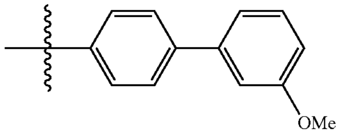 | 0 | H |
| A-081 | H | H | 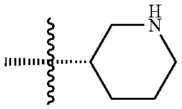 | 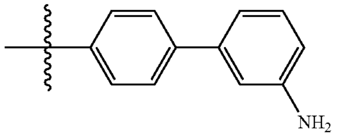 | 0 | H |
| A-082 | H | H | 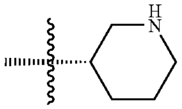 | 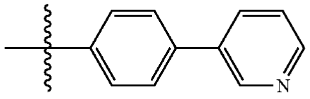 | 0 | H |
| A-083 | H | H | 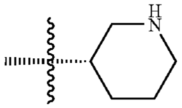 | 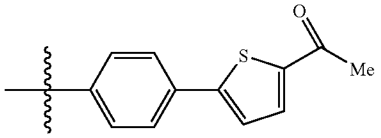 | 0 | H |
| A-084 | H | H | 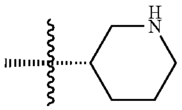 | 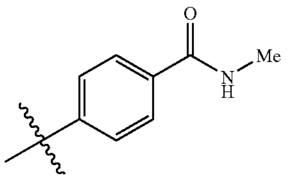 | 0 | H |
| A-085 | H | H | 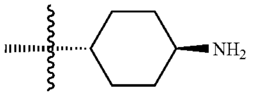 | 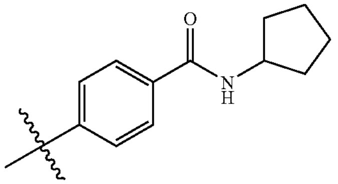 | 0 | H |

TABLE A-continued
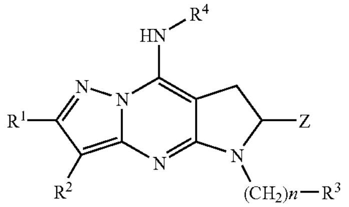
| Compound No. | $R^1$ | $R^2$ | $R^3$ | $R^4$ | n | Z |
|---|---|---|---|---|---|---|
| A-086 | H | H | 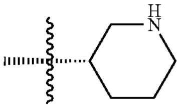 | 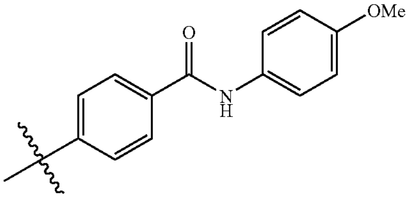 | 0 | H |
| A-087 | H | H | 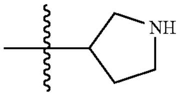 | 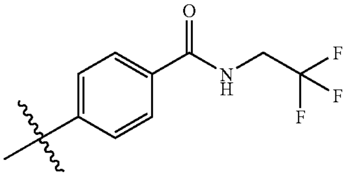 | 0 | H |
| A-088 | H | H | 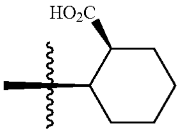 | 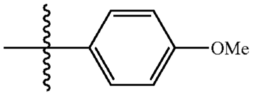 | 0 | H |
| A-089 | H | H | 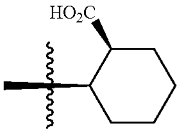 | 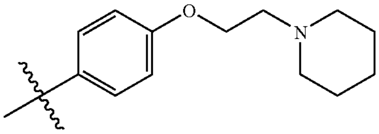 | 0 | H |
| A-090 | H | H | 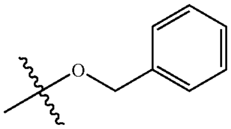 | 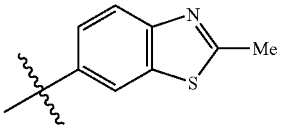 | 0 | H |
| A-091 | H | H | 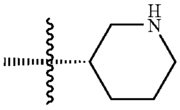 | 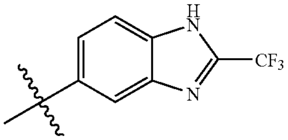 | 0 | H |
| A-092 | H | H | 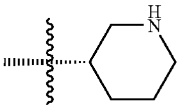 | H | 0 | H |
| A-093 | H | H | 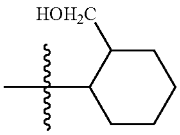 | H | 0 | H |

TABLE A-continued
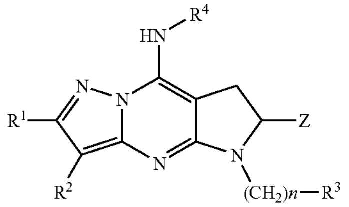
| Compound No. | $R^1$ | $R^2$ | $R^3$ | $R^4$ | n | Z |
|---|---|---|---|---|---|---|
| A-094 | H | H | 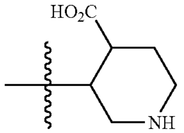 | H | 0 | H |
| A-095 | H | H | 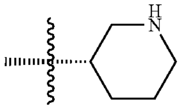 | 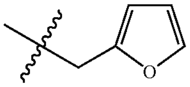 | 0 | H |
| A-096 | H | H | 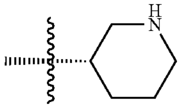 | Me | 0 | H |
| A-97 | H | H | 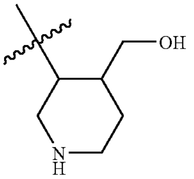 | 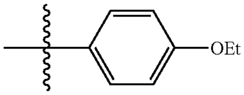 | 0 | H |
| A-98 | H | H | 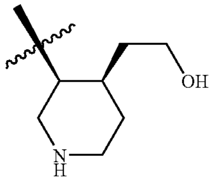 | 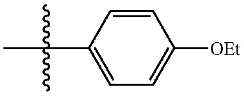 | 0 | H |
| A-99 | H | H | 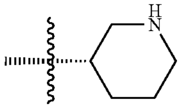 | 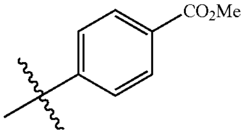 | 0 | H |
| A-100 | H | H | 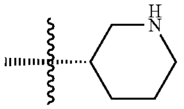 | 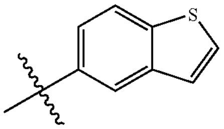 | 0 | H |
| A-101 | H | Cl | 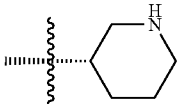 | 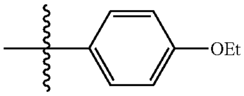 | 0 | H |
| A-102 | H | Br | 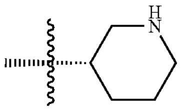 | 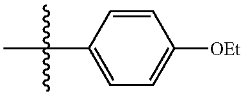 | 0 | H |

TABLE B
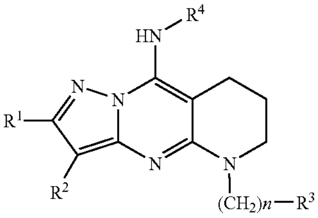
| Compound No. | $R^1$ | $R^2$ | $R^3$ | $R^4$ | n |
|---|---|---|---|---|---|
| B-001 | H | H | 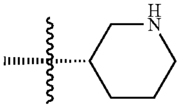 | 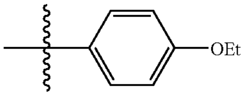 | 0 |
| B-002 | H | H | 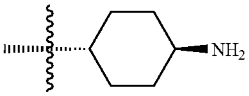 | 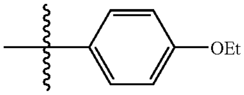 | 0 |
| B-003 | H | H | 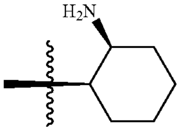 | 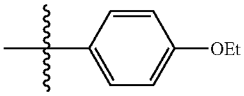 | 0 |
| B-004 | H | H | 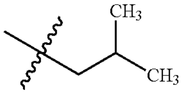 | 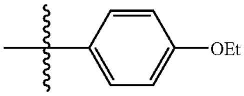 | 0 |
| B-005 | H | H | 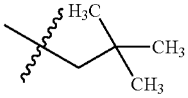 | 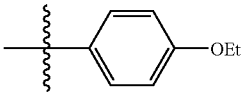 | 0 |
| B-006 | H | H | 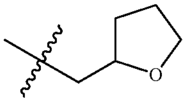 | 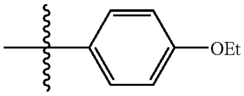 | 0 |
| B-007 | H | H | 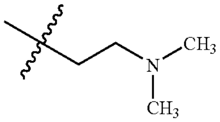 | 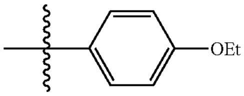 | 0 |
| B-008 | H | H | 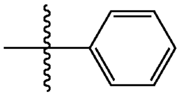 | 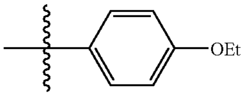 | 1 |
| B-009 | H | H | 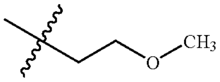 | 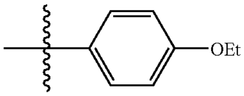 | 0 |
| B-010 | H | H | 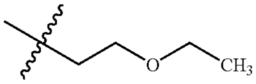 | 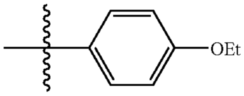 | 0 |
| B-011 | H | H | 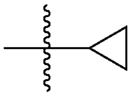 | 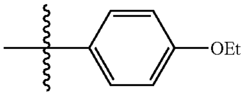 | 0 |

TABLE B-continued
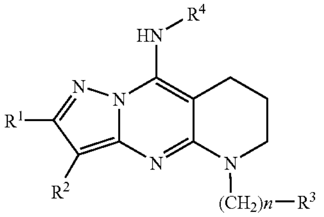
| Compound No. | $R^1$ | $R^2$ | $R^3$ | $R^4$ | n |
|---|---|---|---|---|---|
| B-012 | H | H | 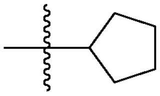 | 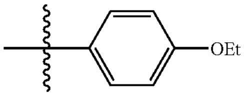 | 0 |
| B-013 | H | H | 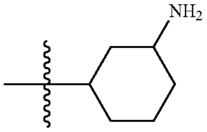 | 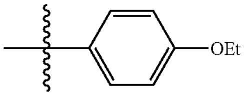 | 0 |
| B-014 | H | H | 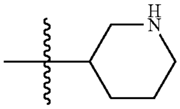 | 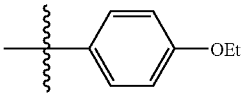 | 0 |
| B-015 | H | H | 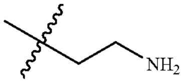 | 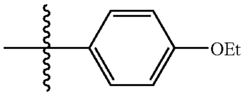 | 1 |
| B-016 | H | H | 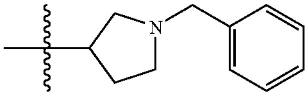 | 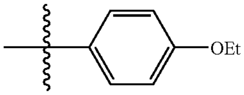 | 0 |
| B-017 | H | H | 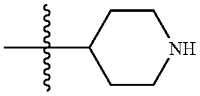 | 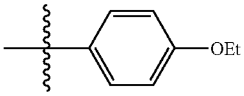 | 0 |
| B-018 | H | H | 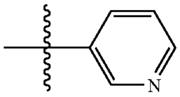 | 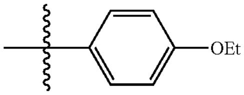 | 1 |
| B-019 | F | H | 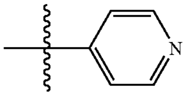 | 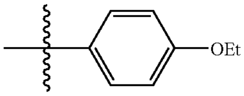 | 1 |
| B-020 | H | H | 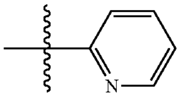 | 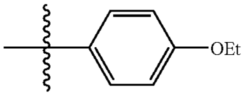 | 1 |
| B-021 | H | H | 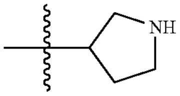 | 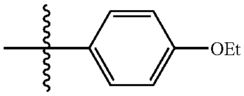 | 0 |
| B-022 | H | H | 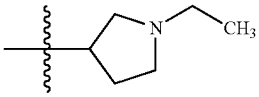 | 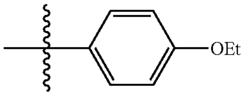 | 0 |

TABLE B-continued
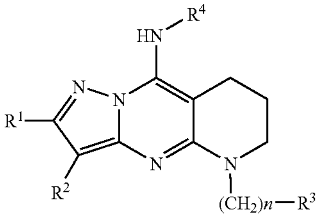
| Compound No. | $R^1$ | $R^2$ | $R^3$ | $R^4$ | n |
|---|---|---|---|---|---|
| B-023 | H | H | 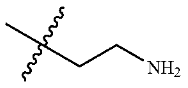 | 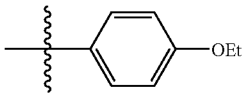 | 0 |
| B-024 | H | H | 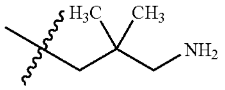 | 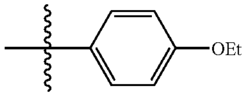 | 0 |
| B-025 | H | H | 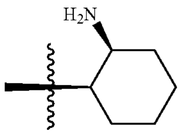 | 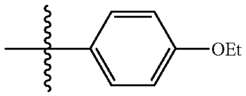 | 0 |
| B-026 | H | H | 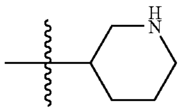 | 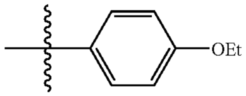 | 1 |
| B-027 | H | H | 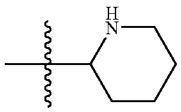 | 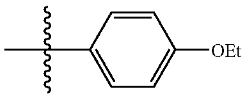 | 1 |
| B-028 | H | H | 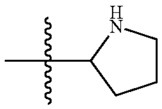 | 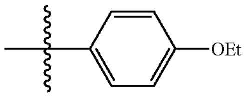 | 1 |
| B-029 | H | H | 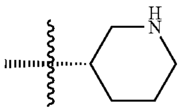 | 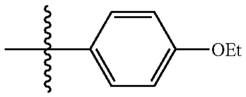 | 0 |
| B-030 | H | H | 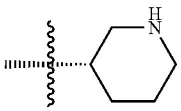 | 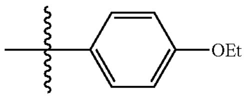 | 0 |
| B-031 | H | H | 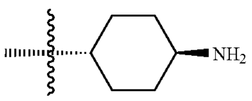 | 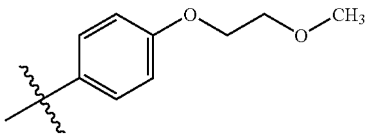 | 0 |
| B-032 | H | H | 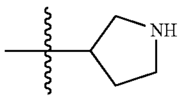 | 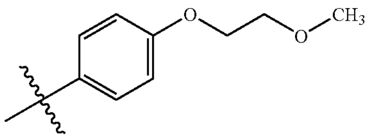 | 0 |

TABLE B-continued
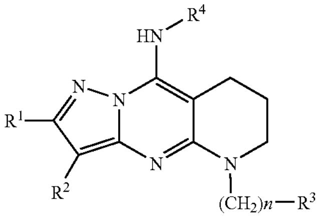
| Compound No. | $R^1$ | $R^2$ | $R^3$ | $R^4$ | n |
|---|---|---|---|---|---|
| B-033 | H | H | 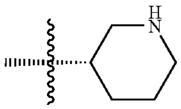 | 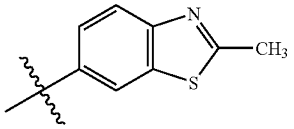 | 0 |
| B-034 | H | H | 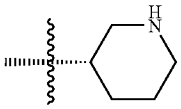 | 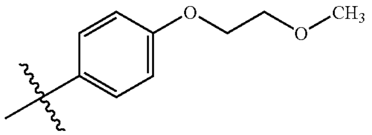 | 0 |
| B-035 | H | H | 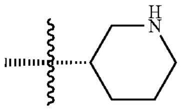 | 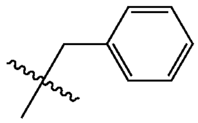 | 0 |
| B-036 | H | H | 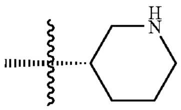 | 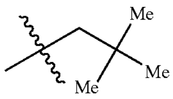 | 0 |
| B-037 | H | H | 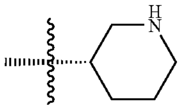 | 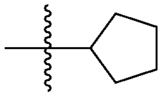 | 0 |
| B-038 | H | H | 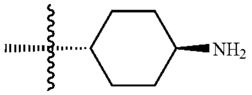 | 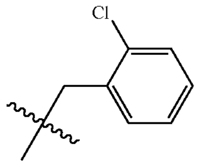 | 0 |
| B-039 | H | H | 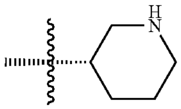 | 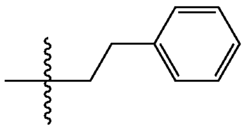 | 0 |
| B-040 | H | H | 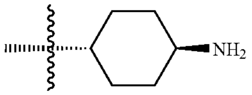 | 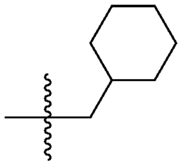 | 0 |
| B-041 | H | H | 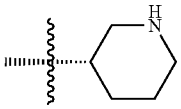 | 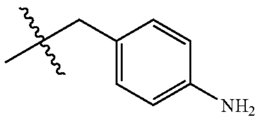 | 0 |

TABLE B-continued
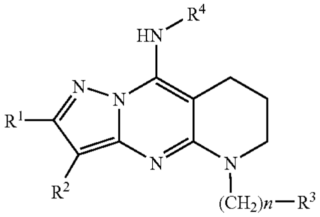
| Compound No. | $R^1$ | $R^2$ | $R^3$ | $R^4$ | n |
| --- | --- | --- | --- | --- | --- |
| B-042 | H | H | 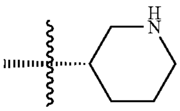 | 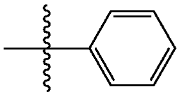 | 0 |
| B-043 | H | H | 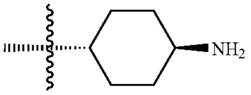 | 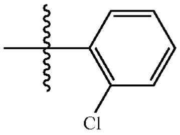 | 0 |
| B-044 | H | H | 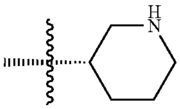 | 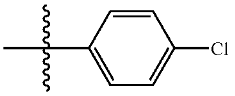 | 0 |
| B-045 | H | H | 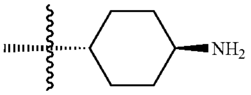 | 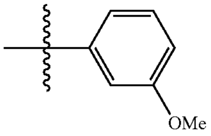 | 0 |
| B-046 | H | H | 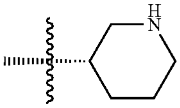 | 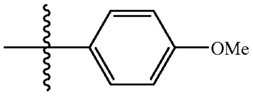 | 0 |
| B-047 | H | H | 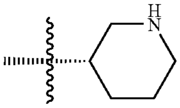 | 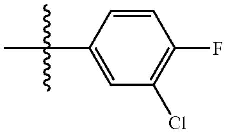 | 0 |
| B-048 | H | H | 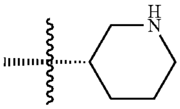 | 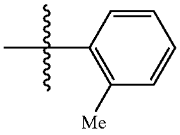 | 0 |
| B-049 | H | H | 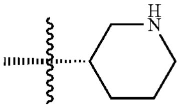 | 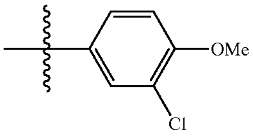 | 0 |
| B-050 | H | H | 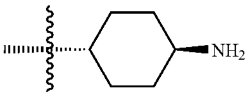 | 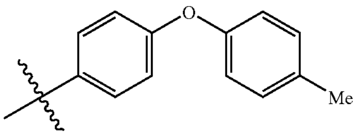 | 0 |

TABLE B-continued
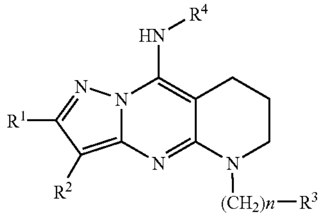
| Compound No. | $R^1$ | $R^2$ | $R^3$ | $R^4$ | n |
|---|---|---|---|---|---|
| B-051 | H | H | 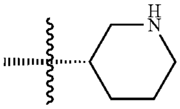 | 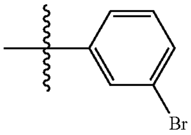 | 0 |
| B-052 | H | H | 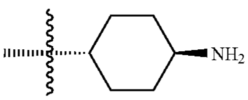 | 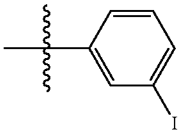 | 0 |
| B-053 | H | H | 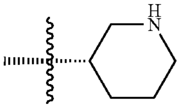 | 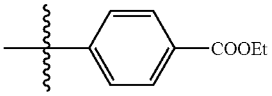 | 0 |
| B-054 | H | H | 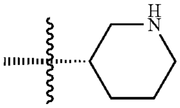 | 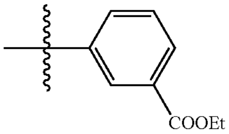 | 0 |
| B-055 | H | H | 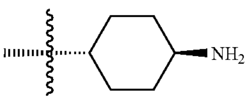 | 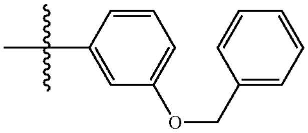 | 0 |
| B-056 | H | H | 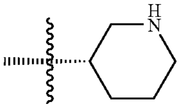 | 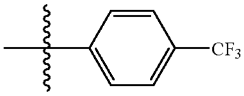 | 0 |
| B-057 | H | H | 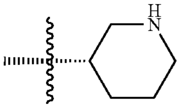 | 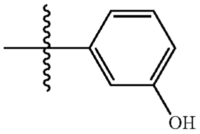 | 0 |
| B-058 | H | H | 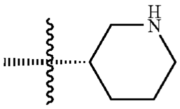 | 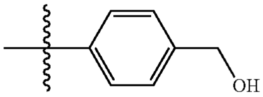 | 0 |
| B-059 | H | H | 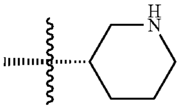 | 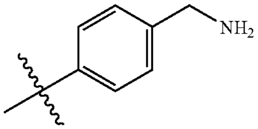 | 0 |

TABLE B-continued
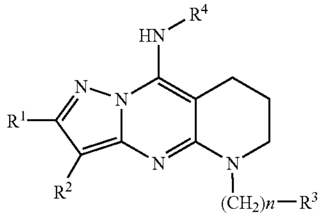
| Compound No. | $R^1$ | $R^2$ | $R^3$ | $R^4$ | n |
|---|---|---|---|---|---|
| B-060 | H | H | 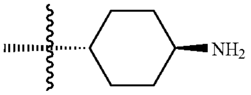 | 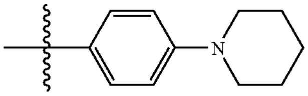 | 0 |
| B-061 | H | H | 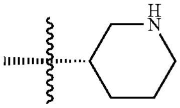 | 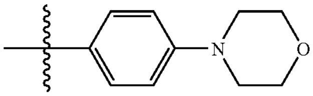 | 0 |
| B-062 | H | H | 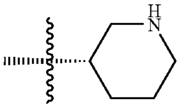 | 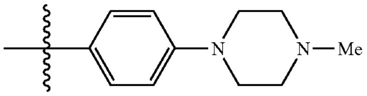 | 0 |
| B-063 | H | H | 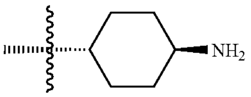 | 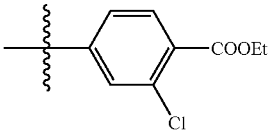 | 0 |
| B-064 | H | H | 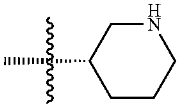 | 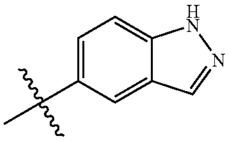 | 0 |
| B-065 | H | H | 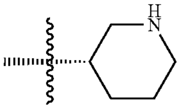 | 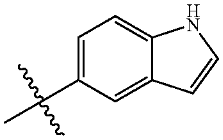 | 0 |
| B-066 | H | H | 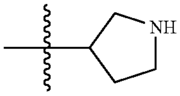 | 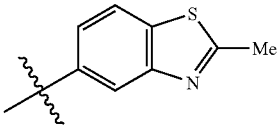 | 0 |
| B-067 | H | H | 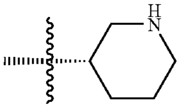 | 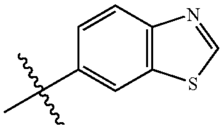 | 0 |
| B-068 | H | H | 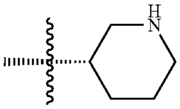 | 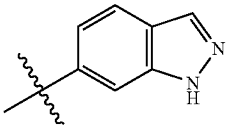 | 0 |

TABLE B-continued
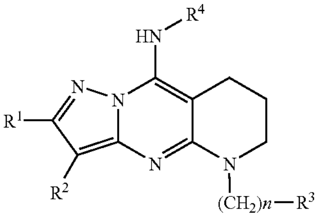
| Compound No. | $R^1$ | $R^2$ | $R^3$ | $R^4$ | n |
|---|---|---|---|---|---|
| B-069 | H | H | 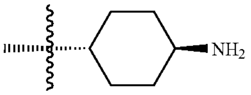 | 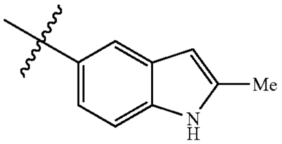 | 0 |
| B-070 | H | H | 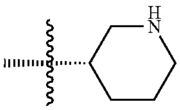 | 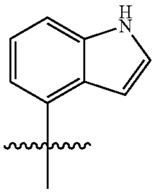 | 0 |
| B-071 | H | H | 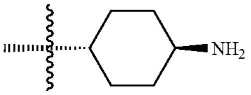 | 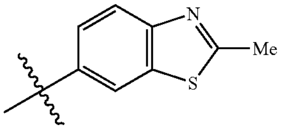 | 0 |
| B-072 | H | H | 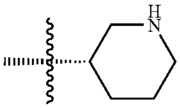 | 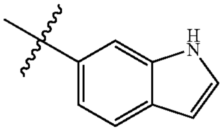 | 0 |
| B-073 | H | H | 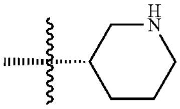 | 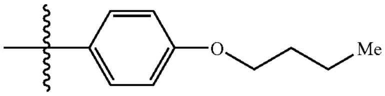 | 0 |
| B-074 | H | H | 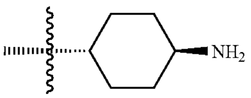 | 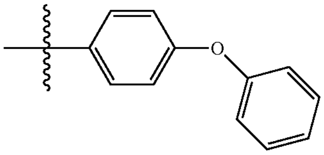 | 0 |
| B-075 | H | H | 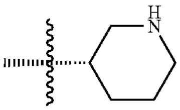 | 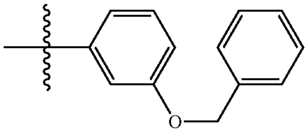 | 0 |
| B-076 | H | H | 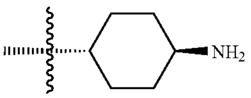 | 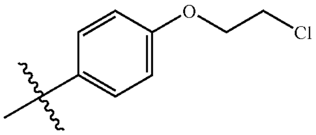 | 0 |

TABLE B-continued
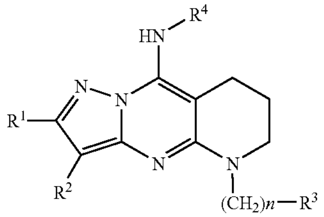
| Compound No. | $R^1$ | $R^2$ | $R^3$ | $R^4$ | n |
|---|---|---|---|---|---|
| B-077 | H | H | 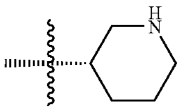 | 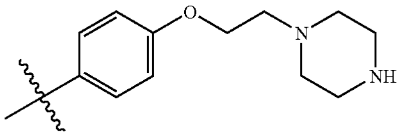 | 0 |
| B-078 | H | H | 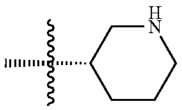 | 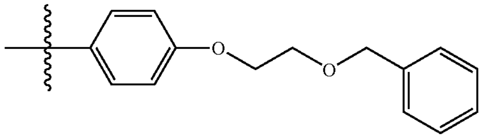 | 0 |
| B-079 | H | H | 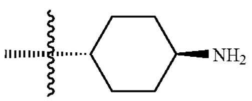 | 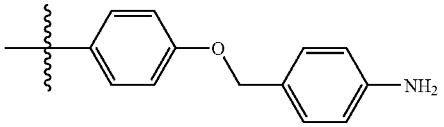 | 0 |
| B-080 | H | H | 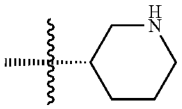 | 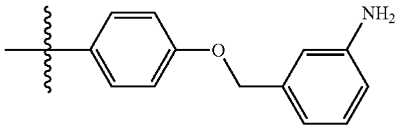 | 0 |
| B-081 | H | H | 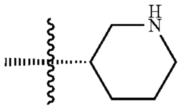 | 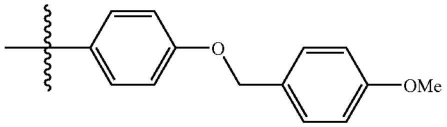 | 0 |
| B-082 | H | H | 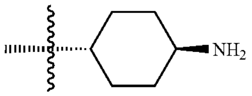 | 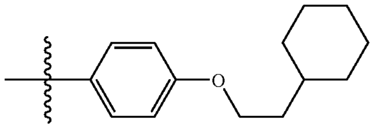 | 0 |
| B-083 | H | H | 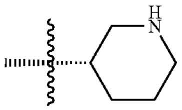 | 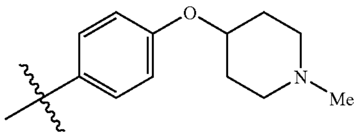 | 0 |
| B-084 | H | H | 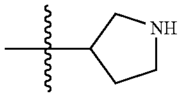 | 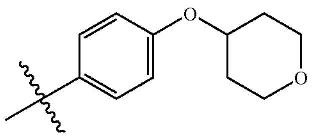 | 0 |
| B-085 | H | H | 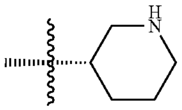 | 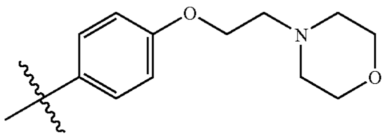 | 0 |

TABLE B-continued
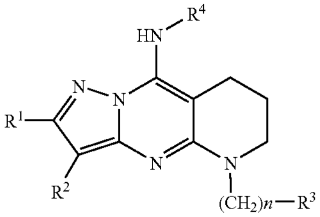
| Compound No. | $R^1$ | $R^2$ | $R^3$ | $R^4$ | n |
|---|---|---|---|---|---|
| B-086 | H | H | 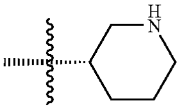 | 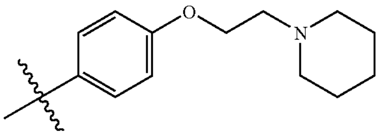 | 0 |
| B-087 | H | H | 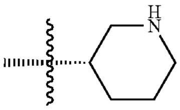 | 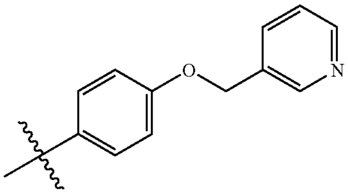 | 0 |
| B-088 | H | H | 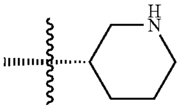 | 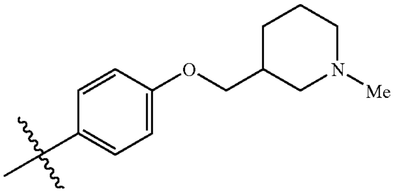 | 0 |
| B-089 | H | H | 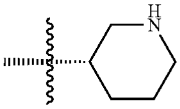 | 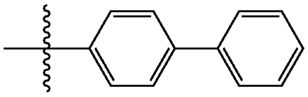 | 0 |
| B-090 | H | H | 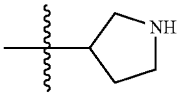 | 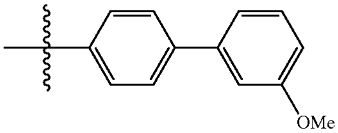 | 0 |
| B-091 | H | H | 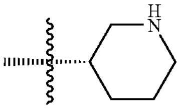 | 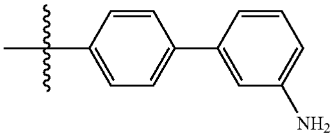 | 0 |
| B-092 | H | H | 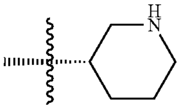 | 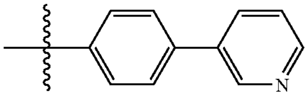 | 0 |
| B-093 | H | H | 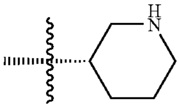 | 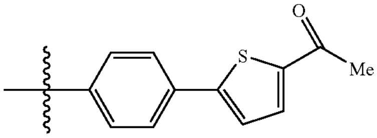 | 0 |

TABLE B-continued
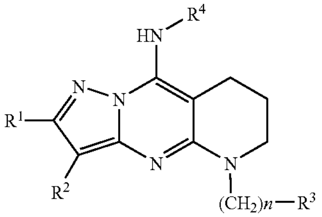
| Compound No. | $R^1$ | $R^2$ | $R^3$ | $R^4$ | n |
|---|---|---|---|---|---|
| B-094 | H | H | 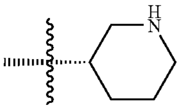 | 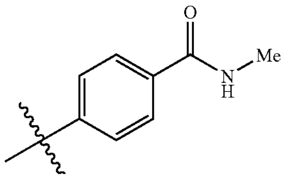 | 0 |
| B-095 | H | H | 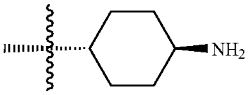 | 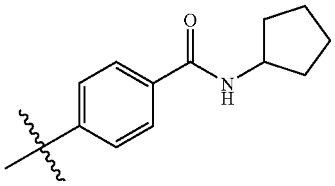 | 0 |
| B-096 | H | H | 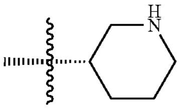 | 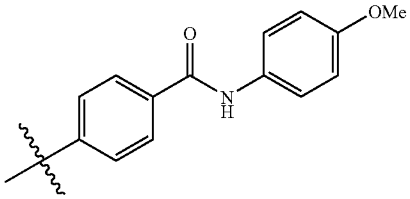 | 0 |
| B-97 | H | H | 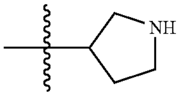 | 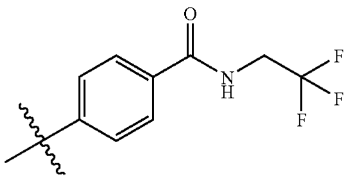 | 0 |
| B-98 | H | H | 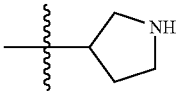 | H | 0 |
| B-99 | H | H | 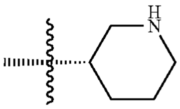 | H | 0 |
| B-100 | H | H | 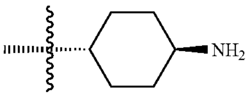 | H | 0 |

TABLE C
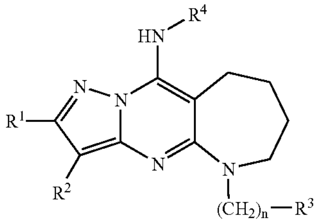
| Compound No. | $R^1$ | $R^2$ | $R^3$ | $R^4$ | n |
|---|---|---|---|---|---|
| C-001 | H | H | 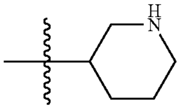 | 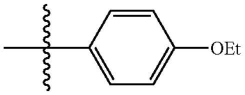 | 0 |
| C-002 | H | H | 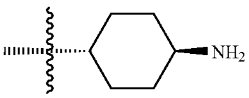 | 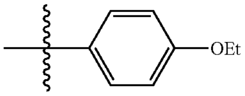 | 0 |
| C-003 | H | H | 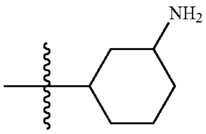 | 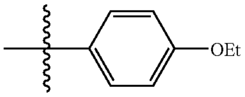 | 0 |
| C-004 | H | H | 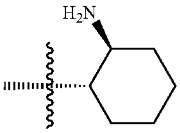 | 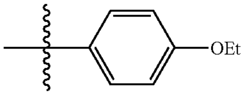 | 0 |
| C-005 | H | H | 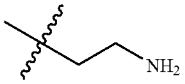 | 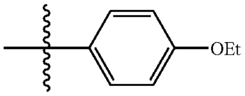 | 0 |
| C-006 | H | H | 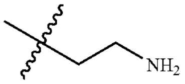 | 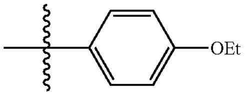 | 1 |
| C-007 | H | H | 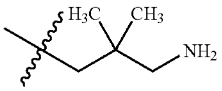 | 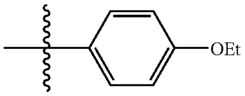 | 0 |
| C-008 | H | H | 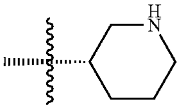 | 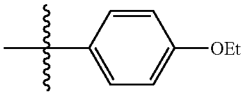 | 0 |
| C-009 | H | H | 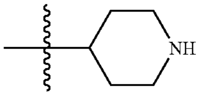 | 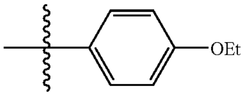 | 0 |
| C-010 | H | H | 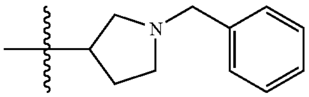 | 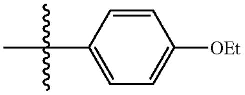 | 0 |

TABLE C-continued
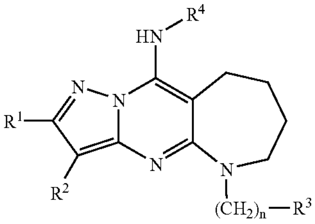
| Compound No. | $R^1$ | $R^2$ | $R^3$ | $R^4$ | n |
| --- | --- | --- | --- | --- | --- |
| C-011 | H | H | 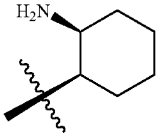 | 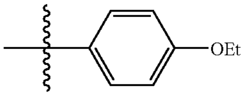 | 0 |
| C-012 | H | H | 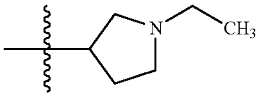 | 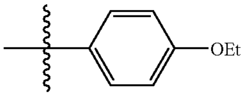 | 0 |
| C-013 | H | H | 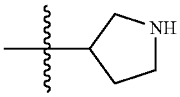 | 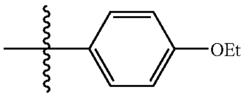 | 0 |
| C-014 | H | H | 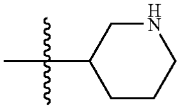 | 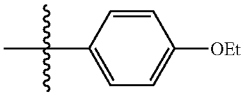 | 1 |
| C-015 | H | H | 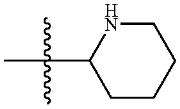 | 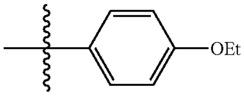 | 1 |
| C-016 | H | H | 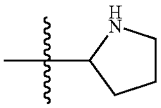 | 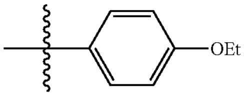 | 1 |
| C-017 | H | H | 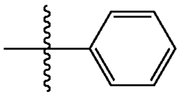 | 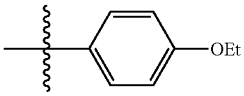 | 1 |
| C-018 | H | F | 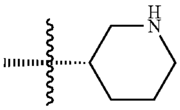 | 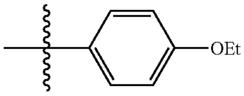 | 0 |
| C-019 | F | F | 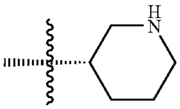 | 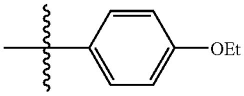 | 0 |
| C-020 | H | H | 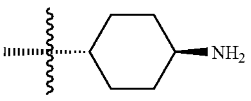 | 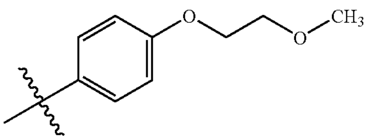 | 0 |

TABLE C-continued
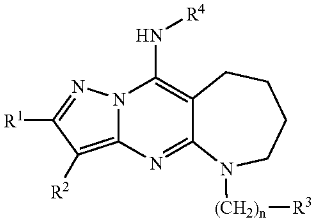
| Compound No. | $R^1$ | $R^2$ | $R^3$ | $R^4$ | n |
|---|---|---|---|---|---|
| C-021 | H | H | 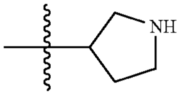 | 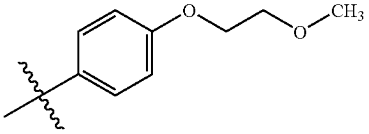 | 0 |
| C-022 | H | H | 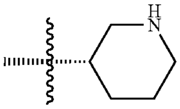 | 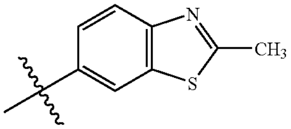 | 0 |
| C-023 | H | H | 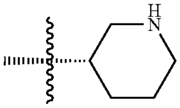 | 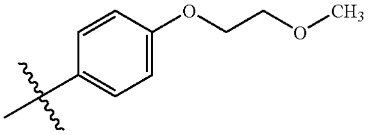 | 0 |
| C-024 | H | H | 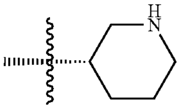 | 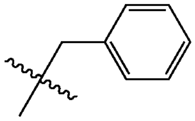 | 0 |
| C-025 | H | H | 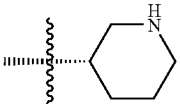 | 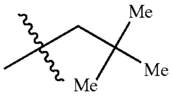 | 0 |
| C-026 | H | H | 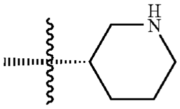 | 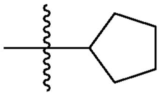 | 0 |
| C-027 | H | H | 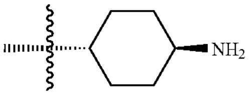 | 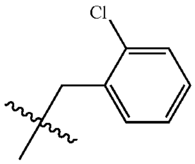 | 0 |
| C-028 | H | H | 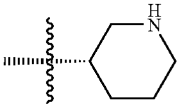 | 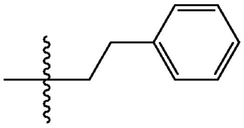 | 0 |
| C-029 | H | H | 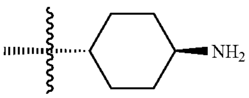 | 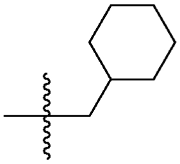 | 0 |

TABLE C-continued
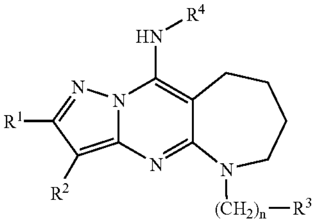
| Compound No. | $R^1$ | $R^2$ | $R^3$ | $R^4$ | n |
|---|---|---|---|---|---|
| C-030 | H | H | 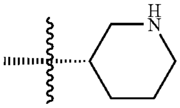 | 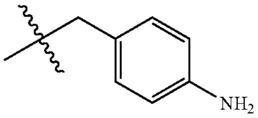 | 0 |
| C-031 | H | H | 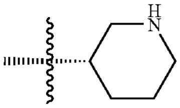 | 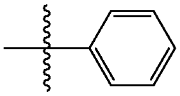 | 0 |
| C-032 | H | H | 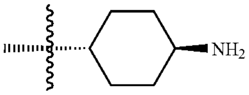 | 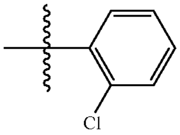 | 0 |
| C-033 | H | H | 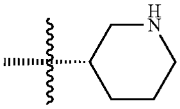 | 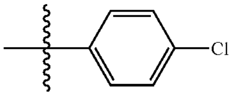 | 0 |
| C-034 | H | H | 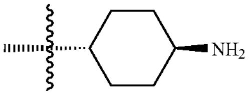 | 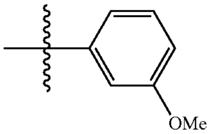 | 0 |
| C-035 | H | H | 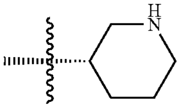 | 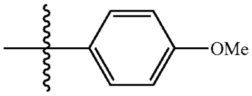 | 0 |
| C-036 | H | H | 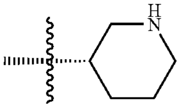 | 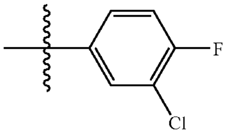 | 0 |
| C-037 | H | H | 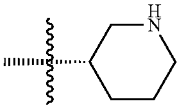 | 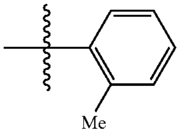 | 0 |
| C-038 | H | H | 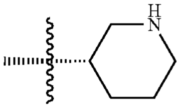 | 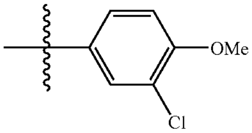 | 0 |

TABLE C-continued
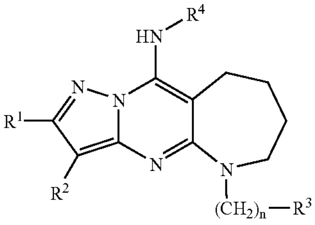
| Compound No. | $R^1$ | $R^2$ | $R^3$ | $R^4$ | n |
|---|---|---|---|---|---|
| C-039 | H | H | 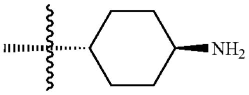 | 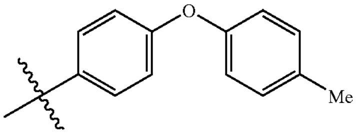 | 0 |
| C-040 | H | H | 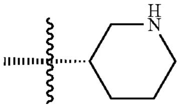 | 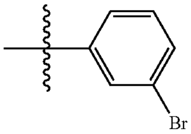 | 0 |
| C-041 | H | H | 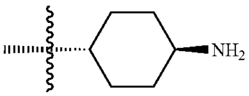 | 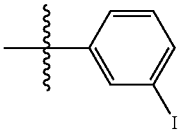 | 0 |
| C-042 | H | H | 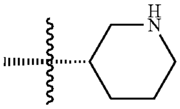 | 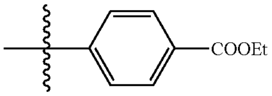 | 0 |
| C-043 | H | H | 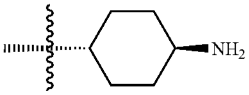 | 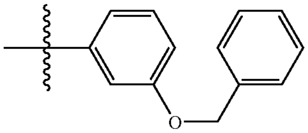 | 0 |
| C-044 | H | H | 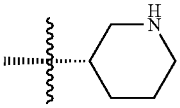 | 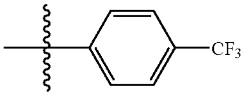 | 0 |
| C-045 | H | H | 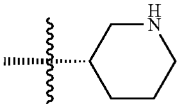 | 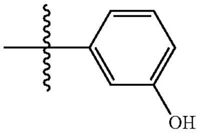 | 0 |
| C-046 | H | H | 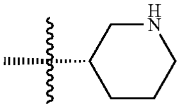 | 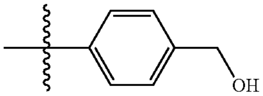 | 0 |
| C-047 | H | H | 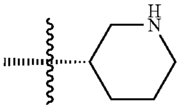 | 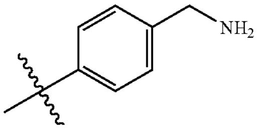 | 0 |

TABLE C-continued
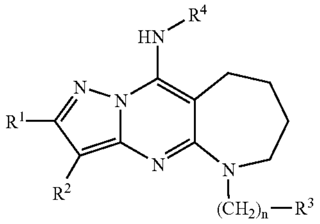
| Compound No. | $R^1$ | $R^2$ | $R^3$ | $R^4$ | n |
|---|---|---|---|---|---|
| C-048 | H | H | 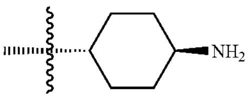 | 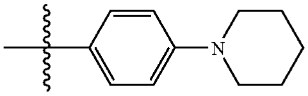 | 0 |
| C-049 | H | H | 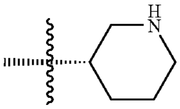 | 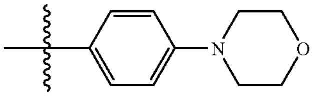 | 0 |
| C-050 | H | H | 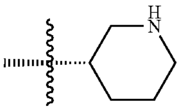 | 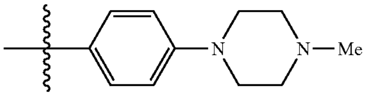 | 0 |
| C-051 | H | H | 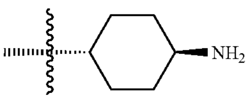 | 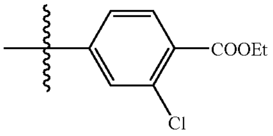 | 0 |
| C-052 | H | H | 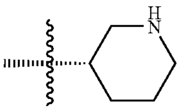 | 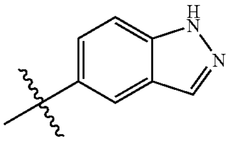 | 0 |
| C-053 | H | H | 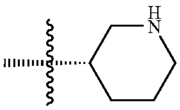 | 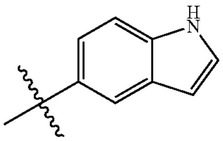 | 0 |
| C-054 | H | H | 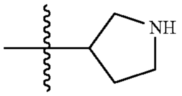 | 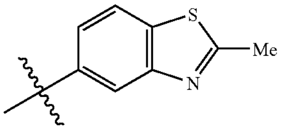 | 0 |
| C-055 | H | H | 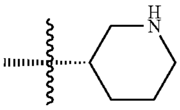 | 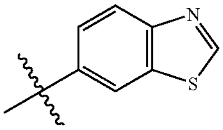 | 0 |
| C-056 | H | H | 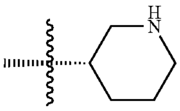 | 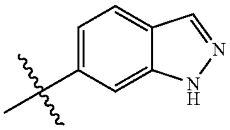 | 0 |

TABLE C-continued
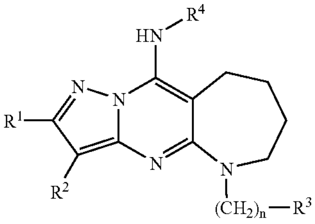
| Compound No. | $R^1$ | $R^2$ | $R^3$ | $R^4$ | n |
|---|---|---|---|---|---|
| C-057 | H | H | 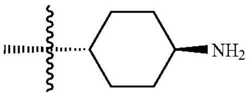 | 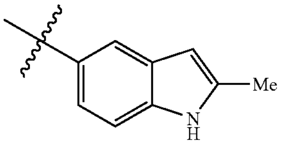 | 0 |
| C-058 | H | H | 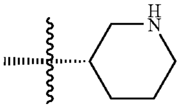 | 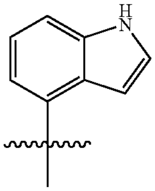 | 0 |
| C-059 | H | H | 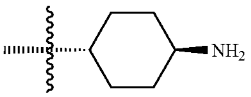 | 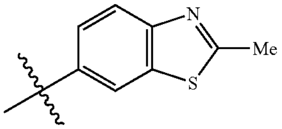 | 0 |
| C-060 | H | H | 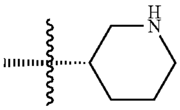 | 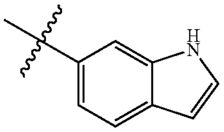 | 0 |
| C-061 | H | H | 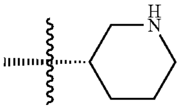 | 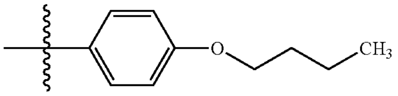 | 0 |
| C-062 | H | H | 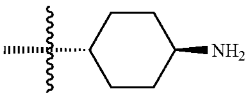 | 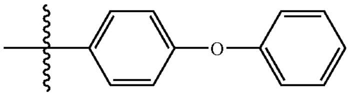 | 0 |
| C-063 | H | H | 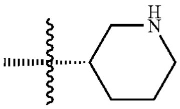 | 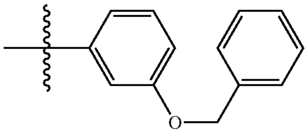 | 0 |
| C-064 | H | H | 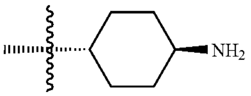 | 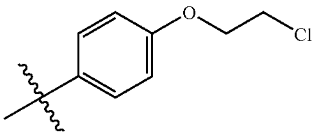 | 0 |
| C-065 | H | H | 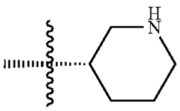 | 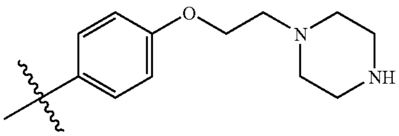 | 0 |

TABLE C-continued
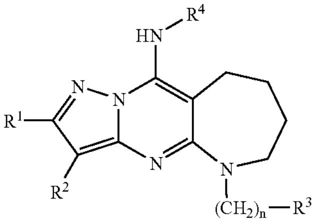
| Compound No. | $R^1$ | $R^2$ | $R^3$ | $R^4$ | n |
| --- | --- | --- | --- | --- | --- |
| C-066 | H | H | 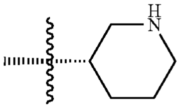 | 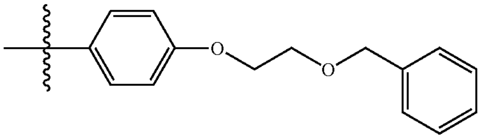 | 0 |
| C-067 | H | H | 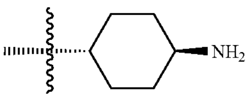 | 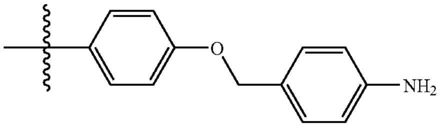 | 0 |
| C-068 | H | H | 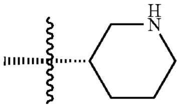 | 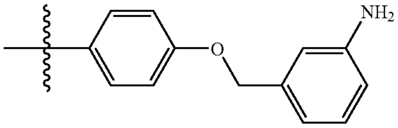 | 0 |
| C-069 | H | H | 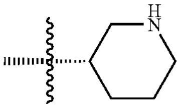 | 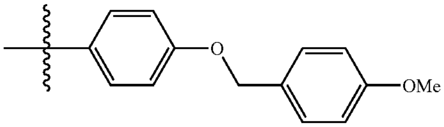 | 0 |
| C-070 | H | H | 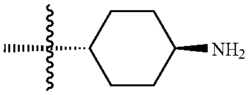 | 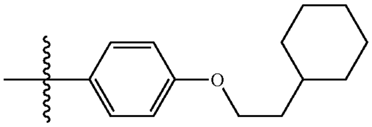 | 0 |
| C-071 | H | H | 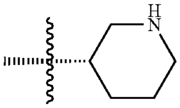 | 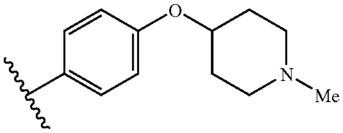 | 0 |
| C-072 | H | H | 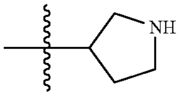 | 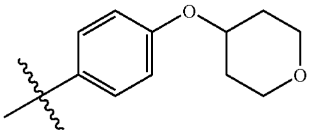 | 0 |
| C-073 | H | H | 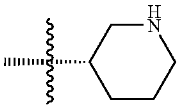 | 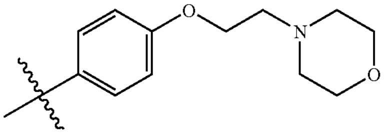 | 0 |
| C-074 | H | H | 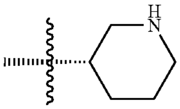 | 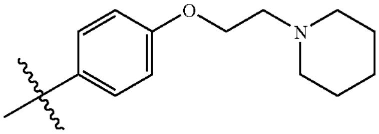 | 0 |

TABLE C-continued
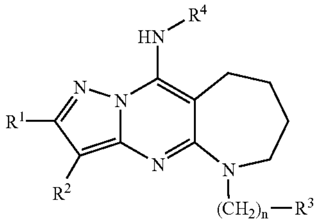
| Compound No. | $R^1$ | $R^2$ | $R^3$ | $R^4$ | n |
|---|---|---|---|---|---|
| C-075 | H | H | 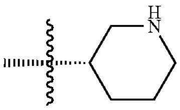 | 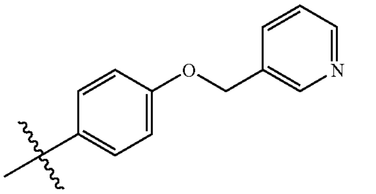 | 0 |
| C-076 | H | H | 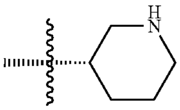 | 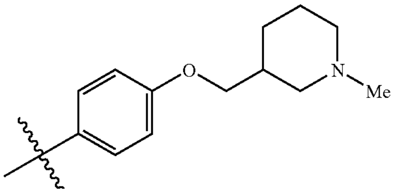 | 0 |
| C-077 | H | H | 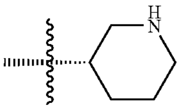 | 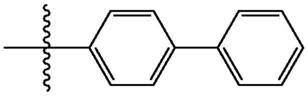 | 0 |
| C-078 | H | H | 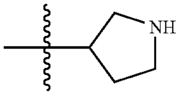 | 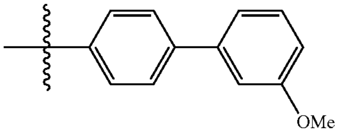 | 0 |
| C-079 | H | H | 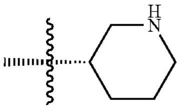 | 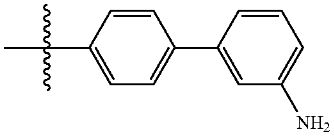 | 0 |
| C-080 | H | H | 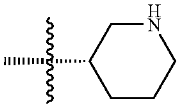 | 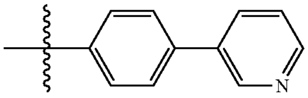 | 0 |
| C-081 | H | H | 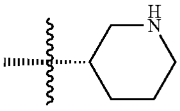 | 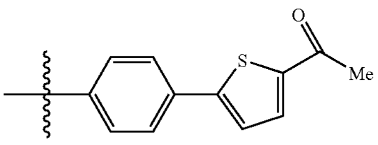 | 0 |
| C-082 | H | H | 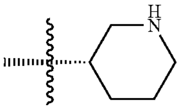 | 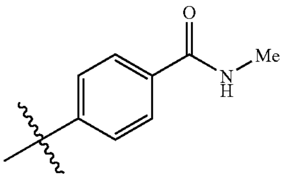 | 0 |

TABLE C-continued
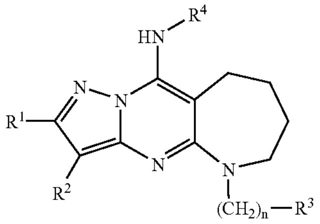
| Compound No. | $R^1$ | $R^2$ | $R^3$ | $R^4$ | n |
|---|---|---|---|---|---|
| C-083 | H | H | 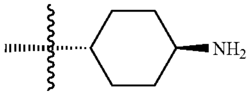 | 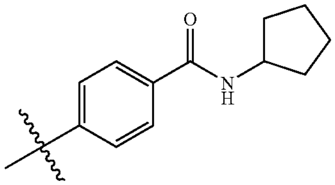 | 0 |
| C-084 | H | H | 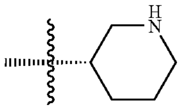 | 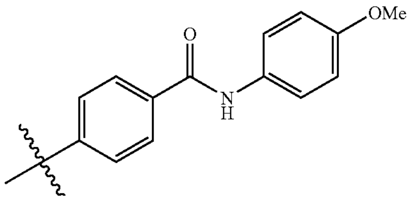 | 0 |
| C-085 | H | H | 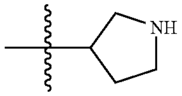 | 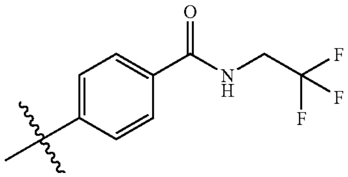 | 0 |
| C-086 | H | H | OH | 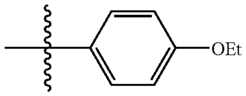 | 0 |
TABLE D
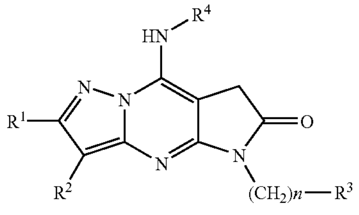
| Compound No. | $R^1$ | $R^2$ | $R^3$ | $R^4$ | n |
|---|---|---|---|---|---|
| D-001 | H | H | 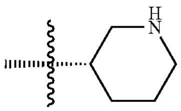 | 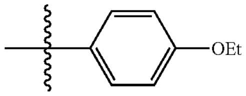 | 0 |
| D-002 | H | H | 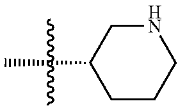 | 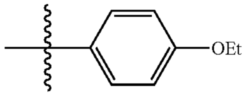 | 1 |

TABLE D-continued
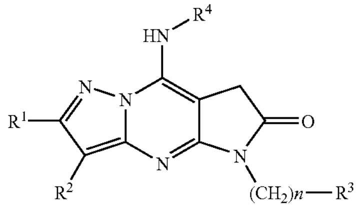
| Compound No. | $R^1$ | $R^2$ | $R^3$ | $R^4$ | n |
|---|---|---|---|---|---|
| D-003 | H | H | 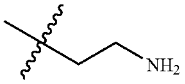 | 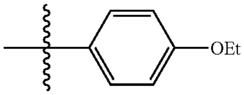 | 0 |
| D-004 | H | H | 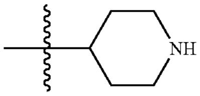 | 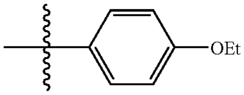 | 0 |
| D-005 | H | H | 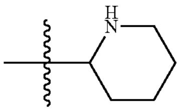 | 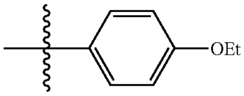 | 1 |
| D-006 | H | H | 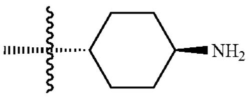 | 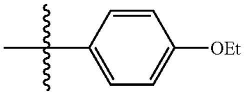 | 0 |
| D-007 | H | H | 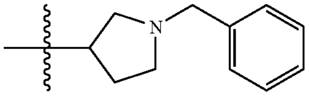 | 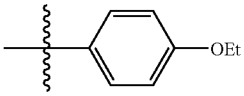 | 0 |
| D-008 | H | H | 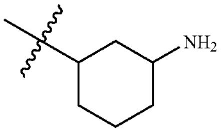 | 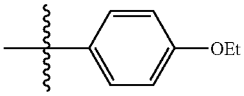 | 0 |
| D-009 | H | H | 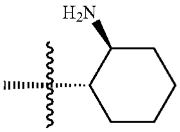 | 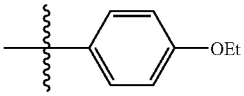 | 0 |
| D-010 | H | H | 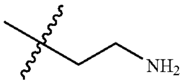 | 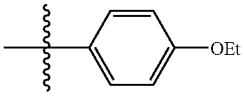 | 1 |
| D-011 | H | H | 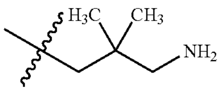 | 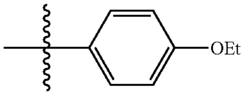 | 0 |
| D-012 | H | H | 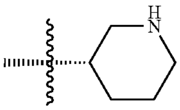 | 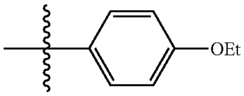 | 0 |

TABLE D-continued
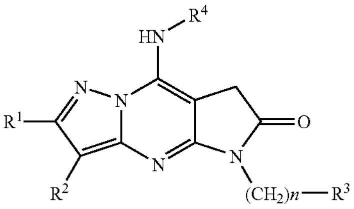
| Compound No. | $R^1$ | $R^2$ | $R^3$ | $R^4$ | n |
|---|---|---|---|---|---|
| D-013 | H | H | 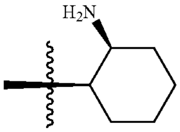 | 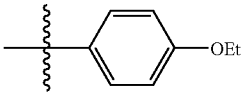 | 0 |
| D-014 | H | H | 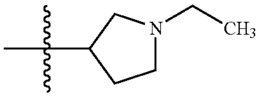 | 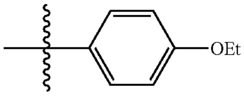 | 0 |
| D-015 | H | H | 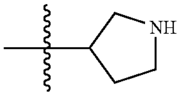 | 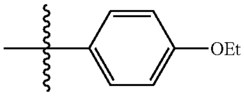 | 0 |
| D-016 | H | H | 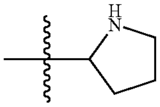 | 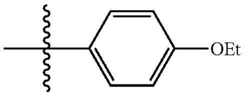 | 1 |
| D-017 | H | H | 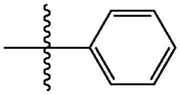 | 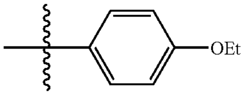 | 1 |
| D-018 | H | F | 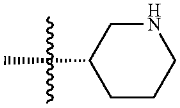 | 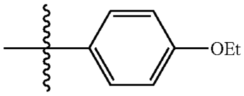 | 0 |
| D-019 | F | F | 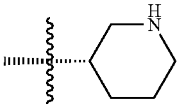 | 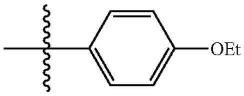 | 0 |
| D-020 | H | H | 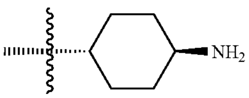 | 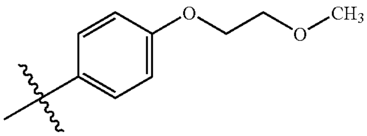 | 0 |
| D-021 | H | H | 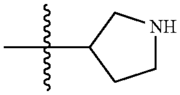 | 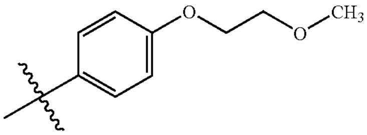 | 0 |
| D-022 | H | H | 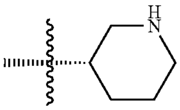 | 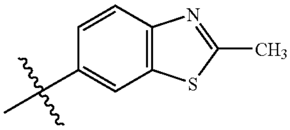 | 0 |

TABLE D-continued
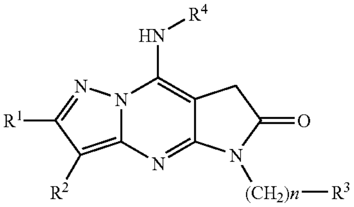
| Compound No. | $R^1$ | $R^2$ | $R^3$ | $R^4$ | n |
|---|---|---|---|---|---|
| D-023 | H | H | 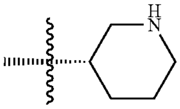 | 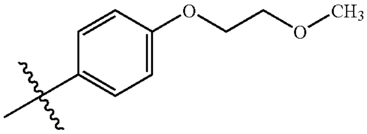 | 0 |
| D-024 | H | H | 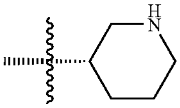 | 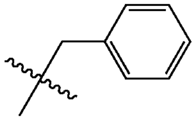 | 0 |
| D-025 | H | H | 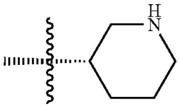 | 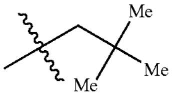 | 0 |
| D-026 | H | H | 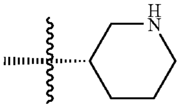 | 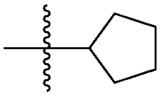 | 0 |
| D-027 | H | H | 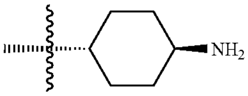 | 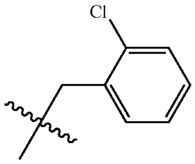 | 0 |
| D-028 | H | H | 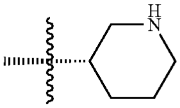 | 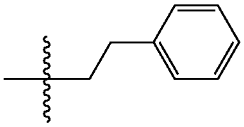 | 0 |
| D-029 | H | H | 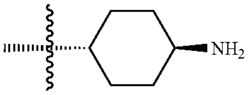 | 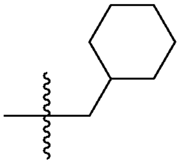 | 0 |
| D-030 | H | H | 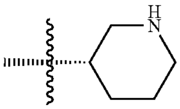 | 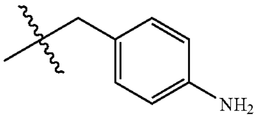 | 0 |
| D-031 | H | H | 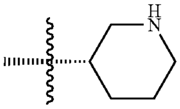 | 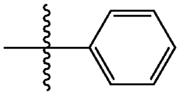 | 0 |

TABLE D-continued
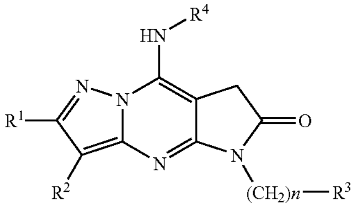
| Compound No. | $R^1$ | $R^2$ | $R^3$ | $R^4$ | n |
|---|---|---|---|---|---|
| D-032 | H | H | 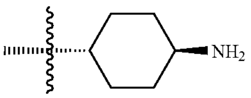 | 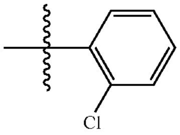 | 0 |
| D-033 | H | H | 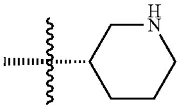 | 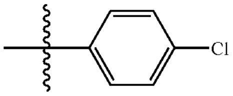 | 0 |
| D-034 | H | H | 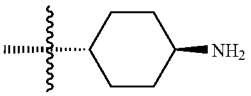 | 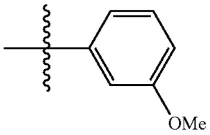 | 0 |
| D-035 | H | H | 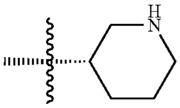 | 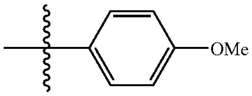 | 0 |
| D-036 | H | H | 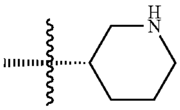 | 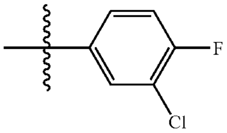 | 0 |
| D-037 | H | H | 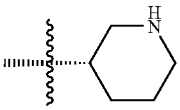 | 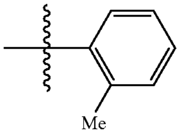 | 0 |
| D-038 | H | H | 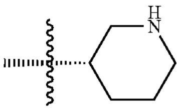 | 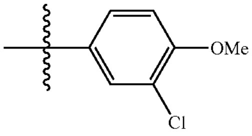 | 0 |
| D-039 | H | H | 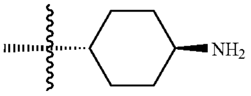 | 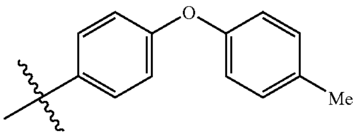 | 0 |
| D-040 | H | H | 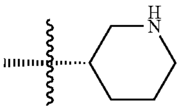 | 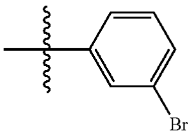 | 0 |

TABLE D-continued
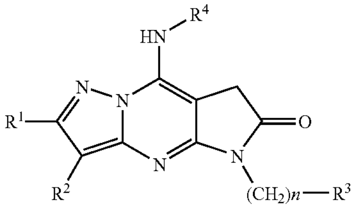
| Compound No. | $R^1$ | $R^2$ | $R^3$ | $R^4$ | n |
|---|---|---|---|---|---|
| D-041 | H | H | 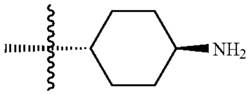 | 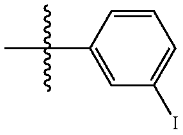 | 0 |
| D-042 | H | H | 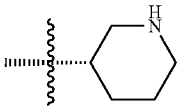 | 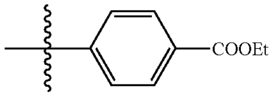 | 0 |
| D-043 | H | H | 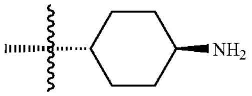 | 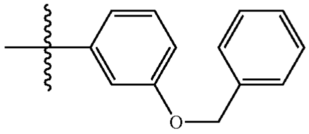 | 0 |
| D-044 | H | H | 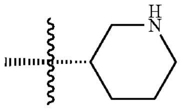 | 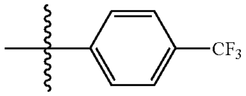 | 0 |
| D-045 | H | H | 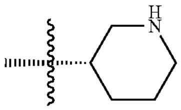 | 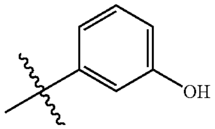 | 0 |
| D-046 | H | H | 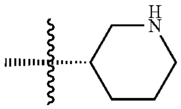 | 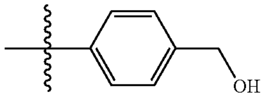 | 0 |
| D-047 | H | H | 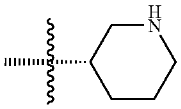 | 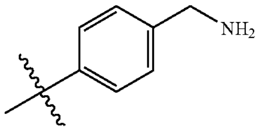 | 0 |
| D-048 | H | H | 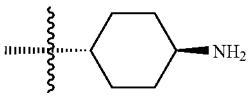 | 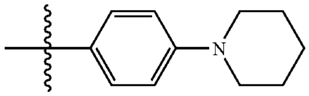 | 0 |
| D-049 | H | H | 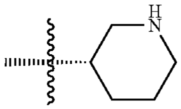 | 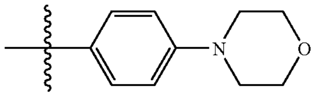 | 0 |
| D-050 | H | H | 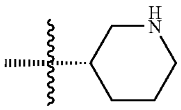 | 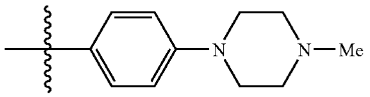 | 0 |

TABLE D-continued
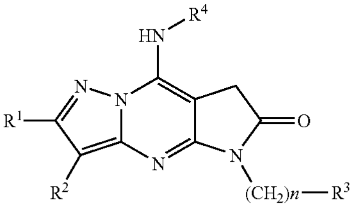
| Compound No. | $R^1$ | $R^2$ | $R^3$ | $R^4$ | n |
|---|---|---|---|---|---|
| D-051 | H | H | 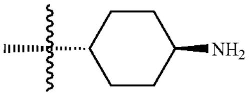 | 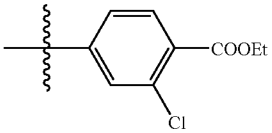 | 0 |
| D-052 | H | H | 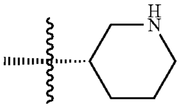 | 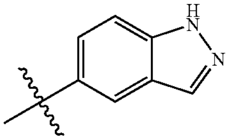 | 0 |
| D-053 | H | H | 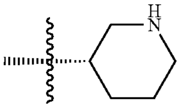 | 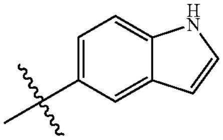 | 0 |
| D-054 | H | H | 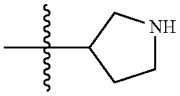 | 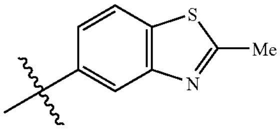 | 0 |
| D-055 | H | H | 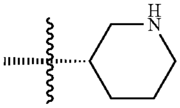 | 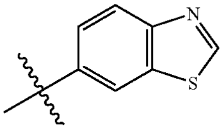 | 0 |
| D-056 | H | H | 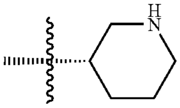 | 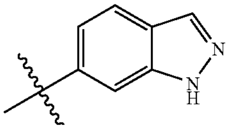 | 0 |
| D-057 | H | H | 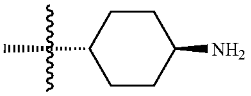 | 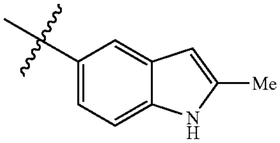 | 0 |
| D-058 | H | H | 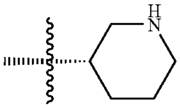 | 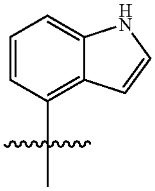 | 0 |

TABLE D-continued
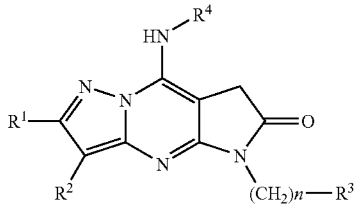
| Compound No. | $R^1$ | $R^2$ | $R^3$ | $R^4$ | n |
|---|---|---|---|---|---|
| D-059 | H | H | 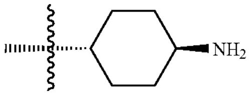 | 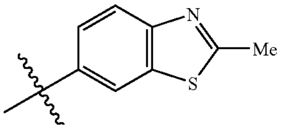 | 0 |
| D-060 | H | H | 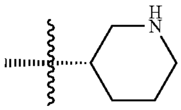 | 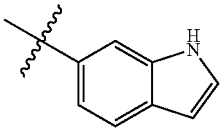 | 0 |
| D-061 | H | H | 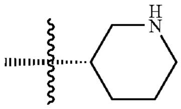 | 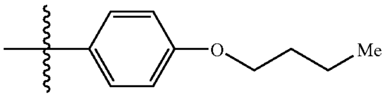 | 0 |
| D-062 | H | H | 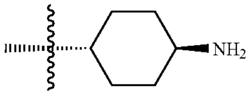 | 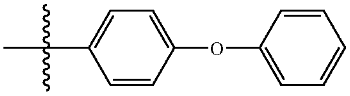 | 0 |
| D-063 | H | H | 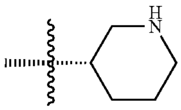 | 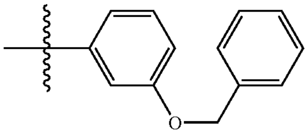 | 0 |
| D-064 | H | H | 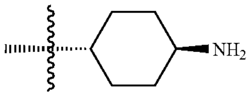 | 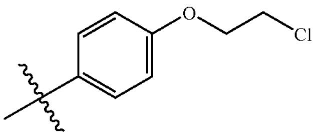 | 0 |
| D-065 | H | H | 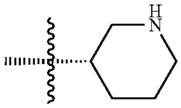 | 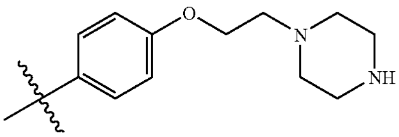 | 0 |
| D-066 | H | H | 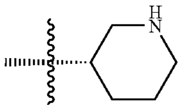 | 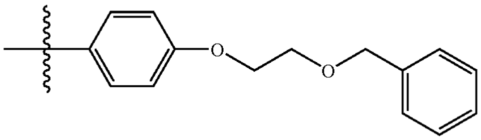 | 0 |
| D-067 | H | H | 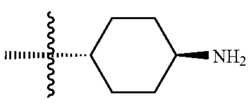 | 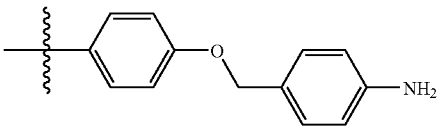 | 0 |

TABLE D-continued
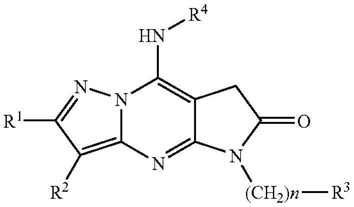
| Compound No. | $R^1$ | $R^2$ | $R^3$ | $R^4$ | n |
|---|---|---|---|---|---|
| D-068 | H | H | 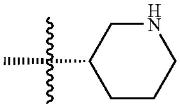 | 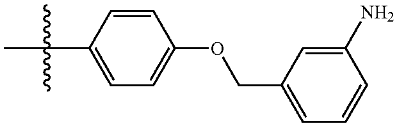 | 0 |
| D-069 | H | H | 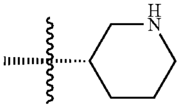 | 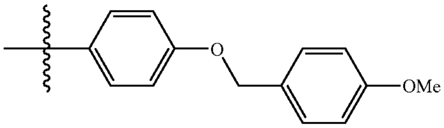 | 0 |
| D-070 | H | H | 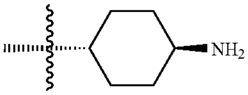 | 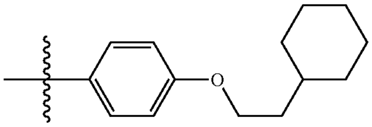 | 0 |
| D-071 | H | H | 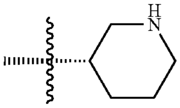 | 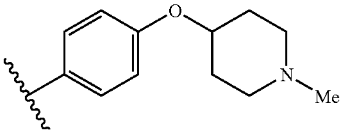 | 0 |
| D-072 | H | H | 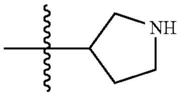 | 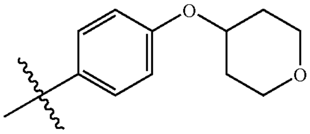 | 0 |
| D-073 | H | H | 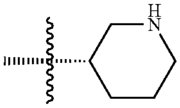 | 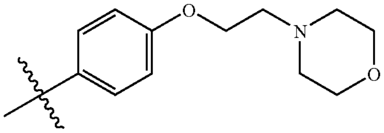 | 0 |
| D-074 | H | H | 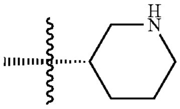 | 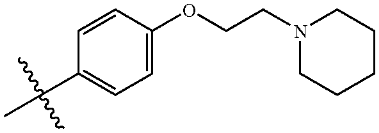 | 0 |
| D-075 | H | H | 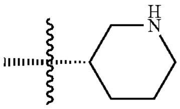 | 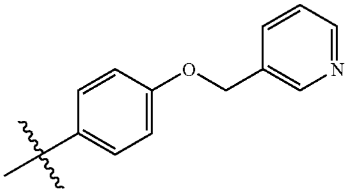 | 0 |

TABLE D-continued
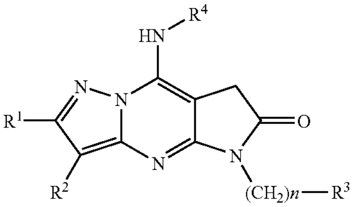
| Compound No. | $R^1$ | $R^2$ | $R^3$ | $R^4$ | n |
| --- | --- | --- | --- | --- | --- |
| D-076 | H | H | 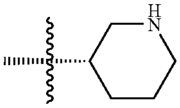 | 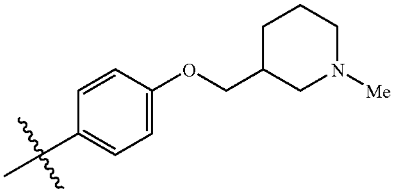 | 0 |
| D-077 | H | H | 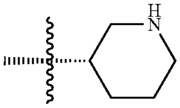 | 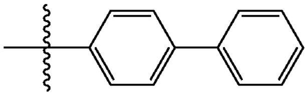 | 0 |
| D-078 | H | H | 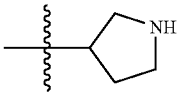 | 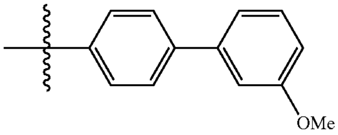 | 0 |
| D-079 | H | H | 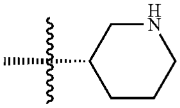 | 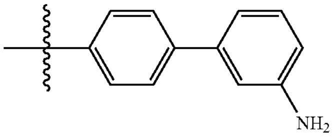 | 0 |
| D-080 | H | H | 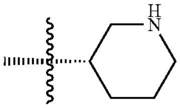 | 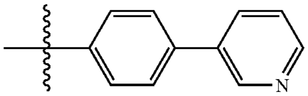 | 0 |
| D-081 | H | H | 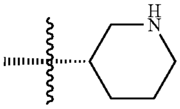 | 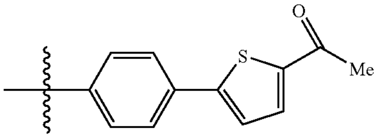 | 0 |
| D-082 | H | H | 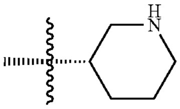 | 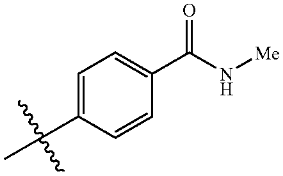 | 0 |
| D-083 | H | H | 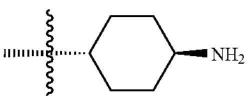 | 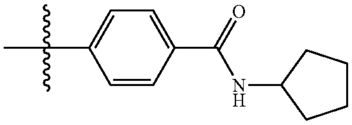 | 0 |

TABLE D-continued
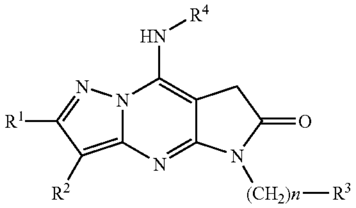
| Compound No. | $R^1$ | $R^2$ | $R^3$ | $R^4$ | n |
|---|---|---|---|---|---|
| D-084 | H | H | 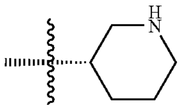 | 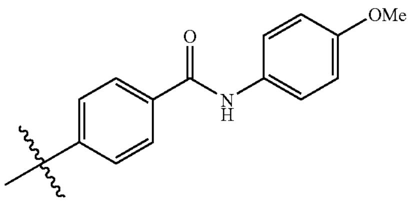 | 0 |
| D-085 | H | H | 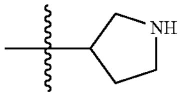 | 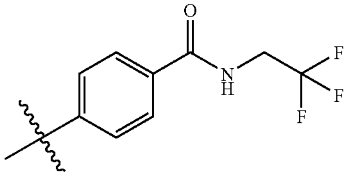 | 0 |
TABLE E
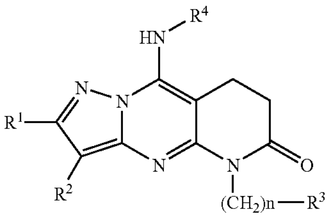
| Compound No. | $R^1$ | $R^2$ | $R^3$ | $R^4$ | n |
|---|---|---|---|---|---|
| E-001 | H | H | 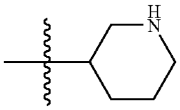 | 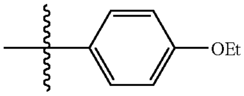 | 0 |
| E-002 | H | H | 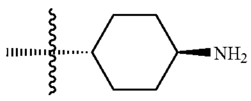 | 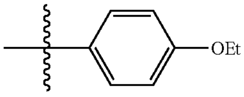 | 0 |
| E-003 | H | H | 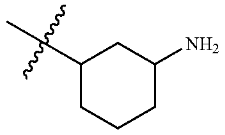 | 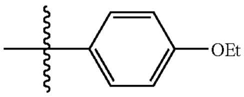 | 0 |
| E-004 | H | H | 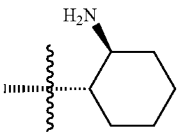 | 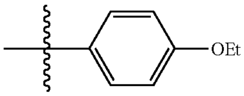 | 0 |

TABLE E-continued
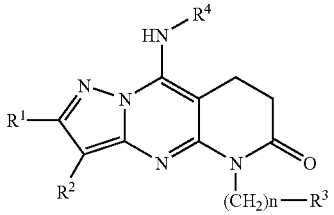
| Compound No. | $R^1$ | $R^2$ | $R^3$ | $R^4$ | n |
|---|---|---|---|---|---|
| E-005 | H | H | 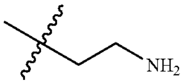 | 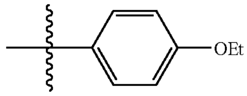 | 0 |
| E-006 | H | H | 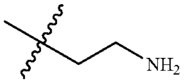 | 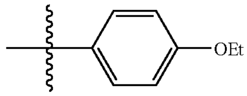 | 1 |
| E-007 | H | H | 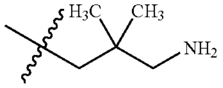 | 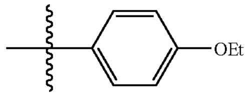 | 0 |
| E-008 | H | H | 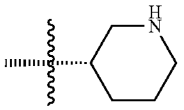 | 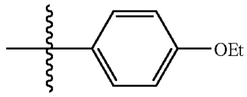 | 0 |
| E-009 | H | H | 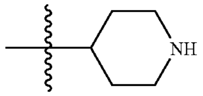 | 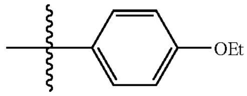 | 0 |
| E-010 | H | H | 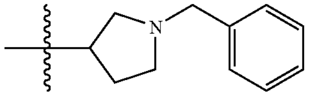 | 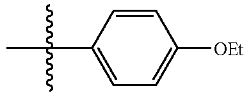 | 0 |
| E-011 | H | H | 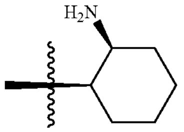 | 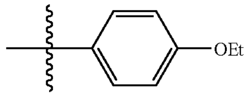 | 0 |
| E-012 | H | H | 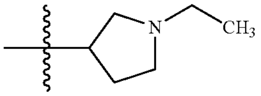 | 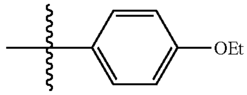 | 0 |
| E-013 | H | H | 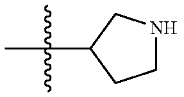 | 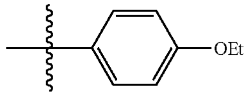 | 0 |
| E-014 | H | H | 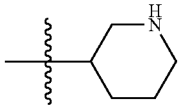 | 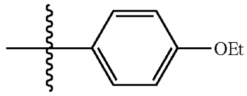 | 1 |
| E-015 | H | H | 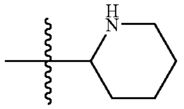 | 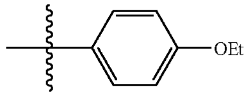 | 1 |

TABLE E-continued
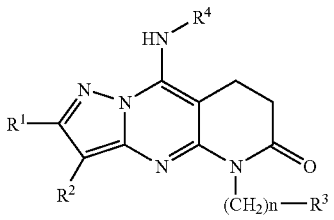
| Compound No. | $R^1$ | $R^2$ | $R^3$ | $R^4$ | n |
|---|---|---|---|---|---|
| E-016 | H | H | 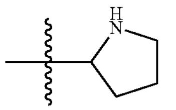 | 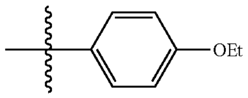 | 1 |
| E-017 | H | H | 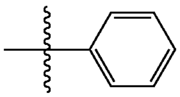 | 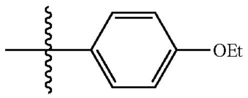 | 1 |
| E-018 | H | F | 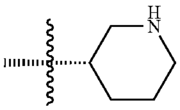 | 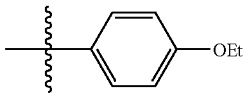 | 0 |
| E-019 | F | F | 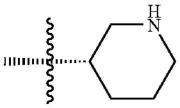 | 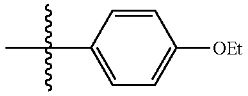 | 0 |
| E-020 | H | H | 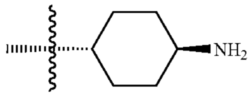 | 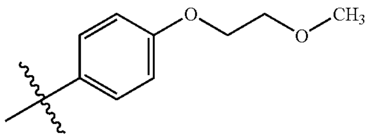 | 0 |
| E-021 | H | H | 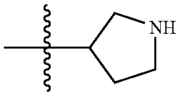 | 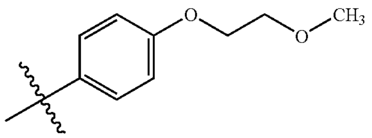 | 0 |
| E-022 | H | H | 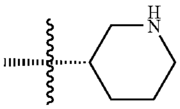 | 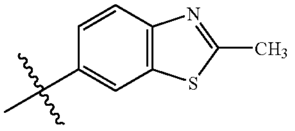 | 0 |
| E-023 | H | H | 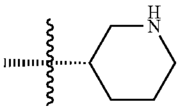 | 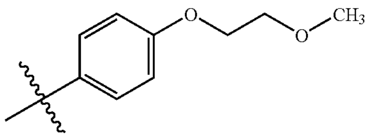 | 0 |
| E-024 | H | H | 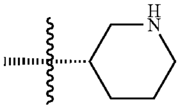 | 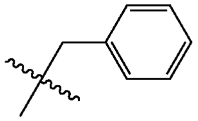 | 0 |

TABLE E-continued
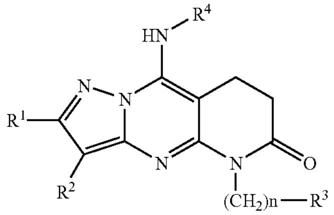
| Compound No. | $R^1$ | $R^2$ | $R^3$ | $R^4$ | n |
|---|---|---|---|---|---|
| E-025 | H | H | 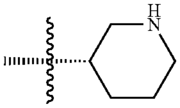 | 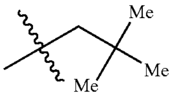 | 0 |
| E-026 | H | H | 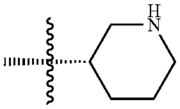 | 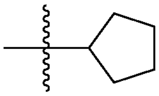 | 0 |
| E-027 | H | H | 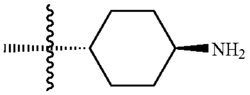 | 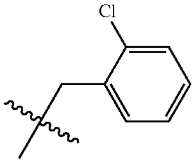 | 0 |
| E-028 | H | H | 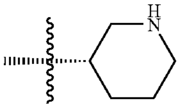 | 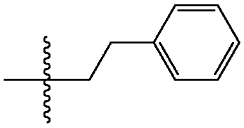 | 0 |
| E-029 | H | H | 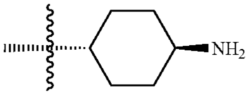 | 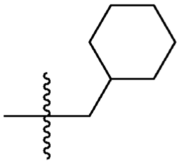 | 0 |
| E-030 | H | H | 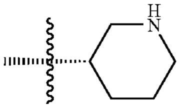 | 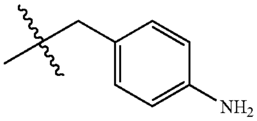 | 0 |
| E-031 | H | H | 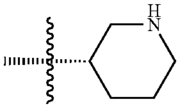 | 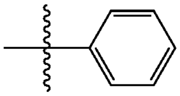 | 0 |
| E-032 | H | H | 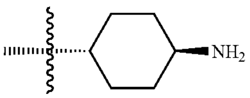 | 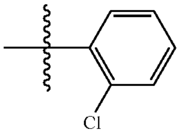 | 0 |
| E-033 | H | H | 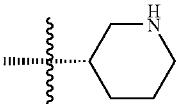 | 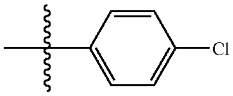 | 0 |

TABLE E-continued
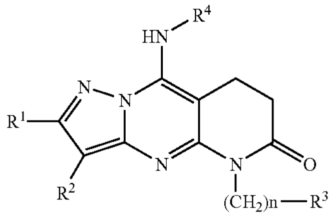
| Compound No. | $R^1$ | $R^2$ | $R^3$ | $R^4$ | n |
|---|---|---|---|---|---|
| E-034 | H | H | 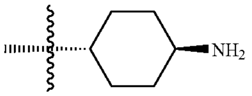 | 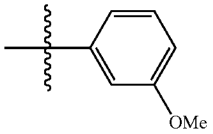 | 0 |
| E-035 | H | H | 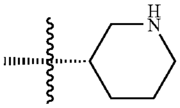 | 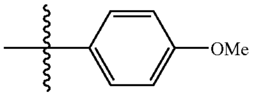 | 0 |
| E-036 | H | H | 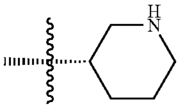 | 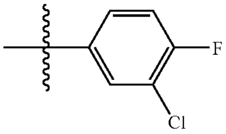 | 0 |
| E-037 | H | H | 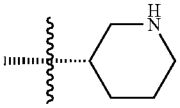 | 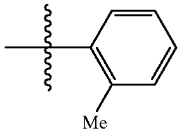 | 0 |
| E-038 | H | H | 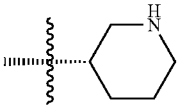 | 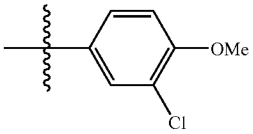 | 0 |
| E-039 | H | H | 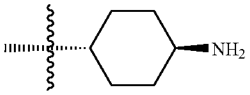 | 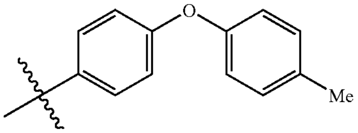 | 0 |
| E-040 | H | H | 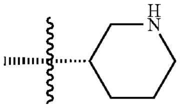 | 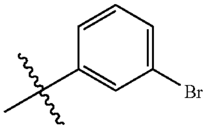 | 0 |
| E-041 | H | H | 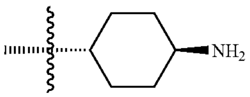 | 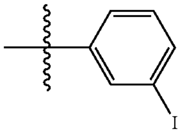 | 0 |
| E-042 | H | H | 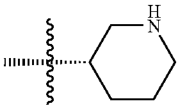 | 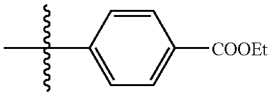 | 0 |

TABLE E-continued
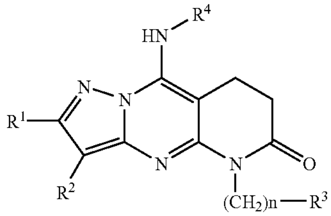
| Compound No. | $R^1$ | $R^2$ | $R^3$ | $R^4$ | n |
|---|---|---|---|---|---|
| E-043 | H | H | 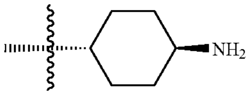 | 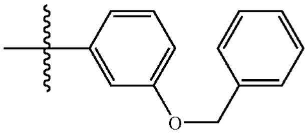 | 0 |
| E-044 | H | H | 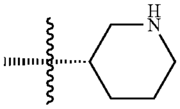 | 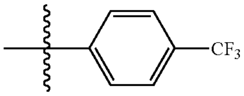 | 0 |
| E-045 | H | H | 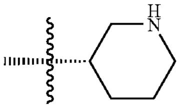 | 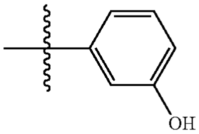 | 0 |
| E-046 | H | H | 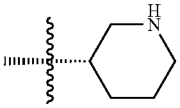 | 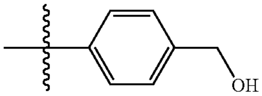 | 0 |
| E-047 | H | H | 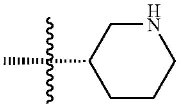 | 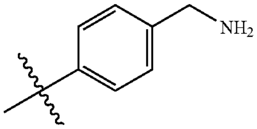 | 0 |
| E-048 | H | H | 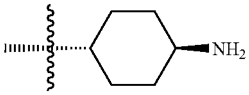 | 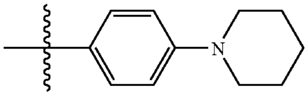 | 0 |
| E-049 | H | H | 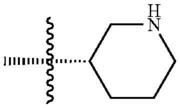 | 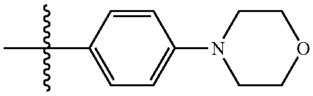 | 0 |
| E-050 | H | H | 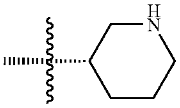 | 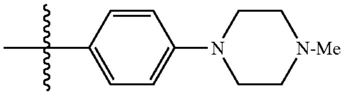 | 0 |
| E-051 | H | H | 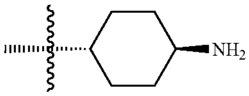 | 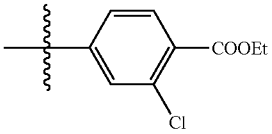 | 0 |

TABLE E-continued
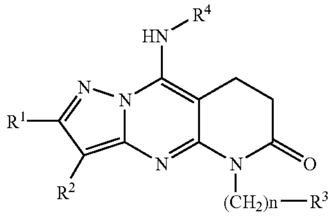
| Compound No. | $R^1$ | $R^2$ | $R^3$ | $R^4$ | n |
|---|---|---|---|---|---|
| E-052 | H | H | 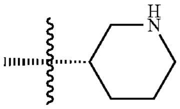 | 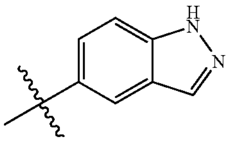 | 0 |
| E-053 | H | H | 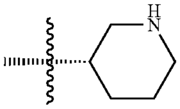 | 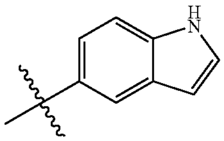 | 0 |
| E-054 | H | H | 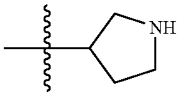 | 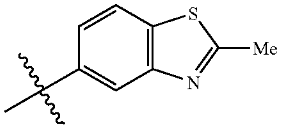 | 0 |
| E-055 | H | H | 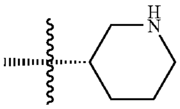 | 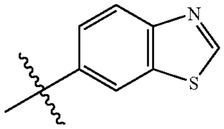 | 0 |
| E-056 | H | H | 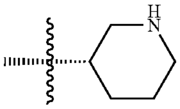 | 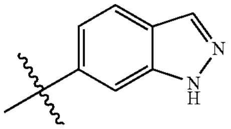 | 0 |
| E-057 | H | H | 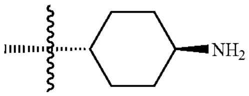 | 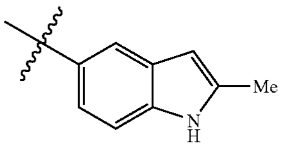 | 0 |
| E-058 | H | H | 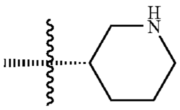 | 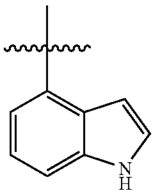 | 0 |
| E-059 | H | H | 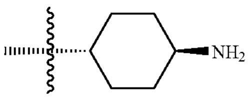 | 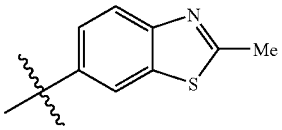 | 0 |

TABLE E-continued
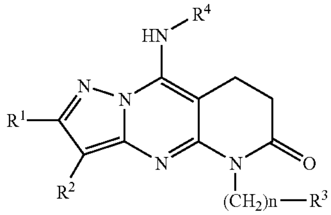
| Compound No. | $R^1$ | $R^2$ | $R^3$ | $R^4$ | n |
|---|---|---|---|---|---|
| E-060 | H | H | 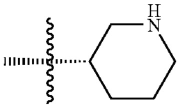 | 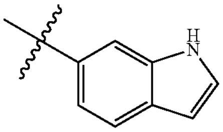 | 0 |
| E-061 | H | H | 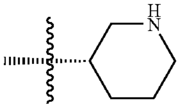 | 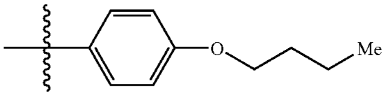 | 0 |
| E-062 | H | H | 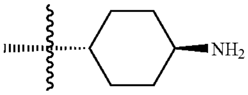 | 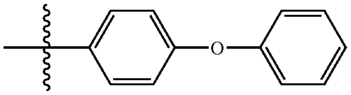 | 0 |
| E-063 | H | H | 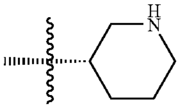 | 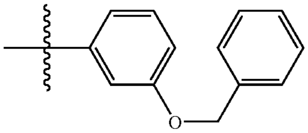 | 0 |
| E-064 | H | H | 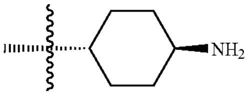 | 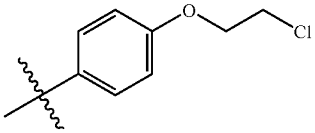 | 0 |
| E-065 | H | H | 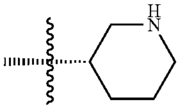 | 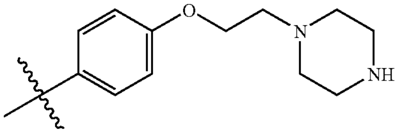 | 0 |
| E-066 | H | H | 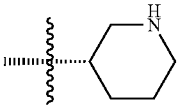 | 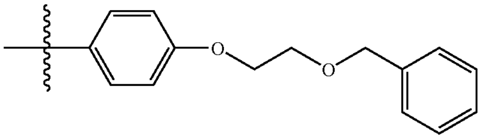 | 0 |
| E-067 | H | H | 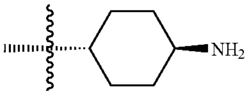 | 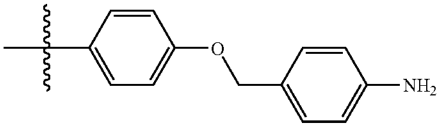 | 0 |
| E-068 | H | H | 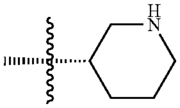 | 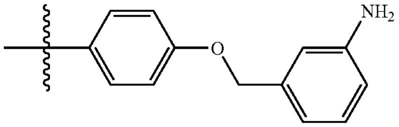 | 0 |

TABLE E-continued
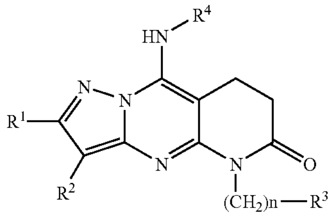
| Compound No. | $R^1$ | $R^2$ | $R^3$ | $R^4$ | n |
|---|---|---|---|---|---|
| E-069 | H | H | 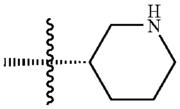 | 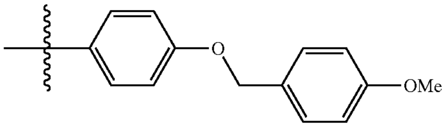 | 0 |
| E-070 | H | H | 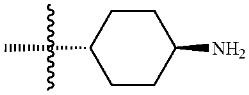 | 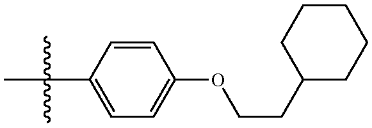 | 0 |
| E-071 | H | H | 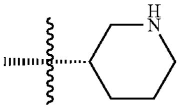 | 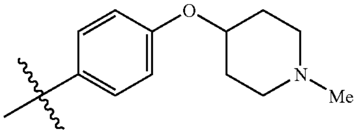 | 0 |
| E-072 | H | H | 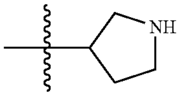 | 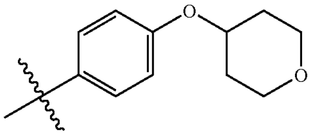 | 0 |
| E-073 | H | H | 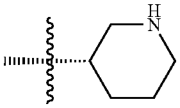 | 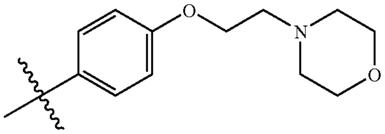 | 0 |
| E-074 | H | H | 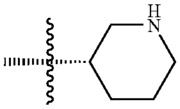 | 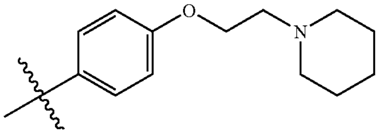 | 0 |
| E-075 | H | H | 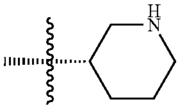 | 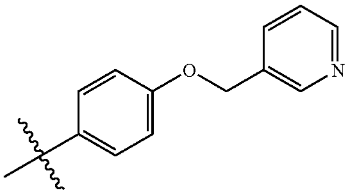 | 0 |
| E-076 | H | H | 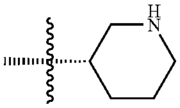 | 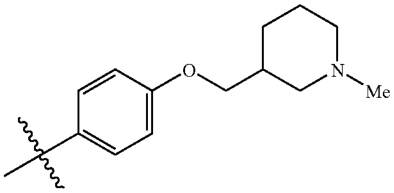 | 0 |

TABLE E-continued
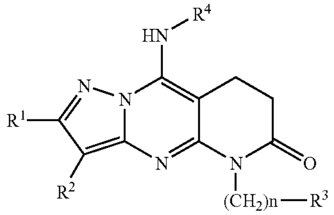
| Compound No. | $R^1$ | $R^2$ | $R^3$ | $R^4$ | n |
|---|---|---|---|---|---|
| E-077 | H | H | 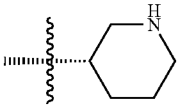 | 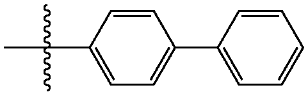 | 0 |
| E-078 | H | H | 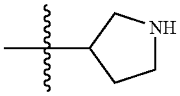 | 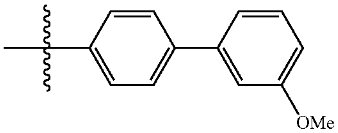 | 0 |
| E-079 | H | H | 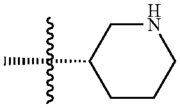 | 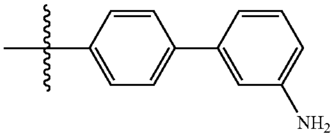 | 0 |
| E-080 | H | H | 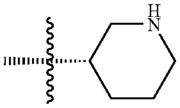 | 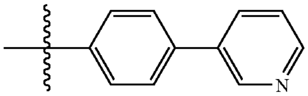 | 0 |
| E-081 | H | H | 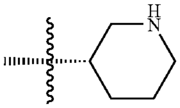 | 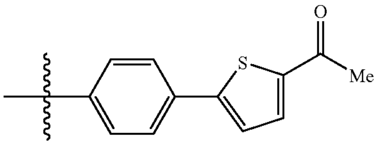 | 0 |
| E-082 | H | H | 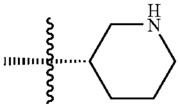 | 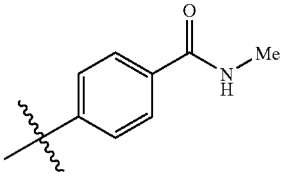 | 0 |
| E-083 | H | H | 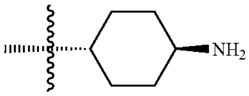 | 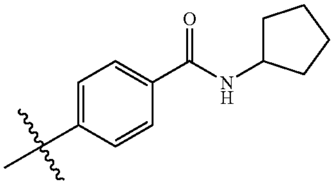 | 0 |
| E-084 | H | H | 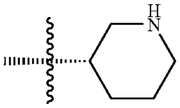 | 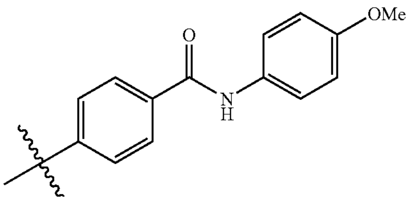 | 0 |

TABLE E-continued
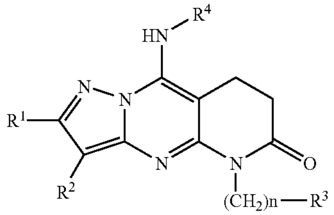
| Compound No. | $R^1$ | $R^2$ | $R^3$ | $R^4$ | n |
|---|---|---|---|---|---|
| E-085 | H | H | 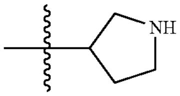 | 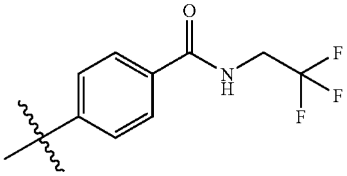 | 0 |
TABLE F
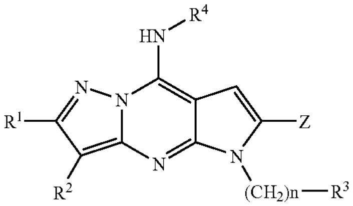
| Compound No. | $R^1$ | $R^2$ | $R^3$ | $R^4$ | n | Z |
|---|---|---|---|---|---|---|
| F-001 | H | H | 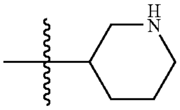 | 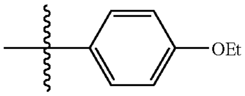 | 0 | H |
| F-002 | H | H | 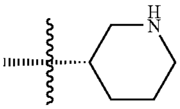 | 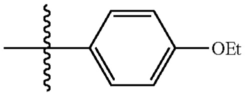 | 0 | 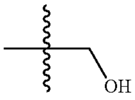 |
| F-003 | H | H | 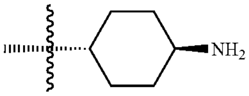 | 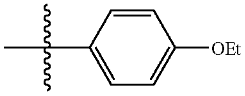 | 0 | H |
| F-004 | H | H | 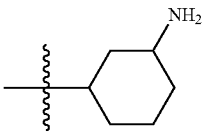 | 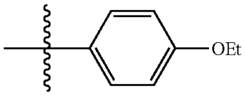 | 0 | H |
| F-005 | H | H | 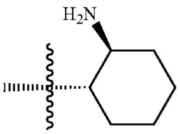 | 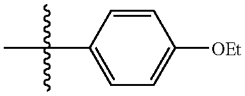 | 0 | H |

TABLE F-continued
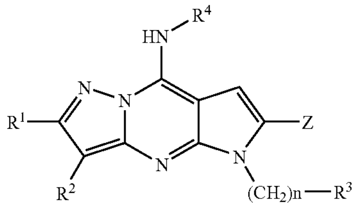
| Compound No. | $R^1$ | $R^2$ | $R^3$ | $R^4$ | n | Z |
|---|---|---|---|---|---|---|
| F-006 | H | H | 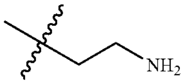 | 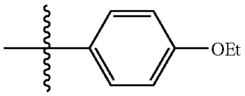 | 0 | H |
| F-007 | H | H | 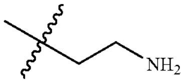 | 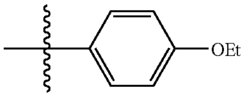 | 1 | H |
| F-008 | H | H | 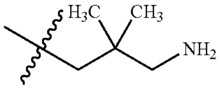 | 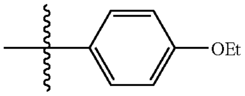 | 0 | H |
| F-009 | H | H | 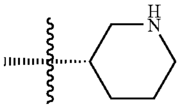 | 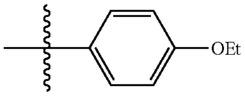 | 0 | H |
| F-010 | H | H | 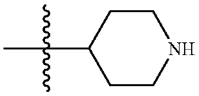 | 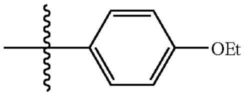 | 0 | H |
| F-011 | H | H | 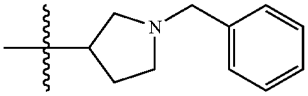 | 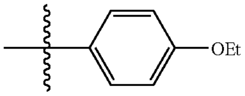 | 0 | H |
| F-012 | H | H | 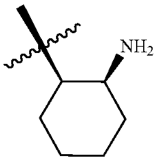 | 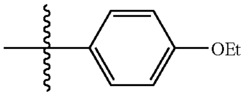 | 0 | H |
| F-013 | H | H | 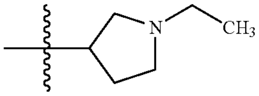 | 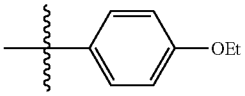 | 0 | H |
| F-014 | H | H | 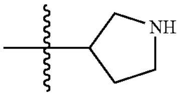 | 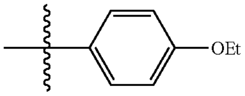 | 0 | H |
| F-015 | H | H | 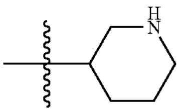 | 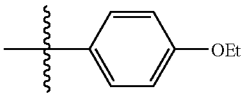 | 1 | H |
| F-016 | H | H | 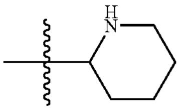 | 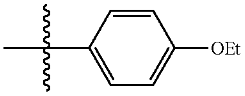 | 1 | H |

TABLE F-continued
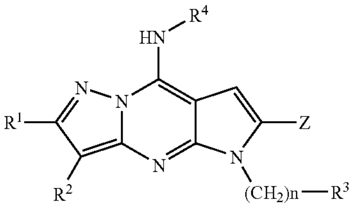
| Compound No. | $R^1$ | $R^2$ | $R^3$ | $R^4$ | n | Z |
|---|---|---|---|---|---|---|
| F-017 | H | H | 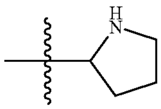 | 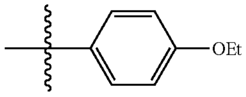 | 1 | H |
| F-018 | H | H | 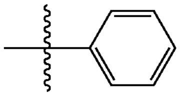 | 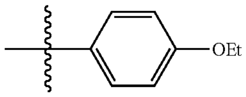 | 1 | H |
| F-019 | H | F | 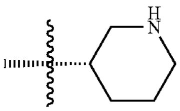 | 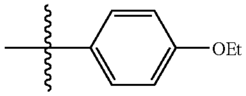 | 0 | H |
| F-020 | F | F | 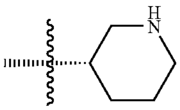 | 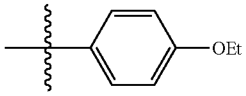 | 0 | H |
| F-021 | H | H | 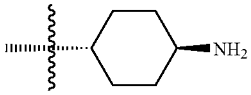 | 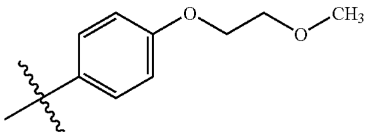 | 0 | H |
| F-022 | H | H | 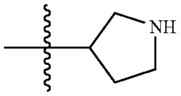 | 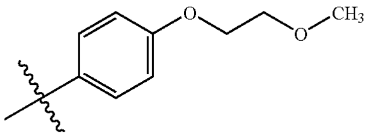 | 0 | H |
| F-023 | H | H | 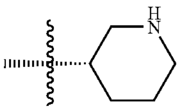 | 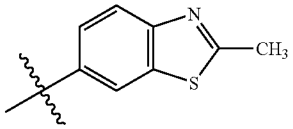 | 0 | H |
| F-024 | H | H | 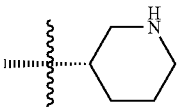 | 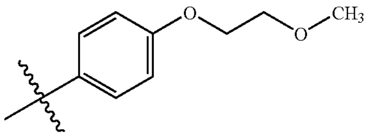 | 0 | H |
| F-025 | H | H | 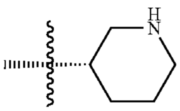 | 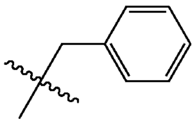 | 0 | H |

TABLE F-continued
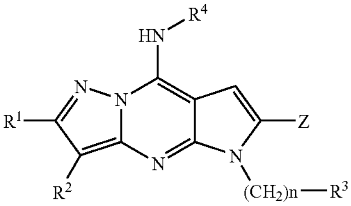
| Compound No. | $R^1$ | $R^2$ | $R^3$ | $R^4$ | n | Z |
|---|---|---|---|---|---|---|
| F-026 | H | H | 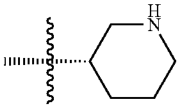 | 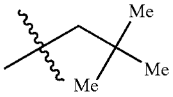 | 0 | H |
| F-027 | H | H | 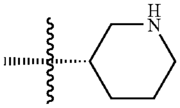 | 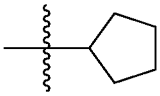 | 0 | H |
| F-028 | H | H | 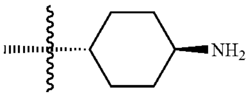 | 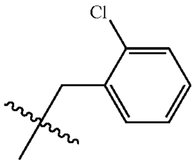 | 0 | H |
| F-029 | H | H | 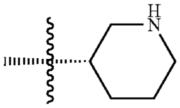 | 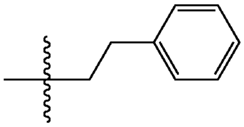 | 0 | H |
| F-030 | H | H | 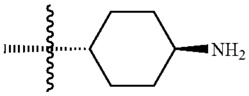 | 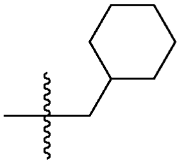 | 0 | H |
| F-031 | H | H | 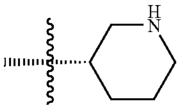 | 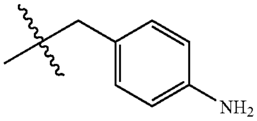 | 0 | H |
| F-032 | H | H | 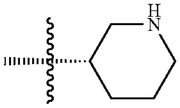 | 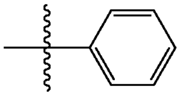 | 0 | H |
| F-033 | H | H | 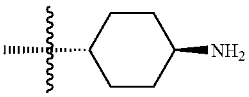 | 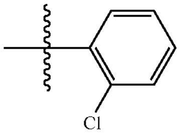 | 0 | H |
| F-034 | H | H | 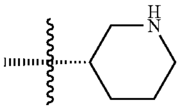 | 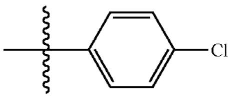 | 0 | H |

TABLE F-continued
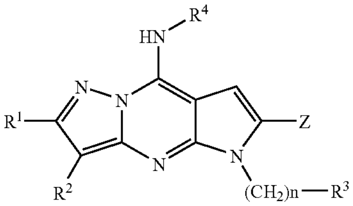
| Compound No. | $R^1$ | $R^2$ | $R^3$ | $R^4$ | n | Z |
|---|---|---|---|---|---|---|
| F-035 | H | H | 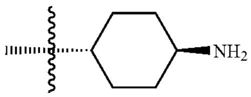 | 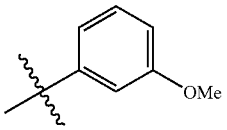 | 0 | H |
| F-036 | H | H | 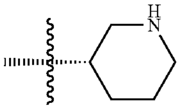 | 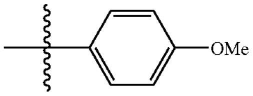 | 0 | H |
| F-037 | H | H | 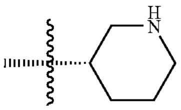 | 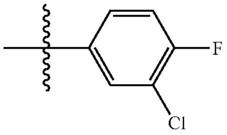 | 0 | H |
| F-038 | H | H | 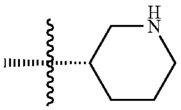 | 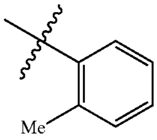 | 0 | H |
| F-039 | H | H | 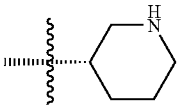 | 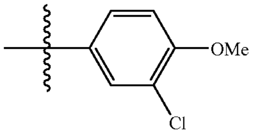 | 0 | H |
| F-040 | H | H | 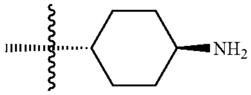 | 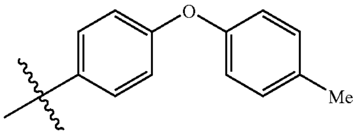 | 0 | H |
| F-041 | H | H | 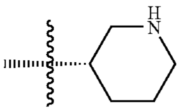 | 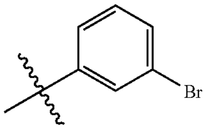 | 0 | H |
| F-042 | H | H | 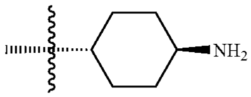 | 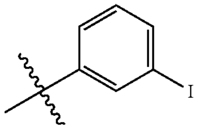 | 0 | H |
| F-043 | H | H | 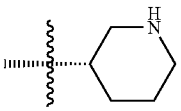 | 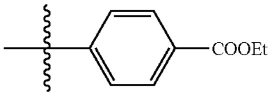 | 0 | H |

TABLE F-continued
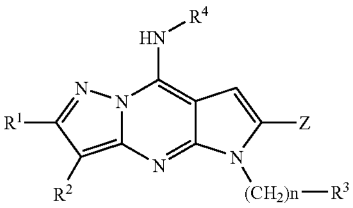
| Compound No. | $R^1$ | $R^2$ | $R^3$ | $R^4$ | n | Z |
|---|---|---|---|---|---|---|
| F-044 | H | H | 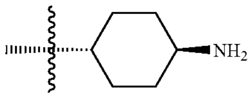 | 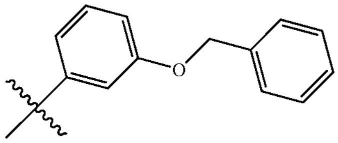 | 0 | H |
| F-045 | H | H | 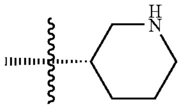 | 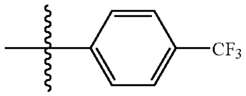 | 0 | H |
| F-046 | H | H | 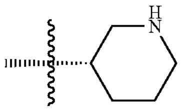 | 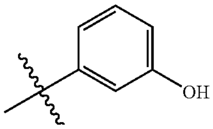 | 0 | H |
| F-047 | H | H | 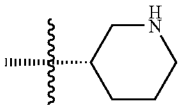 | 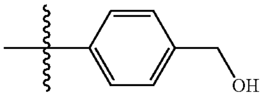 | 0 | H |
| F-048 | H | H | 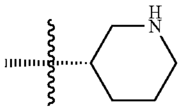 | 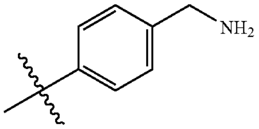 | 0 | H |
| F-049 | H | H | 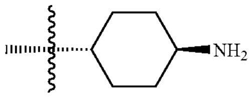 | 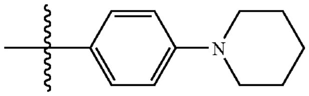 | 0 | H |
| F-050 | H | H | 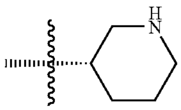 | 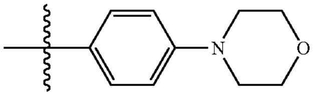 | 0 | H |
| F-051 | H | H | 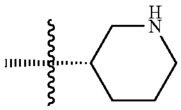 | 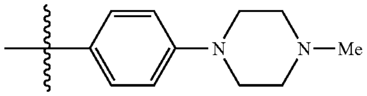 | 0 | H |
| F-052 | H | H | 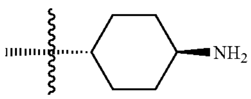 | 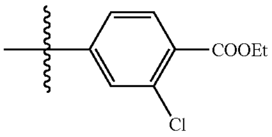 | 0 | H |

TABLE F-continued
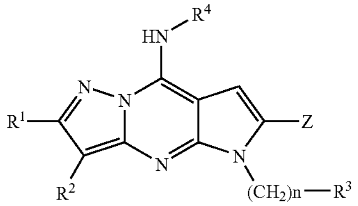
| Compound No. | $R^1$ | $R^2$ | $R^3$ | $R^4$ | n | Z |
|---|---|---|---|---|---|---|
| F-053 | H | H | 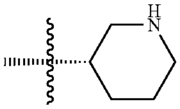 | 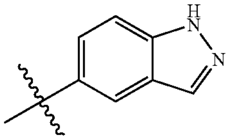 | 0 | H |
| F-054 | H | H | 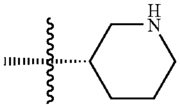 | 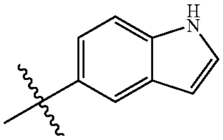 | 0 | H |
| F-055 | H | H | 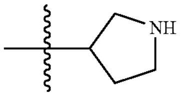 | 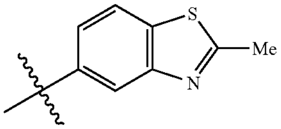 | 0 | H |
| F-056 | H | H | 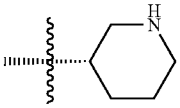 | 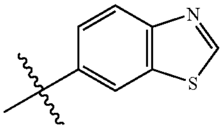 | 0 | H |
| F-057 | H | H | 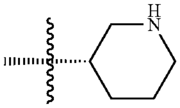 | 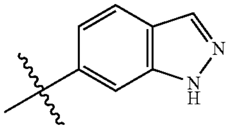 | 0 | H |
| F-058 | H | H | 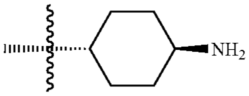 | 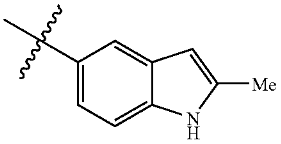 | 0 | H |
| F-059 | H | H | 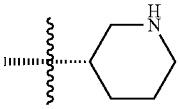 | 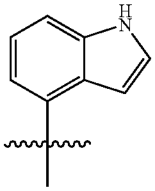 | 0 | H |
| F-060 | H | H | 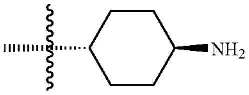 | 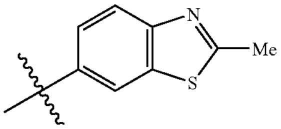 | 0 | H |

TABLE F-continued
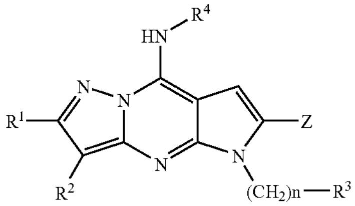
| Compound No. | $R^1$ | $R^2$ | $R^3$ | $R^4$ | n | Z |
|---|---|---|---|---|---|---|
| F-061 | H | H | 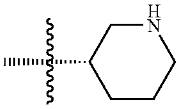 | 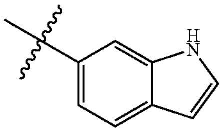 | 0 | H |
| F-062 | H | H | 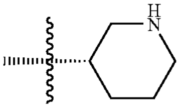 | 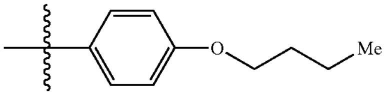 | 0 | H |
| F-063 | H | H | 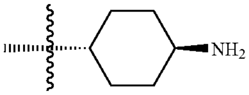 | 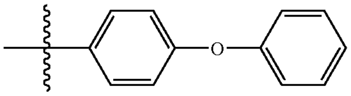 | 0 | H |
| F-064 | H | H | 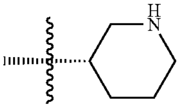 | 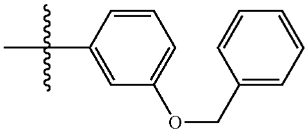 | 0 | H |
| F-065 | H | H | 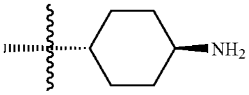 | 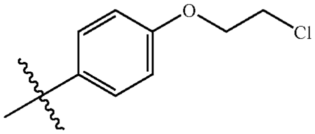 | 0 | H |
| F-066 | H | H | 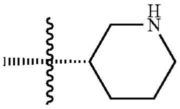 | 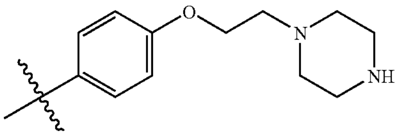 | 0 | H |
| F-067 | H | H | 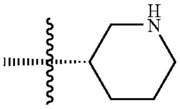 | 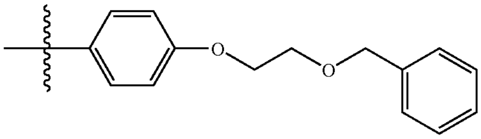 | 0 | H |
| F-068 | H | H | 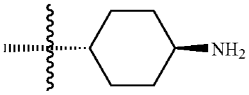 | 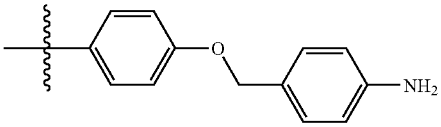 | 0 | H |
| F-069 | H | H | 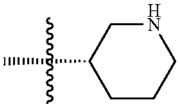 | 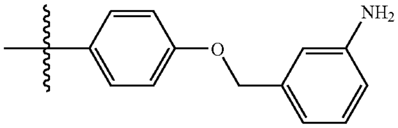 | 0 | H |

TABLE F-continued
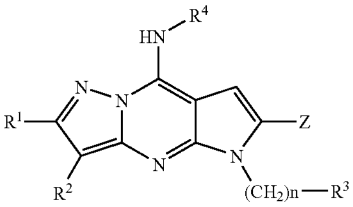
| Compound No. | $R^1$ | $R^2$ | $R^3$ | $R^4$ | n | Z |
|---|---|---|---|---|---|---|
| F-070 | H | H | 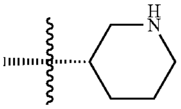 | 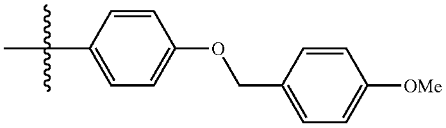 | 0 | H |
| F-071 | H | H | 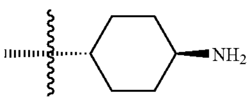 | 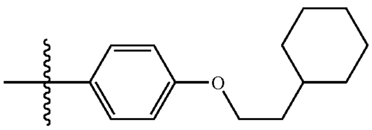 | 0 | H |
| F-072 | H | H | 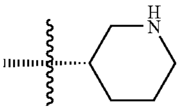 | 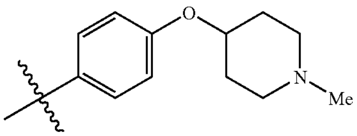 | 0 | H |
| F-073 | H | H | 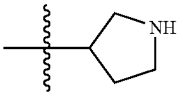 | 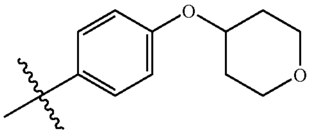 | 0 | H |
| F-074 | H | H | 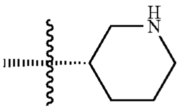 | 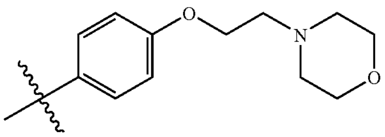 | 0 | H |
| F-075 | H | H | 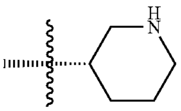 | 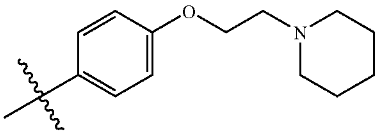 | 0 | H |
| F-076 | H | H | 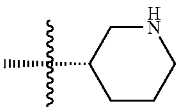 | 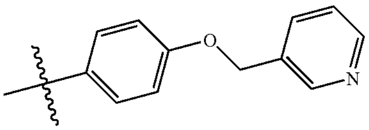 | 0 | H |
| F-077 | H | H | 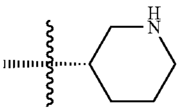 | 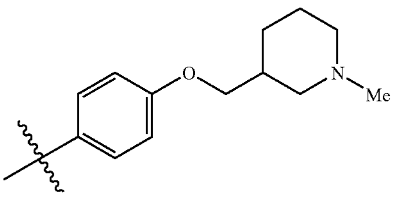 | 0 | H |

TABLE F-continued
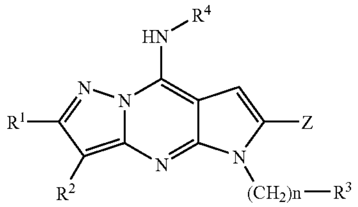
| Compound No. | $R^1$ | $R^2$ | $R^3$ | $R^4$ | n | Z |
|---|---|---|---|---|---|---|
| F-078 | H | H | 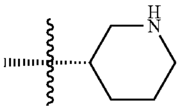 | 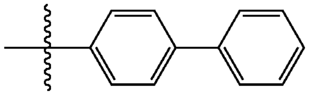 | 0 | H |
| F-079 | H | H | 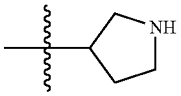 | 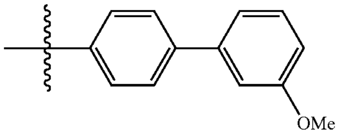 | 0 | H |
| F-080 | H | H | 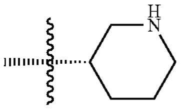 | 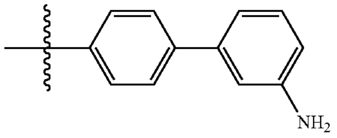 | 0 | H |
| F-081 | H | H | 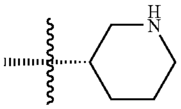 | 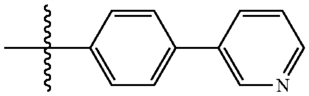 | 0 | H |
| F-082 | H | H | 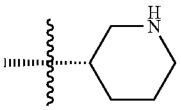 | 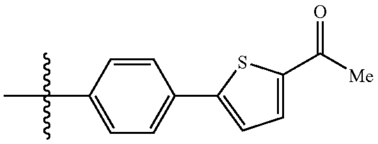 | 0 | H |
| F-083 | H | H | 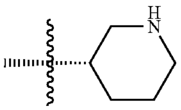 | 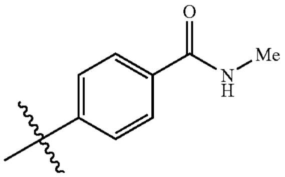 | 0 | H |
| F-084 | H | H | 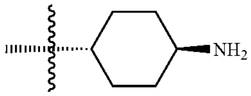 | 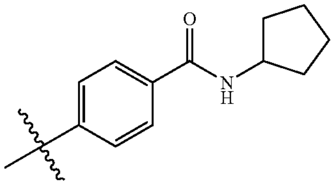 | 0 | H |
| F-085 | H | H | 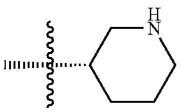 | 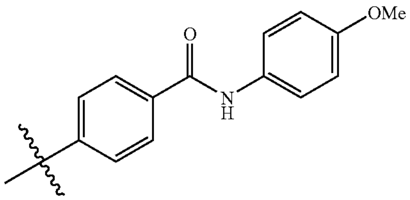 | 0 | H |

TABLE F-continued
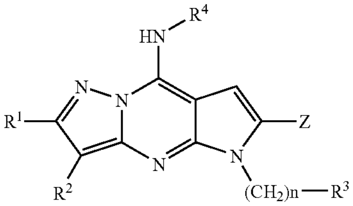
| Compound No. | $R^1$ | $R^2$ | $R^3$ | $R^4$ | n | Z |
|---|---|---|---|---|---|---|
| F-086 | H | H | 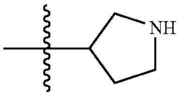 | 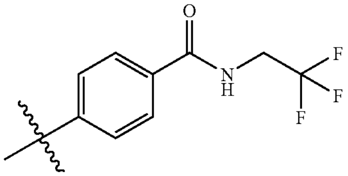 | 0 | H |
| F-87 | H | H | 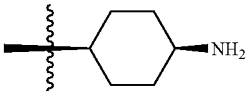 | 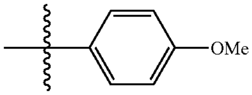 | 0 | H |
| F-88 | H | H | 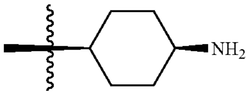 | 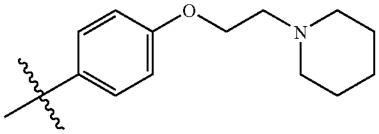 | 0 | H |
| F-89 | H | H | 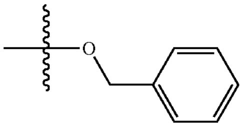 | 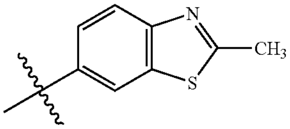 | 0 | H |
| F-90 | H | H | 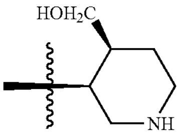 | 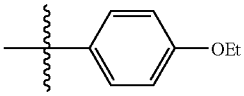 | 0 | H |
TABLE G
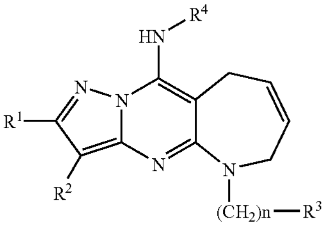
| Compound No. | $R^1$ | $R^2$ | $R^3$ | $R^4$ | n |
|---|---|---|---|---|---|
| G-001 | H | H | 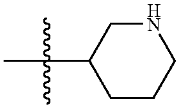 | 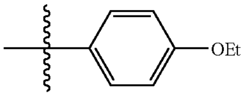 | 0 |

TABLE G-continued
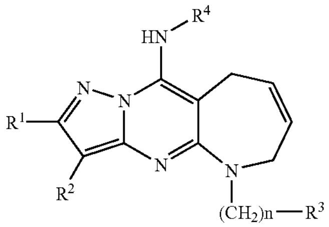
| Compound No. | $R^1$ | $R^2$ | $R^3$ | $R^4$ | n |
|---|---|---|---|---|---|
| G-002 | H | H | 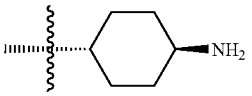 | 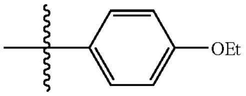 | 0 |
| G-003 | H | H | 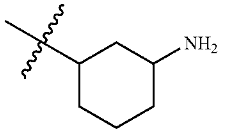 | 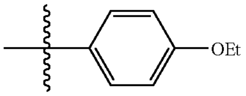 | 0 |
| G-004 | H | H | 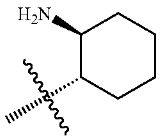 | 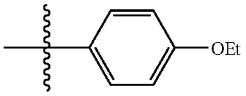 | 0 |
| G-005 | H | H | 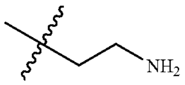 | 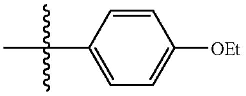 | 0 |
| G-006 | H | H | 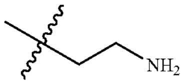 | 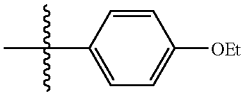 | 1 |
| G-007 | H | H | 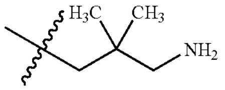 | 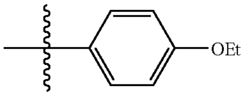 | 0 |
| G-008 | H | H | 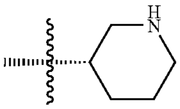 | 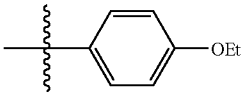 | 0 |
| G-009 | H | H | 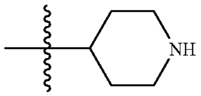 | 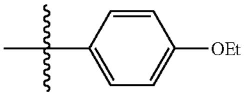 | 0 |
| G-010 | H | H | 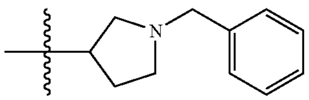 | 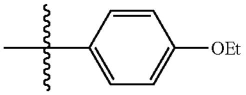 | 0 |
| G-011 | H | H | 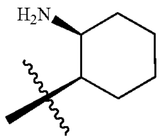 | 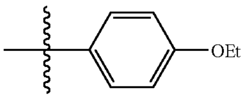 | 0 |

TABLE G-continued
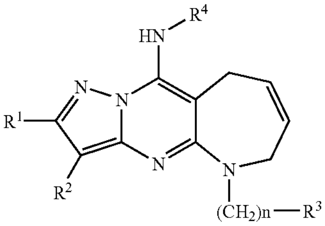
| Compound No. | $R^1$ | $R^2$ | $R^3$ | $R^4$ | n |
|---|---|---|---|---|---|
| G-012 | H | H | 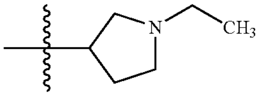 | 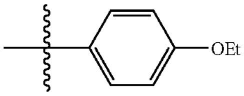 | 0 |
| G-013 | H | H | 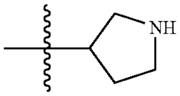 | 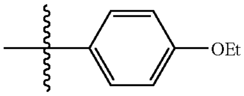 | 0 |
| G-014 | H | H | 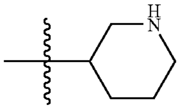 | 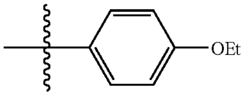 | 1 |
| G-015 | H | H | 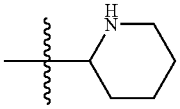 | 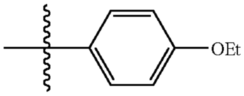 | 1 |
| G-016 | H | H | 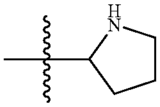 | 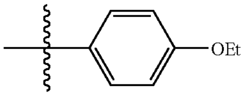 | 1 |
| G-017 | H | H | 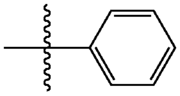 | 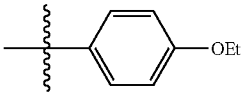 | 1 |
| G-018 | H | F | 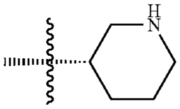 | 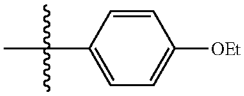 | 0 |
| G-019 | F | F | 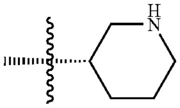 | 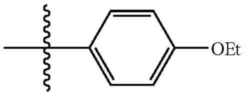 | 0 |
| G-020 | H | H | 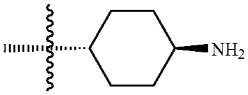 | 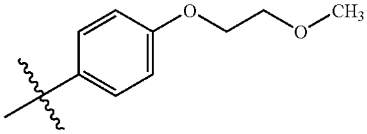 | 0 |
| G-021 | H | H | 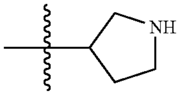 | 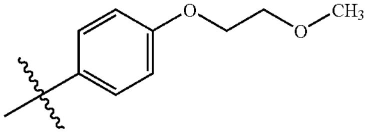 | 0 |

TABLE G-continued
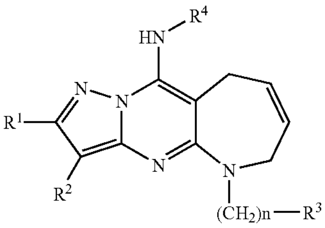
| Compound No. | $R^1$ | $R^2$ | $R^3$ | $R^4$ | n |
|---|---|---|---|---|---|
| G-022 | H | H | 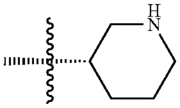 | 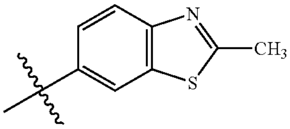 | 0 |
| G-023 | H | H | 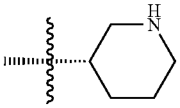 | 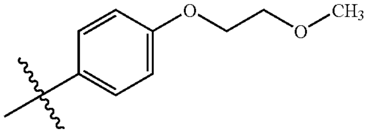 | 0 |
| G-024 | H | H | 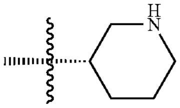 | 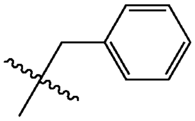 | 0 |
| G-025 | H | H | 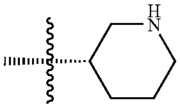 | 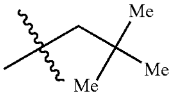 | 0 |
| G-026 | H | H | 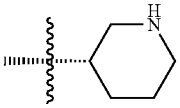 | 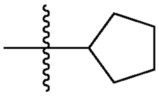 | 0 |
| G-027 | H | H | 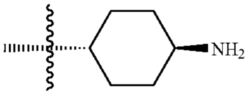 | 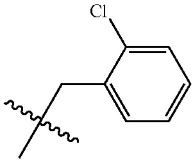 | 0 |
| G-028 | H | H | 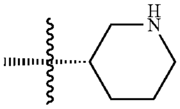 | 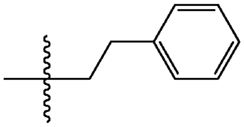 | 0 |
| G-029 | H | H | 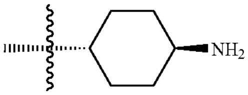 | 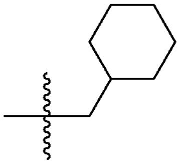 | 0 |
| G-030 | H | H | 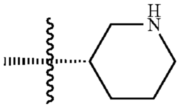 | 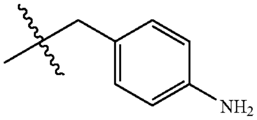 | 0 |

TABLE G-continued
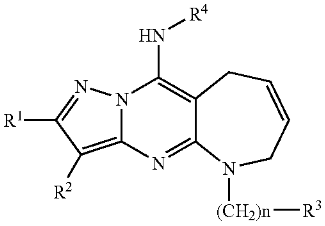
| Compound No. | $R^1$ | $R^2$ | $R^3$ | $R^4$ | n |
|---|---|---|---|---|---|
| G-031 | H | H | 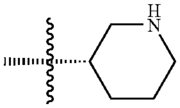 | 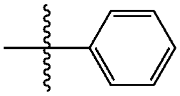 | 0 |
| G-032 | H | H | 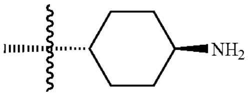 | 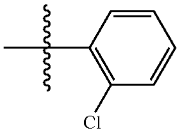 | 0 |
| G-033 | H | H | 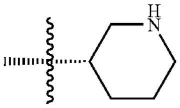 | 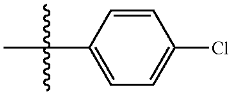 | 0 |
| G-034 | H | H | 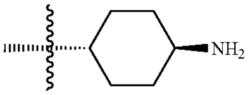 | 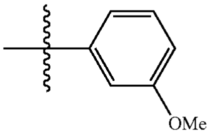 | 0 |
| G-035 | H | H | 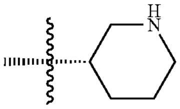 | 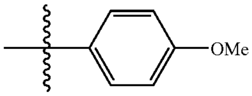 | 0 |
| G-036 | H | H | 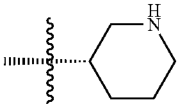 | 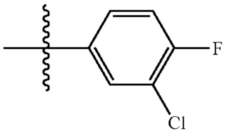 | 0 |
| G-037 | H | H | 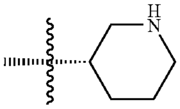 | 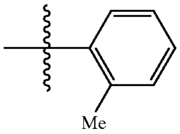 | 0 |
| G-038 | H | H | 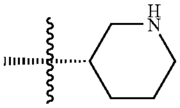 | 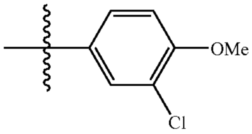 | 0 |
| G-039 | H | H | 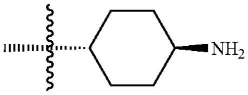 | 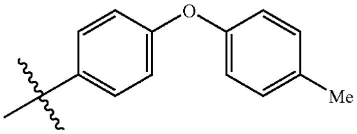 | 0 |

TABLE G-continued
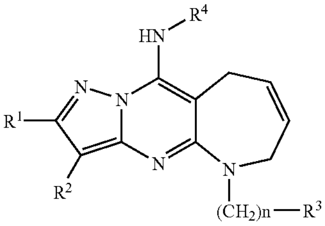
| Compound No. | $R^1$ | $R^2$ | $R^3$ | $R^4$ | n |
|---|---|---|---|---|---|
| G-040 | H | H | 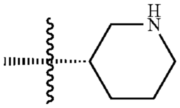 | 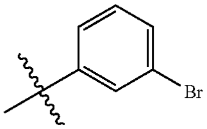 | 0 |
| G-041 | H | H | 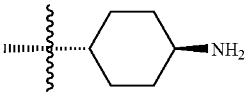 | 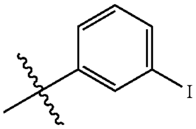 | 0 |
| G-042 | H | H | 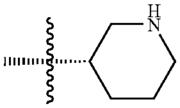 | 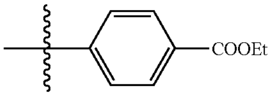 | 0 |
| G-043 | H | H | 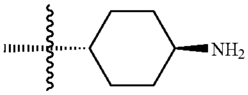 | 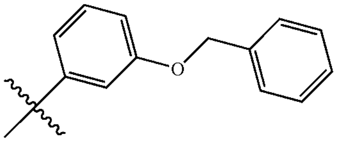 | 0 |
| G-044 | H | H | 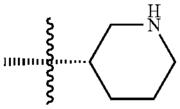 | 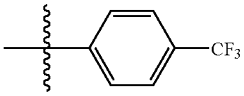 | 0 |
| G-045 | H | H | 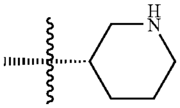 | 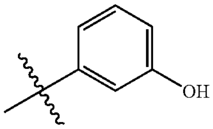 | 0 |
| G-046 | H | H | 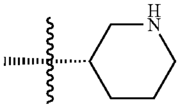 | 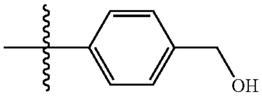 | 0 |
| G-047 | H | H | 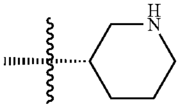 | 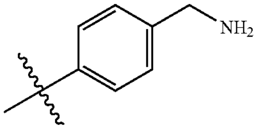 | 0 |
| G-048 | H | H | 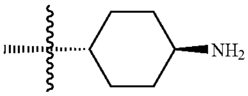 | 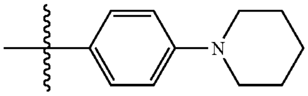 | 0 |

TABLE G-continued
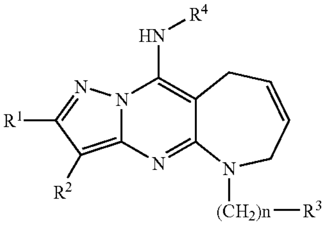
| Compound No. | $R^1$ | $R^2$ | $R^3$ | $R^4$ | n |
|---|---|---|---|---|---|
| G-049 | H | H | 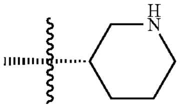 | 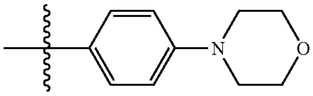 | 0 |
| G-050 | H | H | 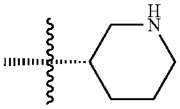 | 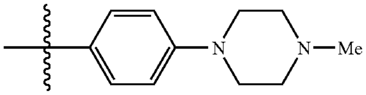 | 0 |
| G-051 | H | H | 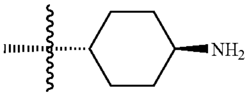 | 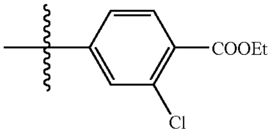 | 0 |
| G-052 | H | H | 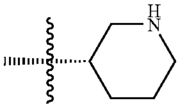 | 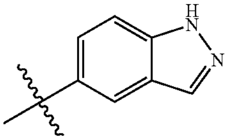 | 0 |
| G-053 | H | H | 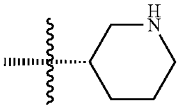 | 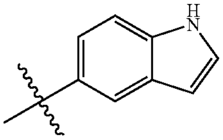 | 0 |
| G-054 | H | H | 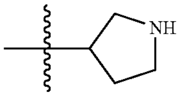 | 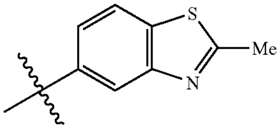 | 0 |
| G-055 | H | H | 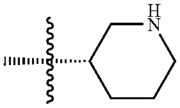 | 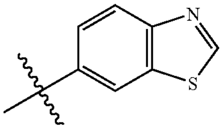 | 0 |
| G-056 | H | H | 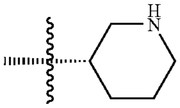 | 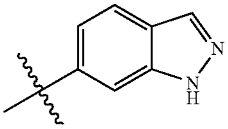 | 0 |
| G-057 | H | H | 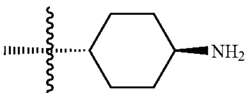 | 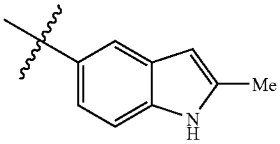 | 0 |

TABLE G-continued
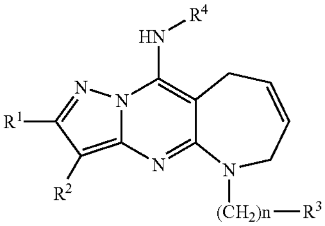
| Compound No. | $R^1$ | $R^2$ | $R^3$ | $R^4$ | n |
|---|---|---|---|---|---|
| G-058 | H | H | 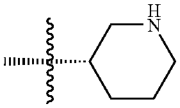 | 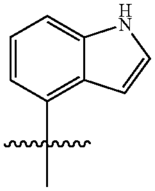 | 0 |
| G-059 | H | H | 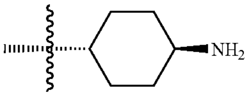 | 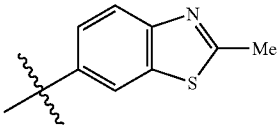 | 0 |
| G-060 | H | H | 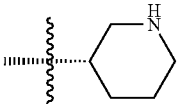 | 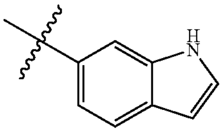 | 0 |
| G-061 | H | H | 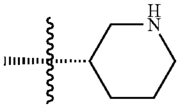 | 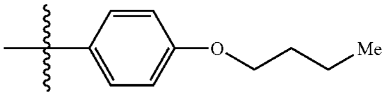 | 0 |
| G-062 | H | H | 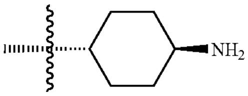 | 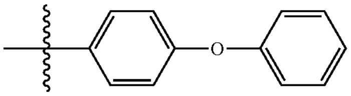 | 0 |
| G-063 | H | H | 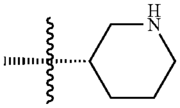 | 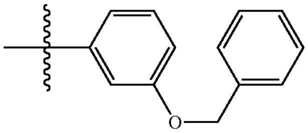 | 0 |
| G-064 | H | H | 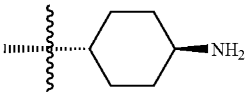 | 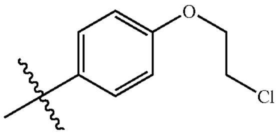 | 0 |
| G-065 | H | H | 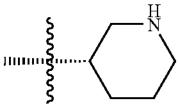 | 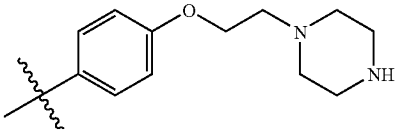 | 0 |

TABLE G-continued
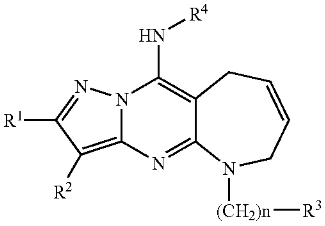
| Compound No. | $R^1$ | $R^2$ | $R^3$ | $R^4$ | n |
| --- | --- | --- | --- | --- | --- |
| G-066 | H | H | 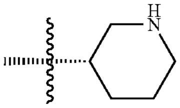 | 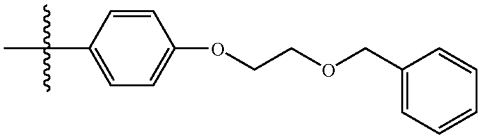 | 0 |
| G-067 | H | H | 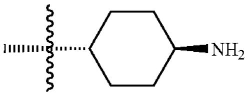 | 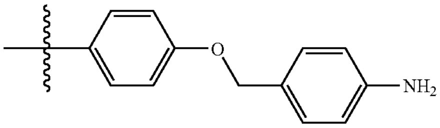 | 0 |
| G-068 | H | H | 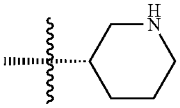 | 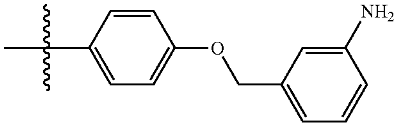 | 0 |
| G-069 | H | H | 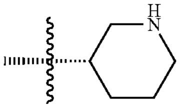 | 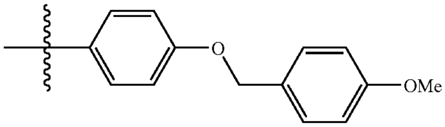 | 0 |
| G-070 | H | H | 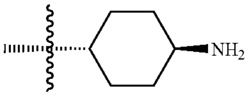 | 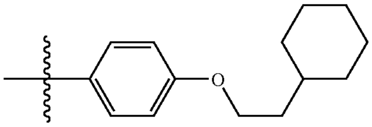 | 0 |
| G-071 | H | H | 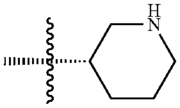 | 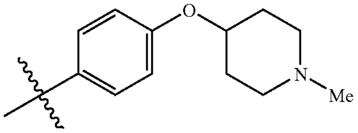 | 0 |
| G-072 | H | H | 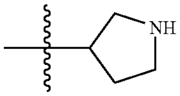 | 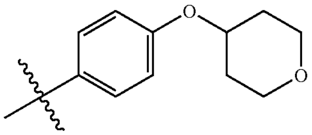 | 0 |
| G-073 | H | H | 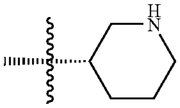 | 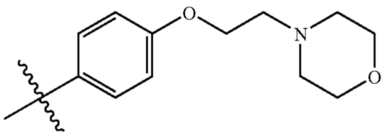 | 0 |
| G-074 | H | H | 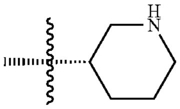 | 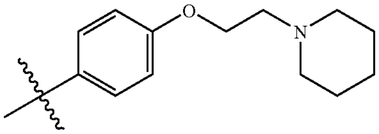 | 0 |

TABLE G-continued
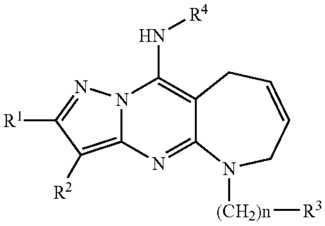
| Compound No. | $R^1$ | $R^2$ | $R^3$ | $R^4$ | n |
|---|---|---|---|---|---|
| G-075 | H | H | 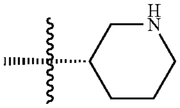 | 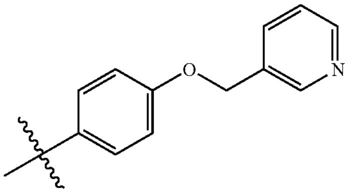 | 0 |
| G-076 | H | H | 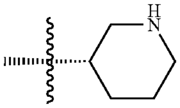 | 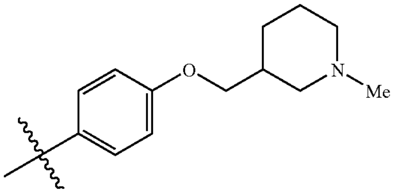 | 0 |
| G-077 | H | H | 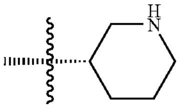 | 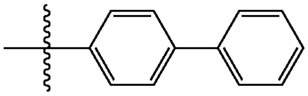 | 0 |
| G-078 | H | H | 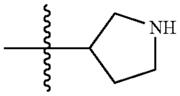 | 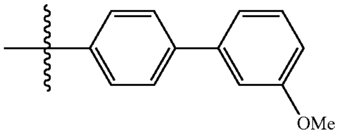 | 0 |
| G-079 | H | H | 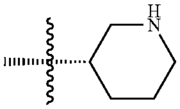 | 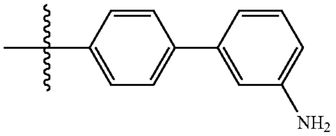 | 0 |
| G-080 | H | H | 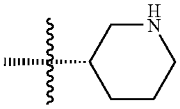 | 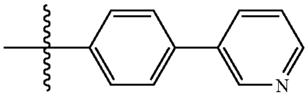 | 0 |
| G-081 | H | H | 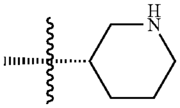 | 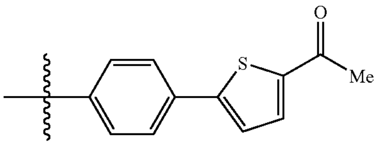 | 0 |
| G-082 | H | H | 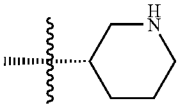 | 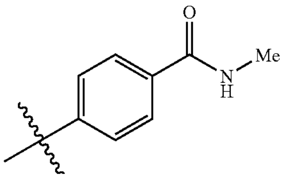 | 0 |

TABLE G-continued
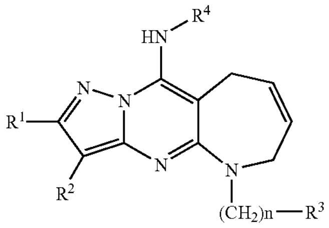
| Compound No. | $R^1$ | $R^2$ | $R^3$ | $R^4$ | n |
|---|---|---|---|---|---|
| G-083 | H | H | 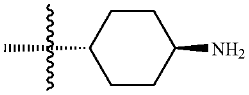 | 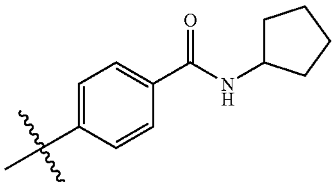 | 0 |
| G-084 | H | H | 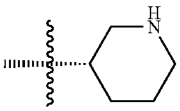 | 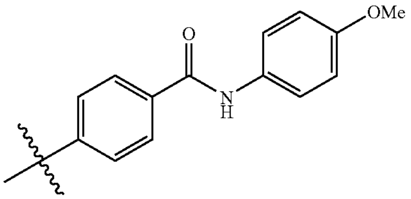 | 0 |
| G-085 | H | H | 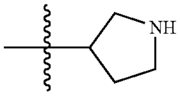 | 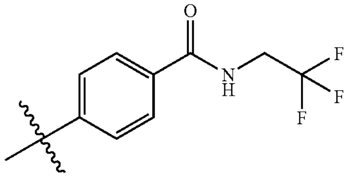 | 0 |
| G-086 | H | H | 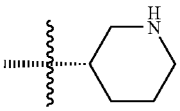 | H | 0 |
| G-087 | H | H | 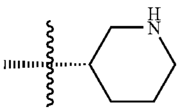 | Me | 0 |
| G-88 | H | H | 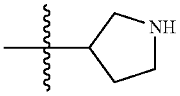 | H | 0 |
| G-089 | H | H | 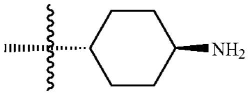 | H | 0 |

The pyrazolopyrimidine derivative represented by the above formula (1) exists in tautomeric forms exemplified by the following formula.

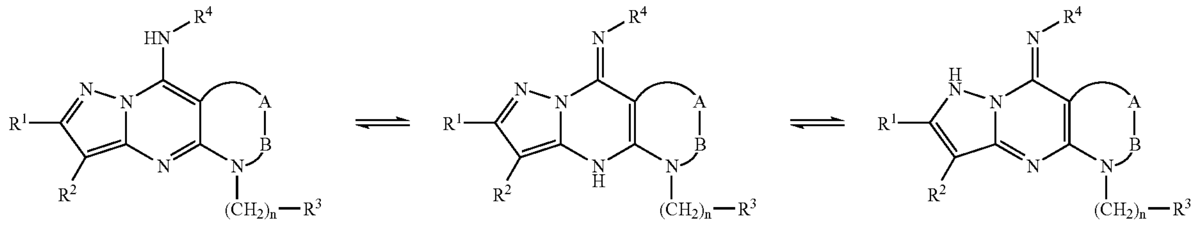

(In the formula, $R^1$, $R^2$, $R^3$, $R^4$, n and -A-B- are as defined for formula (1)).

These tautomers are also included in the scope of the present invention.

As examples of compound represented by formula (2) in the present invention, there may be mentioned compounds having $R^1$, $R^2$, $R^3$, $R^4$, n and -A-B- listed in Tables A to G.

The compounds of the present invention can be synthesized by the following method. In each formula, $R^1$-$R^4$, -A-B- and n are as defined in the above formula (1). Reagents and solvents shown as conditions in chemical formulae are examples, as mentioned in the text. Each of abbreviations of substituents, reagents and solvents in the text and tables represent the following.

Me: methyl

Et: ethyl $^i$Pr: isopropyl $^t$Bu: tert-butyl

Cy: cyclohexyl

Ms: methanesulfonyl

Boc: tert-butoxycarbonyl

TBS: tert-butyldimethylsilyl

TBAF: tetrabutylammonium fluoride

TFA: trifluoroacetic acid

HATU: O-(7-azabenzotriazol-1-yl)-N,N,N',N'-tetramethyluronium hexafluorophosphate Dess-Martin periodinane: 1,1,1-tris(acetoxy)-1,1-dihydro-1,2-benziodoxol-3(1H)-one DMAP: 4-N,N-dimethylaminopyridine NMO: N-methylmorpholine-N-oxide DMF: N,N-dimethylformamide THF: tetrahydrofuran PTLC: preparative thin layer chromatography Grubbs reagent: benzylidene-bis(tricyclohexylphosphine) dichlororuthenium NBS: N-bromosuccinimide NCS: N-chlorosuccinimide

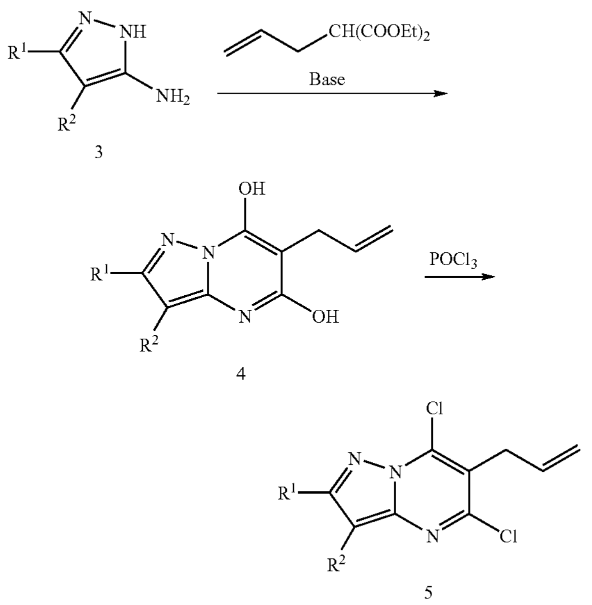

1) The compound represented by formula (4) can be obtained by reaction of the compound represented by formula (3) and allylmalonic diester in an appropriate organic solvent (for example, ethanol or methanol) under a condition from room temperature to heating under reflux in the presence of a base (for example, sodium ethoxide or sodium methoxide). (References: J. Med. Chem., 1976, 19, 296 and J. Med. Chem., 1977, 20, 296)

2) The compound represented by formula (5) can be obtained by reaction of the compound represented by formula (4) and a halogenating agent (for example, phosphoryl chloride) either in an appropriate organic solvent (for example, acetonitrile) or without solvent under a condition from room temperature to heating under reflux in the presence or absence of an appropriate base (for example, dimethylaniline).

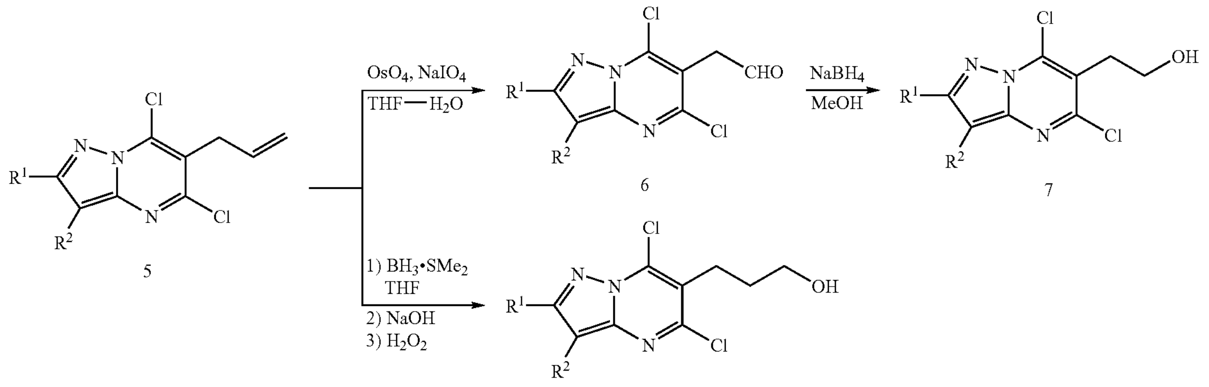
5 6 7 8
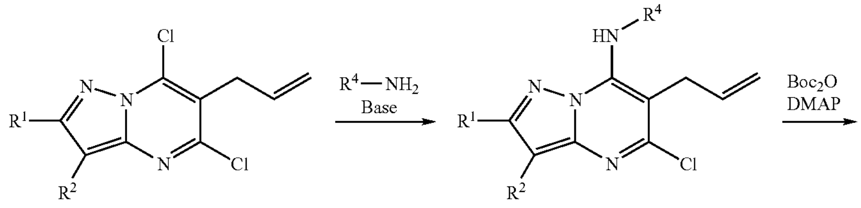
5 13
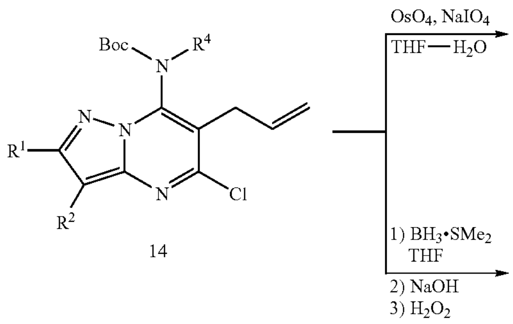
14
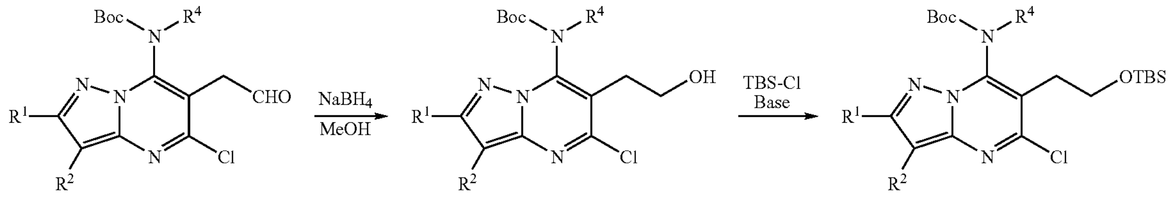
15 16 17
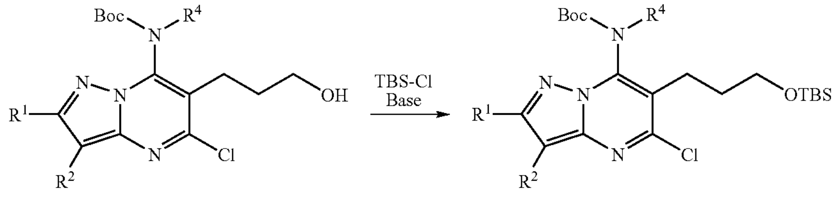
18 19

3) The compound represented by formula (6) or (15) can be obtained by reaction of the compound represented by formula (5) or (14), respectively, with an oxidizing agent (for example, sodium periodate and osmium tetraoxide) in an appropriate solvent (for example, THF-water mixed solvent) at a temperature ranging from 0° C. to room temperature.

4) The compound represented by formula (7) or (16) can be obtained by reaction of the compound represented by formula (6) or (15), respectively, with a reducing agent (for example, sodium borohydride) in an appropriate organic solvent (for example, ethanol or methanol) at a temperature ranging from 0° C. to 40° C.

5) The compound represented by formula (8) or (18) can be obtained by reaction of the compound represented by formula (5) or (14), respectively, with a borane agent (for example, borane-dimethylsulfide complex) in an appropriate organic solvent (for example, THF) at a temperature ranging from 0° C. to room temperature followed by reaction with aqueous hydrogen peroxide in aqueous sodium hydroxide solution.

6) The compound represented by formula (10), (17), (19) or (42) can be obtained by reaction of the compound represented by formula (9), (16), (18) or (41), respectively, with tert-butylchlorodimethylsilane in an appropriate organic solvent (for example, methylene chloride or DMF) at a temperature ranging from 0° C. to 40° C. in the presence of a base (for example, triethylamine or imidazole). (Reference: Protective Groups in Organic Synthesis, 3rd edition, John Wiley & Sons Inc.)

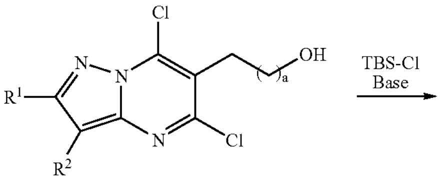

9

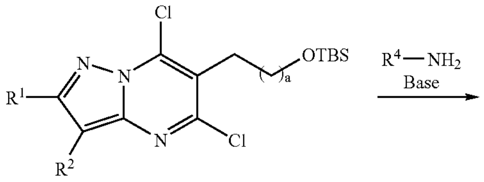

10

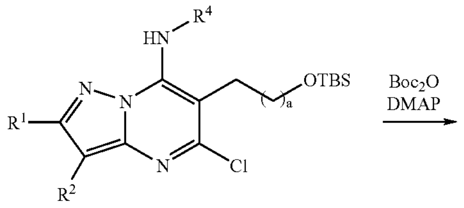

11

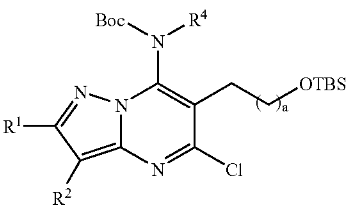

12

-continued a = 1, 2

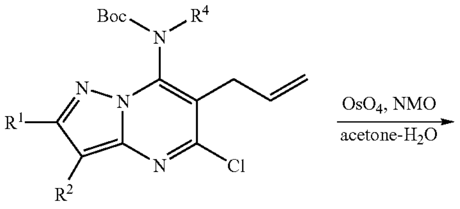

14

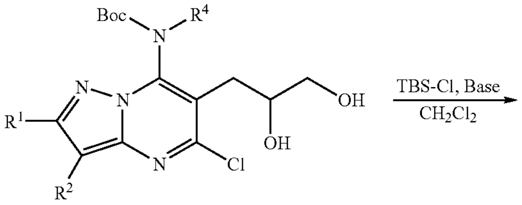

41

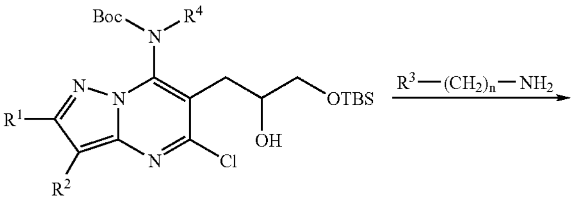

42

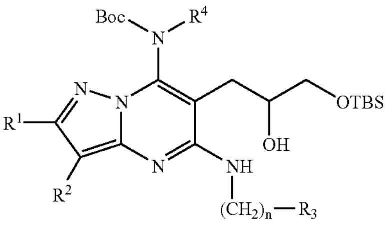

43

7) The compound represented by formula (11) or (13) can be obtained by reaction of the compound represented by formula (10) or (5), respectively, with an amine compound represented as $R^4NH_2$ in an appropriate organic solvent (for example, 2-propanol, DMF, THF or DMF-THF mixed solvent) under a condition from room temperature to heating under reflux in the presence of a base (for example triethylamine or sodium hydride).

8) The compound represented by formula (41) can be obtained by reaction of the compound represented by formula (14) with an oxidizing agent (for example, osmium tetraoxide and N-methylmorpholine-N-oxide) in an appropriate solvent (for example, acetone-water mixed solvent) at a temperature ranging from 0° C. to room temperature. (References: Tetrahedron Lett., 1973 (1976) and Org. Synth. Collective volume 6, 342)

9) The compound represented by formula (12) or (14) can be obtained by reaction of the compound represented by formula (11) or (13), respectively, with di-tert-butyl dicarbonate in an appropriate organic solvent (for example, 1,4-dioxane) under a condition from room temperature to heating under reflux in the presence of a base (for example triethylamine or 4-N,N-dimethylaminopyridine). (Reference: Protective Groups in Organic Synthesis, 3rd edition, John Wiley & Sons Inc.)

10) The compound represented by formula (25) or (27) can be obtained by reaction of the compound represented by formula (15) or (26), respectively, with an oxidizing agent (for example, sodium chlorite in the presence of 2-methyl-2-butene and sodium dihydrogenphosphate) in an appropriate solvent (for example, tert-butanol-water mixed solvent) at a temperature ranging from 0° C. to room temperature.

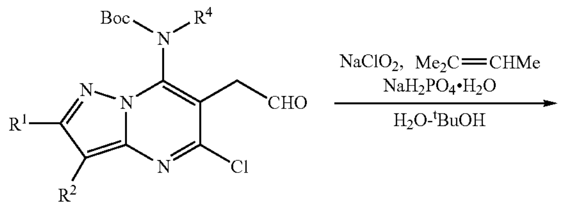

15

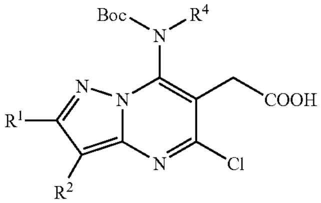

25

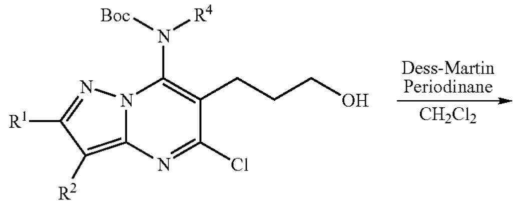

18

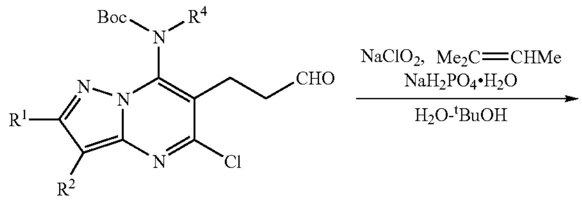

26

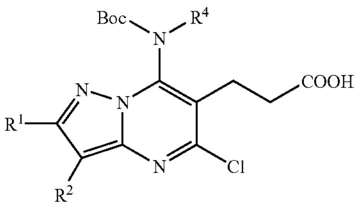

27

11) The compound represented by formula (26) can be obtained by reaction of the compound represented by formula (18) with an oxidizing agent [for example, Dess-Martin periodinane, i.e., 1,1,1-tris(acetoxy)-1,1-dihydro-1,2-benziodoxol-3(1H)-one] in an appropriate organic solvent (for example, methylene chloride) at a temperature ranging from 0° C. to room temperature. (References: J. Org. Chem., 48, 4155 (1983); J. Am. Chem. Soc., 113, 7277 (1991))

12) The compound represented by formula (20), (32) or (43) can be obtained by reaction of the compound represented by formula (12), (14) or (42), respectively, with an amine represented by formula $R^3—(CH_2)_n—NH_2$ in an appropriate organic solvent (for example, acetonitrile) or without solvent under a condition from room temperature to heating under reflux. (When $R^3$ in the compound represented by formula $R^3—(CH_2)_n—NH_2$ contains an unprotected primary amino group, the compound represented by formula (12), (14) or (42) is reacted with $R^3—(CH_2)_n—NH_2$ by the above-mentioned method and then the amino group in $R^3$ moiety is protected by treatment with di-tert-butyl dicarbonate in an appropriate organic solvent (for example, 1,4-dioxane or methylene chloride) under a condition from room temperature to heating under reflux in the presence of bases (for example, triethylamine and 4-N,N-dimethylaminopyridine) to obtain the corresponding tert-butoxycarbonyl-protected compound, which is defined as the compound represented by formula (20), (32) or (43), respectively.)

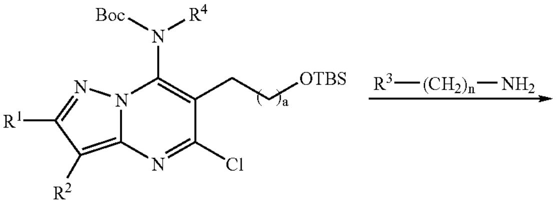

12

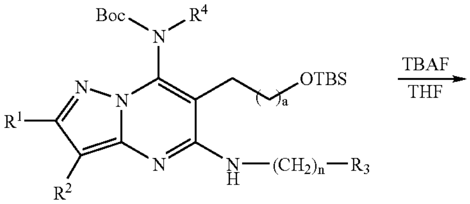

20

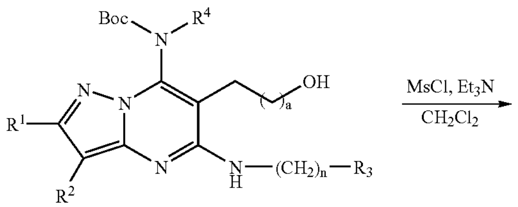

21

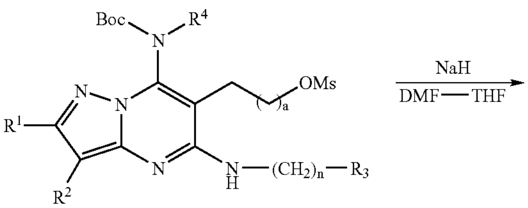

22

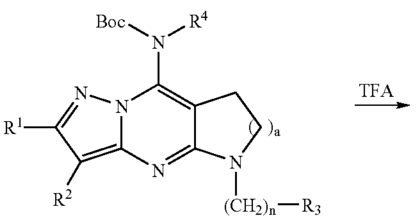

23

-continued

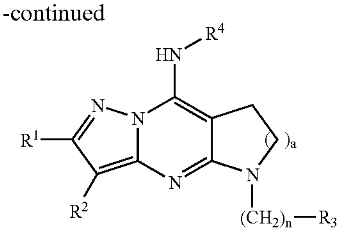

24 a = 1, 2

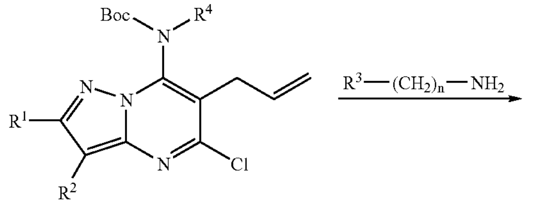

14

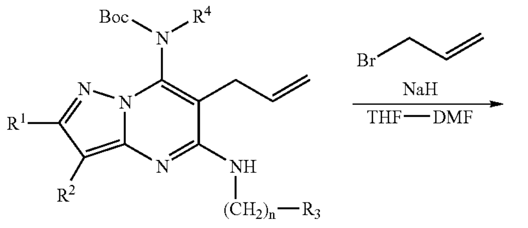

32

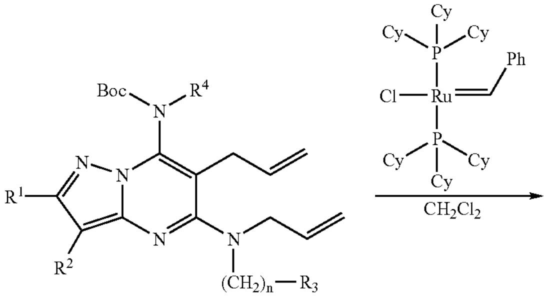

33

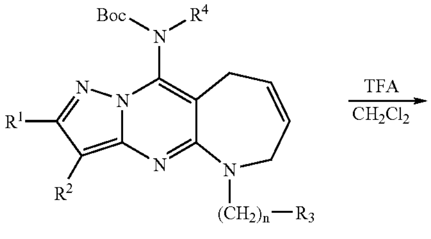

34

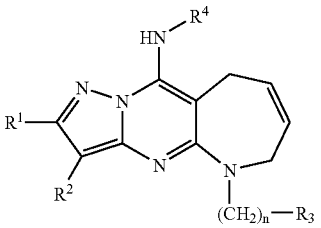

35

13) The compound represented by formula (21) can be obtained by reaction of the compound represented by formula (20) with a fluoride ion agent (for example, n-tetrabutylammonium fluoride) in an appropriate organic solvent (for example, THF) at a temperature ranging from 0° C. to room temperature. (Reference: Protective Groups in Organic Synthesis, 3rd edition, John Wiley & Sons Inc.)

14) The compound represented by formula (22) or (46) can be obtained by reaction of the compound represented by formula (21) or (43), respectively, with a mesylating agent (for example, methanesulfonyl chloride) in an appropriate organic solvent (for example, methylene chloride) at a temperature ranging from 0° C. to room temperature in the presence of a base (for example, triethylamine). (Reference: Protective Groups in Organic Synthesis, 3rd edition, John Wiley & Sons Inc.)

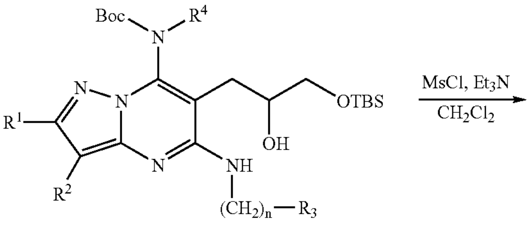

43

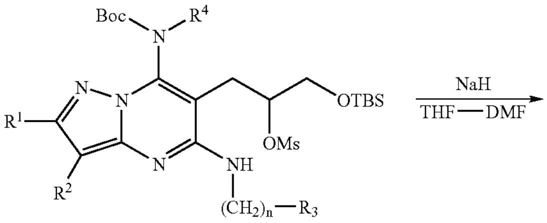

46

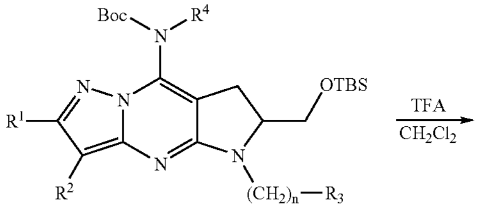

47

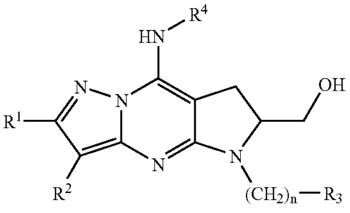

48

15) The compound represented by formula (23) or (47) can be obtained by reaction of the compound represented by formula (22) or (46), respectively, with a base (for example, sodium hydride) in an appropriate organic solvent (for example, DMF, THF or DMF-THF mixed solvent) at a temperature ranging from 0° C. to 60° C.

16) The compound represented by formula (29) can be obtained by reaction of the compound represented by formula (28) with an amine compound represented by formula $R^3$—$(CH_2)_n$—$NH_2$ in an appropriate organic solvent (for example, DMF) at a temperature ranging from 0° C. to 40° C. in the presence of a peptide condensing agent [for example, O-(7-azabenzotriazol-1-yl)-N,N,N',N'-tetramethyluronium hexafluorophosphate] and a base (for example, diisopropyethylamine).

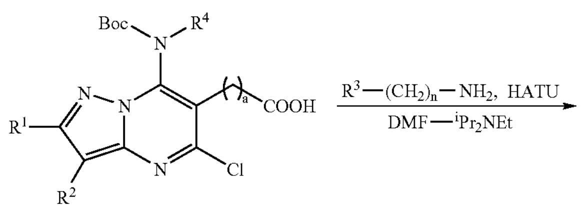

28

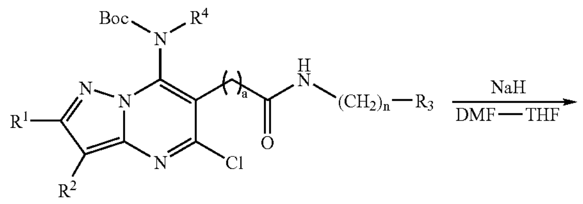

29

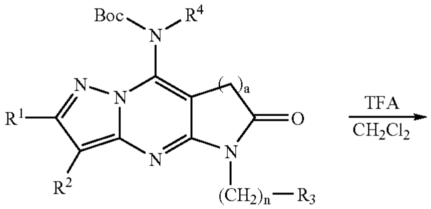

30

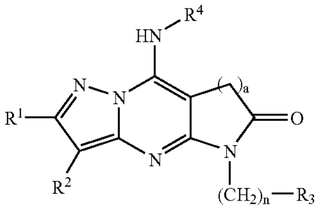

31 a = 1, 2

17) The compound represented by formula (30) can be obtained by reaction of the compound represented by formula (29) with a base (for example, sodium hydride) in an appropriate organic solvent (for example, DMF, THF or DMF-THF mixed solvent) at a temperature ranging from 0° C. to 60° C.

18) The compound represented by formula (38) can be obtained by reaction of the compound represented by formula (15) with hydroxylamine in the presence of a reducing agent (for example, sodium cyanoborohydride) in an appropriate organic solvent (for example, methanol or ethanol) under a condition from 0° C. to heating under reflux.

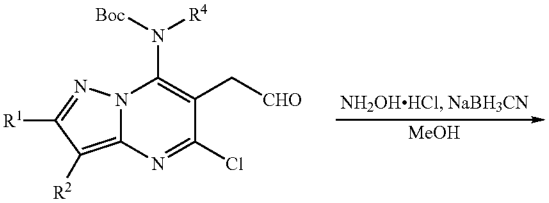

15

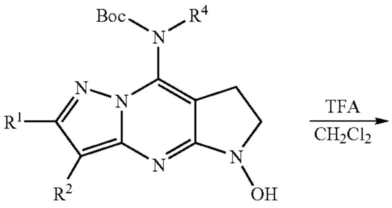

38

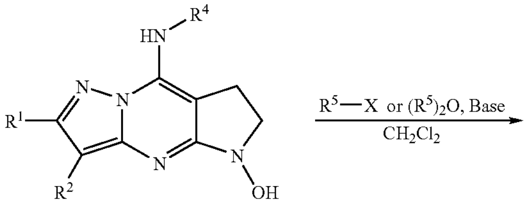

39

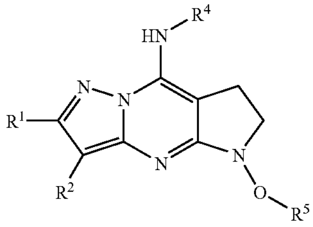

40

19) The compound represented by formula (40) can be obtained by reaction of the compound represented by formula (39) with an appropriate reagent (for example, acetic anhydride) in the presence of a base (for example, triethylamine) in an appropriate organic solvent (for example, methylene chloride) at a temperature ranging from 0° C. to 40° C.

20) The compound represented by formula (33) can be obtained by reaction of the compound represented by formula (32) with an allylating agent (for example, allyl bromide) in the presence of a base (for example, sodium hydride) in an appropriate organic solvent (for example, DMF, THF or DMF-THF mixed solvent) at a temperature ranging from 0° C. to 70° C.

21) The compound represented by formula (34) can be obtained by reaction of the compound represented by formula (33) with an olefin metathesis catalyst [for example, Grubbs catalyst, i.e., benzylidenebis(tricyclohexylphosphine)dichlororuthenium] in an appropriate organic solvent (for example, toluene) at a temperature ranging from 0° C. to 40° C. (Reference: Angew. Chem. Int. Ed., 2002, 41, 176)

22) The compound represented by formula (36) can be obtained by reaction of the compound represented by formula (34) with hydrogen in the presence of a palladium catalyst (for example, palladium-carbon) in an appropriate organic solvent (for example, methanol, ethanol or 1,4-dioxane-ethanol mixed solvent) at room temperature.

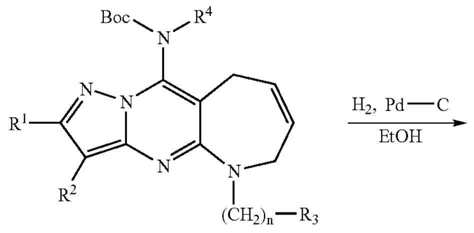

34

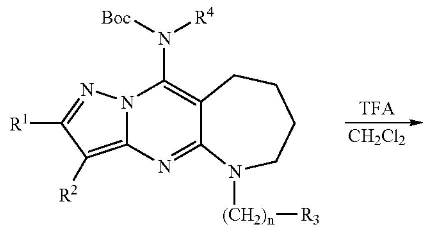

36

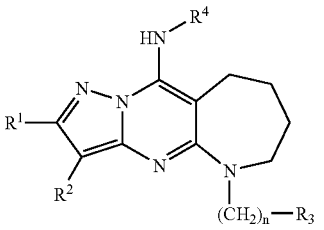

37

23) The compound represented by formula (44) can be obtained by reaction of the compound represented by formula (43) with an oxidizing agent [for example, Dess-Martin periodinane, i.e., 1,1,1-tris(acetyloxy)-1,1-dihydro-1,2-benziodoxol-3(1H)-one] in an appropriate organic solvent (for example, methylene chloride) at a temperature ranging from 0° C. to 40° C.

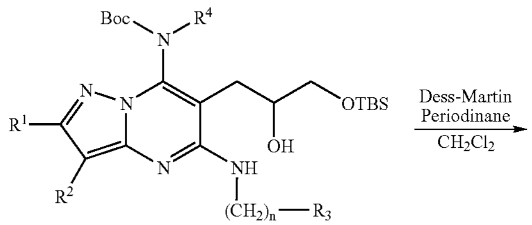

43

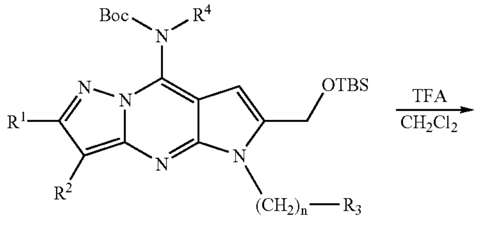

44

-continued

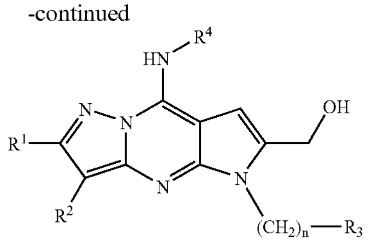

45

24) Each compound represented by formula (49) can be obtained by reaction of the corresponding compound represented by formula (32) with an oxidizing agent (for example, sodium periodate and osmium tetraoxide) in an appropriate solvent (for example, THF-water mixed solvent) at a temperature ranging from 0° C. to 40° C.

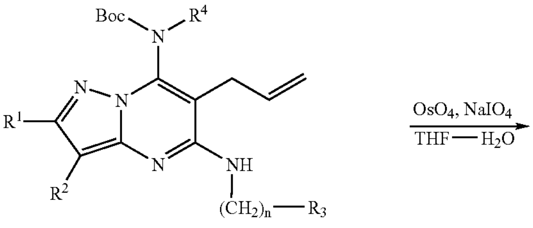

32

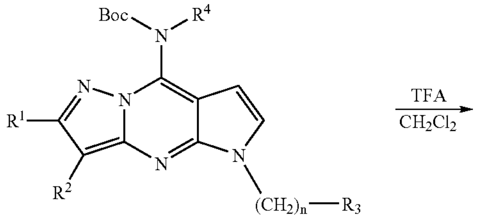

49

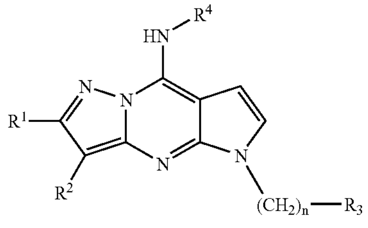

50

25) The compound represented by formula (52) or (53) can be obtained by reaction of the compound represented by formula (51) with a nucleophilic halogenatigen agent (for example, 1-chloromethyl-4-fluoro-1,4-diazobicyclo [2.2.2]octane bis(tetrafluoroborate), N-bromosuccinimide, or N-chlorosucciminde) in an appropriate organic solvent (for example, DMF, methylene chloride, or THF) at a temperature ranging from 0° C. to 40° C. (Reference: J. Chem. Soc. Perkin 1, 1996, 2069.)

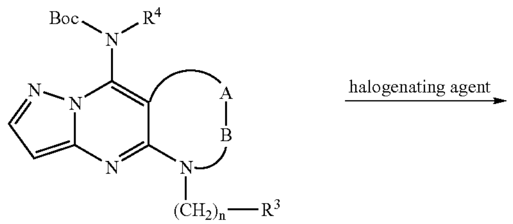

51

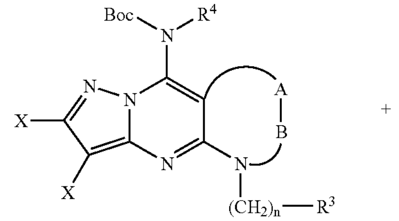

52

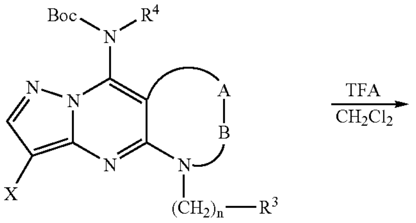

53

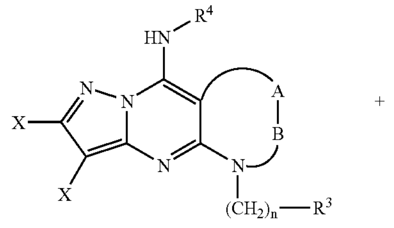

54

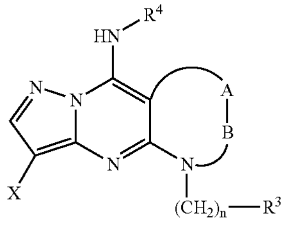

55

X = F, Cl, Br, I

26) The compound represented by formula (1) can be obtained by reaction of the compound represented by formula (2) with an acid (for example, trifluroacetic acid) in an appropriate organic solvent (for example, methylene chloride) at a temperature ranging from 0° C. to room temperature. (Reference: Protective Groups in Organic Synthesis, 3rd edition, John Wiley & Sons Inc.)

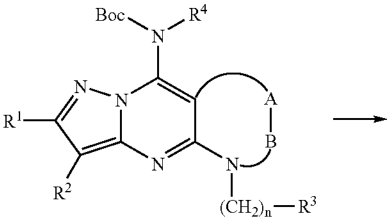

2

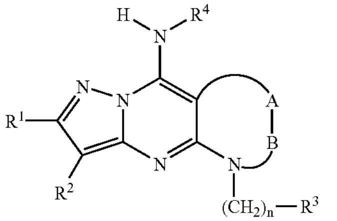

1

27) The compound represented by formula (45) or (48) can be obtained by reaction of the compound represented by formula (44) or (47), respectively, with an acid (for example, trifluroacetic acid) in an appropriate organic solvent (for example, methylene chloride) at a temperature ranging from 0° C. to room temperature.

A preparation comprising the compound of the present invention or a medically acceptable salt thereof as an active ingredient is prepared by using carriers, excipients or other additives usually used for formulation. As carriers and excipients used for formulation, either solid or liquid may be used, and for example, there may be mentioned lactose, magnesium stearate, starch, talc, gelatin, agar, pectin, gum arabic, olive oil, sesame oil, cacao butter, ethylene glycol and others conventionally used. The preparation may be administrated either orally as tablets, pills, capsules, granule, powder, liquid or the like or parenterally through injection such as an intravenous injection and an intramuscular injection, suppository, percutaneous administration or the like.

As diseases for which the MAPKAP-K2 inhibitor of the present invention is effective, there may be mentioned neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

As autoimmune diseases, specifically, there may be mentioned rheumatoid arthritis, ankylosing spondylitis, juvenile rheumatoid arthritis, psoriatic arthritis, graft-versus-host disease, diabetes mellitus or Crohn's disease.

The dose of the compound of the present invention is, although it varies depending on the kind of disease, the administration route, the age and sex of patient and the degree of disease, usually 1-500 mg/day for one adult.

EXAMPLES

The present invention will be explained with specific examples, although the present invention is not limited to these examples.

The compound number of each compound in the following examples corresponds to the compound number given to the compound mentioned as preferred example in Tables A to G.

The structures of novel compounds isolated were confirmed by $^1$H NMR and/or mass analysis measured on a single quadrupole instrumentation equipped with an electrospray source or other appropriate analytical methods.

For $^1$H NMR spectra (400 MHz, DMSO-$d_6$ or $CDCl_3$), chemical shifts (δ: ppm) and coupling constants (J: Hz) are shown. For results of mass analysis, M+H, that is, the measured value observed as the molecular mass of compound (M) with one proton (H) added, is shown. "HPLC retention time" represents the retention time (unit: min) of compound in HPLC analysis under the following analytical conditions.

Conditions for HPLC (High Performance Liquid Chromatography)

Instrumental system: Hewlett-Packard 1100HPLC

Column: Cadenza CD-C18 (Intact) 100 mm×4.6 mm (i.d.)

Column Temperature: 40° C.

[HPLC Condition A]

Solvent: A: $H_2O$/acetonitrile=95/5, 0.05% TFA (trifluoroacetic acid)

B: $H_2O$/acetonitrile=5/95, 0.05% TFA (trifluoroacetic acid)

Flow rate: 1.0 mL/min

Gradient:
0 to 1 min; Solvent B: 10%, Solvent A: 90%
1 to 13 min; Solvent B: 10% to 70%, Solvent A: 90% to 30%
13 to 14 min; Solvent B: 70% to 100%, Solvent A: 30% to 0%
14 to 16 min; Solvent B: 100%, Solvent A: 0%
16 to 19 min; Solvent B: 100% to 10%, Solvent A: 0% to 90%

[HPLC Condition B]

Solvent: A: $H_2O$/acetonitrile=95/5, 0.05% TFA (trifluoroacetic acid)

B: $H_2O$/acetonitrile=5/95, 0.05% TFA (trifluoroacetic acid)

Flow rate: 1.0 mL/min

Gradient:
0 to 1 min; Solvent B: 1%, Solvent A: 99%
1 to 13 min; Solvent B: 1% to 55%, Solvent A: 99% to 45%
13 to 14 min; Solvent B: 55% to 100%, Solvent A: 45% to 0%
14 to 16 min; Solvent B: 100%, Solvent A: 0%
16 to 19 min; Solvent B: 100% to 1%, Solvent A: 0% to 99%

Reference Example 1

Synthesis of 6-allyl-5,7-dichloropyrazolo[1,5-a]pyrimidine

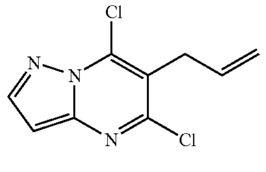

To an ethanolic solution (0.2 L) containing sodium ethoxide (7.8 g, 0.11 mol), 3-aminopyrazole (5.0 g, 0.6 mol) and diethyl allylmalonate (12 mL, 0.61 mol) were added at room temperature. The resultant mixture was heated under reflux for 24 hr. After the mixture was cooled down to room temperature, the solvent was distilled off. The residue was dissolved in water (150 mL) and the aqueous solution was washed with ethyl acetate. This aqueous layer was acidified by adding 6 mol/L hydrochloric acid, and the resultant precipitate was collected by filtration and dried under reduced pressure to obtain 6-allyl-5,7-dihydroxypyrazolo[1,5-a]pyrimidine (9.3 g).

The above dihydroxy compound was suspended in phosphoryl chloride (0.21 kg). After this suspension was stirred at 120° C. for 5 hr, the excessive phosphoryl chloride was distilled off. The residue was neutralized by adding aqueous sodium hydrogen carbonate, and the mixture was extracted with ethyl acetate. The combined ethyl acetate layer was washed with brine and dried over sodium sulfate. After the sodium sulfate was filtered off, the solvent was distilled off and the residue was purified with column chromatography (15% ethyl acetate-hexane) to obtain the title compound (5.2 g, yield 40% in two steps).

$^1$H NMR ($CDCl_3$, 400 MHz) δ(ppm): 8.19 (d, J=2.2 Hz, 1H), 6.72 (d, J=2.2 Hz, 1H), 5.98-5.88 (m, 1H), 5.20-5.13 (m, 2H), 3.72 (dt, J=6.1 and 1.6 Hz, 2H).

Reference Example 2

Synthesis of 2-(5,7-dichloropyrazolo[1,5-a]pyrimidin-6-yl)ethanol

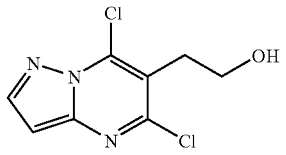

To a mixed solution of THF (24 mL) and water (6 mL) containing 6-allyl-5,7-dichloropyrazolo[1,5-a]pyrimidine (1.82 g, 7.89 mmol), sodium periodate (5.12 g, 23.9 mmol) and osmium tetraoxide (2.5w/v % in tert-butanol, 3 mL, 0.23 mmol) were added with ice-cooling. After this mixture was stirred at room temperature for 3 hr, aqueous sodium sulfite was added here. The resultant mixture was extracted with ethyl acetate and the organic layer was washed with aqueous sodium hydrogen carbonate and then brine and dried over sodium sulfate. After the sodium sulfate was filtered off, the solvent was distilled off to obtain 5,7-dichloro-6-(2-oxoethyl)pyrazolo[1,5-a]pyrimidine.

The above aldehyde (1.82 mmol) was dissolved in methanol (27 mL), and sodium borohydride (302 mg, 7.98 mmol) was added to this solution with ice-cooling. After this mixture was stirred for 30 min, aqueous ammonium chloride was added here. The resultant mixture was extracted with ethyl acetate, and the organic layer was washed with brine and dried over sodium sulfate. After the sodium sulfate was filtered off, the solvent was distilled off, and the residue was purified with column chromatography (15% ethyl acetate-hexane) to obtain the title compound (617 mg).

$^1$H NMR ($CDCl_3$, 400 MHz) δ(ppm): 8.17 (d, J=2.2 Hz, 1H), 6.70 (d, J=1.9 Hz, 1H), 3.90 (t, 2H), 3.21 (t, 2H).

Reference Example 3

Synthesis of 6-[2-(tert-butyldimethylsilanyloxy) ethyl]-5,7-dichloropyrazolo[1,5-a]pyrimidine

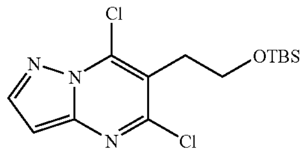

To a methylene chloride (50 mL) solution containing 2-(5,7-dichloropyrazolo[1,5-a]pyrimidin-6-yl)ethanol (640 mg, 2.77 mmol), triethylamine (3.86 mL, 27.7 mmol) and tert-butylchlorodimethylsilane (1.25 g, 8.31 mmol) were added, and this mixture was stirred at room temperature for 16 hr. After the reaction, aqueous ammonium chloride was added to the reaction solution, and the mixture was extracted with ethyl acetate. The combined ethyl acetate layer was washed with saturated aqueous sodium hydrogen carbonate and then brine and dried over sodium sulfate. After the sodium sulfate was filtered off, the solvent was distilled off and the residue was purified with column chromatography (15% ethyl acetate-hexane) to obtain the title compound (1.04 g).

$^1$H NMR ($CDCl_3$, 400 MHz) δ(ppm): 8.17 (s, J=2.4 Hz, 1H), 6.70 (d, J=2.2 Hz, 1H), 3.91 (dd, J=13.2 and 6.3 Hz, 2H), 3.24-3.19 (m, 2H), 0.84 (s, 9H), 0.00 (s, 6H).

Reference Example 4

Synthesis of 3-(5,7-dichloropyrazolo[115-a]pyrimidin-6-yl)propan-1-ol

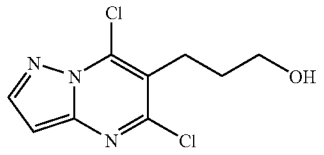

To a tetrahydrofuran (85 mL) solution containing 6-allyl-5,7-dichloropyrazolo[1,5-a]pyrimidine (5.8 g, 25 mmol), borane-dimethyl sulfide complex (2 mol/L tetrahydrofuran solution, 20 mL, 41 mmol) was added with ice-cooling over 30 min. This mixture was stirred at room temperature for 1 hr and again cooled on ice. Here, aqueous sodium hydroxide (1 mol/L, 40 mL) was added over 20 min, and hydrogen peroxide (30% aqueous solution, 3 mL) was further added, and the mixture was stirred for 1 hr. After the reaction, the mixture was extracted with ethyl acetate. The ethyl acetate layer was washed with brine and dried over sodium sulfate. After the sodium sulfate was filtered off, the solvent was distilled off and the residue was purified with column chromatography (25 to 50% ethyl acetate-hexane) to obtain the title compound (3.4 g, yield 31%).

Reference Example 5

Synthesis of {6-[2-(tert-butyldimethylsilanyloxy) ethyl]-5-chloropyrazolo[1,5-a]pyrimidin-7-yl}[4-(2-methoxyethoxy)phenyl]amine

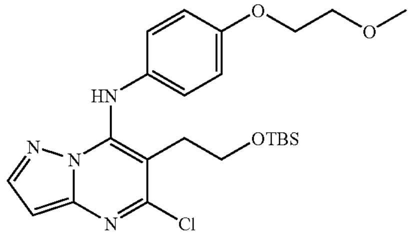

To an isopropanol (3.0 mL) solution containing 6-[2-(tert-butyldimethylsilanyloxy)ethyl]-5,7-dichloropyrazolo[1,5-a] pyrimidine (512 mg, 1.49 mmol), triethylamine (836 μL, 5.96 mmol) and 4-(2-methoxyethoxy)phenylamine (299 mg, 1.79 mmol) were added, and this mixture was heated at 85° C. with stirring. After the reaction, the solvent was concentrated, sodium hydrogen carbonate was added here, and the mixture was extracted with ethyl acetate. The combined ethyl acetate layer was dried over sodium sulfate. After the sodium sulfate was filtered off, the solvent was distilled off to obtain the title compound.

Reference Example 6

Synthesis of tert-butyl {6-[2-(tert-butyldimethylsilanyloxy)ethyl]-5-chloropyrazolo[1,5-a]pyrimidin-7-yl}[4-(2-methoxyethoxy)phenyl]carbamate

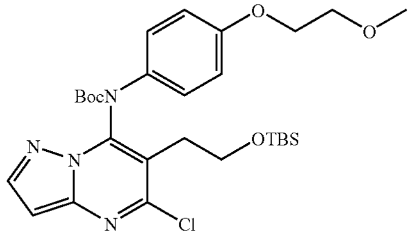

To a 1,4-dioxane (7.0 mL) solution containing {6-[2-(tert-butyldimethylsilanyloxy)ethyl]-5-chloropyrazolo[1,5-a]pyrimidin-7-yl}[4-(2-methoxyethoxy)phenyl]amine (570 mg, 1.20 mmol), di-tert-butyl dicarbonate (515 μL, 2.24 mmol) and N,N-dimethylaminopyridine (35.2 mg, 0.29 mmol) were added, and this mixture was stirred with heating at 40° C. After the reaction, the solvent was concentrated, sodium hydrogen carbonate was added here, and the mixture was extracted with methylene chloride. The combined methylene chloride layer was washed with brine and dried over sodium sulfate. After the sodium sulfate was filtered off, the filtrate was concentrated to obtain the residue, which was used for the subsequent reaction without purification.

Reference Example 7

Synthesis of tert-butyl (S)-3-{7-{tert-butoxycarbonyl-[4-(2-methoxyethoxy)phenyl]amino}-6-[2-(tert-butyldimethylsilanyloxy)ethyl]pyrazolo[1,5-a]pyrimidin-5-ylamino}piperidine-1-carboxylate

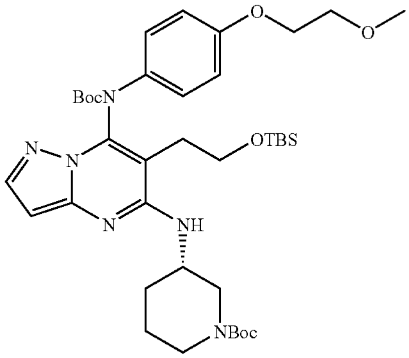

To an acetonitrile (5 mL) solution containing tert-butyl {6-[2-(tert-butyldimethylsilanyloxy)ethyl]-5-chloropyrazolo[1,5-a]pyrimidin-7-yl}[4-(2-methoxyethoxy)phenyl] carbamate (570 mg, 1.20 mmol), (S)-3-amino-1-tert-butoxycarbonylpiperidine (1.51 g) was added, and this mixture was stirred at 85° C. for 48 hr. The reaction solution was concentrated, and the residue was purified with column chromatography (35% ethyl acetate-hexane) to obtain the title compound (204 mg).

Reference Example 8

Synthesis of tert-butyl (S)-3-[7-{tert-butoxycarbonyl-[4-(2-methoxyethoxy)phenyl]amino}-6-(2-hydroxyethyl)pyrazolo[1,5-a]pyrimidin-5-ylamino] piperidine-1-carboxylate

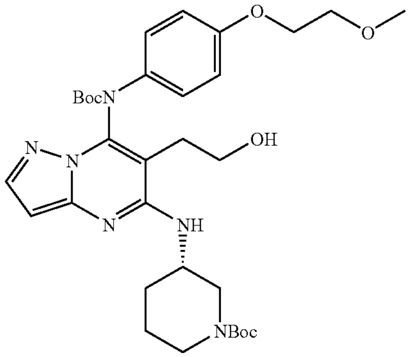

To a tetrahydrofuran (5 mL) solution containing tert-butyl (S)-3-{7-{tert-butoxycarbonyl-[4-(2-methoxyethoxy)phenyl]amino}-6-[2-(tert-butyldimethylsilanyloxy)ethyl]pyrazolo[1,5-a]pyrimidin-5-ylamino}piperidine-1-carboxylate (193 mg, 0.261 mmol), tetrabutylammonium fluoride (474 µL, 0.474 mmol) was added, and this mixture was stirred at room temperature for 1.5 hr. After the reaction, aqueous ammonium chloride was added to the reaction solution, and the mixture was extracted with ethyl acetate. The combined ethyl acetate layer was dried over sodium sulfate. After the sodium sulfate was filtered off, the filtrate was concentrated to obtain the title compound (233 mg).

Reference Example 9

Synthesis of tert-butyl (S)-3-[7-{tert-butoxycarbonyl-[4-(2-methoxyethoxy)phenyl]amino}-6-(2-methanesulfonyloxyethyl)pyrazolo[1,5-a]pyrimidin-5-ylamino]piperidine-1-carboxylate

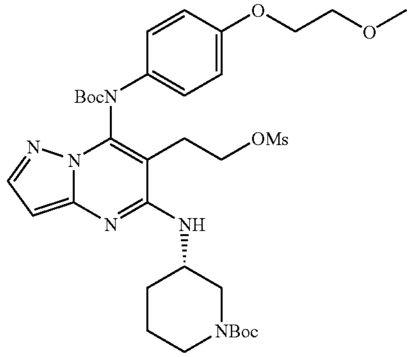

To a methylene chloride (5 mL) solution containing tert-butyl (S)-3-[7-{tert-butoxycarbonyl-[4-(2-methoxyethoxy) phenyl]amino}-6-(2-hydroxyethyl)pyrazolo[1,5-a]pyrimidin-5-ylamino]piperidine-1-carboxylate (216 mg, 0.345 mmol), triethylamine (480 µL, 3.45 mmol) and methanesulfonyl chloride (80 µL, 1.04 mmol) were added, and this mixture was stirred at room temperature for 30 min. After the reaction, aqueous ammonium chloride was added to the reaction solution, and the mixture was extracted with methylene chloride. The combined methylene chloride layer was dried over sodium sulfate. After the sodium sulfate was filtered off, the filtrate was concentrated to obtain the title compound (258 mg).

Reference Example 10

Synthesis of tert-butyl {5-(4-tert-butoxycarbonylaminocyclohexylamino)-6-[2-(tert-butyldimethylsilanyloxy)ethyl]pyrazolo[1,5-a]pyrimidin-7-yl}-(4-ethoxyphenyl)carbamate

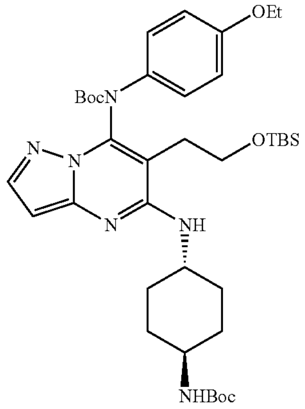

To a methylene chloride solution (0.5 mL) of tert-butyl {5-(4-aminocyclohexylamino)-6-[2-(tert-butyldimethylsilanyloxy)ethyl]pyrazolo[1,5-a]pyrimidin-7-yl}-(4-ethoxyphenyl)carbamate (50 mg, 0.08 mmol), triethylamine (33 μL, 0.24 mmol), di-tert-butyl dicarbonate (32 mg, 0.16 mmol) and 4-N,N-dimethylaminopyridine (2 mg, 0.02 mmol) were added and the mixture was stirred at room temperature. After the reaction, aqueous ammonium chloride solution was added to the reaction solution and the mixture was extracted with ethyl acetate. The combined ethyl acetate layer was washed with brine and dried over sodium sulfate. The sodium sulfate was filtered off and the filtrate was concentrated to obtain the title compound.

Example 1

Synthesis of tert-butyl (S)-3-(8-{tert-butoxycarbonyl-[4-(2-methoxyethoxy)phenyl]amino}-6,7-dihydro-1,4,5,8a-tetraaza-s-indacen-5-yl)piperidine-1-carboxylate

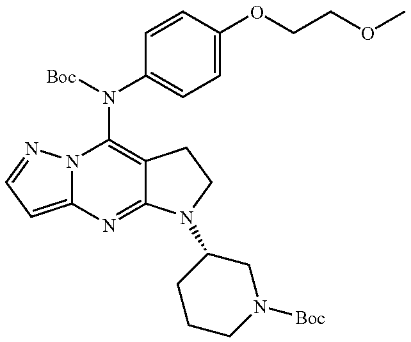

To a mixed solution of tetrahydrofuran (5 mL) and N,N-dimethylformamide (1.8 mL) containing tert-butyl (S)-3-[7-f{tert-butoxycarbonyl-[4-(2-methoxyethoxy)phenyl]amino}-6-(2-methanesulfonyloxyethyl)pyrazolo[1,5-a]pyrimidin-5-ylamino]piperidine-1-carboxylate (162 mg, 0.231 mmol), sodium hydride (with 40% mineral oil added) (22 mg, 0.55 mmol) was added, and this mixture was stirred at room temperature for 30 min. After the reaction, aqueous ammonium chloride was added to the reaction solution, and the mixture was extracted with methylene chloride. The combined methylene chloride layer was dried over sodium sulfate. After the sodium sulfate was filtered off, the filtrate was concentrated to obtain the title compound.

HPLC retention time (HPLC condition A): 15.42 min

ESI/MS: 610.15 (M+H, $C_{32}H_{44}N_6O_8$)

Example 2

Synthesis of tert-butyl (S)-3-{8-[tert-butoxycarbonyl-(2-methylbenzothiazol-6-yl)amino]-6,7-dihydro-1,4,5,8a-tetraaza-s-indacen-5-yl}piperidine-1-carboxylate

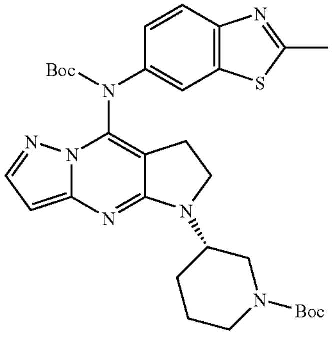

The title compound was synthesized using tert-butyl (S)-3-[7-{tert-butoxycarbonyl-(2-methylbenzothiazol-6-yl)amino}-6-(2-methanesulfonyloxyethyl)pyrazolo[1,5-a]pyrimidin-5-ylamino]piperidine-1-carboxylate by the same method as Example 1.

HPLC retention time (HPLC condition A): 15.55 min

ESI/MS: 606.10 (M+H, $C_{31}H_{39}N_7O_4S_1$)

Reference Example 11

Synthesis of (6-ally-5-chloropyrazolo[1,5-a]pyrimidin-7-yl)(4 ethoxyphenyl)amine

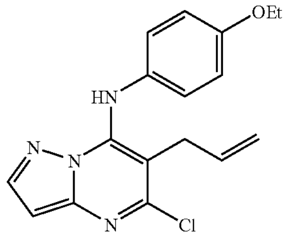

To an isopropanol (52 mL) solution containing 6-allyl-5,7-dichloropyrazolo[1,5-a]pyrimidine (5.98 g), triethylamine (12.7 mL) and phenethidine (4.30 g) were added, and this mixture was stirred at 40° C. for 5 hr. After the reaction, the solvent was distilled off. Saturated aqueous sodium hydrogen carbonate was added to the residue, and the mixture was extracted with ethyl acetate. The combined ethyl acetate layer was dried over sodium sulfate. After the sodium sulfate was filtered off, the filtrate was concentrated to obtain the title compound (8.62 g).

Reference Example 12

Synthesis of 3-[5-chloro-7-(4-ethoxyphenylamino)pyrazolo[1,5-a]pyrimidin-6-yl]propan-1-ol

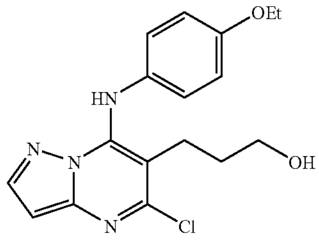

To an isopropanol (3 mL) solution containing 3-(5,7-dichloropyrazolo[1,5-a]pyrimidin-6-yl)propan-1-ol (224 mg, 0.910 mmol), triethylamine (253 μL, 1.82 mmol) and phenethidine (128 μL, 1.00 mmol) were added, and this mixture was stirred at 40° C. for 5 hr. After the reaction, the solvent was distilled off, aqueous sodium hydrogen carbonate was added to the residue, and the mixture was extracted with ethyl acetate. The combined ethyl acetate layer was dried over sodium sulfate. After the sodium sulfate was filtered off, the filtrate was concentrated and the residue was purified with column chromatography (30% ethyl acetate-hexane) to obtain the title compound (212 mg).

$^1$H NMR ($CDCl_3$, 400 MHz) δ(ppm): 8.17 (s, 1H), 7.98 (d, J=2.2 Hz, 2H), 7.17(d, J=8.3 Hz, 2H), 6.91 (d, J=8.8 Hz, 2H), 6.48 (d, J=2.2 Hz, 1H), 4.05 (q, J=7.1 Hz, 2H), 3.33 (t, J=6.3 Hz, 2H), 2.49 (m, 2H), 1.59 (m, 2H), 1.44 (t, J=7.1 Hz, 2H).

Reference Example 13

Synthesis of {6-[3-(tert-butyldimethylsilanyloxy)propyl]-5-chloropyrazolo[1,5-a]pyrimidin-7-yl}(4-ethoxyphenyl)amine

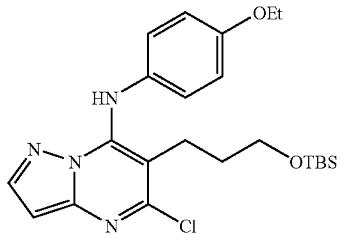

To a methylene chloride (14 mL) solution containing [6-(3-hydroxypropyl)-5-chloropyrazolo[1,5-a]pyrimidin-7-yl](4-ethoxyphenyl)amine (1.43 g, 4.12 mmol), triethylamine (861 μL, 6.18 mmol) and tert-butylchlorodimethylsilane (808 mg, 5.36 mmol) were added with ice-cooling, and this mixture was stirred at room temperature for 16 hr. After the reaction, 1 mol/L hydrochloric acid was added to the reaction solution, and the mixture was extracted with ethyl acetate. The ethyl acetate layer was washed with aqueous sodium hydrogen carbonate and then brine and dried over sodium sulfate. After the sodium sulfate was filtered off, the filtrate was concentrated and the residue was purified with column chromatography (10 to 15% ethyl acetate-hexane) to obtain the title compound (2.03 g, yield 100%).

$^1$H NMR ($CDCl_3$, 400 MHz) δ(ppm): 8.08 (s, 1H), 7.98 (d, J=2.2 Hz, 1H), 7.16 (d, J=8.8 Hz, 2H), 6.90 (d, J=8.8 Hz, 2H), 6.47 (d, J=2.4 Hz, 1H), 4.04 (q, J=7.1 Hz, 2H), 3.30 (t, J=6.3 Hz, 2H), 2.45 (m, 2H), 1.56 (s, 9H), 1.55 (m, 2H), 1.44 (t, J=7.1 Hz, 3H), 0.84 (s, 9H), −0.03 (s, 9H).

Reference Example 14

Synthesis of tert-butyl (6-allyl-5-chloropyrazolo[1,5-a]pyrimidin-7-yl) (4-ethoxyphenyl)carbamate

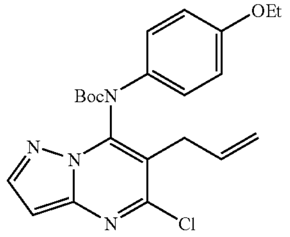

To a 1,4-dioxane (130 mL) solution containing (6-allyl-5-chloropyrazolo[1,5-a]pyrimidin-7-yl)(4-ethoxyphenyl)amine (8.62 g), di-tert-butoxycarboxylate (11.4 g) and N,N-dimethylaminopyridine (0.80 g) were added, and this mixture was stirred at room temperature for 2 hr. After the reaction, the solvent was distilled off, and the residue was purified with column chromatography (10% ethyl acetate-hexane) to obtain the title compound (10.49 g, yield 93%).

$^1$H NMR ($CDCl_3$, 400 MHz) δ(ppm): 8.16 (s, 1H), 7.18 (d, J=9.0 Hz, 2H), 6.83 (d, J=8.9 Hz, 2H), 6.69 (d, J=2.2 Hz, 1H), 5.64 (s, 1H), 5.00 (td, J=15.4 and 4.2 Hz, 2H), 3.99 (q, J=7.1 Hz, 2H), 3.44 (m, 2H), 1.39 (t, J=7.1 Hz, 3H), 1.26 (s, 9H).

Reference Example 15

Synthesis of tert-butyl[5-chloro-6-(2-oxoethyl)pyrazolo[1,5-a]pyrimidin-7-yl](4-ethoxyphenyl)carbamate

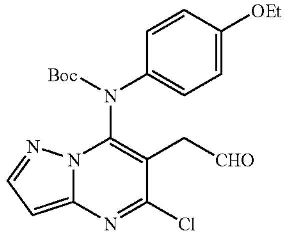

To a mixed solution of tetrahydrofuran (12 mL) and water (3 mL) containing tert-butyl (6-allyl-5-chloropyrazolo[1,5-a]pyrimidin-7-yl)(4-ethoxyphenyl)carbamate (1.5 g, 3.5 mmol), sodium periodate (2.3 g, 10.5 mmol) and osmium tetraoxide (2.5w/v % in tert-butanol, 1.8 mL, 0.15 mmol) were added with ice-cooling. After the reaction mixture was stirred at room temperature for 5 hr, aqueous sodium sulfite was added here, and the mixture was extracted with ethyl acetate. The organic layer was washed with aqueous sodium hydrogen carbonate and then brine, and dried over sodium sulfate. After the sodium sulfate was filtered off, the solvent was distilled off, and the residue was purified with column chromatography (20% ethyl acetate-hexane) to obtain the title compound (895 mg, 2.08 mmol, yield 59%). $^1$H NMR ($CDCl_3$, 400 MHz) δ(ppm): 9.44 (s, 1H), 8.19 (s, 1H), 7.14 (dt, J=9.8 and 2.9 Hz, 2H), 6.81 (d, J=6.8 Hz, 2H), 6.73 (d, J=2.2 Hz, 1H), 3.98 (q, J=7.1 Hz, 2H), 3.84 (d, J=37.3 Hz, 1H), 1.56 (s, 2H), 1.38 (t, J=7.1 Hz, 3H).

Reference Example 16

Synthesis of {7-[tert-butoxycarbonyl-(4-ethoxyphenyl)amino]-5-chloropyrazolo[1,5-a]pyrimidin-6-yl}acetic acid

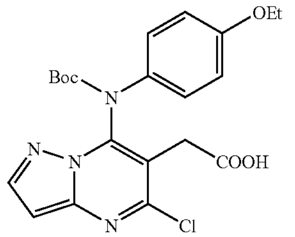

To a mixed solution of water (0.5 mL) and tert-butanol (5 mL) containing tert-butyl [5-chloro-6-(2-oxoethyl)pyrazolo[1,5-a]pyrimidin-7-yl](4-ethoxyphenyl)carbamate (431 mg, 1.0 mmol), sodium dihydrogen phosphate (1.56 g, 10 mmol), 2-methyl-2-butene (1.1 mL, 10 mmol) and sodium chlorite (181 mg, 2.0 mmol) were added, and this mixture was stirred at room temperature for 4 hr. After the reaction, water was added to the reaction solution, and the mixture was extracted with ethyl acetate. The organic layer was dried over sodium sulfate. After the sodium sulfate was filtered off, the solvent was distilled off to obtain the title compound (468 mg).

Reference Example 17

Synthesis of tert-butyl[5-chloro-6-(3-oxopropyl)pyrazolo[1,5-a]pyrimidin-7-yl](4-ethoxyphenyl)carbamate

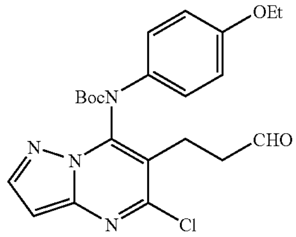

To a methylene chloride (1.7 mL) solution containing tert-butyl[5-chloro-6-(3-hydroxypropyl)pyrazolo[1,5-a]pyrimidin-7-yl](4-ethoxyphenyl)carbamate (155 mg, 0.346 mmol), Dess-Martin periodinane (152 mg, 0.381 mmol) was added with ice-cooling, and this mixture was stirred at room temperature for 16 hr. The reaction mixture was filtered through celite and the filtrate was concentrated. The residue was purified with column chromatography (10 to 20% ethyl acetate-hexane) to obtain the title compound (117 mg, yield 76%).

$^1$H NMR ($CDCl_3$, 400 MHz) δ(ppm): 9.68 (s, 1H), 8.16 (s, 1H), 7.15 (d, J=9.0 Hz, 2H), 6.81 (d, J=9.0 Hz, 2H), 6.69 (d, J=1.9 Hz, 1H), 3.98 (q, J=6.8 Hz, 2H), 3.03 (m, 2H), 2.69 (m, 1H), 1.97 (m, 1H), 1.39 (t, 3H), 1.26 (s, 9H).

Reference Example 18

Synthesis of tert-butyl {6-[3-(tert-butyldimethylsilanyloxy)propyl]-5-chloropyrazolo[1,5-a]pyrimidin-7-yl}(4-ethoxyphenyl)carbamate

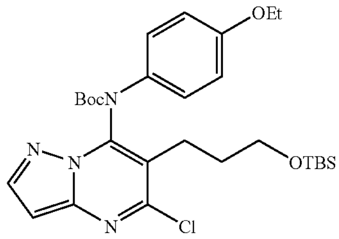

To a 1,4-dioxane (13 mL) solution containing {6-[3-(tert-butyldimethylsilanyloxy)propyl]-5-chloropyrazolo[1,5-a]pyrimidin-7-yl}(4-ethoxyphenyl)amine (1.89 g, 4.12 mmol), were added triethylamine (861 μL, 6.18 mmol), di-tert-butyl dicarbonate (1.08 g, 4.84 mmol) and N,N-dimethylaminopyridine (50.3 mg, 0.412 mmol), and this mixture was stirred at room temperature for 2 hr. After the reaction, aqueous ammonium chloride was added to the reaction solution, and the mixture was extracted with ethyl acetate. The combined ethyl acetate layer was washed with aqueous sodium hydrogen carbonate and then brine and dried over sodium sulfate. After the sodium sulfate was filtered off, the solvent was distilled off and the residue was purified with column chromatography (10% ethyl acetate-hexane) to obtain the title compound (2.03 g).

$^1$H NMR ($CDCl_3$, 400 MHz) δ(ppm): 8.13 (d, J=2.0 Hz, 1H), 7.20 (d, J=9.0 Hz, 2H), 6.80 (d, J=8.8 Hz, 2H), 6.66 (d, J=2.2 Hz, 1H), 3.98 (q, J=7.1 Hz, 2H), 3.62 (m, 2H), 2.77 (m, 2H), 1.74 (m, 1H), 1.48 (m, 1H), 1.38 (t, J=7.1 Hz, 3H), 1.26 (s, 9H), 0.91 (s, 9H), 0.064 (s, 6H).

Reference Example 19

Synthesis of tert-butyl[5-chloro-6-(3-hydroxypropyl)pyrazolo[1,5-a]pyrimidin-7-yl](4-ethoxyphenyl)carbamate

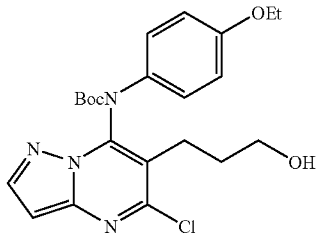

To a tetrahydrofuran (23 mL) solution containing tert-butyl (6-allyl-5-chloropyrazolo[1,5-a]pyrimidin-7-yl)(4-ethoxyphenyl)carbamate (3.0 g, 7.0 mmol), borane-dimethyl sulfide complex (2 mol/L tetrahydrofuran solution, 5.6 mL, 23 mmol) was added over 30 min with ice-cooling. This mixture was stirred at room temperature for 2 hr and then again cooled on ice. Here, 1 mol/L aqueous sodium hydroxide (11.2 mL, 11.2 mmol) was added over 20 min, and hydrogen peroxide (30% aqueous solution, 0.81 mL, 8.4 mmol) was added. The resultant mixture was stirred for 1 hr. After the reaction, the reaction mixture was extracted with ethyl acetate. The combined ethyl acetate layer was washed with brine and dried over sodium sulfate. After the sodium sulfate was filtered off, the solvent was distilled off and the residue was purified with column chromatography (20% ethyl acetate-hexane) to obtain the title compound (2.02 g, yield 65%).

$^1$H NMR ($CDCl_3$, 400 MHz) δ(ppm): 8.15 (s, 1H), 7.19 (d, J=8.3 Hz, 2H), 6.82 (d, J=8.3 Hz, 2H), 6.68 (d, J=2.2 Hz, 1H), 3.99 (q, J=7.0 Hz, 2H), 3.64 (J=6.0 Hz, 2H), 2.79 (s, 2H), 1.39 (t, J=7.0 Hz, 3H), 1.26 (s, 9H).

Reference Example 20

Synthesis of tert-butyl[5-chloro-6-(2-hydroxyethyl)pyrazolo[1,5-a]pyrimidin-7-yl](4-ethoxyphenyl)carbamate

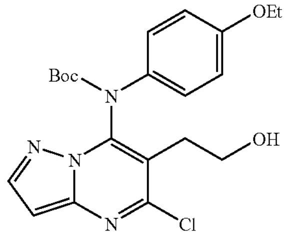

To a mixed solution of tetrahydrofuran (12 mL) and water (3 mL) containing tert-butyl (6-allyl-5-chloropyrazolo[1,5-a]pyrimidin-7-yl)(4-ethoxyphenyl)carbamate (1.5 g, 3.5 mmol), sodium periodate (2.3 g, 10.5 mmol) and osmium tetraoxide (2.5w/v % in tert-butanol, 1.8 mL, 0.15 mmol) were added with ice-cooling. After this mixture was stirred at room temperature for 5 hr, aqueous sodium sulfite was added here. The resultant mixture was extracted with ethyl acetate. The organic layer was washed with aqueous sodium hydrogen carbonate and then brine and dried over sodium sulfate. After the sodium sulfate was filtered off, the solvent was distilled off to obtain tert-butyl[5-chloro-6-(2-oxoethyl)pyrazolo[1,5-a]pyrimidin-7-yl](4-ethoxyphenyl)carbamate.

The above product was dissolved in methanol (6 mL) and sodium borohydride (0.14 g, 3.5 mmol) was added to this solution with ice-cooling. After the reaction mixture was stirred for 30 min, aqueous ammonium chloride was added here. The mixture was extracted with ethyl acetate, and the organic layer was washed with brine and dried over sodium sulfate. After the sodium sulfate was filtered off, the solvent was distilled off and the residue was purified with column chromatography (15% ethyl acetate-hexane) to obtain the title compound (1.0 g).

$^1$H NMR ($CDCl_3$, 400 MHz) δ(ppm): 8.17 (s, 1H), 7.20 (d, J=8.8 Hz, 2H), 6.83 (d, J=8.0 Hz, 2H), 6.70 (d, J=2.2 Hz, 1H), 3.99 (q, J=7.0 Hz, 2H), 3.80 (br, 1H), 3.58 (br, 1H), 3.00 (br, 2H), 1.61 (s, 9H), 1.39 (t, J=6.8 Hz, 3H).

Reference Example 21

Synthesis of tert-butyl[5-chloro-6-(2,3-dihydroxypropyl)pyrazolo[1,5-a]pyrimidin-7-yl](4-ethoxyphenyl)carbamate

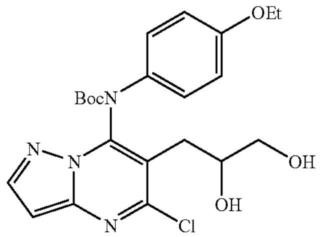

To a mixed solution of acetone (11 mL) and water (22 mL) containing tert-butyl (6-allyl-5-chloropyrazolo[1,5-a]pyrimidin-7-yl)(4-ethoxyphenyl)carbamate (1.0 g, 2.33 mmol), N-methylmorpholine-N-oxide (327 mg, 2.79 mmol) and osmium tetraoxide (2.5w/v % in tert-butanol, 1.46 mL, 0.116 mmol) were added with ice-cooling. The mixture was allowed to warm to room temperature and stirred for 16 hr. After the reaction, aqueous sodium sulfite was added here, and the mixture was extracted with ethyl acetate. The combined ethyl acetate layer was washed with brine and dried over sodium sulfate. After the sodium sulfate was filtered off, the solvent was distilled off and the residue was purified with column chromatography (50% ethyl acetate-hexane) to obtain the title compound (947 mg).

Reference Example 22

Synthesis of tert-butyl {6-[3-(tert-butyldimethylsilanyloxy)-2-hydroxypropyl]-5-chloropyrazolo[1,5-a]pyrimidin-7-yl}(4-ethoxyphenyl)carbamate

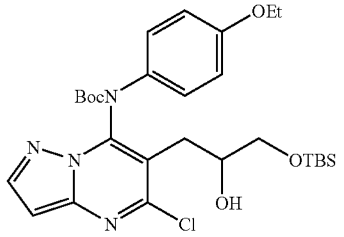

To a methylene chloride (3.6 mL) solution containing tert-butyl[5-chloro-6-(2,3-dihydroxypropyl)pyrazolo[1,5-a]pyrimidin-7-yl](4-ethoxyphenyl)carbamate (500 mg, 1.08 mmol), triethylamine (300 μL, 2.16 mmol), tert-butylchlorodimethylsilane (195 mg, 1.30 mmol) and N,N-dimethylpyridine (13 mg, 0.108 mmol) were added. After the reaction mixture was stirred at room temperature for 5 hr, 1 mol/L hydrochloric acid was added here, and the mixture was extracted with ethyl acetate. The combined ethyl acetate layer was washed with aqueous sodium hydrogen carbonate and then brine and dried over sodium sulfate. After the sodium sulfate was filtered off, the solvent was distilled off and the residue was purified with column chromatography to obtain the title compound (503 mg).

Reference Example 23

Synthesis of tert-butyl (S)-3-[7-[tert-butoxycarbonyl-(4-ethoxyphenyl)amino]-6-(2-hydroxyethyl)pyrazolo[1,5-a]pyrimidin-5-ylamino]piperidine-1-carboxylate

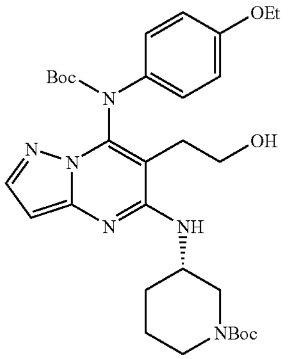

A mixture of tert-butyl[5-chloro-6-(2-hydroxyethyl)pyrazolo[1,5-a]pyrimidin-7-yl](4-ethoxyphenyl)carbamate (300 mg) and (S)-3-amino-1-tert-butoxycarbonylpiperidine (900 mg) was stirred at 90° C. for 16 hr. To the reaction solution, 1 mol/L hydrochloric acid was added, and the mixture was extracted with ethyl acetate. The ethyl acetate layer was washed with aqueous sodium hydrogen carbonate and then brine and dried over sodium sulfate. After the sodium sulfate was filtered off, the solvent was distilled off to obtain the title compound.

Reference Example 24

Synthesis of tert-butyl (S)-3-[7-[tert-butoxycarbonyl-(4-ethoxyphenyl)amino]-6-(3-hydroxypropyl)pyrazolo[1,5-a]pyrimidin-5-ylamino]piperidine-1-carboxylate

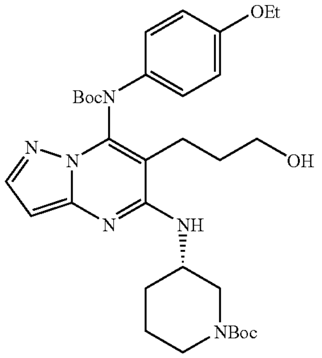

To a tetrahydrofuran (1.3 mL) solution containing tert-butyl (S)-3-[7-[tert-butoxycarbonyl-(4-ethoxyphenyl)amino]-6-(3-tert-butyldimethylsiloxypropyl)pyrazolo[1,5-a]pyrimidin-5-ylamino]piperidine-1-carboxylate (13.3 mg), was added tetrabutylammonium fluoride (1 mol/L tetrahydrofuran solution, 26 μL), and the mixture was stirred at room temperature for 3 hr. After the reaction, the mixture was purified with PTLC (50% ethyl acetate-hexane) to obtain the title compound (7.7 mg).

Reference Example 25

Synthesis of tert-butyl (S)-3-[7-[tert-butoxycarbonyl-(4-ethoxyphenyl)amino]-6-(2-methanesulfonyloxyethyl)pyrazolo[1,5-a]pyrimidin-5-ylamino]piperidine-1-carboxylate

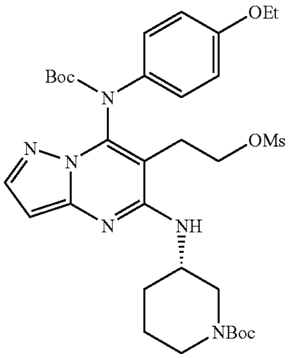

To a methylene chloride (2 mL) solution containing tert-butyl (S)-3-[7-[tert-butoxycarbonyl-(4-ethoxyphenyl)amino]-6-(2-hydroxyethyl)pyrazolo[1,5-a]pyrimidin-5-ylamino]piperidine-1-carboxylate (0.693 mmol), triethylamine (290 μL, 2.08 mmol) and methanesulfonyl chloride (80 μL, 1.04 mmol) were added with ice-cooling, and the mixture was stirred for 30 min. After the reaction, 1 mol/L hydrochloric acid was added to the reaction solution, and the mixture was extracted with ethyl acetate. The organic layer was washed with aqueous sodium hydrogen carbonate and then brine and dried over sodium sulfate. After the sodium sulfate was filtered off, the solvent was distilled off to obtain the title compound.

Example 3

Synthesis of tert-butyl (S)-3-{8-[tert-butoxycarbonyl-(4-ethoxyphenyl)amino]-6,7-dihydro-1,4,5,8a-tetraaza-s-indacen-5-yl}piperidine-1-carboxylate

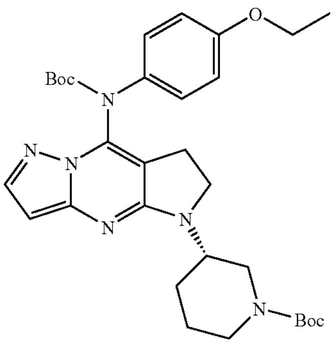

To a mixed solution of tetrahydrofuran (3 mL) and N,N-dimethylformamide (1 mL) containing tert-butyl (S)-3-[7-

[tert-butoxycarbonyl-(4-ethoxyphenyl)amino]-6-(2-methanesulfonyloxyethyl)pyrazolo[1,5-a]pyrimidin-5-ylamino]piperidine-1-carboxylate (0.693 mmol), sodium hydride (with 40% mineral oil added) (55 mg) was added with ice-cooling, and the mixture was stirred for 2 hr. After the reaction, water was added to the reaction solution, and the mixture was extracted with ethyl acetate. The ethyl acetate layer was washed with brine and dried over sodium sulfate. After the sodium sulfate was filtered off, the solvent was distilled off to obtain the title compound.

HPLC retention time (HPLC condition A): 15.92 min

ESI/MS: 579.20 (M+H, $C_{31}H_{42}N_6O_5$)

Reference Example 26

Synthesis of tert-butyl (S)-3-(2-{7-[tert-butoxycarbonyl-(4-ethoxyphenyl)amino]-5-chloropyrazolo[1,5-a]pyrimidin-6-yl}acetylamino)piperidine-1-carboxylate

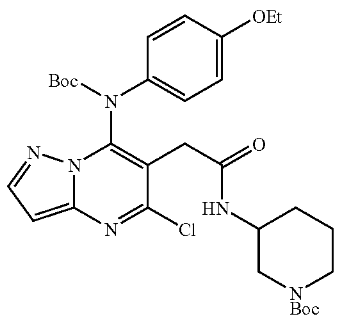

To an N,N-dimethylformamide (0.5 mL) solution containing {7-[tert-butoxycarbonyl-(4-ethoxyphenyl)amino]-5-chloropyrazolo[1,5-a]pyrimidin-6-yl} acetic acid (10.3 mg, 0.023 mmol) and (S)-3-amino-1-tert-butoxycarbonylpipridine (9.2 mg, 0.046 mmol), diisopropylamine (50 μL) and O-(7-benzotriazol-1-yl)-N,N,N',N'-tetramethyluronium hexafluorophosphate (13.1 mg, 0.0345 mmol) were added, and the mixture was stirred at room temperature for 16 hr. To the reaction solution, aqueous ammonium chloride was added, and the mixture was extracted with ethyl acetate. The organic layer was dried over sodium sulfate. After the sodium sulfate was filtered off, the solvent was distilled off, and the residue was purified with PTLC (50% ethyl acetate-hexane) to obtain the title compound (10.8 mg). $^1H$ NMR ($CDCl_3$, 400 MHz) δ(ppm): 8.16 (s, 1H), 7.22 (t, J=6.3 Hz, 2H), 6.92 (d, J=7.8 Hz, 2H), 6.69 (d, J=2.0 Hz, 1H), 3.97 (q, J=5.5 Hz, 2H), 3.92 (m, 1H), 3.57-3.07 (m, 6H), 2.47-2.31 (m, 1H), 1.81 (m, 1H), 1.62 (s, 9H), 1.47 (s, 9H), 1.26 (t, J=6.2 Hz, 3H).

Example 4

Synthesis of tert-butyl (S)-3-{8-[tert-butoxycarbonyl-(4-ethoxyphenyl)amino]-6-oxo-6,7-dihydro-1,4,5,8a-tetraaza-s-indacen-5-yl}piperidine-1-carboxylate

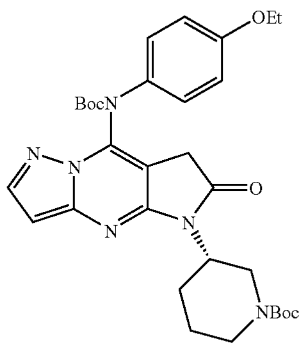

To a mixed solution of tetrahydrofuran (0.3 mL) and N,N-dimethylformamide (0.1 mL) containing tert-butyl (S)-3-(2-{7-[tert-butoxycarbonyl-(4-ethoxyphenyl)amino]-5-chloropyrazolo[1,5-a]pyrimidin-6-yl}acetylamino)piperidine-1-carboxylate (4.3 mg), sodium hydride (with 40% mineral oil added) (10 mg) was added, and the mixture was stirred at room temperature for 1 hr. To the reaction solution, aqueous ammonium chloride was added, and the mixture was extracted with ethyl acetate. The ethyl acetate layer was dried over sodium sulfate. After the sodium sulfate was filtered off, the solvent was distilled off to obtain the title compound.

Reference Example 27

Synthesis of tert-butyl (S)-3-(allyl-{6-allyl-7-[tert-butoxycarbonyl-(4-ethoxyphenyl)amino)pyrazolo[1,5-a]pyrimidin-5-yl}amino)piperidine-1-carboxylate

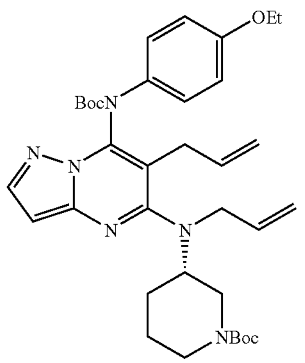

To a mixed solution of tetrahydrofuran (0.6 mL) and N,N-dimethylformamide containing tert-butyl (S)-3-{6-allyl-7-[tert-butoxycarbonyl-(4-ethoxyphenyl)amino]pyrazolo[1,5-a]pyrimidin-5-ylamino}piperidine-1-carboxylate (100 mg, 0.168 mmol), sodium hydride and allyl bromide were added at 0° C., and the mixture was stirred at 70° C. for 5 hr. To the reaction solution, water was added, and the mixture was extracted with ethyl acetate. The combined ethyl acetate layer was dried over sodium sulfate. After the sodium sulfate was filtered off, the solvent was distilled off to obtain the title compound (102 mg).

Example 5

Synthesis of tert-butyl (S)-3-{10-[tert-butoxycarbonyl-(4-ethoxyphenyl)amino]-6,9-dihydro-1,4,5,10a-tetraazacyclohepta[f]inden-5-yl}piperidine-1-carboxylate

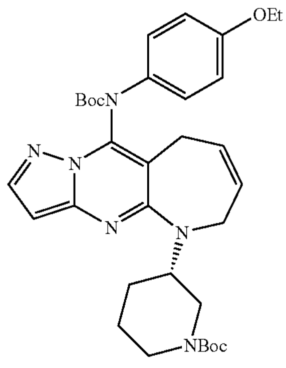

To a toluene (0.7 mL) solution containing tert-butyl (S)-3-(allyl-{6-allyl-7-[tert-butoxycarbonyl-(4-ethoxyphenyl)amino]pyrazolo[1,5-a]pyrimidin-5-yl}amino)piperidine-1-carboxylate (28.5 mg, 0.035 mmol), Grubbs catalyst (8.4 mg, 0.0103 mmol) was added. After the mixture was stirred at 40° C. for 16 hr, the solvent was distilled off, and the residue was purified with PTLC (30% ethyl acetate-hexane) to obtain the title compound (10 mg).

Example 6

Synthesis of tert-butyl (S)-3-{10-[tert-butoxycarbonyl-(4-ethoxyphenyl)amino]-6,7,8,9-tetrahydro-1,4,5,10a-tetraazacyclohepta[f]inden-5-yl}piperidine-1-carboxylate

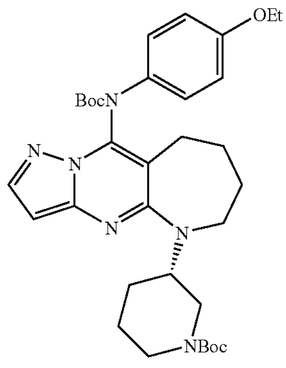

tert-Butyl(S)-3-{10-[tert-butoxycarbonyl-(4-ethoxyphenyl)amino]-6,9-dihydro-1,4,5,10a-tetraazacyclohepta[f]inden-5-yl}piperidine-1-carboxylate (12.5 mg) was hydrogenated in the presence of palladium-carbon (15 mg) in ethanol (1.2 mL) under a hydrogen atmosphere. After the reaction, the palladium-carbon was filtered off, and the filtrate was concentrated. The residue was used for the subsequent reaction without purification.

Example 7

Synthesis of tert-butyl (4-ethoxyphenyl)(5-hydroxy-6,7-dichloro-5H-1,4,5,8a-tetraaza-s-indacen-8-yl) carbamate

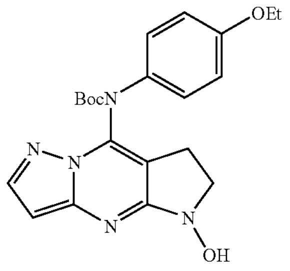

To a methanol (30 mL) solution containing tert-butyl[5-chloro-6-(2-oxoethyl)pyrazolo[1,5-a]pyrimidin-7-yl](4-ethoxyphenyl)carbamate (1.0 g, 2.3 mmol) and hydroxylamine hydrochloride (0.81 g, 11.6 mmol), sodium cyanoborohydride (0.73 g, 11.6 mmol) was added, and the mixture was heated at 50° C. for 16 hr. To the reaction solution, aqueous sodium hydrogen carbonate was added, and the mixture was extracted with ethyl acetate. The combined ethyl acetate layer was washed with brine and dried over sodium sulfate. After the sodium sulfate was filtered off, and the solvent was distilled off to obtain the title compound.

$^1$H NMR ($CDCl_3$, 400 MHz) δ(ppm): 7.85 (d, J=2.0 Hz, 1H), 7.19 (dd, J=2.2 and 6.8 Hz, 2H), 6.80 (dd, J=2.2 and 6.6 Hz, 2H), 6.26 (d, 1H), 3.97 (q, J=7.1 Hz, 2H), 3.79 (t, J=7.6 Hz, 2H), 2.71 (br, 2H), 1.37 (s, 9H), 1.26 (t, J=7.1 Hz, 3H).

Example 8

Synthesis of tert-butyl (S)-3-{8-[tert-butoxycarbonyl-(4-ethoxyphenyl)amino]-1,4,5,8a-tetraaza-s-indacen-5-yl}piperidine-1-carboxylate

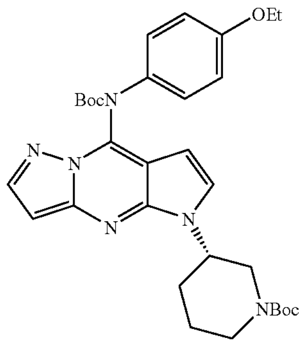

To a mixed solution of tetrahydrofuran (3.2 mL) and water (0.8 mL) containing tert-butyl (S)-3-{6-allyl-7-[tert-butoxycarbonyl-(4-ethoxyphenyl)amino]pyrazolo[1,5-a]pyrimidin-5-ylamino}piperidine-1-carboxylate (375 mg, 0.632 mmol), sodium periodate (405 mg, 1.89 mmol) and osmium tetraoxide (2.5w/v % tert-butanol solution, 793 μL, 0.063 mmol) were added, and the mixture was stirred. After the reaction, aqueous sodium sulfite was added to the solution, and the mixture was extracted with ethyl acetate. The combined ethyl acetate layer was washed with brine and dried over sodium sulfate. After the sodium sulfate was filtered off, and the solvent was distilled off to obtain the title compound.

Example 9

Synthesis of tert-butyl (S)-3-[8-[tert-butoxycarbonyl-(4-ethoxyphenyl)amino]-6-(tert-butyldimethylsilanyloxymethyl)-1,4,5,8a-tetraaza-s-indacen-5-yl]piperidine-1-carboxylate

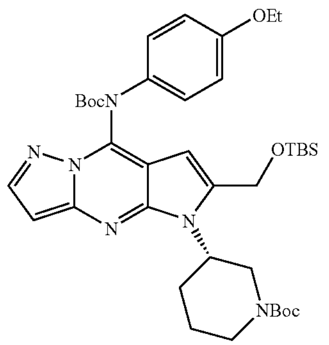

To a methylene chloride (1 mL) solution containing tert-butyl (S)-3-{7-[tert-butoxycarbonyl-(4-ethoxyphenyl)amino]-6-[3-(tert-butyldimethylsilanyloxy)-2-hydroxypropyl]pyrazolo[1,5-a]pyrimidin-5-ylamino}piperidine-1-carboxylate (28.6 mg, 0.0495 mmol), Dess-Martin periodinane (25.2 mg, 0.0594 mmol) was added at 0° C., and the mixture was allowed to warm to room temperature and stirred for 3 hr. After the reaction, the reaction solution was concentrated, and the residue was purified with PTLC (30% ethyl acetate-hexane) to obtain the title compound (14.5 mg).

$^1$H NMR ($CDCl_3$, 400 MHz) δ(ppm): 8.05 (d, J=2.2 Hz, 1H), 7.26 (dt, J=9.8 and 2.8 Hz, 2H), 6.74 (dt, J=9.8 and 2.8 Hz, 2H), 6.40 (d, J=2.2 Hz, 1H), 6.04 (s, 1H), 4.66 (d, J=12.9 Hz, 1H), 4.58 (d, J=13.4 Hz, 1H), 4.19-4.02 (m, 2H), 3.90 (q, J=7.0 Hz, 2H), 2.84 (br, 2H), 1.91 (m, 1H), 1.80 (m, 1H), 1.38 (s, 9H), 1.30 (t, J=7.1 Hz, 3H), 1.28 (s, 9H), 0.83 (s, J=13.0 Hz, 9H), 0.02 (d, J=16.8 Hz, 6H).

Reference Example 28

Synthesis of tert-butyl (S)-3-[7-{tert-butoxycarbonyl-(4-ethoxyphenyl)amino}-6-{3-(tert-butyldimethylsilanyloxy)-2-hydroxypropyl}pyrazolo[1,5-a]pyrimidin-5-ylamino]piperidine-1-carboxylate

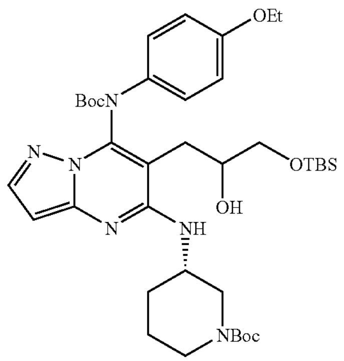

By using tert-butyl {6-[3-(tert-butyldimethylsilanyloxy)-2-hydroxypropyl]-5-chloropyrazolo[1,5-a]pyrimidin-7-yl}(4-ethoxyphenyl)carbamate, the title compound was synthesized by the same method as Reference example 7.

Reference Example 29

Synthesis of tert-butyl (S)-3-[7-{tert-butoxycarbonyl-(4-ethoxyphenyl)amino}-6-{3-(tert-butyldimethylsilanyloxy)-2-methanesulfonyloxypropyl}pyrazolo[1,5-a]pyrimidin-5-ylamino]piperidine-1-carboxylate

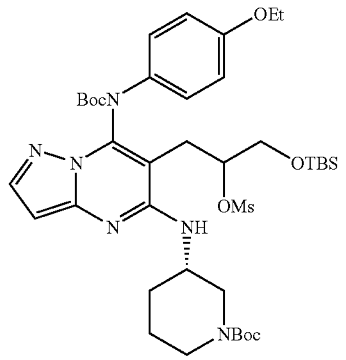

By using tert-butyl (S)-3-[7-{tert-butoxycarbonyl-(4-ethoxyphenyl)amino}-6-{3-(tert-butyldimethylsilanyloxy)-2-hydroxypropyl}pyrazolo[1,5-a]pyrimidin-5-ylamino]piperidine-1-carboxylate, the title compound was synthesized by the same method as Reference example 25.

Example 10

Synthesis of tert-butyl (S)-3-[8-{tert-butoxycarbonyl-(4-ethoxyphenyl)amino}-6-(tert-butyldimethylsilanyloxymethyl)-6,7-dihydro-1,4,5,8a-tetraaza-s-indacen-5-yl]piperidine-1-carboxylate

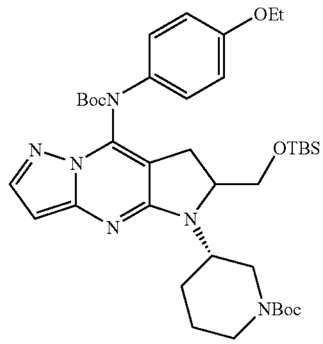

By using tert-butyl (S)-3-[7-{tert-butoxycarbonyl-(4-ethoxyphenyl)amino}-6-{3-(tert-butyldimethylsilanyloxy)-2-methanesulfonyloxypropyl}pyrazolo[1,5-a]pyrimidin-5-ylamino]piperidine-1-carboxylate, the title compound was synthesized by the same method as Example 1.

Example 11

Synthesis of (S)-(4-ethoxyphenyl)(5-piperidin-3-yl-6,7-dihydro-5H-1,4,5,8a-tetraaza-s-indacen-8-yl) amine (Compound No.: A-008)

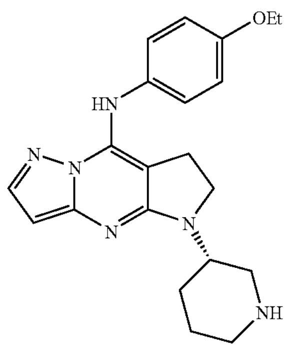

To a methylene chloride (4 mL) solution containing tert-butyl (S)-3-{8-[tert-butoxycarbonyl-(4-ethoxyphenyl) amino]-6,7-dihydro-1,4,5,8a-tetraaza-s-indacen-5-yl}piperidine-1-carboxylate (0.693 mmol), trifluoroacetic acid (2 mL) was added with ice-cooling, and the mixture was allowed to warm to room temperature and stirred for 16 hr. After the reaction, the reaction solution was poured into aqueous sodium hydrogen carbonate, and the mixture was extracted with ethyl acetate. The ethyl acetate layer was washed with brine and dried over sodium sulfate. After the sodium sulfate was filtered off, the solvent was distilled off and the residue was purified with PTLC {10% (2 mol/L ammonia/methanol)-methylene chloride} to obtain the title compound (97.0 mg).

$^{1}$H NMR ($CDCl_3$, 400 MHz) δ(ppm): 7.74 (d, J=2.2 Hz, 1H), 7.55 (s, 1H), 7.17 (d, J=8.8 Hz, 2H), 6.99 (d, J=8.8 Hz, 2H), 6.06 (d, J=2.2 Hz, 1H), 4.05 (t, J=7.1 Hz, 2H), 3.43 (m, 2H), 3.13 (m, 1H), 3.03 (m, 1H), 2.67 (t, 1H), 2.54 (m, 1H), 2.30 (t, 2H), 1.79 (m, 3H), 1.60 (m, 1H), 1.44 (t, 3H).

HPLC retention time (HPLC condition A): 7.30 min

ESI/MS: 379.15 (M+H, $C_{21}H_{26}N_6O$)

Example 12

Synthesis of (S)-(4-ethoxyphenyl)(5-piperidin-3-yl-5H-14,5,8a-tetraaza-s-indacen-8-yl)amine (Compound No.: F-001)

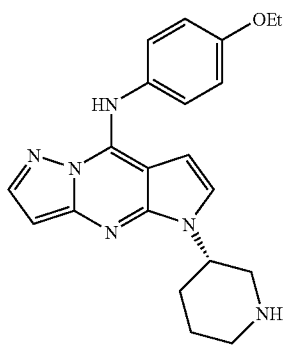

By using tert-butyl (S)-3-{8-[tert-butoxycarbonyl-(4-ethoxyphenyl)amino]-1,4,5,8a-tetraaza-s-indacen-5-yl}piperidine-1-carboxylate, the title compound was synthesized by the same method as Example 11.

$^{1}$H NMR ($CDCl_3$, 400 MHz) δ(ppm): 8.30 (br, 1H), 8.04 (d, J=2.4 Hz, 1H), 7.35 (dd, J=2.2 and 6.6 Hz, 2H), 6.99 (dd, J=2.2 and 6.6 Hz, 2H), 6.82 (d, J=3.9 Hz, 1H), 6.31 (d, J=2.2 Hz, 1H), 5.42 (d, J=3.9 Hz, 1H), 4.70 (m, 1H), 4.10 (q, J=7.1 Hz, 2H), 3.33 (m, 1H), 3.10 (m, 1H), 2.80 (m, 1H), 2.68 (m, 1H), 2.13-1.67 (m, 4H), 1.47 (t, J=7.1 Hz, 3H).

HPLC retention time: 7.91 min

ESI/MS: 377.14 (M+H, $C_{21}H_{24}N_6O$)

Example 13

Synthesis of (S)-(4-ethoxyphenyl)(5-piperidin-3-yl-6,9-dihydro-5H-1,4,5,10a-tetraazacyclohepta[f]inden-10-yl)amine (Compound No.: G-001)

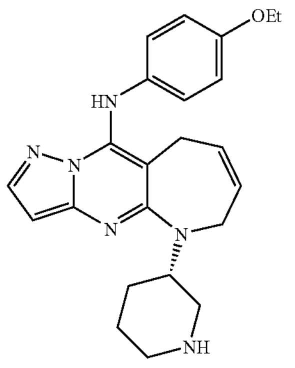

By using tert-butyl (S)-3-{10-[tert-butoxycarbonyl-(4-ethoxyphenyl)amino]-6,9-dihydro-1,4,5,10a-tetraazacyclohepta[f]inden-5-yl}piperidine-1-carboxylate, the title compound was synthesized by the same method as Example 11.

$^{1}$H NMR ($CDCl_3$, 400 MHz) δ(ppm): 7.81 (d, J=2.2 Hz, 1H), 7.54 (s, 1H), 7.02 (d, J=8.8 Hz, 2H), 6.85 (d, J=8.8 Hz, 2H), 6.16 (d, J=2.2 Hz, 1H), 5.71 (m, 2H), 4.47 (m, 1H), 4.02 (q, J=6.8 Hz, 2H), 3.82 (m, 2H), 3.31 (m, 1H), 3.05 (m, 1H), 2.98 (d, J=5.6 Hz, 2H), 2.74 (t, J=11.2 Hz, 1H), 2.55 (m, 1H), 2.02 (m, 1H), 1.96 (m, 2H), 1.67 (m, 2H), 1.42 (t, J=6.8 Hz, 3H).

HPLC retention time (HPLC condition A): 9.17 min

ESI/MS: 405.04 (M+H, $C_{23}H_{28}N_6O_1$)

Example 14

Synthesis of (S)-(4-ethoxyphenyl)(5-piperidin-3-yl-6,7,8,9-tetrahydro-5H-1,4,5,10a-tetraazacyclohepta [f]inden-10-yl)amine (Compound No.: C-001)

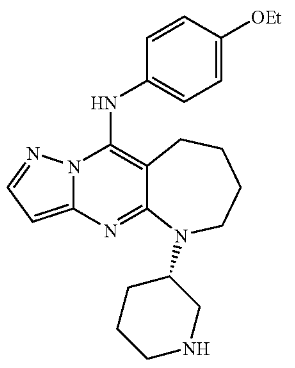

By using tert-butyl (S)-3-{10-[tert-butoxycarbonyl-(4-ethoxyphenyl)amino]-6,7,8,9-tetrahydro-1,4,5,10a-tetraaza-cyclohepta[f]inden-5-yl}piperidine-1-carboxylate, the title compound was synthesized by the same method as Example 11.

$^1$H NMR ($CDCl_3$, 400 MHz) δ(ppm): 7.76 (d, J=2.2 Hz, 1H), 7.50 (s,1H), 7.03 (d, J=8.8 Hz, 2H), 6.85 (d, J=9.0 Hz, 2H), 6.06 (d, J=2.2 Hz, 1H), 4.59 (m, 1H), 4.03 (q, J=7.1 Hz, 2H), 3.38 (m, 2H), 3.26 (m, 1H), 3.10 (m, 1H), 2.82 (m, 1H), 2.66 (t, J=11.0 Hz, 1H), 2.56 (m, 1H), 2.17 (m, 3H), 2.00 (m, 1H), 1.82-1.66 (m, 5H), 1.42 (t, J=7.1 Hz, 3H).

HPLC retention time: 8.59 min

ESI/MS: 407.12 (M+H, $C_{23}H_{30}N_6O_1$)

Example 15

Synthesis of 8-(4-ethoxyphenylamino)-6,7-dihydro-1,4,5,8a-tetraaza-s-indacen-5-ol (Compound No.: A-020)

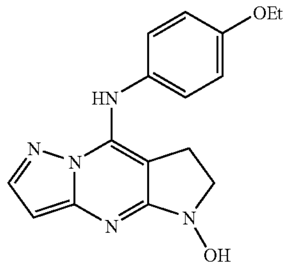

By using tert-butyl (4-ethoxyphenyl)(5-hydroxy-6,7-dichloro-5H-1,4,5,8a-tetraaza-s-indacen-8-yl)carbamate, the title compound was synthesized by the same method as Example 11.

$^1$H NMR ($CDCl_3$, 400 MHz) δ(ppm): 7.84 (d, J=2.2 Hz, 1H), 7.82 (s, 1H), 7.16 (dd, J=2.2 and 6.6 Hz, 2H), 6.90 (dd, J=2.2 and 6.6 Hz), 6.26 (d, J=2.2 Hz, 1H), 4.05 (q, J=7.1 Hz, 2H), 3.53 (t, J=7.6 Hz, 2H), 2.23 (t, J=7.6 Hz, 2H), 1.44 (t, J=7.1 Hz, 3H).

HPLC retention time (HPLC condition A): 7.74 min

ESI/MS: 312.15 (M+H, $C_{16}H_{17}N_5O_2$)

Example 16

Synthesis of 8-(4-ethoxyphenylamino)-6,7-dihydro-1,4,5,8a-tetraaza-s-indacen-5-yl acetate (Compound No.: A-021)

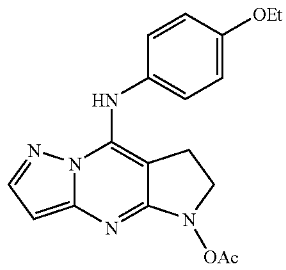

To a methylene chloride (0.5 mL) solution containing 8-(4-ethoxyphenylamino)-6,7-dihydro-1,4,5,8a-tetraaza-s-indacen-5-ol (2.8 mg), triethylamine (50 μL) and acetic anhydride (50 μL) were added. After this solution was stirred at room temperature for 30 min, the solvent was concentrated, and the residue was purified with PTLC (70% ethyl acetate-hexane) to obtain the title compound (2.3 mg).

$^1$H NMR ($CDCl_3$, 400 MHz) δ(ppm): 7.93 (s, 1H), 7.90 (d, 2H), 7.19 (dd, J=2.2 and 6.6 Hz, 2H), 6.91 (dd, J=2.2 and 6.6 Hz, 2H), 6.35 (d, 1H), 4.06 (q, J=6.8 Hz, 2H), 3.58 (t, J=7.6 Hz, 2H), 2.36 (t, J=7.3 Hz, 2H), 2.57 (s, 3H), 1.45 (t, J=7.1 Hz, 3H).

HPLC retention time (HPLC condition A): 10.8 min

ESI/MS: 354.06 (M+H, $C_{18}H_{19}N_5O_3$)

Example 17

Synthesis of [5-(4-aminocyclohexyl)-5,6,7,8-tetrahydro-1,4,5,9a-tetraazacyclopenta[b]naphthalen-9-yl](4-ethoxyphenyl)amine (Compound No.: B-002)

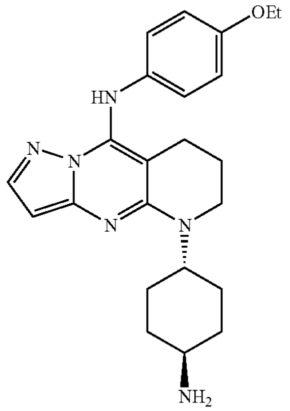

By using tert-butyl[5-(4-tert-butoxycarbonylaminocyclohexyl)-5,6,7,8-tetrahydro-1,4,5,9a-tetraazacyclopenta[b]naphthalen-9-yl](4-ethoxyphenyl)carbamate, the title compound was synthesized by the same method as Example 11.

$^1$H NMR ($CDCl_3$, 400 MHz) δ(ppm): 7.75 (d, J=2.2 Hz,1H), 7.46 (s, 1H), 7.01 (d, J=8.8 Hz, 2H), 6.85 (d, J=8.8 Hz, 2H), 6.03 (d, J=2.2 Hz, 1H), 4.95 (m, 1H), 4.02 (q, J=7.1 Hz, 2H), 3.21 (t, J=5.6 Hz, 2H), 2.76 (m, 1H), 2.10 (t, J=6.1 Hz, 2H), 2.00 (m, 2H), 1.78 (m, 4H), 1.53 (m, 2H), 1.42 (t, J=6.8 Hz, 3H).

HPLC retention time (HPLC condition A): 7.2 min

ESI/MS: 407.34 (M+H, $C_{23}H_{30}N_6O$)

Example 18

Synthesis of (S)-(2-methylbenzothiazol-6-yl)(5-piperidin-3-yl-6,7-dihydro-5H-1,4,5,8a-tetraaza-s-indacen-8-yl)amine (Compound No.: A-022)

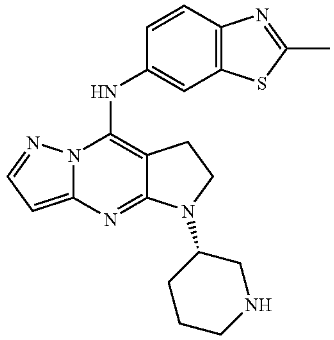

By using tert-butyl (S)-3-(8-{tert-butoxycarbonyl-[4-(2-methylbenzothiazol-6-yl)]-6,7-dihydro-1,4,5,8a-tetraaza-s-indacen-5-yl}piperidine-1-carboxylate, the title compound was synthesized by the same method as Example 11.

$^1H$ NMR ($CDCl_3$, 400 MHz) δ(ppm): 10.63 (s, 2H), 9.71 (s, 1H), 8.49 (s, 1H), 8.04 (d, J=8.5 Hz, 1H), 7.89 (d, J=2.2 Hz, 2H), 7.82 (d, J=2.2 Hz, 2H), 7.41 (dd, J=8.5 and 2.2 Hz, 1H), 6.42 (d, J=2.0 Hz, 1H), 4.68 (t, J=11.3 Hz, 1H), 3.72 (dq, J=31.1 and 9.0 Hz, 2H), 3.48-3.34 (m, 3H), 3.01 (m, 1H), 2.99 (s, 3H), 2.39 (t, J=8.5 Hz, 2H), 2.08-1.79 (m, 4H).

HPLC retention time (HPLC condition A): 6.19 min

ESI/MS: 406.10 (M+H, $C_{21}H_{23}N_7S$)

Example 19

Synthesis of (S)-[4-(2-methoxyethoxy)phenyl](5-piperidin-3-yl-6,7-dihydro-5H-1,4,5,8a-tetraaza-s-indacen-8-yl)amine (Compound No.: A-023)

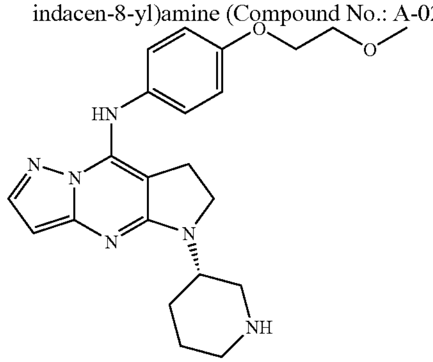

By using tert-butyl (S)-3-(8-{tert-butoxycarbonyl-[4-(2-methoxyethoxy)phenyl]amino}-6,7-dihydro-1,4,5,8a-tetraaza-s-indacen-5-yl)piperidine-1-carboxylate, the title compound was synthesized by the same method as Example 11.

$^1H$ NMR ($CDCl_3$, 400 MHz) δ(ppm): 10.93 (s, 1H), 9.65 (s, 1H), 8.29 (s, 1H), 7.86 (d, J=2.2 Hz, 1H), 7.26 (d, J=7.8 Hz, 2H), 7.00 (dd, J=9.6 and 2.8 Hz, 2H), 6.39 (d, J=2.0 Hz, 1H), 4.67 (t, J=11.8 Hz, 1H), 4.17 (t, J=4.5 Hz, 2H), 3.80 (dd, J=5.4 and 3.7 Hz, 2H), 3.71 (dq, J=28.4 and 6.8 Hz, 2H), 3.48 (s, 3H), 3.48-3.30 (m, 3H), 3.04 (m, 1H), 2.37 (t, 2H, J=8.5 Hz), 2.08-1.79 (m, 4H).

HPLC retention time (HPLC condition A): 6.19 min

ESI/MS: 409.15 (M+H, $C_{22}H_{28}N_6O_2$)

Example 20

Synthesis of (S)-(4-ethoxyphenyl)(3-fluoro-5-piperidin-3-yl-6,7-dihydro-5H-1,4,5,8a-tetraaza-s-indacen-8-yl)amine (Compound No.: A-018) and (S)-(2,3-difluoro-5-piperidin-3-yl-6,7-dihydro-5H-1,4,5,8a-tetraaza-s-indacen-8-yl)(4-ethoxyphenyl)amine (Compound No.: A-019)

Compound No.: A-018

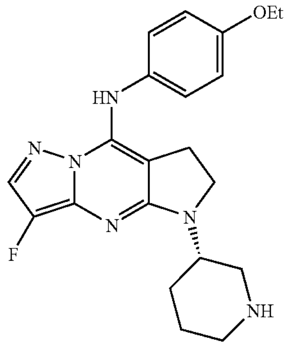

-continued

Compound No.: A-019

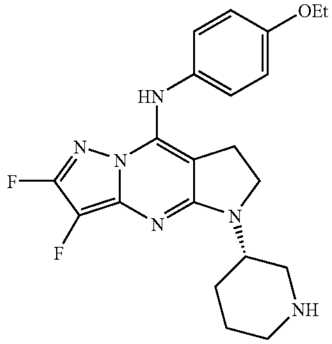

To an N,N-dimethylformamide (1.3 mL) solution containing tert-butyl (S)-3-{8-[tert-butoxycarbonyl-(4-ethoxyphenyl)amino]-6,7-dihydro-1,4,5,8a-tetraaza-s-indacen-5-yl}piperidine-1-carboxylate (78 mg, 0.14 mmol), an N,N-dimethylformamide (1.4 mL) solution containing 1-chloromethyl-4-fluoro-1,4-diazoniabicyclo[2.2.2]octane bis(tetrafluoroborate) (38.3 mg, 0.108 mmol) was added with ice-cooling, and this mixture was stirred at room temperature for 4 days. After the reaction, 0.2 mol/L hydrochloric acid was added to the reaction solution, and the mixture was extracted with ethyl acetate. The ethyl acetate layer was washed with aqueous sodium hydrogen carbonate and then brine and dried over sodium sulfate. After the sodium sulfate was filtered off, the solvent was distilled off. To the residue, methylene chloride (3.0 mL) and trifluoroacetic acid (0.3 mL) were added, and this solution was stirred at room temperature. The solvent was distilled off under reduced pressure, and the residue was purified with preparative HPLC to obtain the title compounds.

(S)-(4-Ethoxyphenyl)(3-fluoro-5-piperidin-3-yl-6,7-dihydro-5H-1,4,5,8a-tetraaza-s-indacen-8-yl)amine (Compound No.: A-018)

Yield: 7.6 mg

HPLC retention time (HPLC condition A): 8.50 min

ESI/MS: 397.08 (M+H, $C_{21}H_{25}FN_6O$)

(S)-(2,3-Difluoro-5-piperidin-3-yl-6,7-dihydro-5H-1,4,5,8a-tetraaza-s-indacen-8-yl)(4-ethoxyphenyl)amine (Compound No.: A-019)

Yield: 14.9 mg

HPLC retention time (HPLC condition A): 10.23 min

ESI/MS: 415.07 (M+H, $C_{21}H_{24}F_2N_6O_1$)

Example 21

Synthesis of (S)-{8-(4-ethoxyphenylamino)-5-piperidin-3-yl-6,7-dihydro-5H-1,4,5,8a-tetraaza-s-indacen-6-yl]methanol (Compound No.: A-024)

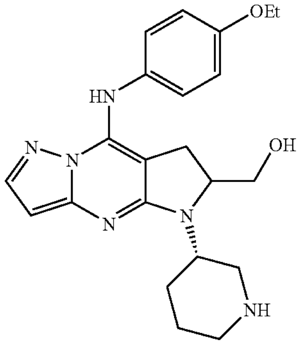

By using tert-butyl (S)-3-[8-{tert-butoxycarbonyl-(4-ethoxyphenyl)amino}-6-(tert-butyldimethylsilanyloxymethyl)-6,7-dihydro-1,4,5,8a-tetraaza-s-indacen-5-yl]piperidine-1-carboxylate, the title compound was synthesized by the same method as Example 11.

HPLC retention time (HPLC condition A): 6.41 min

ESI/MS: 409.10 (M+H, $C_{22}H_{28}N_6O_2$)

Example 22

Synthesis of tert-butyl (S)-3-{3-chloro-8-[tert-butoxycarbonyl-(4-ethoxyphenyl)amino]-6,7-dihydro-1,4,5,8a-tetraaza-s-indacen-5-yl}piperidine-1-carboxylate

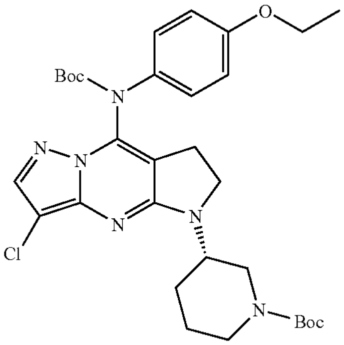

To a THF solution (2.0 mL) of tert-butyl (S)-3-{8-[tert-butoxycarbonyl-(4-ethoxyphenyl)amino]-6,7-dihydro-1,4,5,8a-tetraaza-s-indacen-5-yl}piperidine-1-carboxylate (12.5 mg, 0.0216 mmol), N-chlorosuccinimide (15.3 mg, 0.114 mmol) was added at room temperature and the mixture was stirred at room temperature for 1 hr. After the reaction, aqueous sodium thiosulfate solution was added to the reaction solution, and the mixture was extracted with ethyl acetate. The ethyl acetate layer was washed with water and then brine and dried over sodium sulfate. After the sodium sulfate was filtered off, the solvent was evaporated to obtain the title compound.

HPLC retention time (HPLC condition A): 16.69 min

ESI/MS: 613.10 (M+H, $C_{31}H_{41}ClN_6O_5$)

Example 23

Synthesis of tert-butyl (S)-3-{3-bromo-8-tert-butoxycarbonyl-(4-ethoxyphenyl)amino}-6,7-dihydro-1,4,5,8a-tetraaza-s-indacen-5-yl}piperidine-1-carboxylate

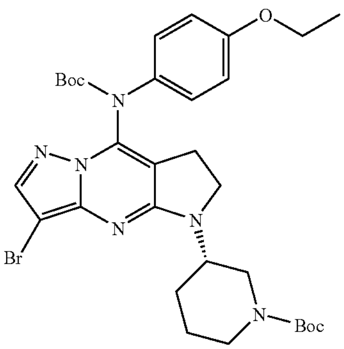

To a THF solution (2.0 mL) of tert-butyl (S)-3-{8-[tert-butoxycarbonyl-(4-ethoxyphenyl)amino]-6,7-dihydro-1,4,5,8a-tetraaza-s-indacen-5-yl}piperidine-1-carboxylate (20.0 mg, 0.0346 mmol), N-bromosuccinimide (31.4 mg, 0.176 mmol) was added on ice-bath cooling and the mixture was stirred for 10 min. After the reaction, aqueous sodium thiosulfate solution was added to the reaction solution, and the mixture was extracted with ethyl acetate. The ethyl acetate layer was washed with water and then brine and dried over sodium sulfate. After the sodium sulfate was filtered off, the solvent was evaporated and the residue was purified with column chromatography (30% ethyl acetate-hexane) to obtain the title compound (16.8 mg).

HPLC retention time (HPLC condition A): 16.79 min

ESI/MS: 657.05, 659.10 (M+H, $C_{31}H_{41}BrN_6O_5$)

Example 24

Synthesis of (S)-(4-ethoxyphenyl)-(3-chloro-5-piperidin-3-yl-6,7-dihydro-5H-1,4,5,8a-tetraaza-s-indacen-8-yl)amine (Compound No.: A-101)

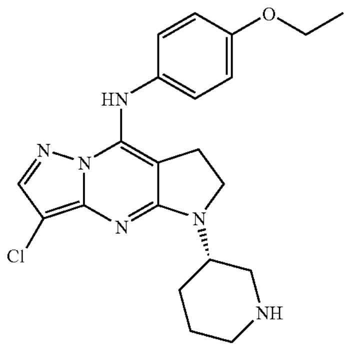

The title compound was synthesized using tert-butyl (S)-3-{3-chloro-8-[tert-butoxycarbonyl-(4-ethoxyphenyl) amino]-6,7-dihydro-1,4,5,8a-tetraaza-s-indacen-5-yl}piperidine-1-carboxylate by the same method as Example 11.

HPLC retention time (HPLC condition A): 9.82 min

ESI/MS: 413.05 (M+H, $C_{21}H_{25}ClN_6O_1$)

Example 25

Synthesis of (S)-(4-ethoxyphenyl)-(3-bromo-5-piperidin-3-yl-6,7-dihydro-5H-1,4,5,8a-tetraaza-s-indacen-8-yl)amine (Compound No.: A-102)

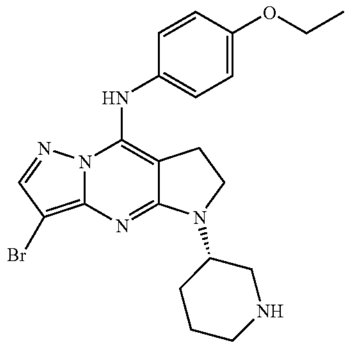

The title compound was synthesized using tert-butyl (S)-3-{3-bromo-8-[tert-butoxycarbonyl-(4-ethoxyphenyl) amino]-6,7-dihydro-1,4,5,8a-tetraaza-s-indacen-5-yl}piperidine-1-carboxylate by the same method as Example 11.

HPLC retention time (HPLC condition A): 10.04 min

ESI/MS: 456.95, 459.00 (M+H, $C_{21}H_{25}BrN_6O_1$)

Example 26

Synthesis of (S)-furan-2-yl-(5-piperidin-3-yl-6,7-dihydro-5H-1,4,5,8a-tetraaza-s-indacen-8-yl)amine (Compound No.: A-095) and (S)-5-piperidin-3-yl-6,7-dihydro-5H-1,4,5,8a-tetraaza-s-indacen-8-ylamine (Compound No.: A-092)

Compound No.: A-095

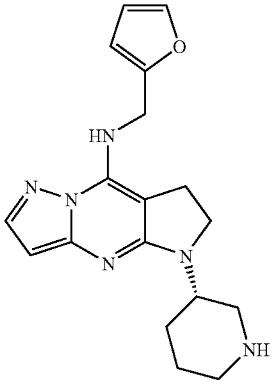

Compound No.: A-092

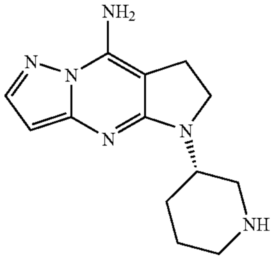

To a methylene chloride solution (2.0 mL) of tert-butyl (S)-3-{8-[tert-butoxycarbonyl-furan-2-ylmethylamino]-6,7-dihydro-1,4,5,8a-tetraaza-s-indacen-5-yl}piperidine-1-carboxylate (60.0 mg, 0.111 mmol), trifluoroacetic acid (1.0 mL) was added on ice-bath cooling and the mixture was allowed to warm up to room temperature and stirred for 4 hr. The reaction mixture was concentrated under reduced pressure and the residue was purified with preparative HPLC to obtain the two title compounds.

(Compound No.: A-095)

Yield: 18.0 mg

HPLC retention time (HPLC condition A): 5.40 min

ESI/MS: 338.95 (M+H, $C_{18}H_{22}N_6O_1$)

(Compound No.: A-092)

Yield: 13.4 mg

HPLC retention time (HPLC condition B): 2.51 min

ESI/MS: 259.00 (M+H, $C_{13}H_{18}N_6O_1$)

Example 27

Synthesis of tert-butyl (S)-3-(3-iodo-8-[tert-butoxycarbonyl-{4-(2-methoxyethoxy)phenyl}amino]-6,7-dihydro-1,4,5,8a-tetraaza-s-indacen-5-yl)piperidine-1-carboxylate

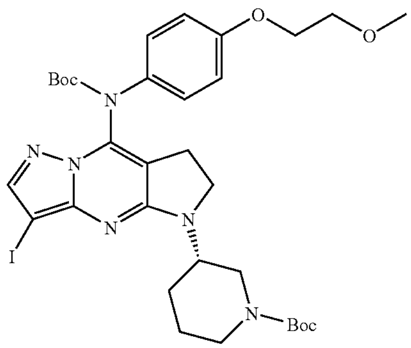

To a THF solution (1.5 mL) of tert-butyl (S)-3-(8-[tert-butoxycarbonyl-{4-(2-methoxyethoxy)phenyl}amino]-6,7-dihydro-1,4,5,8a-tetraaza-s-indacen-5-yl}piperidine-1-carboxylate (110.6 mg, 0.182 mmol), N-iodosuccinimide (49.1 mg, 0.218 mmol) was added at room temperature and the mixture was stirred for 3 hr. After the reaction, the reaction mixture was extracted with ethyl acetate. The ethyl acetate layer was washed with water and then brine and dried over sodium sulfate. After the sodium sulfate was filtered off, the solvent was removed under reduced pressure and the residue was purified with column chromatography (30% ethyl acetate-hexane) to obtain the title compound (118.9 mg).

HPLC retention time (HPLC condition A): 16.48 min

ESI/MS: 735.24 (M+H, $C_{32}H_{43}IN_6O_6$)

Example 28

Synthesis of tert-butyl (S)-3-[3-iodo-8-{tert-butoxycarbonyl-(2-methylbenzothiazol-6-yl)amino}-6,7-dihydro-1,4,5,8a-tetraaza-s-indacen-5-yl]piperidine-1-carboxylate

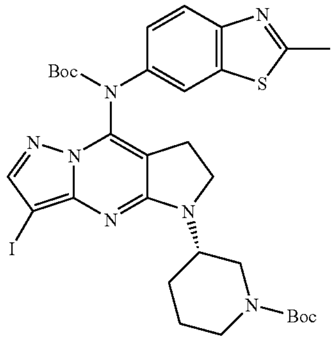

To a THF solution (1.5 mL) of tert-butyl (S)-3-[8-{tert-butoxycarbonyl-(2-methylbenzothiazol-6-yl)amino}-6,7-dihydro-1,4,5,8a-tetraaza-s-indacen-5-yl]piperidine-1-carboxylate (97.6 mg, 0.161 mmol), N-iodosuccinimide (43.5 mg, 0.193 mmol) was added at room temperature and the mixture was stirred for 3 hr. After the reaction, the reaction mixture was extracted with ethyl acetate. The ethyl acetate layer was washed with water and then brine and dried over sodium sulfate. After the sodium sulfate was filtered off, the solvent was removed under reduced pressure and the residue was purified with column chromatography (30% ethyl acetate-hexane) to obtain the title compound (109.7 mg).

HPLC retention time (HPLC condition A): 16.68 min

ESI/MS: 732.18 (M+H, $C_{31}H_{38}IN_7O_4S$)

Example 29

The compounds listed in the following Table H were synthesized from the corresponding starting material and reagent according to each method described in Examples 11 to 21, and 24 to 26. The compound number assigned to each compound in Table H corresponds to the compound number of the example listed in the above Tables A to G. The structures of novel compounds isolated were confirmed by $^1H$ NMR and/or mass analysis on a single quadrupole instrumentation equipped with an electrospray source or other appropriate analytical methods.

For results of mass analysis, M+H, that is, the measured value observed as the molecular mass of compound (M) with one proton (H) added, is shown. "HPLC retention time" represents the retention time (unit: min) of compound in HPLC analysis under the above-mentioned analytical conditions. "Conditions for HPLC" represents the conditions for HPLC analysis on that occasion.

TABLE H

| Compound NO. | ESI/MS M + H | HPLC Retention Time (min) | Conditions for HPLC |
|---|---|---|---|
| A-001 | 379.30 | 7.22 | A |
| A-002 | 393.18 | 6.75 | A |
| A-003 | 393.18 | 6.78 | A |
| A-004 | 393.18 | 7.20 | A |
| A-005 | 339.16 | 6.44 | A |
| A-006 | 353.18 | 6.25 | A |
| A-007 | 381.17 | 8.60 | A |
| A-009 | 379.22 | 6.42 | A |
| A-010 | 455.22 | 8.27 | A |
| A-011 | 393.25 | 7.82 | A |
| A-012 | 393.20 | 7.95 | A |
| A-013 | 365.20 | 6.87 | A |
| A-014 | 393.12 | 6.74 | A |
| A-015 | 393.12 | 7.84 | A |
| A-016 | 379.09 | 7.78 | A |
| A-017 | 386.10 | 11.25 | A |
| A-025 | 349.15 | 6.13 | A |
| A-026 | 329.20 | 6.89 | A |
| A-027 | 327.20 | 5.69 | B |
| A-032 | 335.05 | 6.03 | A |
| A-058 | 375.10 | 5.02 | A |
| A-091 | 443.10 | 5.84 | A |
| A-096 | 273.10 | 1.55 | B |
| A-099 | 393.05 | 6.65 | A |
| A-100 | 391.00 | 9.28 | A |
| B-001 | 393.12 | 8.81 | A |
| B-003 | 407.28 | 9.12 | A |
| B-004 | 366.30 | 11.14 | A |
| B-005 | 380.32 | 11.74 | A |
| B-006 | 394.29 | 10.24 | A |
| B-007 | 381.30 | 8.56 | A |
| B-009 | 368.31 | 9.66 | A |
| B-010 | 382.27 | 10.18 | A |
| B-011 | 350.32 | 9.72 | A |
| B-012 | 378.31 | 11.13 | A |
| B-013 | 407.28 | 7.72 | A |
| B-014 | 393.31 | 7.84 | A |

TABLE H-continued

| Compound NO. | ESI/MS M + H | HPLC Retention Time (min) | Conditions for HPLC |
|---|---|---|---|
| B-015 | 367.27 | 6.77 | A |
| B-016 | 469.32 | 11.31 | A |
| B-017 | 393.31 | 6.91 | A |
| B-018 | 401.30 | 8.77 | A |
| B-019 | 401.24 | 7.86 | A |
| B-020 | 401.17 | 8.64 | A |
| B-021 | 379.00 | 7.88 | A |
| B-022 | 407.06 | 9.10 | A |
| D-001 | 393.15 | 6.94 | A |
| D-002 | 407.08 | 7.78 | A |
| D-003 | 353.11 | 7.22 | A |
| D-004 | 393.12 | 7.97 | A |
| D-005 | 407.15 | 8.16 | A |
| D-006 | 407.08 | 8.36 | A |
| D-007 | 469.06 | 10.19 | A |
| E-001 | 407.12 | 8.84 | A |
| F-002 | 407.25 | 8.08 | A |

Example 30

General Measurement Method for Determining Inhibition of MAPKAP-K2 Enzyme Activity (Preparation of Solutions of Compounds)

Each compound was dissolved to DMSO to prepare a solution with a concentration of 20 mmol/L and this solution was stored at −20° C. This stock solution was diluted with DMSO successively to prepare solutions with 200-fold concentrations of a necessary range. These solutions were further diluted with water at a ratio of 1:20 to prepare solutions with 10-fold concentrations of a necessary range. Each of these solutions (5 μL) was used for each reaction in 50 μL-scale. Through the dilution series of all compounds, the final DMSO concentration was kept at 0.5%. Conventional tests for the compounds were carried out at a final concentration ranging from 100 μmol/L to 0.03 μmol/L, but in some cases, tests were carried out at lower concentrations, depending on activity.

(Measurements of MAPKAP-K2 Enzyme Activity)

To a DMSO solution (5 μL) containing a test compound at 5%, a solution (25 μL) containing a peptide substrate [peptide substrate 60 mmol/L, ATP 20 μmol/L, Tris buffer 60 mmol/L (pH 7.5), EGTA 0.2 mmol/L, β-mercaptoethanol 0.2%, magnesium acetate 20 mmol/L, [γ-33P]ATP 0.1 μCi (specific radioactivity ca. 110 TBq/mmol)] was added. The reaction was initiated by further adding a solution (20 μL) containing MAPKAP-K2 enzyme [recombinant human MAPKAP-K2 10 mU, Tris buffer 50 mmol/L (pH 7.5), EGTA 0.1 mmol/L, β-mercaptoethanol 0.1%, BSA 0.1%]. After the reaction was carried out at room temperature for 30 min, 200 mmol/L phosphoric acid (50 μL) was added to quench the reaction, and 90 μL of the reaction mixture was adsorbed on a multiscreen PH plate (Millipore). The plate was washed with 100 mmol/L phosphoric acid. After the plate was dried, 30 μL of MicroScint™-O (Perkin-Elmer) was added here, and the radioactivity (cpm) was measured on a scintillation counter to determine the inhibitory activity. The peptide substrate was Lys-Lys-Leu-Asn-Arg-Thr-Leu-Ser-Val-Ala.

(Note)

$$\%\ \text{Reference}=(X-B)/(Tot-B)\times 100$$

$$\%\ \text{Inhibition}=100\%-\%\ \text{Reference}$$

X=count per minute of the well with a test compound

B=count per minute of the well without the enzyme

Tot=count per minute of the well with only DMSO solvent and without a test compound (Calculation of MAPKAP-K2 Inhibitory Activity)

IC50 value=a concentration of compound at which 50% inhibition is observed

The efficacy of each compound in Tables A to G against MAPKAP-K2 is listed in the following Table J.

TABLE J

| Compound No. | Activity strength |
|---|---|
| A-001 | +++ |
| A-002 | +++ |
| A-003 | ++ |
| A-004 | + |
| A-005 | +++ |
| A-006 | +++ |
| A-007 | + |
| A-008 | +++ |
| A-009 | +++ |
| A-010 | ++ |
| A-012 | ++ |
| A-013 | +++ |
| A-014 | + |
| A-018 | +++ |
| A-019 | ++ |
| A-020 | +++ |
| A-022 | +++ |
| A-023 | +++ |
| A-024 | +++ |
| A-025 | +++ |
| A-026 | +++ |
| A-027 | +++ |
| A-032 | +++ |
| A-058 | +++ |
| A-091 | +++ |
| A-092 | +++ |
| A-095 | +++ |
| A-096 | +++ |
| A-099 | +++ |
| A-100 | +++ |
| B-001 | +++ |
| B-002 | +++ |
| B-003 | ++ |
| B-007 | + |
| B-013 | + |
| B-014 | +++ |
| B-015 | ++ |
| B-016 | ++ |
| B-017 | +++ |
| B-018 | + |
| B-021 | +++ |
| B-022 | ++ |
| C-001 | +++ |
| D-001 | ++ |
| D-002 | + |
| D-003 | + |
| D-006 | ++ |
| F-001 | +++ |
| F-002 | ++ |
| G-001 | +++ |

(For activity strength in the table, +++ represents IC50 value < 10 μmol/L, ++ represents 10 μmol/L ≦ IC50 value < 50 μmol/L and + represents 50 μmol/L ≦ IC50 value < 100 μmol/L.)

FIELD OF INDUSTRIAL APPLICATION

The compounds of the present invention are useful as MAPKAP-K2 inhibitors. Further, by using the compounds of the present invention as active ingredients, there is provided a therapeutic agent for neurodegenerative and/or neurological disorders (including dementia), inflammatory disease, sepsis, autoimmune diseases, destructive osteopathy, diabetes mellitus, cancer, ischemic reperfusion injury, angiodysplasia, cachexia, obesity, angiogenesis, asthma and/or chronic obstructive pulmonary disease (COPD).

What is claimed is:

1. A pyrazolopyrimidine derivative or medically acceptable salt thereof represented by formula (1):

(1)

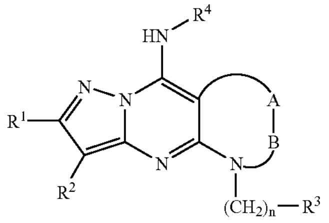

wherein, $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally substituted heterocyclic group, an optionally substituted C6-C14 aryl group or —$OR^5$;

$R^5$ represents a hydrogen atom, an optionally substituted C1-C8 alkyl group or —(C═O)$R^6$;

$R^6$ represents an optionally substituted C1-C8 alkyl group;

n represents 0 or 1, or n represents 0 when $R^3$ is —$OR^5$;

$R^4$ represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted heterocyclylalkyl group or an optionally substituted C7-C16 aralkyl group; the substituents in the optionally substituted C6-C14 aryl group as are one or more substituents selected from the group consisting of halogen, —CN, —$NO_2$, —CHO, —OH, —COOH, optionally substituted C1-C8 alkyl group, optionally substituted C2-C8 alkenyl, optionally substituted C2-C8 alkynyl, optionally substituted C3-C8 cycloalkyl group, —O—$(CH_2)_m$—W, optionally substituted C6-C14 aryl group, optionally substituted heterocyclic group, —C(═O)—$R^{133}$, —O—C(═O)$R^{26}$, —C(═O)$OR^{27}$, —$NR^{28}$C(═O)$R^{29}$, —$NR^{30}R^{31}$, —C(═O)$NR^{32}R^{33}$, —$NR^{34}$C(═$X^1$)$OR^{35}$, —$NR^{36}$C(═$X^2$)$NR^{37}R^{38}$, —$NR^{39}$—$SO_2R^{40}$, —$S(O)_r$—$R^{41}$ and —$SO_2NR^{42}R^{43}$, wherein $X^1$ or $X^2$ represents O, S, N—CN or NH and r represents 0 to 2;

W represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group or an optionally substituted heterocyclic group, and in this case m represents 0 to 4; or W represents an optionally substituted C1-C8 alkoxy group, —$NR^{150}R^{151}$ or an optionally substituted phenoxy group and in this case m represents 1 to 4;

$R^{26}$ to $R^{43}$, $R^{133}$, $R^{150}$ and $R^{151}$ may be identical or different and each represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted aralkyl group or an optionally substituted heterocyclylalkyl group, or, when $R^{30}$ and $R^{31}$, $R^{32}$ and $R^{33}$, $R^{37}$ and $R^{38}$, $R^{42}$ and $R^{43}$ or $R^{150}$ and $R^{151}$ are optionally substituted C1-C8 alkyl groups, the substituents in each combination may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(-Z^1)-$, $—(CH_2)_p—$, $—CH═C(-Z^2)-$ or $—(CH_2)_q—C(═O)—$;

p represents 3 and q represents 1 or 2;

$Z^1$ and $Z^2$ may be identical or different and each represents a hydrogen atom or $—CH_2—OR^{11}$; and $R^{11}$ represents a hydrogen atom, an optionally substituted C1-C8 alkyl group or a substituted silyl group.

2. A pyrazolopyrimidine derivative or medically acceptable salt thereof represented by formula (1):

(1)

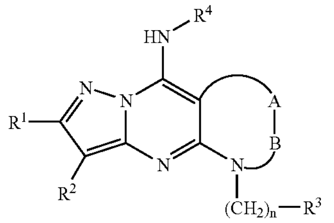

wherein $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally substituted heterocyclic group, an optionally substituted C6-C14 aryl group or $—OR^5$;

$R^5$ represents a hydrogen atom, an optionally substituted C1-C8 alkyl group or $—(C═O)R^6$;

$R^6$ represents an optionally substituted C1-C8 alkyl group;

n represents 0 or 1 or n represents 0 and when $R^3$ is $—OR^5$;

$R^4$ represents an optionally substituted C1-C8 alkyl group, an optionally substituted C3-C8 cycloalkyl group, an optionally substituted C6-C14 aryl group, an optionally substituted heterocyclic group or an optionally substituted C7-C16 aralkyl group; the substituents in the optionally substituted C6-C14 aryl group as $R^4$ are one or more substituents selected from the group consisting of halogen, —CN, $—NO_2$, optionally substituted C1-C8 alkyl group, $—O—(CH_2)_m—W$, optionally substituted C6-$C_{14}$ aryl group, optionally substituted heterocyclic group, $—C(═O)OR^7$, $—NR^8C(═O)R^9$, $—NR^{10}R^{127}$, $—C(═O)NR^{128}R^{129}$ and $—SO_2NR^{130}R^{131}$;

W represents a hydrogen atom, an optionally substituted C1-C8 alkyl group, an optionally substituted C3-C8 cycloalkyl group, an optionally substituted C6-C14 aryl group or an optionally substituted heterocyclic group and in this case m represents 0 to 4; or W represents an optionally substituted C1-C8 alkoxy group or an optionally substituted phenoxy group and in this case m represents 1 to 4;

$R^7$ to $R^{10}$ and $R^{127}$ to $R^{131}$ may be identical or different and each represents a hydrogen atom, an optionally substituted C1-C8 alkyl group, an optionally substituted C3-C8 cycloalkyl group or an optionally substituted C6-C14 aryl group, or, when $R^{10}$ and $R^{127}$, $R^{128}$ and $R^{129}$ or $R^{130}$ and $R^{131}$ are optionally substituted C1-C8 alkyl groups, they may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(-Z^3)-$, $—(CH_2)_p—$, $—CH═C(-Z^4)-$ or $—(CH_2)_q—C(═O)—$;

p represents 3 and q represents 1 or 2;

$Z^3$ and $Z^4$ may be identical or different and each represents a hydrogen atom or $—CH_{20}R^{11}$; and $R^{11}$ represents a hydrogen atom or an optionally substituted C1-C8 alkyl group.

3. The pyrazolopyrimidine derivative or medically acceptable salt thereof according to claim 1 or 2, wherein $R^1$ is hydrogen atom.

4. The pyrazolopyrimidine derivative or medically acceptable salt thereof according to claim 1 or 2, wherein $R^2$ is a hydrogen atom.

5. The pyrazolopyrimidine derivative or medically acceptable salt thereof according to claim 1 or 2, wherein $R^2$ is a halogen.

6. The pyrazolopyrimidine derivative or medically acceptable salt thereof according to claim 1 or 2, wherein $R^3$ is an optionally substituted C1-C8 alkyl group, an optionally substituted C3-C8 cycloalkyl group or an optionally substituted heterocyclic group.

7. The pyrazolopyrimidine derivative or medically acceptable salt thereof according to claim 1 or 2, wherein $R^3$ is an unsubstituted C1-C4 alkyl group, a substituted C1-C4 alkyl group wherein the substituents are 1 to 3 substituents selected from the group consisting of halogen, phenyl group, C1-C4 alkyl group substituted with 1 to 9 halogens, C1-C4 alkoxy group, C1-C4 alkoxy group substituted with 1 to 9 halogens, —CN, —CHO, —OH, —(C═O)OH, $—(C═O)OR^{86}$, $—(C═O)NR^{87}R^{88}$ and $—NR^{89}R^{90}$; $R^{86}$ represents a C1-C4 alkyl group, a 0308 cycloalkyl group or a phenyl group; $R^{87}$ and $R^{88}$ may be identical or different and each represents a hydrogen atom, a C1-C8 alkyl group, a C3-C8 cycloalkyl group, a phenyl group or an aralkyl group; $R^{89}$ represents a hydrogen atom, a C1-C4 alkyl group, a phenyl group or a benzyl group; $R^{90}$ represents a hydrogen atom, a C1-C4 alkyl group, a benzyl group, an acetyl group, a tert-butoxycarbonyl group or a benzyloxycarbonyl group, or, when $R^{89}$ and $R^{90}$ are alkyl groups, they may form a saturated or unsaturated 5- to 7-membered ring together with the nitrogen atom to which they bond; further this ring may contain 1 or 2 heteroatoms selected from the group consisting of oxygen atom, nitrogen atom and sulfur atom besides the nitrogen atom to which $R^{89}$ and $R^{90}$ bond, an unsubstituted C3-C8 cycloalkyl group, a substituted C3-C8 cycloalkyl group wherein the substituents are 1 to 3 substituents selected from the group consisting of halogen, —OH, —(C═O)OH, C1-4 alkyl group, C1-C4 alkoxy group and $—NR^{91}R^{92}$, wherein $R^{91}$ represents a hydrogen atom, a C1-C8 alkyl group, a phenyl group or a benzyl group and $R^{92}$ represents a hydrogen atom, a C1-C8 alkyl group, a benzyl group, an acetyl group, a tert-butoxycarbonyl group or a benzyloxycarbonyl group, an unsubstituted heterocyclic group or a substituted heterocyclic group wherein, when carbon atom(s) in the substituted heterocyclic group are substituted, the substituent(s) are 1 to 3 substituents selected from the group consisting of halogen, —(C═O)OH, C1-C4 alkyl group, C1-C4 alkyl group substituted with 1 to 9 halogens, phenyl group, benzyl group, C1-C4 alkoxy group, C1-C4 alkoxy group substituted with 1 to 9 halogens and $NR^{93}R^{94}$, wherein $R^{93}$ represents a hydrogen atom, a C1-C8 alkyl group, a phenyl group or a benzyl group and $R^{94}$ represents a hydrogen atom, a C1-C8 alkyl group, a benzyl group, an acetyl group, a tert-butoxycarbonyl group or a benzyloxycarbonyl group, wherein, when nitrogen atom(s) in the heterocycle are substituted, the substituents are one or more substituents selected from the group consisting of C1-C4 alkyl group, benzyl group, acetyl group, tert-butoxycarbonyl group and benzyloxycarbonyl group.

8. The pyrazolopyrimidine derivative or medically acceptable salt thereof according to claim 1 or 2, wherein $R^3$ is an unsubstituted heterocyclic group wherein the heterocyclic group represents a monocyclic 5- to 8-membered heterocyclic group containing 1 or 2 heteroatoms selected from the group consisting of N, O and S, a substituted saturated heterocyclic group wherein the heterocyclic group represents a monocyclic 5- to 8-membered heterocyclic group containing 1 or 2 heteroatoms selected from the group consisting of N, O and S, and the substituent bonds to a nitrogen atom in the heterocycle and the substituents represent one or more substituents selected from the group consisting of C1-C4 alkyl group, benzyl group and tert-butoxycarbonyl group, a C1-C4 alkyl group substituted with one amino group or a C3-C8 cycloalkyl group substituted with one amino group.

9. The pyrazolopyrimidine derivative or medically acceptable salt thereof according to claim 1 or 2, wherein $R^3$ is a piperidyl group, a pyrrolidinyl group or a cyclohexyl group substituted with an amino group.

10. The pyrazolopyrimidine derivative or medically acceptable salt thereof according to claim 1 or 2, wherein n is 0.

11. The pyrazolopyrimidine derivative or medically acceptable salt thereof according to claim 1 or 2, wherein $R^4$ san optionally substituted C6-C14 aryl group.

12. The pyrazolopyrimidine derivative or medically acceptable salt thereof according to claim 1 or 2, wherein $R^4$ is an optionally substituted C6-C14 aryl group and the substituents are one or more substituents selected from the group consisting of halogen, —CN, optionally substituted C1-C8 alkyl group, $—O—(CH_2)_m—W$, optionally substituted C6-C14 aryl group, optionally substituted heterocyclic group, $—C(═O)OR^7$ and $—C(═O)NR^9R^{10}$.

13. The pyrazolopyrimidine derivative or medically acceptable salt thereof according to claim 1 or 2, wherein $R^4$ is an optionally substituted C6-C14 aryl group and the substituents are one or more substituents selected from the group consisting of halogen, —CN, optionally substituted C1-C8 alkyl group and $—O—(CH_2)_m—W$.

14. The pyrazolopyrimidine derivative or medically acceptable salt thereof according to claim 1 or 2, wherein $R^4$ is an optionally substituted C6-C14 aryl group and the substituents are one or more $—O—(CH_2)_m—W$, wherein W is a hydrogen atom, an optionally substituted C1-C8 alkyl group, an optionally substituted heterocyclic group or an optionally substituted C1-C8 alkoxy group.

15. The pyrazolopyrimidine derivative or medically acceptable salt thereof according to claim 1 or 2, wherein $R^4$ is an optionally substituted C6-C14 aryl group and the substituents are one or more substituents selected from the group consisting of halogen, —CN, optionally substituted C1-C8 alkyl group, optionally substituted C6-C14 aryl group and optionally substituted heterocyclic group.

16. The pyrazolopyrimidine derivative or medically acceptable salt thereof according to claim 1 or 2, wherein $R^4$ is an optionally substituted C6-C14 aryl group and the substituents are one or more substituents selected from the group consisting of halogen, —CN, optionally substituted C1-C8 alkyl group, $—C(═O)OR^7$ and $—C(═O)NR^9R^{10}$.

17. The pyrazolopyrimidine derivative or medically acceptable salt thereof according to claim 1 or 2, wherein $R^4$ is an optionally substituted C6-C14 aryl group wherein the substituents are 1 to 3 substituents selected from the group consisting of halogen, —CN, optionally substituted C1-C8 alkyl group, $—O—(CH_2)_m—W$ and $—C(═O)OR^{113}$, wherein W represents a hydrogen atom, an optionally substituted C1-C4 alkyl group, an optionally substituted C3-C8 cycloalkyl group, an optionally substituted phenyl group or an optionally substituted monocyclic or bicyclic heterocyclic group and m represents 0 to 4; or W represents an optionally substituted C1-C4 alkoxy group and m represents 1 to 4, and $R^{113}$ represents an optionally substituted 0108 alkyl group, an optionally substituted C3-C8 cycloalkyl group or an optionally substituted phenyl group.

18. The pyrazolopyrimidine derivative or medically acceptable salt thereof according to claim 1 or 2, wherein $R^4$ is an optionally substituted phenyl group wherein the substituent is one $—O—(CH_2)_m—W$, wherein W represents a hydrogen atom or an optionally substituted C1-C4 alkyl group and m represents 0 to 4; or W represents an optionally substituted C1-C4 alkoxy group and m represents 1 to 4.

19. The pyrazolopyrimidine derivative or medically acceptable salt thereof according to claim 1 or 2, wherein $R^4$ is an optionally substituted C6-C14 aryl group wherein the substituents are one or more substituents selected from the group consisting of halogen, —CN, optionally substituted C1-C4 alkyl group, optionally substituted phenyl group and optionally substituted monocyclic or bicyclic heterocyclic group.

20. The pyrazolopyrimidine derivative or medically acceptable salt thereof according to claim 1 or 2, wherein $R^4$ is an optionally substituted C6-C14 aryl group wherein the substituents are one or more substituents selected from the group consisting of halogen, —CN, optionally substituted C1-C4 alkyl group, $—C(═O)OR^{113}$ and $—C(═O)NR^{118}R^{119}$, wherein $R^{113}$, $R^{118}$ and $R^{119}$ may be identical or different and each represents a hydrogen atom, an optionally substituted C1-C8 alkyl group, an optionally substituted C3-C8 cycloalkyl group or an optionally substituted C6-C14 aryl group; and when $R^{118}$ and $R^{119}$ are alkyl groups, they may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which they bond.

21. The pyrazolopyrimidine derivative or medically acceptable salt thereof according to claim 1 or 2, wherein $R^4$ is an optionally substituted heterocyclic group.

22. The pyrazolopyrimidine derivative or medically acceptable salt thereof according to claim 1 or 2, wherein $R^4$ is an optionally substituted bicyclic heteroaryl group wherein, when carbon atom(s) in the bicyclic heteroaryl group are substituted, the substituents are 1 to 3 substituents selected from the group consisting of halogen, —CN, C1-C8 alkyl group, C1-C4 alkyl group substituted with 1 to 9 halogens, C1-C8 alkoxy group, C1-C4 alkoxy group substituted with 1 to 9 halogens, phenyl group, monocyclic or bicyclic heterocyclic group, $—C(═O)OR^{122}$, $—NR^{123}R^{124}$ and $—C(═O)NR^{125}R^{126}$, wherein $R^{123}$ represents a hydrogen atom, a C1-C8 alkyl group, a phenyl group or a benzyl group, $R^{124}$ represents a hydrogen atom, a C1-C8 alkyl group, a benzyl group, an acetyl group, a tert-butoxycarbonyl group or a benzyloxycarbonyl group, $R^{122}$ represents a C1-C8 alkyl group, a C3-C8 cycloalkyl group or a phenyl group, and $R^{125}$ and $R^{126}$ may be identical or different and each represents a hydrogen atom, a C1-C8 alkyl group, a C3-C8 cycloalkyl group, a phenyl group or a benzyl group; when nitrogen atom(s) in the heterocycle are substituted, the substituents are one or more substituents selected from the group consisting of C1-C4 alkyl group, benzyl group, acetyl group, tert-butoxycarbonyl group and benzyloxycarbonyl group.

23. The pyrazolopyrimidine derivative or medically acceptable salt thereof according to claim 1 or 2, wherein $R^4$ is an optionally substituted bicyclic heteroaryl group wherein the bicyclic heteroaryl group means a bicyclic heteroaryl group wherein a phenyl group is fused with an aromatic heterocycle containing 1 or 2 heteroatoms selected from the group consisting of N, O and S; when carbon atom(s) in the bicyclic heteroaryl group are substituted, the substituents are 1 to 3 substituents selected from the group consisting of halogen, C1-C4 alkyl group and C1-C4 alkyl group substituted with 1 to 9 halogens; when nitrogen atom(s) in the heterocycle are substituted, the substituent represents one or more C1-C4 alkyl group.

24. The pyrazolopyrimidine derivative or medically acceptable salt thereof according to claim 1 or 2, wherein $R^4$ is a hydrogen atom, an optionally substituted C1-C8 alkyl group, an optionally substituted C3-C8 cycloalkyl group, an optionally substituted C7-C16 aralkyl group or an optionally substituted heterocyclylalkyl group.

25. The pyrazolopyrimidine derivative or medically acceptable salt thereof according to claim 1 or 2, wherein $R^4$ is an optionally substituted heterocyclylalkyl group.

26. The pyrazolopyrimidine derivative or medically acceptable salt thereof according to claim 1 or 2, wherein -A-B- is $—CH_2—CH_2—$, $—(CH_2)_p—$, or —CH═CH—.

27. The pyrazolopyrimidine derivative or medically acceptable salt thereof according to claim 1 or 2, wherein -A-B- is $—CH_2—CH_2$.

28. A pyrazolopyrimidine derivative represented by formula (2):

(2)

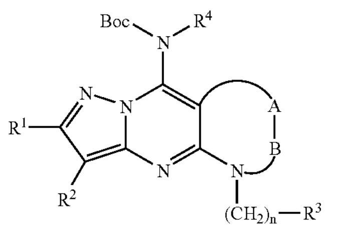

wherein, $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally susbstituted heterocyclic group, an optionally substituted C6-C14 aryl group ot $—OR^5$ ;

$R^5$ represents a hydrogen atom, an optionally substituted C1-C8 alkyl group or $—(C═O)R^6$;

$R^5$ represents an optionally substituted C1-C8 alkyl group;

n represents 0 or 1 , or n represents 0 when $R^3$ is $—OR^5$;

$R^4$ represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted heterocyclylalkyl group or an optionally substituted C7-C16 aralkyl group; the substituents in the optionally substituted C6-C14 aryl group as $R^4$ are one or more substituents selected from the group consisting of halogen, —CN, $-NO_2$, —CHO, —OH, —COOH, optionally substituted C1-C8 alkyl group, optionally substituted C2-C8 alkenyl, optionally substituted C2-C8 alkynyl, optionally substituted C3-C8 cycloalkyl group, $—O—(CH_2)_m—W$, optionally substituted $C_6$-$C_{14}$ aryl group, optionally substituted heterocyclic group, $—(═O)—R^{133}$, $—O—C(═O)R^{26}$, $—C(═O)OR^{27}$, $—NR^{28}C(═O)R^{29}$, $—NR^{30}R^{31}$, $—C(═O)NR^{32}R^{33}$, $—NR^{34}C(═X^1)OR^{35}$, $—NR^{36}C(═C^2)NR^{37}R^{38}$, $—NR^{39}SO_2R^{40}$, $—S(O)_r—R^{41}$ and $—SO_2NR^{42}R^{43}$, wherein $X^1$ or $X^2$ represents O, S, N—CN or NH and r represents 0 to 2;

W represents a hydrogen atom, optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group or an optionally substituted heterocyclic group, and in this case m represents 0 to 4; or W represents an optionally substituted C1-C8 alkoxy group, $—NR^{150}R^{151}$ or an optionally substituted phenoxy group an in this case m represents 1 to 4;

$R^{26}$ to $R^{43}$, $R^{133}$, $R^{150}$ and $R^{151}$ may be identical or different and each represents a hydrogen atom, an optionally substituted C1-C8 alkyl group, an optionally substituted C2-C8 alkenyl, an optionally substituted C2-C8 alkynyl, an optionally substituted C3-C8 cycloalkyl group, an optionally substituted C6-C14 aryl group, an optionally substituted heterocyclic group, an optionally substituted aralkyl group or an optionally substituted hereocyclylalkyl group, or, when $R^{30}$ and $R^{31}$, $R^{32}$ and $R^{33}$, $R^{37}$ and $R^{38}$, $R^{42}$ and $R^{43}$ or $R^{150}$ and $R^{151}$ are optionally substituted C1-C8 alkyl groups, the substituents in each combination may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(-Z^1)-$, $—(CH_2)_p—$, $—CH═C(-Z^2)-$ or $—(CH_2)_q—C(═O)—$;

p represents 3 and q represents 1 or 2;

$Z^1$ and $Z^2$ may be identical or different and each represents a hydrogen atom or $—CH_2—OR^{11}$; and $R^{11}$ represents a hydrogen atom, an optionally substituted C1-C8 alkyl group or a substituted silyl group, and Boc represents tert-butoxycarbonyl.

29. A pyrazolopyrimidine derivative represented by formula (2):

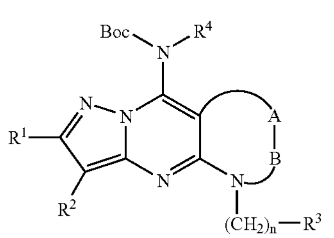

(2)

wherein, $R^1$ represents a hydrogen atom or a halogen;

$R^2$ represents a hydrogen atom or a halogen;

$R^3$ represents a hydrogen atom, an optionally substituted C1-C8 alkyl group, an optionally substituted C3-C8 cycloalkyl group, an optionally substituted heterocyclic group, an optionally substituted C6-C14 aryl group or $—OR^5$;

$R^5$ represents a hydrogen atom, an optionally substituted C1-C8 alkyl group or $—(C{=}O)R^6$;

$R^6$ represents an optionally substituted C1-C8 alkyl group;

n represents 0 or 1 or n represents 0 and when $R^3$ is $—OR^5$;

$R^4$ represents an optionally substituted C1-C8 alkyl group, an optionally substituted C3-C8 cycloalkyl group, an optionally substituted C6-C14 aryl group, an optionally substituted heterocyclic group or an optionally substituted C7-C16 aralkyl group; the substituents in the optionally substituted C6-C14 aryl group as $R^4$ are one or more substituents selected from the group consisting of halogen, —CN, $—NO_2$, optionally substituted C1-C8 alkyl group, $—O—(CH_2)_m—W$, optionally substituted C6-C14 aryl group, optionally substituted heterocyclic group, $—C({=}O)OR^7$, $—NR^8C({=}O)R^9$, $—NR^{10}R^{127}$, $—C({=}O)NR^{128}R^{129}$ and $—SO_2NR^{130}R^{131}$;

W represents a hydrogen atom, an optionally substituted C1-C8 alkyl group, an optionally substituted C3-C8 cycloalkyl group, an optionally substituted C6-C14 aryl group or an optionally substituted heterocyclic group and in this case m represents 0 to 4; or W represents an optionally substituted C1-C8 alkoxy group or an optionally substituted phenoxy group and in this case m represents 1 to 4;

$R^7$ to $R^{10}$ and $R^{127}$ to $R^{131}$ may be identical or different and each represents a hydrogen atom, an optionally substituted C1-C8 alkyl group, an optionally substituted C3-C8 cycloalkyl group or an optionally substituted C6-C14 aryl group, or, when $R^{10}$ and $R^{127}$, $R^{128}$ and $R^{129}$ or $R^{130}$ and $R^{131}$ are optionally substituted C1-C8 alkyl groups, they may form a saturated or unsaturated 5- to 7-membered ring together with the nitrogen atom to which they bond, and this ring may contain 1 or 2 heteroatoms selected from the group consisting of oxygen atom, nitrogen atom and sulfur atom besides the nitrogen atom to which these substituents bond;

-A-B- represents $—CH_2—CH(\text{-}Z^3)\text{-}$, $—(CH_2)_p—$, $—CH{=}C(\text{-}Z^4)\text{-}$ or $—(CH_2)_q—C({=}O)$;

p represents 3 and q represents 1 or 2;

$Z^3$ and $Z^4$ may be identical or different and each represents a hydrogen atom or $—CH_2OR^{11}$; and $R^{11}$ represents a hydrogen atom or an optionally substituted C1-C8 alkyl group, and Boc represents tert-butoxycarbonyl.

30. The pyrazolopyrimidine derivative according to claim 28 or 29, wherein $R^1$ and $R^2$ are a hydrogen atom.

31. The pyrazolopyrimidine derivative according to claim 28 or 29, wherein $R^1$ is a hydrogen atom and $R^2$ is a halogen.

32. The pyrazolopyrimidine derivative according to claim 28 or 29, wherein $R^3$ is an optionally substituted C1-C8 alkyl group, an optionally substituted cyclohexyl group or an optionally substituted heterocyclic group wherein the heterocyclic group means a 3- to 10-membered monocyclic or bicyclic heterocyclic group containing 1 to 4 heteroatoms selected from the group consisting of N, O and S.

33. The pyrazolopyrimidine derivative according to claim 28 or 29, wherein $R^3$ is an unsubstituted heterocyclic group wherein the heterocyclic group means a 5- to 8-membered monocyclic heterocyclic group containing 1 or 2 heteroatoms selected from the group consisting of N, O and S, a substituted heterocyclic group wherein the heterocyclic group means a 5- to 8-membered monocyclic heterocyclic group containing 1 or 2 heteroatoms selected from the group consisting of N, O and S, and the substituent bonds to a nitrogen atom in a saturated heterocyclic group and the substituents represent one or more substituents selected from the group consisting of C1-C4 alkyl group, benzyl group, acetyl group, tert butoxycarbonyl group and benzyloxycarbonyl group, a C1-C4 alkyl group substituted with an amino group or a C3-C8 alkyl group substituted with an amino group.

34. The pyrazolopyrimidine derivative according to claim 28 or 29, wherein $R^4$ is an optionally substituted C1-C8 alkyl group, an optionally substituted C3-C8 cycloalkyl group, an optionally substituted C6-C14 aryl group, an optionally substituted heterocyclic group or an optionally substituted heterocyclylalkyl group.

35. The pyrazolopyrimidine derivative according to claim 28 or 29, wherein $R^4$ is an optionally substituted phenyl group or an optionally substituted bicyclic heteroaryl group.

36. The pyrazolopyrimidine derivative according to claim 28 or 29, wherein $R^4$ is an optionally substituted phenyl group wherein the substituents are one or more $—O—(CH_2)_m—W$, wherein W represents a hydrogen atom or an optionally substituted C1-C4 alkyl group and m is 0 to 4, or W represents an optionally substituted C1-C4 alkoxy group and m is 2 to 4.

37. The pyrazolopyrimidine derivative according to claim 28 or 29, wherein $R^4$ is an optionally substituted bicyclic heteroaryl group wherein the substituents are 1 to 3 substituents selected from the group consisting of halogen, C1-C4 alkyl group and C1-C4 alkyl group substituted with 1 to 9 halogens.

38. The pyrazolopyrimidine derivative according to any of claim 28 or 29, wherein -A-B- is $—CH_2—CH_2—$, $—(CH_2)_p—$, or $—CH{=}CH—$.

39. The pyrazolopyrimidine derivative according to claim 28 or 29, wherein -A-B- is $—CH_2—CH_2$.

40. The pyrazolopyrimidine derivative according to claim 28 or 29, wherein n is 0.

41. A pharmaceutical composition comprising the pyrazolopyrimidine derivative or medically acceptable salt thereof according to claim 1 or 2, and a pharmaceutically acceptable carrier.

42. A MAPKAP-K2 inhibitor comprising the pyrazolopyrimidine derivative or medically acceptable salt thereof according to claims 1 or 2, as an active ingredient.

* * * * *